United States Patent
Peters et al.

(10) Patent No.: US 10,220,048 B2
(45) Date of Patent: *Mar. 5, 2019

(54) COMPOSITIONS AND METHODS FOR TREATING OCULAR DISEASES

(71) Applicant: Aerpio Therapeutics, Inc., Cincinnati, OH (US)

(72) Inventors: Kevin Peters, Cincinnati, OH (US); Robert Shalwitz, Bexley, OH (US)

(73) Assignee: AERPIO THERAPEUTICS, INC., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/355,910

(22) Filed: Nov. 18, 2016

(65) Prior Publication Data

US 2017/0319602 A1 Nov. 9, 2017

Related U.S. Application Data

(63) Continuation of application No. 14/214,413, filed on Mar. 14, 2014, now abandoned.

(60) Provisional application No. 61/792,868, filed on Mar. 15, 2013.

(51) Int. Cl.

| | |
|---|---|
| *A61K 31/635* | (2006.01) |
| *A61K 31/04* | (2006.01) |
| *A61K 31/10* | (2006.01) |
| *C07D 277/22* | (2006.01) |
| *A61K 39/395* | (2006.01) |
| *A61K 31/426* | (2006.01) |
| *A61K 31/427* | (2006.01) |
| *A61K 31/497* | (2006.01) |
| *A61K 31/4439* | (2006.01) |
| *A61K 31/428* | (2006.01) |
| *A61K 31/496* | (2006.01) |
| *A61K 31/513* | (2006.01) |
| *A61K 31/538* | (2006.01) |
| *C07D 277/52* | (2006.01) |
| *C07D 417/04* | (2006.01) |
| *C07D 277/64* | (2006.01) |
| *C07K 16/22* | (2006.01) |
| *A61K 38/05* | (2006.01) |
| *A61K 47/40* | (2006.01) |
| *C07D 413/04* | (2006.01) |
| *C07D 417/12* | (2006.01) |
| *C07D 417/14* | (2006.01) |
| *C07D 263/32* | (2006.01) |
| *C07D 277/28* | (2006.01) |
| *A61K 39/00* | (2006.01) |
| *A61K 9/00* | (2006.01) |

(52) U.S. Cl.
CPC ............ *A61K 31/635* (2013.01); *A61K 31/04* (2013.01); *A61K 31/10* (2013.01); *A61K 31/426* (2013.01); *A61K 31/427* (2013.01); *A61K 31/428* (2013.01); *A61K 31/4439* (2013.01); *A61K 31/496* (2013.01); *A61K 31/497* (2013.01); *A61K 31/513* (2013.01); *A61K 31/538* (2013.01); *A61K 38/05* (2013.01); *A61K 39/3955* (2013.01); *A61K 47/40* (2013.01); *C07D 263/32* (2013.01); *C07D 277/22* (2013.01); *C07D 277/28* (2013.01); *C07D 277/52* (2013.01); *C07D 277/64* (2013.01); *C07D 413/04* (2013.01); *C07D 417/04* (2013.01); *C07D 417/12* (2013.01); *C07D 417/14* (2013.01); *C07K 16/22* (2013.01); *A61K 9/0019* (2013.01); *A61K 2039/505* (2013.01)

(58) Field of Classification Search
None
See application file for complete search history.

(56) References Cited

U.S. PATENT DOCUMENTS

| | | |
|---|---|---|
| 5,078,486 A | 1/1992 | Evans |
| 5,736,536 A | 4/1998 | Siegall et al. |
| 5,919,813 A | 7/1999 | De, Jr. et al. |
| 5,980,929 A | 11/1999 | De Juan, Jr. |
| 6,455,035 B1 | 9/2002 | Suri et al. |
| 7,052,695 B2 | 5/2006 | Kalish |
| 7,226,755 B1 | 6/2007 | Peters et al. |
| 7,309,483 B2 | 12/2007 | Wiegand et al. |

(Continued)

FOREIGN PATENT DOCUMENTS

| | | |
|---|---|---|
| CN | 101506183 A | 8/2009 |
| EP | 1165115 B1 | 5/2003 |

(Continued)

OTHER PUBLICATIONS

Co-pending U.S. Appl. No. 15/462,326, filed Mar. 17, 2017.

(Continued)

*Primary Examiner* — Kortney L. Klinkel
*Assistant Examiner* — William Y Lee
(74) *Attorney, Agent, or Firm* — Wilson Sonsini Goodrich & Rosati

(57) ABSTRACT

Disclosed herein are compositions and methods for treating ocular diseases, inter alia, diabetic macular edema, age-related macular degeneration (wet form), choroidal neovascularization, diabetic retinopathy, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition.

13 Claims, 5 Drawing Sheets

(56) References Cited

U.S. PATENT DOCUMENTS

| | | |
|---|---|---|
| 7,354,579 B2 | 4/2008 | Holash et al. |
| 7,442,185 B2 | 10/2008 | Amark et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,691,963 B2 | 4/2010 | Prickett et al. |
| 7,740,846 B2 | 6/2010 | Gerber et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,029,808 B2 | 10/2011 | Srivastava et al. |
| 8,038,649 B2 | 10/2011 | Kronestedt |
| 8,062,255 B2 | 11/2011 | Brunnberg et al. |
| 8,075,517 B2 | 12/2011 | Karlsson et al. |
| 8,106,078 B2 | 1/2012 | Gray et al. |
| 8,178,570 B2 | 5/2012 | Chen et al. |
| 8,188,125 B2 | 5/2012 | Gray et al. |
| 8,235,952 B2 | 8/2012 | Wikner |
| 8,258,311 B2 | 9/2012 | Gray et al. |
| 8,277,412 B2 | 10/2012 | Kronestedt |
| 8,329,916 B2 | 12/2012 | Gray et al. |
| 8,338,615 B2 | 12/2012 | Gray et al. |
| 8,524,235 B2 | 9/2013 | Rotello et al. |
| 8,529,510 B2 | 9/2013 | Giambattista et al. |
| 8,551,054 B2 | 10/2013 | Guillermo |
| 8,569,348 B2 | 10/2013 | Shalwitz et al. |
| 8,591,890 B2 | 11/2013 | Srivastava et al. |
| 8,846,685 B2 | 9/2014 | Gray et al. |
| 8,883,774 B2 | 11/2014 | Shalwitz et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,968,766 B2 | 3/2015 | Hughes et al. |
| 8,999,325 B2 | 4/2015 | Peters et al. |
| 8,999,953 B2 | 4/2015 | Loftsson et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,248,172 B2 | 2/2016 | Srivastava et al. |
| 9,284,285 B2 | 3/2016 | Gray et al. |
| 9,403,789 B2 | 8/2016 | Eissenstat et al. |
| 9,440,963 B2 | 9/2016 | Peters et al. |
| 9,539,245 B2 | 1/2017 | Peters et al. |
| RE46,592 E | 10/2017 | Gray et al. |
| 9,795,594 B2 | 10/2017 | Gray et al. |
| 9,926,367 B2 | 3/2018 | Rotello et al. |
| 9,949,956 B2 | 4/2018 | Shalwitz et al. |
| 2003/0040463 A1 | 2/2003 | Wiegand et al. |
| 2003/0055006 A1 | 3/2003 | Siemeister et al. |
| 2003/0158199 A1 | 8/2003 | Stieber et al. |
| 2004/0077065 A1 | 4/2004 | Evdokimov et al. |
| 2005/0059639 A1 | 3/2005 | Wei |
| 2007/0173538 A1 | 7/2007 | Han et al. |
| 2007/0299116 A1 | 12/2007 | Gray et al. |
| 2008/0004267 A1 | 1/2008 | Gray et al. |
| 2008/0076764 A1 | 3/2008 | Peters et al. |
| 2008/0108631 A1 | 5/2008 | Gray et al. |
| 2008/0268051 A1 | 10/2008 | Hughes et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0129375 A1 | 5/2010 | Junge et al. |
| 2010/0226992 A1 | 9/2010 | Kabra |
| 2010/0227904 A1 | 9/2010 | Kabra et al. |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2011/0319455 A1 | 12/2011 | Klein et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2012/0207682 A1 | 8/2012 | Ashton |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0137741 A1 | 5/2013 | Kabra et al. |
| 2013/0190324 A1 | 7/2013 | Kompella et al. |
| 2013/0259952 A1 | 10/2013 | Ohto et al. |
| 2013/0324558 A1 | 12/2013 | Gray et al. |
| 2013/0331386 A1 | 12/2013 | Shalwitz et al. |
| 2014/0010805 A1 | 1/2014 | Hart et al. |
| 2014/0044707 A1 | 2/2014 | Rotello et al. |
| 2014/0066458 A1 | 3/2014 | Shalwitz et al. |
| 2014/0073566 A1 | 3/2014 | Koh et al. |
| 2014/0107391 A1 | 4/2014 | Srivastava et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0175676 A1 | 6/2015 | Fandl et al. |
| 2015/0190432 A1 | 7/2015 | Doiron et al. |
| 2015/0210656 A1 | 7/2015 | Gray et al. |
| 2015/0232425 A1 | 8/2015 | Alberico |
| 2015/0232575 A1 | 8/2015 | Peters et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297740 A1 | 10/2015 | Rau et al. |
| 2016/0000871 A1 | 1/2016 | Quaggin |
| 2016/0008327 A1 | 1/2016 | Shalwitz et al. |
| 2016/0030393 A1 | 2/2016 | Breslin et al. |
| 2016/0038467 A1 | 2/2016 | Peters |
| 2016/0045566 A1 | 2/2016 | Purcell et al. |
| 2016/0058828 A1 | 3/2016 | Dumont et al. |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0220541 A1 | 8/2016 | Peters et al. |
| 2016/0251421 A1 | 9/2016 | Brown et al. |
| 2016/0252526 A1 | 9/2016 | Bergmann et al. |
| 2016/0374996 A1 | 12/2016 | Gray et al. |
| 2017/0079959 A1 | 3/2017 | Peters |
| 2017/0260265 A1 | 9/2017 | Duerr et al. |
| 2017/0349649 A1 | 12/2017 | Rotello et al. |
| 2018/0009890 A1 | 1/2018 | Peters et al. |
| 2018/0022741 A1* | 1/2018 | Peters ............... A61K 31/426 |
| 2018/0037579 A1 | 2/2018 | Peters et al. |

FOREIGN PATENT DOCUMENTS

| | | |
|---|---|---|
| EP | 1292335 B1 | 5/2007 |
| EP | 2004697 A2 | 12/2008 |
| EP | 2371865 A2 | 10/2011 |
| EP | 2385763 A1 | 11/2011 |
| EP | 2451279 A1 | 5/2012 |
| EP | 2142189 B1 | 2/2013 |
| EP | 2592072 A2 | 5/2013 |
| EP | 2592073 A2 | 5/2013 |
| EP | 2624916 A2 | 8/2013 |
| EP | 2766043 A1 | 8/2014 |
| EP | 2766044 A1 | 8/2014 |
| EP | 2041129 B1 | 9/2014 |

(56) References Cited

FOREIGN PATENT DOCUMENTS

| | | |
|---|---|---|
| EP | 2041102 B1 | 11/2014 |
| EP | 2803663 A1 | 11/2014 |
| EP | 2038265 B1 | 3/2015 |
| EP | 2967066 A1 | 1/2016 |
| EP | 3168234 A1 | 5/2017 |
| WO | WO-9631598 A1 | 10/1996 |
| WO | WO-9818914 A1 | 5/1998 |
| WO | WO-0057901 A1 | 10/2000 |
| WO | WO-03084565 A2 | 10/2003 |
| WO | WO-2004043927 A1 | 5/2004 |
| WO | WO-2004043928 A2 | 5/2004 |
| WO | WO-2005000900 A1 | 1/2005 |
| WO | WO-2006068953 A2 | 6/2006 |
| WO | WO-2006116713 A1 | 11/2006 |
| WO | WO-2007033216 A2 | 3/2007 |
| WO | WO-2007076448 A2 | 7/2007 |
| WO | WO-2007116360 A2 | 10/2007 |
| WO | WO-2008002569 A2 | 1/2008 |
| WO | WO-2008002570 A2 | 1/2008 |
| WO | WO-2008002571 A2 | 1/2008 |
| WO | WO-2008002570 B1 | 4/2008 |
| WO | WO-2008002571 B1 | 4/2008 |
| WO | WO-2010010689 A1 | 1/2010 |
| WO | WO-2010081172 A1 | 7/2010 |
| WO | WO-2011005330 A1 | 1/2011 |
| WO | WO-2011057112 A1 | 5/2011 |
| WO | WO-2011057115 A1 | 5/2011 |
| WO | WO-2011057121 A1 | 5/2011 |
| WO | WO-2011134056 A1 | 11/2011 |
| WO | WO-2012047966 A2 | 4/2012 |
| WO | WO-2012073627 A1 | 6/2012 |
| WO | WO-2013056233 A1 | 4/2013 |
| WO | WO-2013056240 A1 | 4/2013 |
| WO | WO-2014145068 A1 | 9/2014 |
| WO | WO-2015126860 A1 | 8/2015 |
| WO | WO-2015138882 A1 | 9/2015 |
| WO | WO-2015152416 A1 | 10/2015 |
| WO | WO-2016022813 A1 | 2/2016 |
| WO | WO-2016049183 A1 | 3/2016 |

OTHER PUBLICATIONS

Co-pending U.S. Appl. No. 15/705,639, filed Sep. 15, 2017.
Co-pending U.S. Appl. No. 15/796,293, filed Oct. 27, 2017.
"Do, et al., The Da Vinci Study: Phase 2 Primary Results of VEGF Trap—Eye in Patients with Diabetic Macular Edema, Ophthalmology, Sep. 2011, 118(9): 1819-25".
"Hashizume, et al., Complementary Actions of Inhibitors of Angiopoietin-2 and VEGF on Tumor Angiogenesis and Growth, AACR, Cancer Res; Mar. 2010, 70(6):2213-23".
"Heier, et al., Intravitreal Aflibercept (VEGF Trap-Eye) Wet Age—related Macular Degeneration, Ophthalmolog, Dec. 2012, 119(12):2537-48".
"Vestweber, et al., Molecular Mechanisms That Control Endothelial Cell Contacts, J. Pathol 2000, 190:281-91".
Amarasinge, et al. Design and synthesis of potent, non-peptidic inhibitors of HPTPbeta. Bioorg Med Chem Lett. Aug. 15, 2006;16(16):4252-6. Epub Jun. 12, 2006.
Berenbaum, et al., Synergy, additivism and antagonism in immunosuppression, C/in. Exp. Immunol. (1977) 28, 1-18.
Brewster, et al. Comparative interaction of 2-hydroxypropyl-beta-cyclodextrin and sulfobutylether-beta-cyclodextrin with itraconazole: phase-solubility behavior and stabilization of supersaturated drug solutions. Eur J Pharm Sci. Jul. 3, 2008;34(2-3):94-103. doi: 10.1016/j.ejps.2008.02.007. Epub Feb. 26, 2008.
Cascone, et al. Targeting the angiopoietin/Tie2 pathway: cutting tumor vessels with a double-edged sword? J Clin Oncol. Feb. 1, 2012;30(4):441-4. doi: 10.1200/JCO.2011.38.7621. Epub Dec. 19, 2011.
Cho, et al. COMP-Ang1: a designed angiopoietin-1 variant with nonleaky angiogenic activity. Proc Natl Acad Sci U S A. Apr. 13, 2004;101(15):5547-52. Epub Apr. 1, 2004.

Davis, et al. Isolation of angiopoietin-1, a ligand for the TIE2 receptor, by secretion-trap expression cloning Cell. Dec. 27, 1996;87(7):1161-9.
Derevjanik, et al. Quantitative assessment of the integrity of the blood-retinal barrier in mice. Invest Ophthalmol Vis Sci. Jul. 2002;43(7):2462-7.
Do, et al. One-year outcomes of the Da Vinci study of VEGF trap-eye in eyes of diabetic macular edema. J. Ophthalmology. Aug. 2012; 119(8): 1658-1665.
Dumont, et al. Dominant-negative and targeted null mutations in the endothelial receptor tyrosine kinase, tek, reveal a critical role in vasculogenesis of the embryo. Genes Dev. Aug. 15, 1994;8(16):1897-909.
Fachinger, et al. Functional interaction of vascular endothelial-protein-tyrosine phosphatase with the angiopoietin receptor Tie-2. Oncogene. Oct. 21, 1999;18(43):5948-53.
Hackett, et al. Angiopoietin 2 expression in the retina: upregulation during physiologic and pathologic neovascularization. J Cell Physiol. Sep. 2000;184(3):275-84.
Hackett, et al. Angiopoietin-2 plays an important role in retinal angiogenesis J Cell Physiol. Aug. 2002;192(2):182-7.
Heiderstadt, et al. Increased juvenile and adult body weights in BALB/cByJ mice reared in a communal nest. J Am Assoc Lab Anim Sci. Jul. 2011;50(4):484-7.
International search report and written opinion dated Jul. 30, 2015 for PCT/US2015/020425.
International search report and written opinion dated Aug. 20, 2014 for PCT/US2014/029723.
Klein, et al. The Wisconsin epidemiologic study of diabetic retinopathy. II. Prevalence and risk of diabetic retinopathy when age at diagnosis is less than 30 years. Arch Ophthalmol. Apr. 1984;102(4):520-6.
Klopfenstein, et al. 1,2,3,4-Tetrahydroisoquinolinyl sulfamic acids as phosphatase PTP1B inhibitors. Bioorg Med Chem Lett. Mar. 15, 2006;16(6):1574-8. Epub Jan. 4, 2006.
Krueger, et al. Structural diversity and evolution of human receptor-like protein tyrosine phosphatases. EMBO J. Oct. 1990;9(10):3241-52.
Nambu, et al. Angiopoietin 1 inhibits ocular neovascularization and breakdown of the blood-retinal barrier. Gene Ther. May 2004;11(10):865-73.
Nguyen, et al. Primary End Point (Six Months) Results of the Ranibizumab for Edema of the mAcula in diabetes (READ-2) study. Ophthalmology. Nov. 2009;116(11):2175-81.e1. doi: 10.1016/j.ophtha.2009.04.023. Epub Aug. 22, 2009.
Nguyen, et al. Supplemental oxygen improves diabetic macular edema: a pilot study. Invest Ophthalmol Vis Sci. Feb. 2004;45(2):617-24.
Nguyen, et al. Vascular endothelial growth factor is a critical stimulus for diabetic macular edema. Am J Ophthalmol. Dec. 2006;142(6):961-9. Epub Aug. 2, 2006.
Office action dated Jul. 17, 2015 for U.S. Appl. No. 14/214,413.
Office action dated Aug. 31, 2016 for U.S. Appl. No. 15/098,955.
Office action dated Oct. 6, 2015 for U.S. Appl. No. 13/999,670.
Office action dated Oct. 21, 2016 for U.S. Appl. No. 15/099,161.
Office action dated May 19, 2016 for U.S. Appl. No. 14/214,413.
Oshima, et al. Angiopoietin-2 enhances retinal vessel sensitivity to vascular endothelial growth factor. J Cell Physiol. Jun. 2004;199(3):412-7.
Ozaki, et al. Intravitreal sustained release of VEGF causes retinal neovascularization in rabbits and breakdown of the blood-retinal barrier in rabbits and primates. Exp Eye Res. Apr. 1997;64(4):505-17.
Pubchem. Compound Summary for: CID 52799544. Create Date: May 20, 2011. Retrieved on Apr. 27, 2015. https://pubchem.ncbi.nlm.nih.gov/compound/52799544.
Tobe, et al. Targeted disruption of the FGF2 gene does not prevent choroidal neovascularization in a murine model. Am J Pathol. Nov. 1998;153(5):1641-6.
U.S. Appl. No. 14/938,526, filed Nov. 11, 2015.
U.S. Appl. No. 15/016,599, filed Feb. 5, 2016.
Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.

(56) References Cited

OTHER PUBLICATIONS

Co-pending U.S. Appl. No. 14/938,526, filed Nov. 11, 2015.
Co-pending U.S. Appl. No. 15/016,599, filed Feb. 5, 2016.
Co-pending U.S. Appl. No. 15/273,068, filed Sep. 22, 2016.
Co-pending U.S. Appl. No. 15/365,186, filed Nov. 30, 2016.
Co-pending U.S. Appl. No. 15/430,100, filed Feb. 10, 2017.
Co-pending U.S. Appl. No. 15/438,218, filed Feb. 21, 2017.
Co-pending U.S. Appl. No. 15/443,353, filed Feb. 27, 2017.
Co-pending U.S. Appl. No. 15/443,622, filed Feb. 27, 2017.
Co-pending U.S. Appl. No. 15/463,340, filed Mar. 20, 2017.
Del Valle, Cyclodextrins and their uses: a review Process biochemistry, May 31, 2004, 39(9):1033-46.
European search report and opinion dated Oct. 6, 2016 for EP Application No. 14762974.
Jambhekar, et al., Cyclodextrins in pharmacy: background and Introduction, J Chronother Drug Deliv, 2013, 4:1-13.
Notice of allowance dated Jul. 22, 2016 for U.S. Appl. No. 13/999,670.
Shintei, et al., Newly Revised Disease and Drugs, Yakuji Nippo Limited, 1986 (Third print), p. 504-510. (English Translation).
Singapore search report dated Jun. 16, 2016 for SG Application No. 11201507131W.
Singapore written opinion dated Jun. 16, 2016 for SG Application No. 11201507131W.
Vadlapudi, et al., Recent Patents on Emerging Therapeutics for the Treatment of Glaucoma, Age Related Macular Degeneration and Uveitis, NIH Public Access, Author manuscript, available in PMC Nov. 18, 2014, 38 pages.
Co-pending U.S. Appl. No. 15/894,442, filed Feb. 12, 2018.
Co-pending U.S. Appl. No. 15/913,392, filed Mar. 6, 2018.
Co-pending U.S. Appl. No. 15/958,346, filed Apr. 20, 2018.
Co-pending U.S. Appl. No. 15/958,355, filed Apr. 20, 2018.
Co-pending U.S. Appl. No. 15/958,358, filed Apr. 20, 2018.
Co-pending U.S. Appl. No. 15/969,109, filed May 2, 2018.
Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.
Mitchell, et al. The Restore study: ranibizumab monotherapy or combined with laser versus laser monotherapy for diabetic macular edema. Ophthalmology Apr. 2011;118 (4): 615-25.
Reagan-Shaw, et al. Dose translation from animal to human studies revisited. FASEB J. Mar. 2008;22(3):659-61.
U.S. Appl. No. 15/443,622 Office Action dated May 4, 2018.

\* cited by examiner

COMPOSITIONS AND METHODS FOR TREATING OCULAR DISEASES

CROSS REFERENCE

This Application is a continuation of U.S. application Ser. No. 14/214,413, filed Mar. 14, 2014, which claims the benefit of U.S. Provisional Application No. 61/792,868, filed Mar. 15, 2013, the contents of each of which is incorporated by reference in its entirety.

FIELD

Disclosed herein are compositions and methods for treating ocular diseases, inter alia, diabetic macular edema, age-related macular degeneration (wet form), choroidal neovascularization, diabetic retinopathy, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition.

BACKGROUND

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States. Vascularization of the cornea secondary to injury or disease is yet another category of ocular vascular disease that can lead to severe impairment of vision.

"Macular degeneration" is a general medical term that applies to any of several disease syndromes which involve a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type may reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly.

Choroidal neovascular membrane (CNVM) is a problem that is related to a wide variety of retinal diseases, but is most commonly linked to age-related macular degeneration. With CNVM, abnormal blood vessels stemming from the choroid (the blood vessel-rich tissue layer just beneath the retina) grow up through the retinal layers. These new vessels are very fragile and break easily, causing blood and fluid to pool within the layers of the retina.

Diabetes (diabetes mellitus) is a metabolic disease caused by the inability of the pancreas to produce insulin or to use the insulin that is produced. The most common types of diabetes are type 1 diabetes (often referred to as Juvenile Onset Diabetes Mellitus) and type 2 diabetes (often referred to as Adult Onset Diabetes Mellitus). Type 1 diabetes results from the body's failure to produce insulin due to loss of insulin producing cells, and presently requires the person to inject insulin. Type 2 diabetes generally results from insulin resistance, a condition in which cells fail to use insulin properly. Type 2 diabetes of the has a component of insulin deficiency as well.

Diabetes is directly responsible for a large number of disease conditions, including conditions or diseases of the eye including diabetic retinopathy (DR) and diabetic macular edema (DME) which are leading causes of vision loss and blindness in most developed countries. The increasing number of individuals with diabetes worldwide suggests that DR and DME will continue to be major contributors to vision loss and associated functional impairment for years to come.

Diabetic retinopathy is a complication of diabetes that results from damage to the blood vessels of the light-sensitive tissue at the back of the eye (retina). At first, diabetic retinopathy may cause no symptoms or only mild vision problems. Eventually, however, diabetic retinopathy can result in blindness. Diabetic retinopathy can develop in anyone who has type 1 diabetes or type 2 diabetes.

At its earliest stage, non-proliferative retinopathy, microaneurysms occur in the retina's tiny blood vessels. As the disease progresses, more of these blood vessels become damaged or blocked and these areas of the retina send signals into the regional tissue to grow new blood vessels for nourishment. This stage is called proliferative retinopathy. The new blood vessels grow along the retina and along the surface of the clear, vitreous gel that fills the inside of the eye.

By themselves, these blood vessels do not cause symptoms or vision loss. However, they have thin, fragile walls and without timely treatment, these new blood vessels can leak blood (whole blood or some constituents thereof) which can result in severe vision loss and even blindness.

Also, fluid can leak into the center of the macula, the part of the eye where sharp, straight-ahead vision occurs. The fluid and the associated protein begin to deposit on or under the macula swell the patient's central vision becomes distorted. This condition is called macular edema. It can occur at any stage of diabetic retinopathy, although it is more likely to occur as the disease progresses. About half of the people with proliferative retinopathy also have macular edema.

Uveitis is a condition in which the uvea becomes inflamed. The eye is shaped much like a tennis ball, hollow on the inside with three different layers of tissue surrounding a central cavity. The outermost is the sclera (white coat of the eye) and the innermost is the retina. The middle layer between the sclera and the retina is called the uvea. The uvea contains many of the blood vessels that nourish the eye. Complications of uveitis include glaucoma, cataracts or new blood vessel formation (neovascularization).

The currently available interventions for exudative (wet form) macular degeneration, diabetic retinopathy, diabetic macular edema, choroidal neovascular membrane and complications from uveitis or trauma, include laser photocoagulation therapy, low dose radiation (teletherapy) and surgical removal of neovascular membranes (vitrectomy). Laser therapy has had limited success and selected choroidal neovascular membranes which initially respond to laser therapy have high disease recurrence rates. There is also a potential loss of vision resulting from laser therapy. Low dose radiation has been applied ineffectively to induce regression of choroidal neovascularization. Recently ranibizumab and pegaptinib which are vascular endothelial growth factor (VEGF) antagonist, have been approved for use in age-related macular degeneration.

Retinal vein occlusion (RVO) is the most common retinal vascular disease after diabetic retinopathy. Depending on the area of retinal venous drainage effectively occluded, it is broadly classified as either central retinal vein occlusion (CRVO), hemispheric retinal vein occlusion (HRVO), or branch retinal vein occlusion (BRVO). It has been observed that each of these has two subtypes. Presentation of RVO in general is with variable painless visual loss with any combination of fundal findings consisting of retinal vascular tortuosity, retinal hemorrhages (blot and flame shaped), cotton wool spots, optic disc swelling and macular edema. In a CRVO, retinal hemorrhages will be found in all four quadrants of the fundus, whilst these are restricted to either the superior or inferior fundal hemisphere in a HRVO. In a BRVO, hemorrhages are largely localized to the area drained by the occluded branch retinal vein. Vision loss occurs secondary to macular edema or ischemia.

There is therefore a long felt and substantial need for methods of treating diseases of the eye which are characterized by vascular instability, vascular leakage, and neovascularization.

BRIEF DESCRIPTION OF THE DRAWINGS

The disclosed Figures represent a control or baseline study used as a benchmark for determining the effectiveness of the disclosed methods for treating ocular diseases (FIGS. 1 and 3) and studies directed to the disclosed methods. Described herein below, four patients with visual acuity loss due to diabetic macular edema (central retinal thickness [CRT] of more than 325 microns and best corrected visual acuity less than 70 letters) were treated with subcutaneous injections of 5 mg of the disclosed compound twice a day for 28 days and then observed for an additional two months (days 28 through 84). At any time during the course of the study, investigators could administer additional therapy consisting of intravitreal injection of an anti-VEGF agent, for example, ranibizumab, bevacizumab and/or aflibercept if considered by the investigator to be medically necessary. Retinal thickness as measured by ocular coherence tomography and best corrected visual acuity as measured by a standard vision test were assessed at regular intervals during the 28 day active treatment phase and through the 2 month post-treatment observation phase, (Screening, Day 1 [baseline], Day 7, Day 14, Day 21, Day 28, Day 42, Day 56 and Day 84). The main efficacy outcomes for the study were change in CRT and visual acuity over time with treatment.

As shown in FIG. 1, the two groups receiving ranibizumab had a reduction in Central Foveal Thickness of approximately 120 to 160 mm from day 7 to 1 month after the first injection of ranibizumab.

FIG. 2 is read in this manner: 1 patient eye had a Central Foveal Reduction of between 50-100 μm, 1 patient eye had a Central Foveal Reduction of between 150-200 μm, 1 patient eye had a Central Foveal Reduction of between 200-250 μm, 1 patient eye had a Central Foveal Reduction of between 300-350 μm, 2 patient eyes had a Central Foveal Reduction of between 350-400 μm, and 1 patient eye had a Central Foveal Reduction of between 450-500 mm at 14-28 days post ranibizumab or aflibercept. The mean change in Central Foveal Thickness was −289 μm, approximately double the reduction seen 7 days to one month after ranibizumab injection in the benchmark study as depicted in FIG. 1.

As shown in FIG. 3, the two groups receiving ranibizumab had an increase in visual acuity of between approximately 4 to 6 letters from day 7 to 1 month after the first injection of ranibizumab.

FIG. 4 is read in this manner: 1 patient eye had an increase of from 16 to 18 letters improvement, 2 patient eyes had an increase of from 14 to 16 letters improvement, 1 patient eye had an increase of from 10 to 12 letters improvement, 1 patient eye had an increase of from 6 to 8 letters improvement, 1 patient eye had an increase of from 2 to 4 letters improvement, and 1 patient eye had a decrease of from 2 to 4 letters at 14-28 days post ranibizumab or aflibercept. The mean change in Visual Acuity was 9 letters, approximately 3 to 5 letters more improvement than seen 7 days to one month after ranibizumab injection in the benchmark study as depicted in FIG. 3.

As seen in FIG. 5, the Central Foveal Thickness of the study eye drops significantly by week 4 (28 days). Without wishing to be limited by theory, it is believed that when the fellow eye is treated with an injection of 0.5 mg of ranibizumab, the ranibizumab enters the study eye systemically. As a result, there is a pronounced reduction in CFT from day 21 to day 28 (approximately 300 μm). As seen in FIG. 5, by the next monitoring point, week 6, the effects of the systemically received ranibizumab is no longer present and the CFT returns to approximately 775 μm. At week 6, the study eye is treated with an intravitreal injection of 0.5 mg of ranibizumab. As depicted in FIG. 5, by week 8, there is an overall reduction in CFT of approximately 690 μm, wherein the CFT of the subject eye is approximately 180 μm.

Although the Fellow Eye began with less CFT than the study eye, nevertheless, treatment with ranibizumab at week 3 (day 21) produced a change in CFT of approximately 430 µm. Compared to the benchmark study depicted in FIG. 1 wherein the average change in CFT was approximately 160 mm, the combination disclosed method proved an approximately 690 mm reduction in CFT at 2 weeks.

Figure 6:
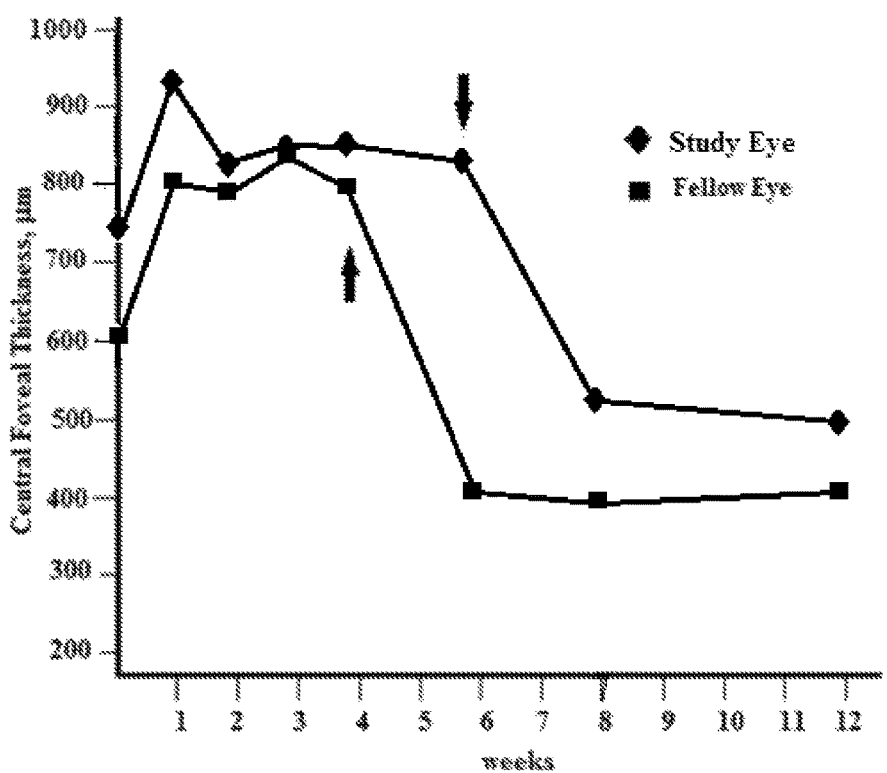

FIG. 6 represents the results of a single patient. The eye having the greater Central Foveal Thickness is chosen as the Treated Eye (Study Eye). The patient from day one was given 5 mg of the disclosed compound subcutaneously twice daily. At week 3 (21 days, indicated by arrow) the fellow eye is rescued with 2 mg of aflibercept. After rescue, the Fellow eye has a CFT reduction of approximately 400 µm. At week 6 (42 days, indicated by arrow) the treated eye is rescued with 2 mg of aflibercept. After rescue, the Study eye has a CFT reduction of approximately 310 µm.

SUMMARY OF THE INVENTION

In some embodiments, the invention provides: a method for treating an ocular disease, comprising administering: a) a compound having the formula:

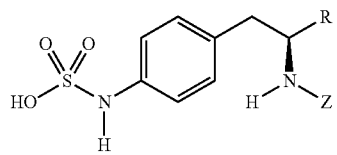

wherein R is a substituted or unsubstituted thiazolyl unit having the formula:

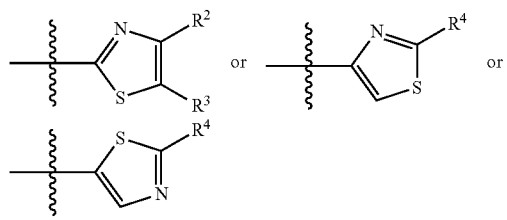

$R^2$, $R^3$, and $R^4$ are each independently:
i) hydrogen; ii) substituted or unsubstituted $C_1$-$C_6$ linear, $C_3$-$C_6$ branched, or $C_3$-$C_6$ cyclic alkyl; iii) substituted or unsubstituted $C_1$-$C_6$ linear, $C_3$-$C_6$ branched, or $C_3$-$C_6$ cyclic alkenyl; iv) substituted or unsubstituted $C_2$-$C_6$ linear or branched alkynyl; v) substituted or unsubstituted $C_6$ or $C_{10}$ aryl; vi) substituted or unsubstituted $C_1$-$C_9$ heteroaryl; vii) substituted or unsubstituted $C_1$-$C_9$ heterocyclic; or viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur; Z is a unit having the formula:

—(L)$_n$-R$^1$ $R^1$ is chosen from: i) hydrogen; ii) hydroxyl; iii) amino; iv) substituted or unsubstituted $C_1$-$C_6$ linear, $C_3$-$C_6$ branched, or $C_3$-$C_6$ cyclic alkyl; v) substituted or unsubstituted $C_1$-$C_6$ linear, $C_3$-$C_6$ branched, or $C_3$-$C_6$ cyclic alkoxy; vi) substituted or unsubstituted $C_6$ or $C_{10}$ aryl; vii) substituted or unsubstituted $C_1$-$C_9$ heterocyclic rings; or viii) substituted or unsubstituted $C_1$-$C_9$ heteroaryl rings; L is a linking unit having the formula:

-[Q]$_y$[C(R$^{5a}$R$^{5b}$)]$_x$[Q$^1$]$_z$[C(R$^{6a}$R$^{6b}$)]$_w$—

Q and Q$^1$ are each independently: i) —C(O)—; ii) —NH—; iii) —C(O)NH—; iv) —NHC(O)—; v) —NHC(O)NH—; vi) —NHC(O)O—; vii) —C(O)O—; viii) —C(O)NHC(O)—; ix) —O—; x) —S—; xi) —SO$_2$—; xii) —C(=NH)—; xiii) —C(=NH)NH—; xiv) —NHC(=NH)—; or xv) —NHC(=NH)NH—; $R^{5a}$ and $R^{5b}$ are each independently: i) hydrogen; ii) hydroxy; iii) halogen; iv) substituted or unsubstituted $C_1$-$C_6$ linear or $C_3$-$C_6$ branched alkyl; or v) a unit having the formula:

—[C(R$^{7a}$R$^{7b}$)]$_t$R$^8$ $R^{7a}$ and $R^{7b}$ are each independently: i) hydrogen; or ii) substituted or unsubstituted $C_1$-$C_6$ linear, $C_3$-$C_6$ branched, or $C_3$-$C_6$ cyclic alkyl; $R^8$ is: i) hydrogen; ii) substituted or unsubstituted $C_1$-$C_6$ linear, $C_3$-$C_6$ branched, or $C_3$-$C_6$ cyclic alkyl; iii) substituted or unsubstituted $C_6$ or $C_{10}$ aryl; iv) substituted or unsubstituted $C_1$-$C_9$ heteroaryl; or v) substituted or unsubstituted $C_1$-$C_9$ heterocyclic; $R^{6a}$ and $R^{6b}$ are each independently: i) hydrogen; or ii) $C_1$-$C_4$ linear or $C_3$-$C_4$ branched alkyl; the index n is 0 or 1; the indices t, w and x are each independently from 0 to 4; the indices y and z are each independently 0 or 1; or a pharmaceutically acceptable salt thereof; and b) one or more anti-VEGF agents.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings: All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

"HPTP beta" or "HPTP-β" are used interchangeably herein and are abbreviations for human protein tyrosine phosphatase beta.

"Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, by a "subject" is meant an individual patient being treated for one or more of the ocular diseases described herein.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a compound of the present invention mitigates a disease or a disorder in a host and/or reduces, inhibits, or eliminates a particular characteristic or event associated with a disorder (e.g., vascular leakage). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The present disclosure relates to compositions and methods for treating ocular diseases, especially ocular disease wherein neovascularization and vascular leakage are present. These diseases are sometimes characterized as diseases wherein there is an elevated angiogenic response in the vessels associated with the eye. The present disclosure provides a Human Protein Tyrosine Phosphatase-beta (HPTP-β) inhibitor that provides vascular stabilization.

Although not wishing to be limited by theory, Vascular Endothelia Growth Factor (VEGF) stimulates angiogenesis in the disclosed ocular diseases. VEGF is a key molecule involved in the development of retinal neovascularization. Studies have demonstrated not only a correlation of the VEGF levels with the severity of proliferative diabetic retinopathy (PDR), but also a reduction in the levels after successful laser treatment of PDR Ischemia in the retina due to microvascular occlusion induces the release of VEGF into the vitreous cavity; highly concentrated VEGF in the ocular fluid leads to the growth of new vessels, VEGF also increases the permeability of capillary vessels and contributes to diabetic macular edema. Retinal fibrovascular membranes, including neovascularization, represent an important risk factor for severe vision loss in patients with diabetic retinopathy. As such, the disclosed HPTP-β inhibitor acts to stabilize ocular vasculature and, as such, serves to counter act the stimulation caused by VEGF and other inflammatory agents that may be present in the diseased retina.

Disclosed is the HPTP-β inhibitor 4-{(S)-2-[(S)-2-(methoxycarbonylamino)-3-phenylpropanamido]-2-[2-(thiophen-2-yl)thiazol-4-yl]ethyl}phenylsulfamic acid. This compound can be used as a treatment in combination with anti-VEGF agents, as a therapy in combination with anti-VEGF agents. HPTP-β can be used to maintain the level of disease reversal after anti-VEGF drugs have withdrawn.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (i.e., carbocyclic and aryl rings) or can comprise one or more heteroatoms in the ring (i.e., heterocyclic and heteroaryl rings). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and Unsubstituted Acyclic Hydrocarbyl:

For the purposes of the present disclosure the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted Cyclic Hydrocarbyl:

For the purposes of the present disclosure the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl (C₆), 2-amino-4-fluorophenyl (C₆), 2-(N,N-diethylamino)phenyl (C₆), 2-cyanophenyl (C₆), 2,6-ditert-butylphenyl (C₆), 3-methoxyphenyl (C₆), 8-hydroxynaphthylen-2-yl (C₁₀), 4,5-dimethoxynaphthylen-1-yl (C₁₀), and 6-cyano-naphthylen-1-yl (C₁₀).

ii) C₆ or C₁₀ aryl rings fused with 1 or 2 saturated rings to afford C₈-C₂₀ ring systems, non-limiting examples of which include, bicyclo[4.2.0]octa-1,3,5-trienyl (C₈), and indanyl (C₉).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which contains the heteroatom is also not an aromatic ring." The following are non-limiting examples of "substituted and unsubstituted heterocyclic rings" which encompass the following categories of units:

i) heterocyclic units having a single ring containing one or more heteroatoms, non-limiting examples of which include, diazirinyl (C₁), aziridinyl (C₂), urazolyl (C₂), azetidinyl (C₃), pyrazolidinyl (C₃), imidazolidinyl (C₃), oxazolidinyl (C₃), isoxazolinyl (C₃), thiazolidinyl (C₃), isothiazolinyl (C₃), oxathiazolidinonyl (C₃), oxazolidinonyl (C₃), hydantoinyl (C₃), tetrahydrofuranyl (C₄), pyrrolidinyl (C₄), morpholinyl (C₄), piperazinyl (C₄), piperidinyl (C₄), dihydropyranyl (C₅), tetrahydropyranyl (C₅), piperidin-2-onyl (valerolactam) (C₅), 2,3,4,5-tetrahydro-1H-azepinyl (C₆), 2,3-dihydro-1H-indole (C₈), and 1,2,3,4-tetrahydroquinoline (C₉).

ii) heterocyclic units having 2 or more rings one of which is a heterocyclic ring, non-limiting examples of which include hexahydro-1H-pyrrolizinyl (C₇), 3a,4,5,6,7,7a-hexahydro-1H-benzo[d]imidazolyl (C₇), 3a,4,5,6,7,7a-hexahydro-1H-indolyl (C₈), 1,2,3,4-tetrahydroquinolinyl (C₉), and decahydro-1H-cycloocta[b]pyrrolyl (C₁₀).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:

i) heteroaryl rings containing a single ring, non-limiting examples of which include, 1,2,3,4-tetrazolyl (C₁), [1,2,3]triazolyl (C₂), [1,2,4]triazolyl (C₂), triazinyl (C₃), thiazolyl (C₃), 1H-imidazolyl (C₃), oxazolyl (C₃), isoxazolyl (C₃), isothiazolyl (C₃), furanyl (C₄), thiophenyl (C₄), pyrimidinyl (C₄), 2-phenylpyrimidinyl (C₄), pyridinyl (C₅), 3-methylpyridinyl (C₅), and 4-dimethylaminopyridinyl (C₅)

ii) heteroaryl rings containing 2 or more fused rings one of which is a heteroaryl ring, non-limiting examples of which include: 7H-purinyl (C₅), 9H-purinyl (C₅), 6-amino-9H-purinyl (C₅), 5H-pyrrolo[3,2-d]pyrimidinyl (C₆), 7H-pyrrolo[2,3-d]pyrimidinyl (C₆), pyrido[2,3-d]pyrimidinyl (C₇), 2-phenylbenzo[d]thiazolyl (C₇), 1H-indolyl (C₈), 4,5,6,7-tetrahydro-1-H-indolyl (C₈), quinoxalinyl (C₈), 5-methylquinoxalinyl (C₈), quinazolinyl (C₈), quinolinyl (C₉), 8-hydroxy-quinolinyl (C₉), and isoquinolinyl (C₉).

5) C₁-C₆ tethered cyclic hydrocarbyl units (whether carbocyclic units, C₆ or C₁₀ aryl units, heterocyclic units, or heteroaryl units) which connected to another moiety, unit, or core of the molecule by way of a C₁-C₆ alkylene unit. Non-limiting examples of tethered cyclic hydrocarbyl units include benzyl C₁-(C₆) having the formula:

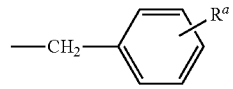

wherein R^a is optionally one or more independently chosen substitutions for hydrogen. Further examples include other aryl units, inter alia, (2-hydroxyphenyl)hexyl C₆-(C₆); naphthalen-2-ylmethyl C₁-(C₁₀), 4-fluorobenzyl C₁-(C₆), 2-(3-hydroxyphenyl)ethyl C₂-(C₆), as well as substituted and unsubstituted C₃-C₁₀ alkylenecarbocyclic units, for example, cyclopropylmethyl C₁-(C₃), cyclopentylethyl C₂-(C₅), cyclohexylmethyl C₁-(C₆). Included within this category are substituted and unsubstituted C₁-C₁₀ alkylene-heteroaryl units, for example a 2-picolyl C₁-(C₆) unit having the formula:

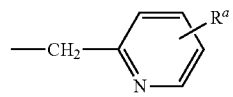

wherein R^a is the same as defined above. In addition, C₁-C₁₂ tethered cyclic hydrocarbyl units include C₁-C₁₀ alkyleneheterocyclic units and alkylene-heteroaryl units, non-limiting examples of which include, aziridinylmethyl C₁-(C₂) and oxazol-2-ylmethyl C₁-(C₃).

For the purposes of the present disclosure carbocyclic rings are from C₃ to C₂₀; aryl rings are C₆ or C₁₀; heterocyclic rings are from C₁ to C₉; and heteroaryl rings are from C₁ to C₉.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

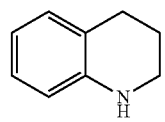

is, for the purposes of the present disclosure, considered a heterocyclic unit. 6,7-Dihydro-5H-cyclopentapyrimidine having the formula:

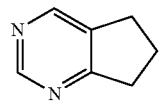

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthpyridine having the formula:

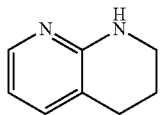

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein below;
v) substituted or unsubstituted $C_1$-$C_9$ heteroaryl rings; as described herein below;
vi) —$(CR^{102a}R^{102b})_aOR^{101}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
vii) —$(CR^{102a}R^{102b})_aC(O)R^{101}$; for example, —COCH$_3$, —CH$_2$COCH$_3$, —COCH$_2$CH$_3$, —CH$_2$COCH$_2$CH$_3$, —COCH$_2$CH$_2$CH$_3$, and CH$_2$COCH$_2$CH$_2$CH$_3$;
viii) —$(CR^{102a}R^{102b})_aC(O)OR^{101}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
ix) —$(CR^{102a}R^{102b})_aC(O)N(R^{101})_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;
x) —$(CR^{102a}R^{102b})_aN(R^{101})_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
xi) halogen; —F, —Cl, —Br, and —I;
xii) —$(CR^{102a}R^{102b})_aCN$;
xiii) —$(CR^{102a}R^{102b})_aNO_2$;
xiv) —CH$_j$X$_k$; wherein X is halogen, the index j is an integer from 0 to 2, j+k=3; for example, —CH$_2$F, —CHF$_2$, —CF$_3$, —CCl$_3$, or —CBr$_3$;
xv) —$(CR^{102a}R^{102b})_aSR^{101}$; —SH, —CH$_2$SH, —SCH$_3$, —CH$_2$SCH$_3$, —SC$_6$H$_5$, and —CH$_2$SC$_6$H$_5$;
xvi) —$(CR^{102a}R^{102b})_aSO_2R^{101}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xvii) —$(CR^{102a}R^{102b})_aSO_3R^{101}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;
wherein each $R^{101}$ is independently hydrogen, substituted or unsubstituted $C_1$-$C_6$ linear, branched, or cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or branched alkyl; the index "a" is from 0 to 4.

For the purposes of the present disclosure the terms "compound," "analog," and "composition of matter" stand equally well for each other and are used interchangeably throughout the specification. The disclosed compounds include all enantiomeric forms, diastereomeric forms, salts, and the like.

The compounds disclosed herein include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The disclosed compounds have Formula (I):

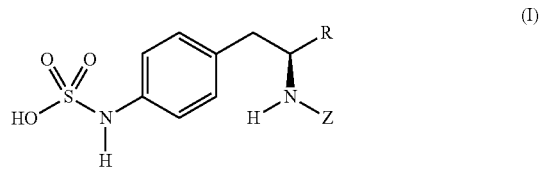

wherein the carbon atom having the amino unit has the (S) stereochemistry as indicated in the following formula:

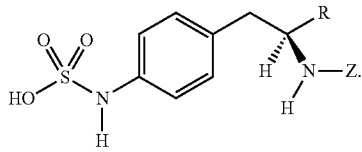

The units which comprise R and Z can comprise units having any configuration, and, as such, the disclosed compounds can be single enantiomers, diastereomeric pairs, or combinations thereof. In addition, the compounds can be isolated as salts or hydrates. In the case of salts, the compounds can comprises more than one cation or anion. In the case of hydrates, any number of water molecules, or fractional part thereof (for example, less than 1 water molecule present for each molecule of analog) can be present.

R Units

R is a substituted or unsubstituted thiazolyl unit having the formula:

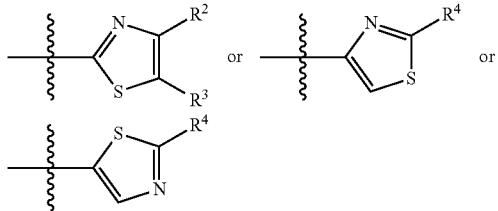

$R^2$, $R^3$, and $R^4$ are substituent groups that can be independently chosen from a wide variety of non-carbon atom containing units (for example, hydrogen, hydroxyl, amino, halogen, nitro, and the like) or organic substituent units, such as substituted and unsubstituted acyclic hydrocarbyl and cyclic hydrocarbyl units as described herein. The carbon comprising units can comprise from 1 to 12 carbon atoms, or 1 to 10 carbon atoms, or 1 to 6 carbon atoms.

An example of compounds of Formula (I) include compounds wherein R units are thiazol-2-yl units having the formula:

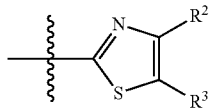

wherein $R^2$ and $R^3$ are each independently chosen from:
  i) hydrogen;
  ii) substituted or unsubstituted $C_1$-$C_6$ linear, $C_3$-$C_6$ branched, or $C_3$-$C_6$ cyclic alkyl;
  iii) substituted or unsubstituted $C_2$-$C_6$ linear, $C_3$-$C_6$ branched, or $C_3$-$C_6$ cyclic alkenyl;
  iv) substituted or unsubstituted $C_2$-$C_6$ linear or $C_3$-$C_6$ branched alkynyl;
  v) substituted or unsubstituted $C_6$ or $C_{10}$ aryl;
  vi) substituted or unsubstituted $C_1$-$C_9$ heteroaryl;
  vii) substituted or unsubstituted $C_1$-$C_9$ heterocyclic; or
  viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen:
  i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
  ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
  iii) substituted or unsubstituted $C_6$ or $C_{10}$ alkylenearyl; for example, benzyl, 2-phenylethyl, naphthylen-2-ylmethyl;
  iv) substituted or unsubstituted $C_1$-$C_9$ heterocyclic rings; as described herein;
  v) substituted or unsubstituted $C_1$-$C_9$ heteroaryl rings; as described herein;
  vi) $-(CR^{21a}R^{21b})_pOR^{20}$; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;
  vii) $-(CR^{21a}R^{21b})_pC(O)R^{20}$; for example, $-COCH_3$, $-CH_2COCH_3$, $-COCH_2CH_3$, $-CH_2COCH_2CH_3$, $-COCH_2CH_2CH_3$, and $-CH_2COCH_2CH_2CH_3$;
  viii) $-(CR^{21a}R^{21b})_pC(O)OR^{20}$; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;
  x) $-(CR^{21a}R^{21b})_pC(O)N(R^{20})_2$; for example, $-CONH_2$, $-CH_2CONH_2$, $-CONHCH_3$, $-CH_2CONHCH_3$, $-CON(CH_3)_2$, and $-CH_2CON(CH_3)_2$;
  x) $-(CR^{21a}R^{21b})_pN(R^{20})_2$; for example, $-NH_2$, $-CH_2NH_2$, $-NHCH_3$, $-CH_2NHCH_3$, $-N(CH_3)_2$, and $-CH_2N(CH_3)_2$;
  xi) halogen; $-F$, $-Cl$, $-Br$, and $-I$;
  xii) $-(CR^{21a}R^{21b})_pCN$;
  xiii) $-(CR^{21a}R^{21b})_pNO_2$;
  xiv) $-(CH_jX_{k'})_hCH_{j'}X_k$; wherein X is halogen, the index j is an integer from 0 to 2, j+k=3, the index j' is an integer from 0 to 2, j'+k'=2, the index h is from 0 to 6; for example, $-CH_2F$, $-CHF_2$, $-CF_3$, $-CH_2CF_3$, $-CHFCF_3$, $-CCl_3$, or $-CBr_3$;
  xv) $-(CR^{21a}R^{21b})_pSR^{20}$; $-SH$, $-CH_2SH$, $-SCH_3$, $-CH_2SCH_3$, $-SC_6H_5$, and $-CH_2SC_6H_5$;
  xvi) $-(CR^{21a}R^{21b})_pSO_2R^{20}$; for example, $-SO_2H$, $-CH_2SO_2H$, $-SO_2CH_3$, $-CH_2SO_2CH_3$, $-SO_2C_6H_5$, and $-CH_2SO_2C_6H_5$; and
  xvii) $-(CR^{21a}R^{21b})_pSO_3R^{20}$; for example, $-SO_3H$, $-CH_2SO_3H$, $-SO_3CH_3$, $-CH_2SO_3CH_3$, $-SO_3C_6H_5$, and $-CH_2SO_3C_6H_5$;
wherein each $R^{20}$ is independently hydrogen, substituted or unsubstituted $C_1$-$C_4$ linear, $C_3$-$C_4$ branched, or $C_3$-$C_4$ cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or $C_3$-$C_4$ branched alkyl; the index p is from 0 to 4.

An example of compounds of Formula (I) includes R units having the formula:

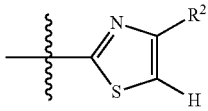

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), cyclopropyl ($C_3$), n-hexyl ($C_6$), 4-methylpentyl ($C_6$), and cyclohexyl ($C_6$).

Another example of compounds of Formula (I) include R units having the formula:

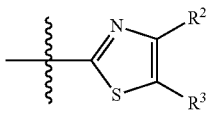

wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

A further example of compounds of Formula (I) includes R units wherein $R^3$ is hydrogen and $R^2$ is a substituted alkyl unit, said substitutions chosen from:
 i) halogen: —F, —Cl, —Br, and —I;
 ii) —N($R^{11}$)$_2$; and
 iii) —O$R^{11}$;
wherein each $R^{11}$ is independently hydrogen or $C_1$-$C_4$ linear or $C_3$-$C_4$ branched alkyl. Non-limiting examples of units that can be a substitute for a $R^2$ or $R^3$ hydrogen atom on R units include —CH$_2$F, —CHF$_2$, —CF$_3$, —CH$_2$CF$_3$, —CH$_2$CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and CH$_2$NH(CH$_2$CH$_3$).

Further non-limiting examples of units that can be a substitute for a $R^2$ or $R^3$ hydrogen atom on R units include 2,2-difluorocyclopropyl, 2-methoxycyclohexyl, and 4-chlorocyclohexyl.

A yet further example of compounds of Formula (I), R units include units wherein $R^3$ is hydrogen and $R^2$ is phenyl or substituted phenyl, wherein non-limiting examples of $R^2$ units include phenyl, 3,4-dimethylphenyl, 4-tert-butylphenyl, 4-cyclopropylphenyl, 4-diethylaminophenyl, 4-(trifluoromethyl)phenyl, 4-methoxyphenyl, 4-(difluoromethoxy)phenyl, 4-(trifluoromethoxy)phenyl, 3-chlorpheny, 4-chlorophenyl, and 3,4-dichloro-phenyl, which when incorporated into the definition of R affords the following R units 4-phenylthiazol-2-yl, 3,4-dimethylphenylthiazol-2-yl, 4-tert-butylphenylthiazol-2-yl, 4-cyclopropylphenylthiazol-2-yl, 4-diethylaminophenylthiazol-2-yl, 4-(trifluoromethyl)-phenylthiazol-2-yl, 4-methoxyphenylthiazol-2-yl, 4-(difluoromethoxy)phenylthiazol-2-yl, 4-(trifluoromethoxy)phenylthiazol-2-yl, 3-chlorophenylthiazol-2-yl, 4-chlorophenylthiazol-2-yl, and 3,4-dichlorophenylthiazol-2-yl.

A still further example of compounds of Formula (I) includes R units wherein $R^2$ is chosen from hydrogen, methyl, ethyl, n-propyl, and iso-propyl and $R^3$ is phenyl or substituted phenyl. A non-limiting example of a R unit according to the fifth aspect of the first category of R units includes 4-methyl-5-phenylthiazol-2-yl and 4-ethyl-5-phenylthiazol-2-yl.

Another further example of compounds of Formula (I) includes R units wherein $R^3$ is hydrogen and $R^2$ is a substituted or unsubstituted heteroaryl unit chosen from 1,2,3,4-tetrazol-1-yl,1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Further non-limiting example of compounds of Formula (I) includes R units wherein $R^2$ is substituted or unsubstituted thiophen-2-yl, for example thiophen-2-yl, 5-chlorothiophen-2-yl, and 5-methylthiophen-2-yl.

A still further example of compounds of Formula (I) includes R units wherein $R^2$ is substituted or unsubstituted thiophen-3-yl, for example thiophen-3-yl, 5-chlorothiophen-3-yl, and 5-methylthiophen-3-yl.

Another example of compounds of Formula (I) includes R units wherein $R^2$ and $R^3$ are taken together to form a saturated or unsaturated ring having from 5 to 7 atoms. Non-limiting examples of the sixth aspect of the first category of R units include 5,6-dihydro-4H-cyclopenta[d]thiazol-2-yl and 4,5,6,7-tetrahydrobenzo[d]thiazol-2-yl.

Further examples of compounds of Formula (I) include R units that are thiazol-4-yl or thiazol-5-yl units having the formula:

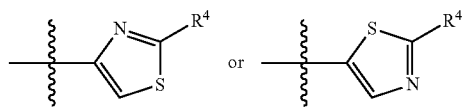

wherein $R^4$ is a unit chosen from:
 i) hydrogen;
 ii) substituted or unsubstituted $C_1$-$C_6$ linear, $C_3$-$C_6$ branched, or $C_3$-$C_6$ cyclic alkyl;
 iii) substituted or unsubstituted $C_2$-$C_6$ linear, $C_3$-$C_6$ branched, or $C_3$-$C_6$ cyclic alkenyl;
 iv) substituted or unsubstituted $C_2$-$C_6$ linear or branched alkynyl;
 v) substituted or unsubstituted $C_6$ or $C_{10}$ aryl;
 vi) substituted or unsubstituted $C_1$-$C_9$ heteroaryl; or
 vii) substituted or unsubstituted $C_1$-$C_9$ heterocyclic.

The following are non-limiting examples of units that can substitute for one or more hydrogen atoms on the $R^4$ units. The following substituents, as well as others not herein described, are each independently chosen:
 i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein below;

v) substituted or unsubstituted $C_1$-$C_9$ heteroaryl rings; as described herein below;

vi) —$(CR^{21a}R^{21b})_pOR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) $(CR^{21a}R^{21b})_pC(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;

viii) —$(CR^{21a}R^{21b})_pC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and $CH_2CO_2CH_2CH_2CH_3$;

xi) —$(CR^{21a}R^{21b})_pC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{21a}R^{21b})_pN(R^{20})_2$; for example, —$NH_2$, —$CH_2NH_2$, —$NHCH_3$, —$CH_2NHCH_3$, —$N(CH_3)_2$, and —$CH_2N(CH_3)_2$;

xi) halogen; —F, —Cl, —Br, and —I;

xii) —$(CR^{21a}R^{21b})_pCN$;

xiii) —$(CR^{21a}R^{21b})_pNO_2$;

xiv) —$(CH_jX_k)_{j'}CH_jX_k$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;

xv) —$(CR^{21a}R^{21b})_pSR^{20}$; —SH, —$CH_2SH$, —$SCH_3$, —$CH_2SCH_3$, —$SC_6H_5$, and —$CH_2SC_6H_5$;

xvi) —$(CR^{21a}R^{21b})_pSO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and xvii) —$(CR^{21a}R^{21b})_pSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{20}$ is independently hydrogen, substituted or unsubstituted $C_1$-$C_4$ linear, $C_3$-$C_4$ branched, or $C_3$-$C_4$ cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or $C_3$-$C_4$ branched alkyl; the index p is from 0 to 4.

An example of compounds of Formula (I) includes R units wherein $R^4$ is hydrogen.

A further example of compounds of Formula (I) includes R units wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylthiazol-4-yl, 2-ethylthiazol-4-yl, 2-(n-propyl)thiazol-4-yl, and 2-(iso-propyl)thiazol-4-yl.

A still further example of compounds of Formula (I) includes R units wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

Yet further example of compounds of Formula (I) includes R units wherein $R^4$ is substituted or unsubstituted heteroaryl, non-limiting examples of which include thiophen-2-yl, thiophen-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Another example of 5-member ring R units includes substituted or unsubstituted imidazolyl units having the formula:

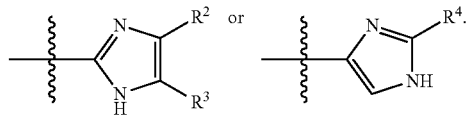

One example of imidazolyl R units includes imidazol-2-yl units having the formula:

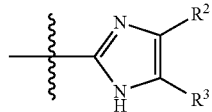

wherein $R^2$ and $R^3$ are each independently chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_2$-$C_6$ linear, $C_3$-$C_6$ branched, or $C_3$-$C_6$ cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl;
vii) substituted or unsubstituted $C_1$-$C_9$ heterocyclic; or
viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen:
i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;

vi) —(CR$^{21a}$R$^{21b}$)$_z$OR$^{20}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

vii) —(CR$^{21a}$R$^{21b}$)$_z$C(O)R$^{20}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;

viii) —(CR$^{21a}$R$^{21b}$)$_z$C(O)OR$^{20}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;

xii) (CR$^{21a}$R$^{21b}$)$_z$C(O)N(R$^{20}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;

x) —(CR$^{21a}$R$^{21b}$)$_z$N(R$^{20}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;

xi) halogen; —F, —Cl, —Br, and —I;

xii) —(CR$^{21a}$R$^{21b}$)$_z$CN;

xiii) —(CR$^{21a}$R$^{21b}$)$_z$NO$_2$;

xiv) —(CH$_j$X$_k$)$_h$CH$_{j'}$X$_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3$;

xv) —(CR$^{21a}$R$^{21b}$)$_z$SR$^{20}$; —SH, —CH$_2$SH, —SCH$_3$, —CH$_2$SCH$_3$, —SC$_6$H$_5$, and —CH$_2$SC$_6$H$_5$;

xvi) —(CR$^{21a}$R$^{21b}$)$_z$SO$_2$R$^{20}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xvii) —(CR$^{21a}$R$^{21b}$)$_z$SO$_3$R$^{20}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{20}$ is independently hydrogen, substituted or unsubstituted C$_1$-C$_4$ linear, C$_3$-C$_4$ branched, or C$_3$-C$_4$ cyclic alkyl, phenyl, benzyl, heterocyclic, or heteroaryl; or two R$^{20}$ units can be taken together to form a ring comprising 3-7 atoms; R$^{21a}$ and R$^{21b}$ are each independently hydrogen or C$_1$-C$_4$ linear or C$_3$-C$_4$ branched alkyl; the index p is from 0 to 4.

One example of R units includes compounds wherein R units have the formula:

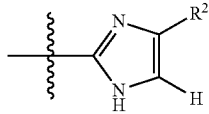

wherein R$^3$ is hydrogen and R$^2$ is a unit chosen from methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$).

Another example of R units includes compounds wherein R$^2$ is a unit chosen from methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$); and R$^3$ is a unit chosen from methyl (C$_1$) or ethyl (C$_2$). Non-limiting examples of this aspect of R includes 4,5-dimethylimidazol-2-yl, 4-ethyl-5-methylimidazol-2-yl, 4-methyl-5-ethylimidazol-2-yl, and 4,5-diethylimidazol-2-yl.

An example of R units includes compounds wherein R$^3$ is hydrogen and R$^2$ is a substituted alkyl unit chosen, said substitutions chosen from:
  i) halogen: —F, —Cl, —Br, and —I;
  ii) —N(R$^{11}$)$_2$; and
  iii) —OR$^{11}$;

wherein each R$^{11}$ is independently hydrogen or C$_1$-C$_4$ linear or C$_3$-C$_4$ branched alkyl.

Non-limiting examples of units comprising this embodiment of R includes: —CH$_2$F, —CHF$_2$, —CF$_3$, —CH$_2$CF$_3$, —CH$_2$Cl, —CH$_2$OH, —CH$_2$OCH$_3$, —CH$_2$CH$_2$OH, —CH$_2$CH$_2$OCH$_3$, —CH$_2$NH$_2$, —CH$_2$NHCH$_3$, —CH$_2$N(CH$_3$)$_2$, and —CH$_2$NH(CH$_2$CH$_3$).

A yet further example of R units include units wherein R$^3$ is hydrogen and R$^2$ is phenyl.

A still further example of R units include units wherein R$^3$ is hydrogen and R$^2$ is a heteroaryl unit chosen from 1,2,3,4-tetrazol-1-yl,1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Z Units

Z is a unit having the formula:

-(L)$_n$-R$^1$

R$^1$ is chosen from:
  i) hydrogen;
  ii) hydroxyl;
  iii) amino;
  iv) substituted or unsubstituted C$_1$-C$_6$ linear, C$_3$-C$_6$ branched or C$_3$-C$_6$ cyclic alkyl;
  v) substituted or unsubstituted C$_1$-C$_6$ linear, C$_3$-C$_6$ branched o C$_3$-C$_6$r cyclic alkoxy;
  vi) substituted or unsubstituted C$_6$ or C$_{10}$ aryl;
  vii) substituted or unsubstituted C$_1$-C$_9$ heterocyclic rings; or
  viii) substituted or unsubstituted C$_1$-C$_9$ heteroaryl rings.

The following are non-limiting examples of units that can substitute for one or more hydrogen atoms on the R$^1$ units. The following substituents, as well as others not herein described, are each independently chosen:
  i) C$_1$-C$_{12}$ linear, C$_3$-C$_{12}$ branched, or C$_3$-C$_{12}$ cyclic alkyl, alkenyl, and alkynyl; methyl (C$_1$), ethyl (C$_2$), ethenyl (C$_2$), ethynyl (C$_2$), n-propyl (C$_3$), iso-propyl (C$_3$), cyclopropyl (C$_3$), 3-propenyl (C$_3$), 1-propenyl (also 2-methylethenyl) (C$_3$), isopropenyl (also 2-methylethen-2-yl) (C$_3$), prop-2-ynyl (also propargyl) (C$_3$), propyn-1-yl (C$_3$), n-butyl (C$_4$), sec-butyl (C$_4$), iso-butyl (C$_4$), tert-butyl (C$_4$), cyclobutyl (C$_4$), buten-4-yl (C$_4$), cyclopentyl (C$_5$), cyclohexyl (C$_6$);
  ii) substituted or unsubstituted C$_6$ or C$_{10}$ aryl; for example, phenyl, naphthyl (also referred to herein as naphthylen-1-yl (C$_{10}$) or naphthylen-2-yl (C$_{10}$));
  iii) substituted or unsubstituted C$_6$ or C$_{10}$ alkylenearyl; for example, benzyl, 2-phenylethyl, naphthylen-2-ylmethyl;
  iv) substituted or unsubstituted C$_1$-C$_9$ heterocyclic rings; as described herein;
  v) substituted or unsubstituted C$_1$-C$_9$ heteroaryl rings; as described herein;
  vi) —(CR$^{31a}$R$^{31b}$)$_q$OR$^{30}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
  vii) —(CR$^{31a}$R$^{31b}$)$_q$C(O)R$^{30}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;

viii) —(CR³¹ᵃR³¹ᵇ)_qC(O)OR³⁰; for example —CONH₂, —CH₂CONH₂, —CONHCH₃, —CH₂CONHCH₃, —CON(CH₃)₂, and —CH₂CON(CH₃)₂; —CH₂CO₂CH₂CH₃;

xiii) —(CR³¹ᵃR³¹ᵇ)_qC(O)N(R³⁰)₂; for example, —CONH₂, —CH₂CONH₂, —CONHCH₃, —CH₂CONHCH₃, —CON(CH₃)₂, and —CH₂CON(CH₃)₂;

x) —(CR³¹ᵃR³¹ᵇ)_qN(R³⁰)₂; for example, —NH₂, —CH₂NH₂, —NHCH₃, —CH₂NHCH₃, —N(CH₃)₂, and —CH₂N(CH₃)₂;

xi) halogen; —F, —Cl, —Br, and —I;

xii) —(CR³¹ᵃR³¹ᵇ)_qCN;

xiii) —(CR³¹ᵃR³¹ᵇ)_qNO₂;

xiv) —(CH_jX_k)_hCH_{j'}X_{k'}; wherein X is halogen, the index j is an integer from 0 to 2, j+k=3, the index j' is an integer from 0 to 2, j'+k'=2, the index h is from 0 to 6; for example, —CH₂F, —CHF₂, —CF₃, —CH₂CF₃, —CHFCF₃, —CCl₃, or —CBr₃;

xv) —(CR³¹ᵃR³¹ᵇ)^qSR³⁰; —SH, —CH₂SH, —SCH₃, —CH₂SCH₃, —SC₆H₅, and —CH₂SC₆H₅;

xvi) —(CR³¹ᵃR³¹ᵇ)^qSO₂R³⁰; for example, —SO₂H, —CH₂SO₂H, —SO₂CH₃, —CH₂SO₂CH₃, —SO₂C₆H₅, and —CH₂SO₂C₆H₅; and xvii) —(CR³¹ᵃR³¹ᵇ)^qSO₃R³⁰; for example, —SO₃H, —CH₂SO₃H, —SO₃CH₃, —CH₂SO₃CH₃, —SO₃C₆H₅, and —CH₂SO₃C₆H₅;

wherein each $R^{30}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{30}$ units can be taken together to form a ring comprising 3-7 atoms; $R^{31a}$ and $R^{31b}$ are each independently hydrogen or $C_1$-$C_4$ linear or $C_3$-$C_4$ branched alkyl; the index q is from 0 to 4.

One example of $R^1$ units includes substituted or unsubstituted phenyl ($C_6$ aryl) units, wherein each substitution is independently chosen from: halogen, $C_1$-$C_4$ linear, branched alkyl, or cyclic alkyl, —OR¹¹, —CN, —N(R¹¹)₂, —CO₂R¹¹, —C(O)N(R¹¹)₂, —NR¹¹C(O)R¹¹, —NO₂, and —SO₂R¹¹; each $R^{11}$ is independently hydrogen; substituted or unsubstituted $C_1$-$C_4$ linear, $C_3$-$C_4$ branched, $C_3$-$C_4$ cyclic alkyl, alkenyl, or alkynyl; substituted or unsubstituted phenyl or benzyl; or two $R^{11}$ units can be taken together to form a ring comprising from 3-7 atoms.

Another example of $R^1$ units includes substituted $C_6$ aryl units chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

A further example of $R^1$ units includes substituted or unsubstituted $C_6$ aryl units chosen from 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

A yet further example of $R^1$ units includes substituted $C_6$ aryl units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Another still further example of $R^1$ units includes substituted $C_6$ aryl units chosen from 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

$R^1$ can comprise heteroaryl units. Non-limiting examples of $C_1$-$C_9$ heteroaryl units include:

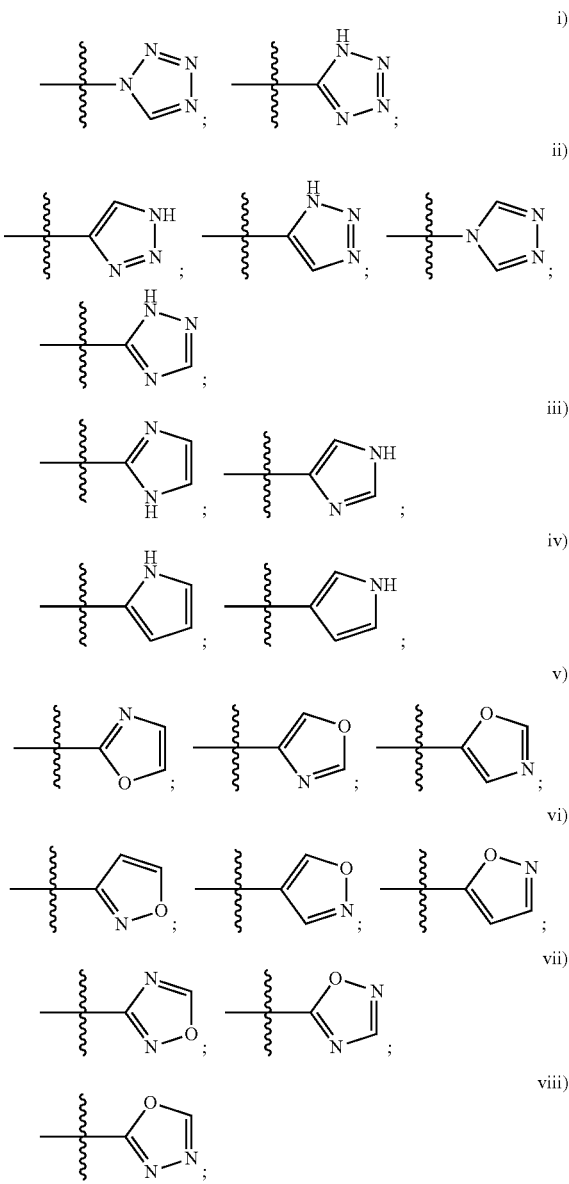

-continued

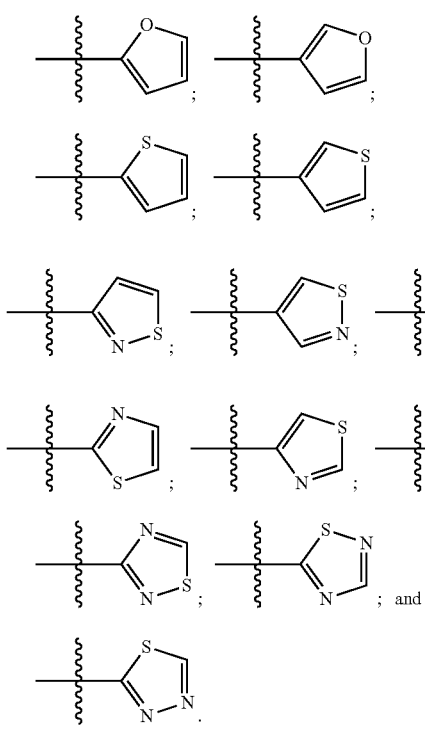

R[1] heteroaryl units can be substituted or unsubstituted. Non-limiting examples of units that can substitute for hydrogen include units chosen from:
i) $C_1$-$C_6$ linear, $C_3$-$C_6$ branched, and $C_3$-$C_6$ cyclic alkyl;
ii) substituted or unsubstituted phenyl and benzyl;
iii) substituted of unsubstituted $C_1$-$C_9$ heteroaryl;
iv) —C(O)R[9]; and
v) —NHC(O)R[9];
wherein R[9] is $C_1$-$C_6$ linear and branched alkyl; $C_1$-$C_6$ linear and $C_3$-$C_6$ branched alkoxy; or —NHCH$_2$C(O)R[10]; R[10] is chosen from hydrogen, methyl, ethyl, and tert-butyl.

An example of R[1] relates to units substituted by an alkyl unit chosen from methyl, ethyl, n-propyl, iso-propyl, n-butyl, iso-butyl, sec-butyl, and tert-butyl.

Another example of R[1] includes units that are substituted by substituted or unsubstituted phenyl and benzyl, wherein the phenyl and benzyl substitutions are chosen from one or more:
i) halogen;
ii) $C_1$-$C_3$ alkyl;
iii) $C_1$-$C_3$ alkoxy;
iv) —CO$_2$R[11]; and
v) —NHCOR[16];
wherein R[11] and R[16] are each independently hydrogen, methyl, or ethyl.

Another example of R[1] relates to phenyl and benzyl units substituted by a carboxy unit having the formula —C(O)R[9]; R[9] is chosen from methyl, methoxy, ethyl, and ethoxy.

A further example of R[1] includes phenyl and benzyl units substituted by an amide unit having the formula —NHC(O)R[9]; R[9] is chosen from methyl, methoxy, ethyl, ethoxy, tert-butyl, and tert-butoxy.

A yet further example of R[1] includes phenyl and benzyl units substituted by one or more fluoro or chloro units.

L Units

L is a linking unit which is present when the index n is equal to 1, but is absent when the index n is equal to 0. L units have the formula:

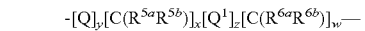

wherein Q and $Q^1$ are each independently:
i) —C(O)—;
ii) —NH—;
iii) —C(O)NH—;
iv) —NHC(O)—;
v) —NHC(O)NH—;
vi) —NHC(O)O—;
vii) —C(O)O—;
viii) —C(O)NHC(O)—;
ix) —O—;
x) —S—;
xi) —SO$_2$—;
xii) —C(=NH)—;
xiii) —C(=NH)NH—;
xiv) —NHC(=NH)—; or
xv) —NHC(=NH)NH—.

When the index y is equal to 1, Q is present. When the index y is equal to 0, Q is absent. When the index z is equal to 1, $Q^1$ is present. When the index z is equal to 0, $Q^1$ is absent. $R^{5a}$ and $R^{5b}$ are each independently:
i) hydrogen;
ii) hydroxy;
iii) halogen;
iv) substituted or unsubstituted $C_1$-$C_6$ linear or $C_3$-$C_6$ branched alkyl; or
v) a unit having the formula:

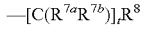

wherein $R^{7a}$ and $R^{7b}$ are each independently:
i) hydrogen; or
ii) substituted or unsubstituted $C_1$-$C_6$ linear, $C_3$-$C_6$ branched, or $C_3$-$C_6$ cyclic alkyl.

$R^8$ is:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_6$ or $C_{10}$ aryl;
iv) substituted or unsubstituted $C_1$-$C_9$ heteroaryl; or
v) substituted or unsubstituted $C_1$-$C_9$ heterocyclic.

$R^{6a}$ and $R^{6b}$ are each independently:
i) hydrogen; or
ii) $C_1$-$C_4$ linear or $C_3$-$C_4$ branched alkyl.

The indices t, w and x are each independently from 0 to 4.

The following are non-limiting examples of units that can substitute for one or more hydrogen atoms on $R^{5a}$, $R^{5b}$, $R^{7a}$, $R^{7b}$, and $R^8$ units. The following substituents, as well as others not herein described, are each independently chosen:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein below;
v) substituted or unsubstituted $C_1$-$C_9$ heteroaryl rings; as described herein below;
vi) —$(CR^{41a}R^{41b})_rOR^{40}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{41a}R^{41b})_rC(O)R^{40}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{41a}R^{41b})_rC(O)OR^{40}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and $CH_2CO_2CH_2CH_2CH_3$;
xiv) —$(CR^{41a}R^{41b})_rC(O)N(R^{40})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{41a}R^{41b})_rN(R^{40})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{41a}R^{41b})_rCN$;
xiii) —$(CR^{41a}R^{41b})_rNO_2$;
xiv) —$(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{41a}R^{41b})_rSR^{40}$; —SH, —$CH_2SH$, —$SCH_3$, —$CH_2SCH_3$, —$SC_6H_5$, and —$CH_2SC_6H_5$;
xvi) —$(CR^{41a}R^{41b})_rSO_2R^{40}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{41a}R^{41b})_rSO_3R^{40}$; for example, —$SO_3H$, —$CH_2SO_3H$, —$SO_3CH_3$, —$CH_2SO_3CH_3$, —$SO_3C_6H_5$, and —$CH_2SO_3C_6H_5$;
wherein each $R^{40}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{40}$ units can be taken together to form a ring comprising 3-7 atoms; $R^{41a}$ and $R^{41b}$ are each independently hydrogen or $C_1$-$C_4$ linear or $C_3$-$C_4$ branched alkyl; the index r is from 0 to 4.

One aspect of L units relates to units having the formula:

—C(O)[C(R$^{5a}$R$^{5b}$)]$_x$NHC(O)— wherein $R^{5a}$ is hydrogen, substituted or unsubstituted $C_1$-$C_4$ alkyl, substituted or unsubstituted phenyl, and substituted or unsubstituted heteroaryl; and the index x is 1 or 2. One embodiment relates to linking units having the formula:
i) —C(O)[C(R$^{5a}$H)]NHC(O)O—;
ii) —C(O)[C(R$^{5a}$H)][CH$_2$]NHC(O)O—;
iii) —C(O)[CH$_2$][C(R$^{5a}$H)]NHC(O)O—;
iv) —C(O)[C(R$^{5a}$H)]NHC(O)—;
v) —C(O)[C(R$^{5a}$H)][CH$_2$]NHC(O)—; or
vi) —C(O)[CH$_2$][C(R$^{5a}$H)]NHC(O)—;
wherein $R^{5a}$ is:
i) hydrogen;
ii) methyl;
iii) ethyl;
iv) isopropyl;
v) phenyl;
vi) benzyl;
vii) 4-hydroxybenzyl;
viii) hydroxymethyl; or
ix) 1-hydroxyethyl.

When the index x is equal to 1, this embodiment provides the following non-limiting examples of L units:

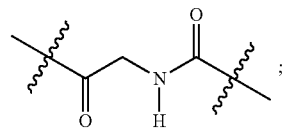

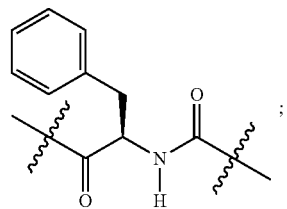

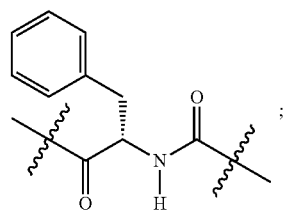

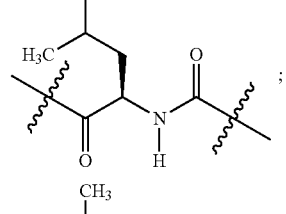

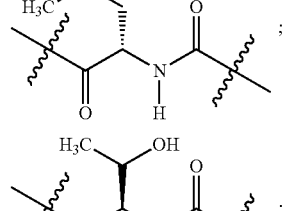

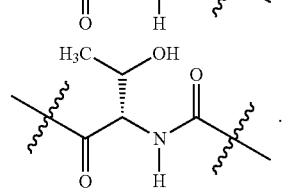; and

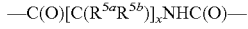.

When the index x is equal to 2, this embodiment provides the following non-limiting examples of L units:

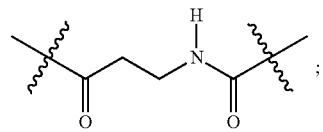;

-continued

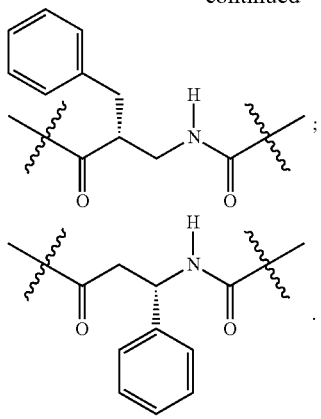

Another embodiment of L units includes units wherein Q is —C(O)—, the indices x and z are equal to 0, w is equal to 1 or 2, a first $R^{6a}$ unit chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl; a second $R^{6a}$ unit is hydrogen and $R^{6b}$ units are hydrogen. For example a linking unit having the formula:

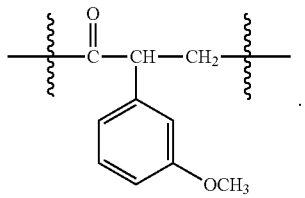 [SMILES: *CC(C(*)=O)c1cccc(OC)c1]

A further example of this embodiment of L includes a first $R^{6a}$ unit as depicted herein above that is a substituted or unsubstituted heteroaryl unit as described herein above.

A yet further example of this embodiment of L includes units having the formula:

—C(O)[C($R^{6a}R^{6b}$)]$_w$—;

wherein $R^{6a}$ and $R^{6b}$ are hydrogen and the index w is equal to 1 or 2; said units chosen from:
i) —C(O)CH$_2$—; and
ii) —C(O)CH$_2$CH$_2$—.

Another embodiment of L units includes units having the formula:

—C(O)[C($R^{5a}R^{5b}$)]—C(O)—;

wherein $R^{5a}$ and $R^{5b}$ are hydrogen and the index x is equal to 1 or 2; said units chosen from:
i) —C(O)CH$_2$C(O)—; and
ii) —C(O)CH$_2$CH$_2$C(O)—.

A still further embodiment of L units includes units having the formula:

—C(O)NH[C($R^{5a}R^{5b}$)]$_x$—;

wherein $R^{5a}$ and $R^{5b}$ are hydrogen and the index w is equal to 0, 1 or 2; said units chosen from:

ii) —C(O)NH—;
ii) —C(O)NHCH$_2$—; and
iii) —C(O)NHCH$_2$CH$_2$—.

A yet still further example of L units includes units having the formula:

—SO$_2$[C($R^{6a}R^{6b}$)]$_w$—;

wherein $R^{8a}$ and $R^{8b}$ are hydrogen or methyl and the index w is equal to 0, 1 or 2; said units chosen from:
i) —SO$_2$—;
ii) —SO$_2$CH$_2$—; and
iii) —SO$_2$CH$_2$CH$_2$—.

The disclosed compounds (analogs) are arranged into several Categories to assist the formulator in applying a rational synthetic strategy for the preparation of analogs which are not expressly exampled herein. The arrangement into categories does not imply increased or decreased efficacy for any of the compositions of matter described herein.

A described herein above the disclosed compounds include all pharmaceutically acceptable salt forms. A compound having the formula:

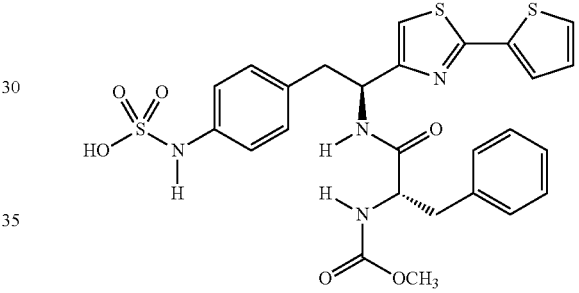

can form salts, for example, a salt of the sulfamic acid:

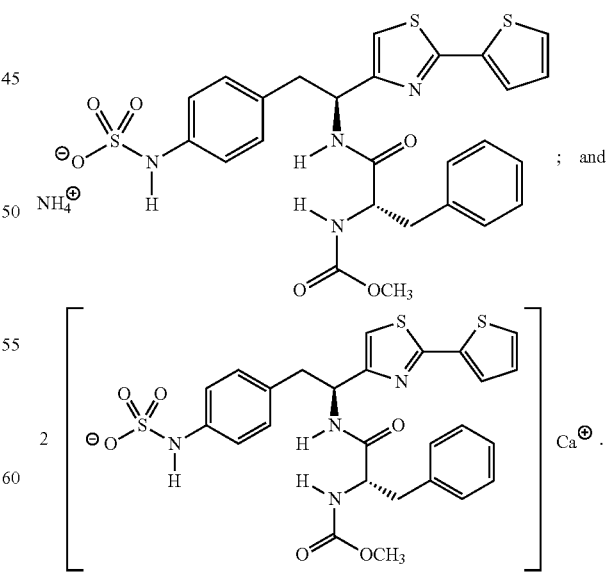

The compounds can also exist in a zwitterionic form, for example:

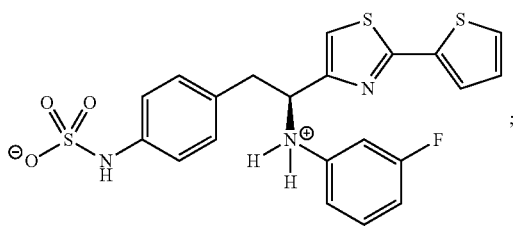 [SMILES: O=S(=O)([O-])Nc1ccc(C[C@H]([NH2+]c2cccc(F)c2)c2csc(-c3cccs3)n2)cc1]

or
as a salt of a strong acid, for example:

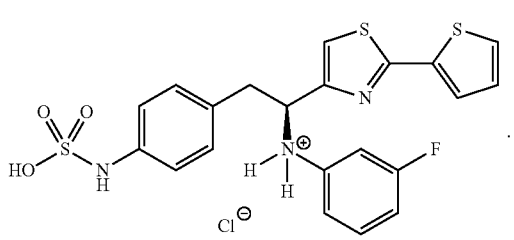 [SMILES: O=S(=O)(O)Nc1ccc(C[C@H]([NH2+]c2cccc(F)c2)c2csc(-c3cccs3)n2)cc1 ; [Cl-]]

The first aspect of Category I of the present disclosure relates to compounds wherein R is a substituted or unsubstituted thiazol-2-yl unit having the formula:

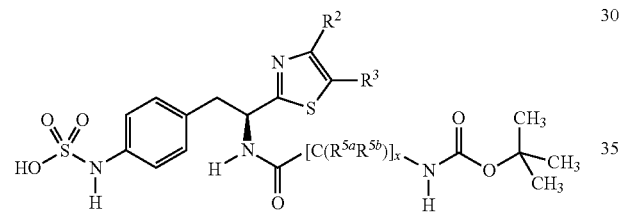

one embodiment of which relates to inhibitors having the formula:

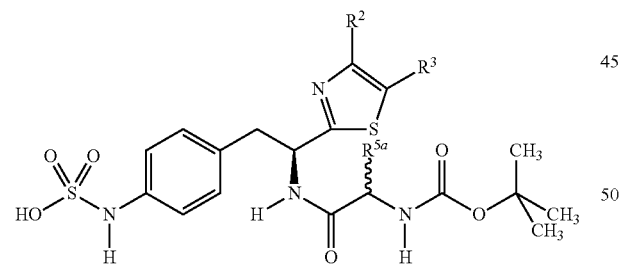

wherein R units are thiazol-2-yl units, that when substituted, are substituted with $R^2$ and $R^3$ units. R and $R^{5a}$ units are further described in Table I.

TABLE I

| No. | R | $R^{5a}$ |
|---|---|---|
| A1 | thiazol-2-yl | (S)-benzyl |
| A2 | 4-methylthiazol-2-yl | (S)-benzyl |
| A3 | 4-ethylthiazol-2-yl | (S)-benzyl |
| A4 | 4-propylthiazol-2-yl | (S)-benzyl |
| A5 | 4-iso-propylthiazol-2-yl | (S)-benzyl |
| A6 | 4-cyclopropylthiazol-2-yl | (S)-benzyl |

TABLE I-continued

| No. | R | $R^{5a}$ |
|---|---|---|
| A7 | 4-butylthiazol-2-yl | (S)-benzyl |
| A8 | 4-tert-butylthiazol-2-yl | (S)-benzyl |
| A9 | 4-cyclohexylthiazol-2-yl | (S)-benzyl |
| A10 | 4-(2,2,2-trifluoroethyl)thiazol-2-yl | (S)-benzyl |
| A11 | 4-(3,3,3-trifluoropropyl)thiazol-2-yl | (S)-benzyl |
| A12 | 4-(2,2-difluorocyclopropyl)thiazol-2-yl | (S)-benzyl |
| A13 | 4-(methoxymethyl)thiazol-2-yl | (S)-benzyl |
| A14 | 4-(carboxylic acid ethyl ester)thiazol-2-yl | (S)-benzyl |
| A15 | 4,5-dimethylthiazol-2-yl | (S)-benzyl |
| A16 | 4-methyl-5-ethylthiazol-2-yl | (S)-benzyl |
| A17 | 4-phenylthiazol-2-yl | (S)-benzyl |
| A18 | 4-(4-chlorophenyl)thiazol-2-yl | (S)-benzyl |
| A19 | 4-(3,4-dimethylphenyl)thiazol-2-yl | (S)-benzyl |
| A20 | 4-methyl-5-phenylthiazol-2-yl | (S)-benzyl |
| A21 | 4-(thiophen-2-yl)thiazol-2-yl | (S)-benzyl |
| A22 | 4-(thiophen-3-yl)thiazol-2-yl | (S)-benzyl |
| A23 | 4-(5-chlorothiophen-2-yl)thiazol-2-yl | (S)-benzyl |
| A24 | 5,6-dihydro-4H-cyclopenta[d]thiazol-2-yl | (S)-benzyl |
| A25 | 4,5,6,7-tetrahydrobenzo[d]thiazol-2-yl | (S)-benzyl |

The compounds encompassed within the first aspect of Category I of the present disclosure can be prepared by the procedure outlined in Scheme I and described in Example 1 herein below Scheme I

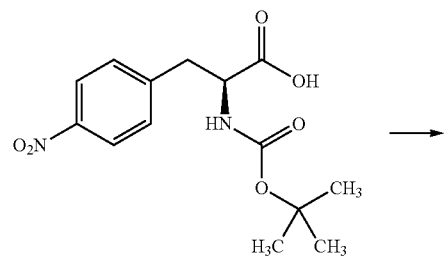

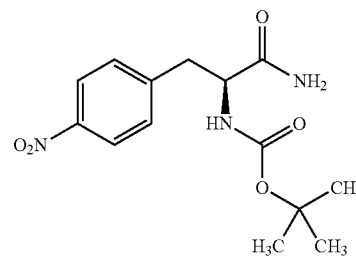

1

33
Reagents and Conditions: (a)(i) (Iso-Butyl)OCOCl, NMM, DMF; 0° C., 20 Min
(ii) NH$_3$; 0° C. for 30 Min
34
Reagents and Conditions: (c) CH$_3$CN; Reflux, 3 hr
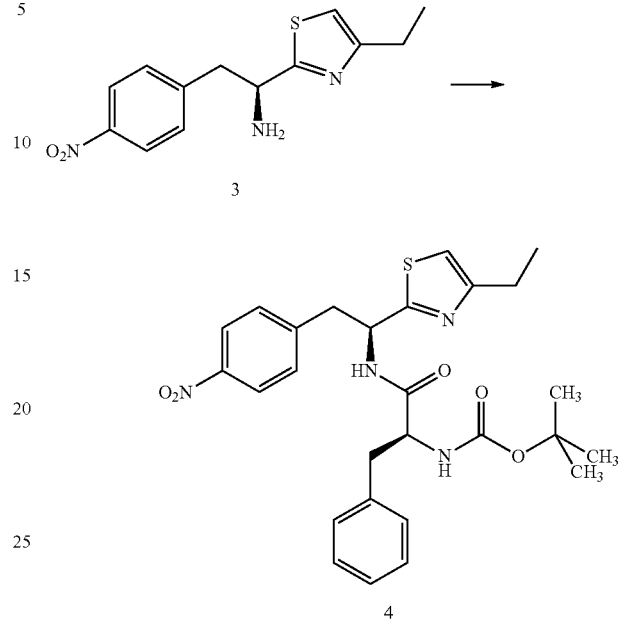
Reagents and Conditions: (d) Boc-Phe, EDCI, HOBt, DIPEA, DMF; Rt, 18 hr
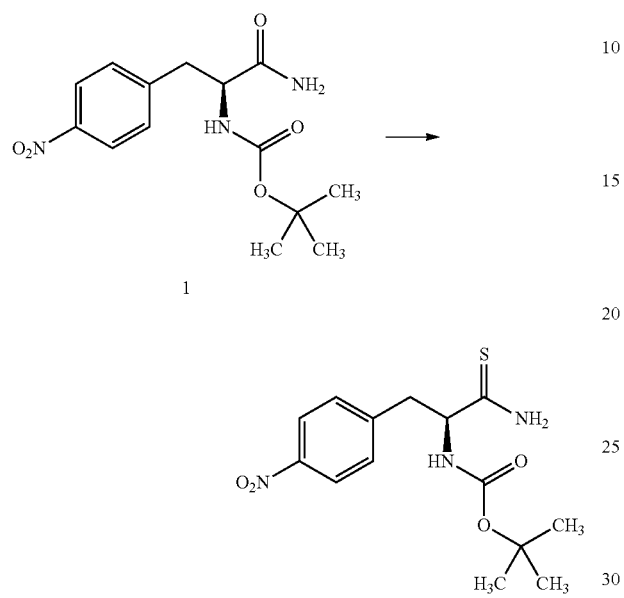
Reagents and Conditions: (b) Lawesson's Reagent, THF; Rt, 3 hr
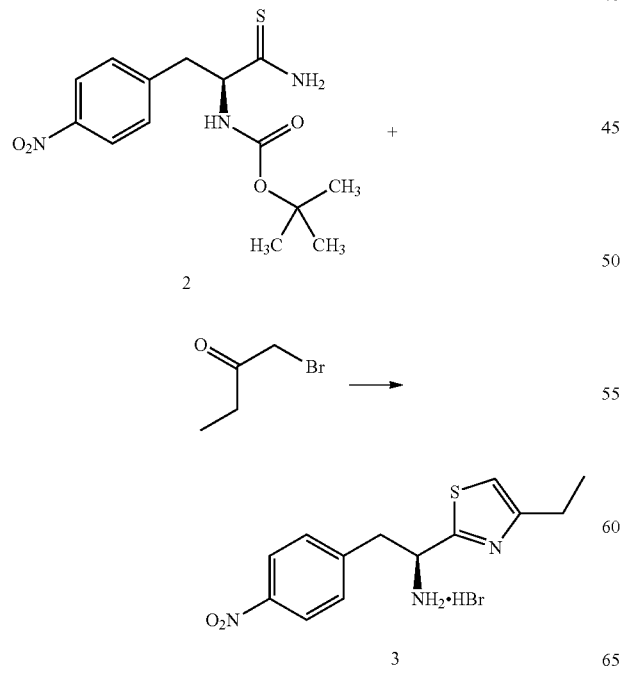

Reagents and Conditions: (e) (i) H₂:Pd/C, MeOH; (ii) SO₃-Pyridine, NH₄OH; Rt, 2 hr

EXAMPLE 1

4-{(S)-2-[(S)-2-(tert-Butoxycarbonylamino)-3-phenylpropanamido]-2-(4-ethylthiazol-2-yl)ethyl}phenylsulfamic Acid (5)

Preparation of [1-(S)-carbamoyl-2-(4-nitrophenyl)ethyl-carbamic acid tert-butyl ester (1): To a 0° C. solution of 2-(S)-tert-butoxycarbonylamino-3-(4-nitrophenyl)-propionic acid and N-methylmorpholine (1.1 mL, 9.65 mmol) in DMF (10 mL) is added dropwise iso-butyl chloroformate (1.25 mL, 9.65 mmol). The mixture is stirred at 0° C. for 20 minutes after which NH₃ (g) is passed through the reaction mixture for 30 minutes at 0° C. The reaction mixture is concentrated and the residue dissolved in EtOAc, washed successively with 5% citric acid, water, 5% NaHCO₃, water and brine, dried (Na₂SO₄), filtered and concentrated in vacuo to a residue that is triturated with a mixture of EtOAc/petroleum ether to provide 2.2 g (74%) of the desired product as a white solid.

Preparation of [2-(4-nitrophenyl)-1-(S)-thiocarbamoyl-ethyl]carbamic acid tert-butyl ester (2): To a solution of [1-(S)-carbamoyl-2-(4-nitrophenyl)ethyl-carbamic acid tert-butyl ester, 1, (0.400 g, 1.29 mmol) in THF (10 mL) is added Lawesson's reagent (0.262 g. 0.65 mmol). The reaction mixture is stirred for 3 hours and concentrated to a residue which is purified over silica to provide 0.350 g (83%) of the desired product. ¹H NMR (300 MHz, CDCl₃) δ 8.29 (s, 1H), 8.10 (d, J=8.4 Hz, 2H), 8.01 (s, 1H), 7.42 (d, J=8.4 Hz, 2H), 5.70 (d, J=7.2 Hz, 1H), 4.85 (d, J=7.2 Hz, 1H), 3.11-3.30 (m, 1H), 1.21 (s, 9H).

Preparation of 1-(S)-(4-ethylthiazol-2-yl)-2-(4-nitrophenyl)ethyl amine (3): A mixture of R-(4-nitrophenyl)-1-(S)-thiocarbamoylethyl)carbamic acid tert-butyl ester, 2, (0.245 g, 0.753 mmol), 1-bromo-2-butanone (0.125 g, 0.828 mmol) in CH₃CN (5 mL) is refluxed 3 hours. The reaction mixture is cooled to room temperature and diethyl ether is added to the solution and the precipitate which forms is removed by filtration. The solid is dried under vacuum to afford 0.242 g (90% yield) of the desired product. ESI+ MS 278 (M+1).

Preparation of {1-[1-(4-ethylthiazol-2-yl)-2-(4-nitrophenyl)ethylcarbamoyl]-2-phenylethyl}carbamic acid tert-butyl ester (4): To a solution of 1-(S)-(4-ethylthiazol-2-yl)-2-(4-nitrophenyl)ethyl amine hydrobromide, 3, (0.393 g, 1.1 mmol), (S)-(2-tert-butoxycarbonylamino)-3-phenylpropionic acid (0.220 g, 0.828 mmol) and 1-hydroxybenzotriazole (HOBt) (0.127 g, 0.828 mmol) in DMF (10 mL) at 0° C., is added 1-(3-dimethylaminopropyl)-3-ethylcarbodiimide (EDCI) (0.159 g, 0.828 mmol) followed by diisopropylamine (0.204 g, 1.58 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.345 g of the desired product which is used without further purification. LC/MS ESI+ 525 (M+1).

Preparation of 4-{(S)-2-[(S)-2-(tert-butoxycarbonylamino)-3-phenylpropanamido]-2-(4-ethylthiazol-2-yl)ethyl}phenylsulfamic acid ammonium salt (5): {1-[1-(4-ethylthiazol-2-yl)-2-(4-nitrophenyl)ethylcarbamoyl]-2-phenylethyl}carbamic acid tert-butyl ester, 4, (0.345 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO₃-pyridine (0.314 g). The reaction is stirred at room temperature for 5 minutes after which a 7% solution of NH₄OH (50 mL) is added. The mixture is then concentrated and the resulting residue is purified by reverse phase chromatography to afford 0.222 g of the desired product as the ammonium salt. ¹H NMR (CD₃OD): δ 7.50-6.72 (m, 10H), 5.44-5.42 (d, 1H, J=6.0 Hz), 4.34 (s, 1H), 3.34-2.79 (m, 4H), 2.83-2.76 (q, 2H, J=7.2 Hz), 1.40 (s, 9H), 1.31 (t, 3H, J=7.5 Hz).

The disclosed inhibitors can also be isolated as the free acid. A non-limiting example of this procedure is described herein below in Example 4.

The following is a non-limiting example of compounds encompassed within this embodiment of the first aspect of Category I of the present disclosure.

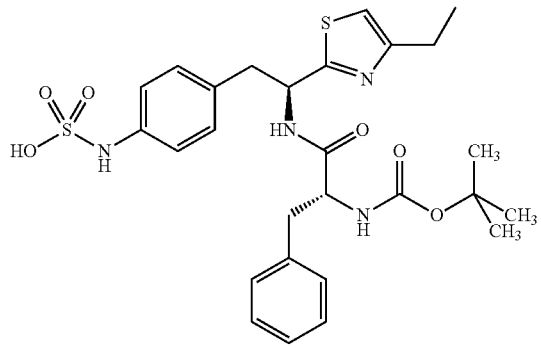 [SMILES: CCc1csc([C@H](Cc2ccc(NS(=O)(=O)O)cc2)NC(=O)[C@@H](Cc2ccccc2)NC(=O)OC(C)(C)C)n1]

4-{(S)-2-[(R)-2-(tert-butoxycarbonylamino)-3-phenylpropanamido]-2-(4-ethylthiazol-2-yl)ethyl}phenylsulfamic acid: ¹H NMR (CD₃OD): δ 7.22-7.02 (m, 10H), 5.39 (s, 1H), 4.34 (s, 1H), 3.24-2.68 (m, 6H), 1.37 (s, 9H), 1.30 (t, 3H, J=7.5 Hz).

Another embodiment of this aspect of Category I relates to inhibitors having the formula:

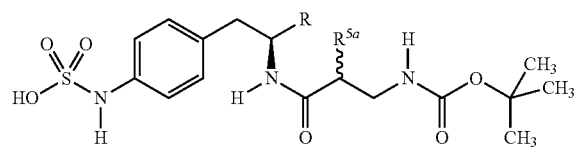

wherein R units and R⁵ᵃ units further described in Table II.

TABLE II

| No. | R | R⁵ᵃ |
|---|---|---|
| B26 | thiazol-2-yl | (S)-benzyl |
| B27 | 4-methylthiazol-2-yl | (S)-benzyl |
| B28 | 4-ethylthiazol-2-yl | (S)-benzyl |
| B29 | 4-propylthiazol-2-yl | (S)-benzyl |
| B30 | 4-iso-propylthiazol-2-yl | (S)-benzyl |
| B31 | 4-cyclopropylthiazol-2-yl | (S)-benzyl |
| B32 | 4-butylthiazol-2-yl | (S)-benzyl |
| B33 | 4-tert-butylthiazol-2-yl | (S)-benzyl |
| B34 | 4-cyclohexylthiazol-2-yl | (S)-benzyl |
| B35 | 4-(2,2,2-trifluoroethyl)thiazol-2-yl | (S)-benzyl |
| B36 | 4-(3,3,3-trifluoropropyl)thiazol-2-yl | (S)-benzyl |
| B37 | 4-(2,2-difluorocyclopropyl)thiazol-2-yl | (S)-benzyl |
| B38 | 4-(methoxymethyl)thiazol-2-yl | (S)-benzyl |

TABLE II-continued

| No. | R | $R^{5a}$ |
|---|---|---|
| B39 | 4-(carboxylic acid ethyl ester)thiazol-2-yl | (S)-benzyl |
| B40 | 4,5-dimethylthiazol-2-yl | (S)-benzyl |
| B41 | 4-methyl-5-ethylthiazol-2-yl | (S)-benzyl |
| B42 | 4-phenylthiazol-2-yl | (S)-benzyl |
| B43 | 4-(4-chlorophenyl)thiazol-2-yl | (S)-benzyl |
| B44 | 4-(3,4-dimethylphenyl)thiazol-2-yl | (S)-benzyl |
| B45 | 4-methyl-5-phenylthiazol-2-yl | (S)-benzyl |
| B46 | 4-(thiophen-2-yl)thiazol-2-yl | (S)-benzyl |
| B47 | 4-(thiophen-3-yl)thiazol-2-yl | (S)-benzyl |
| B48 | 4-(5-chlorothiophen-2-yl)thiazol-2-yl | (S)-benzyl |
| B49 | 5,6-dihydro-4H-cyclopenta[d]thiazol-2-yl | (S)-benzyl |
| B50 | 4,5,6,7-tetrahydrobenzo[d]thiazol-2-yl | (S)-benzyl |

The compounds of this embodiment can be prepared according to the procedure outlined above in Scheme I and described in Example 1 by substituting the appropriate Boc-β-amino acid for (S)-(2-tert-butoxycarbonylamino)-3-phenylpropionic acid in step (d).

The following are non-limiting examples of compounds according to this embodiment.

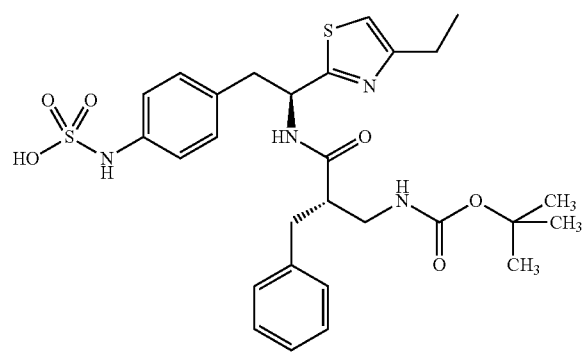 [SMILES: CCc1csc([C@H](Cc2ccc(NS(=O)(=O)O)cc2)NC(=O)[C@H](CNC(=O)OC(C)(C)C)Cc2ccccc2)n1]

{1-[1-(4-Ethylthiazol-2-yl)-(S)-2-(4-sulfoaminophenyl) ethylcarbamoyl]-(S)-2-phenylethyl}methyl carbamic acid tert-butyl ester: $^1$H NMR (300 MHz, MeOH-d$_4$) δ 8.36 (d, J=8.1 Hz, 1H), 7.04-7.22 (m, 9H), 5.45 (s, 1H), 3.01-3.26 (m, 2H), 2.60-2.88 (m, 4H), 2.33 (s, 3H), 1.30 (s, 9H).

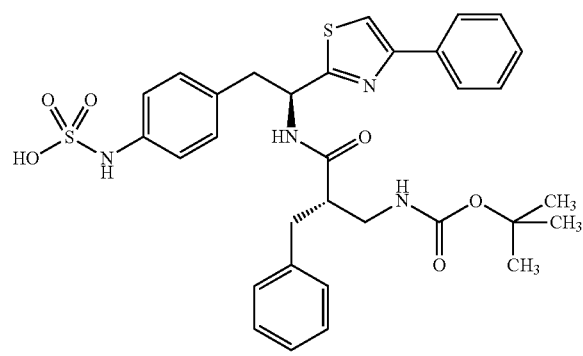 [SMILES: CC(C)(C)OC(=O)NC[C@H](Cc1ccccc1)C(=O)N[C@@H](Cc1ccc(NS(=O)(=O)O)cc1)c1nc(-c2ccccc2)cs1]

{1-[1-(4-Phenylthiazol-2-yl)-(S)-2-(4-sulfoaminophenyl) ethylcarbamoyl]-(S)-2-phenylethyl}methyl carbamic acid tert-butyl ester: $^1$H NMR (300 MHz, MeOH-d$_4$) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The second aspect of Category I of the present disclosure relates to compounds wherein R is a substituted or unsubstituted thiazol-4-yl having the formula:

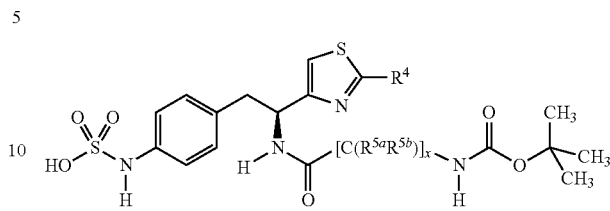

one embodiment of which relates to inhibitors having the formula:

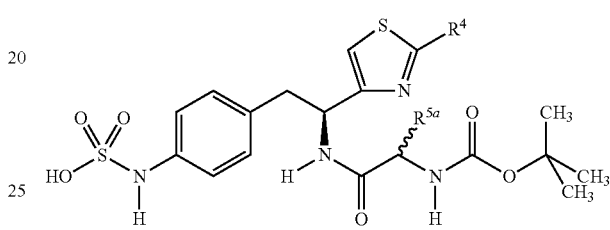

wherein R units and $R^{5a}$ units further described in Table III.

TABLE III

| No. | R | $R^{5a}$ |
|---|---|---|
| C51 | thiazol-4-yl | (S)-benzyl |
| C52 | 2-methylthiazol-4-yl | (S)-benzyl |
| C53 | 2-ethylthiazol-4-yl | (S)-benzyl |
| C54 | 2-propylthiazol-4-yl | (S)-benzyl |
| C55 | 2-iso-propylthiazol-4-yl | (S)-benzyl |
| C56 | 2-cyclopropylthiazol-4-yl | (S)-benzyl |
| C57 | 2-butylthiazol-4-yl | (S)-benzyl |
| C58 | 2-tert-butylthiazol-4-yl | (S)-benzyl |
| C59 | 2-cyclohexylthiazol-4-yl | (S)-benzyl |
| C60 | 2-(2,2,2-trifluoroethyl)thiazol-4-yl | (S)-benzyl |
| C61 | 2-(3,3,3-trifluoropropyl)thiazol-4-yl | (S)-benzyl |
| C62 | 2-(2,2-difluorocyclopropyl)thiazol-4-yl | (S)-benzyl |
| C63 | 2-phenylthiazol-4-yl | (S)-benzyl |
| C64 | 2-(4-chlorophenyl)thiazol-4-yl | (S)-benzyl |
| C65 | 2-(3,4-dimethylphenyl)thiazol-4-yl | (S)-benzyl |
| C66 | 2-(thiophen-2-yl)thiazol-4-yl | (S)-benzyl |
| C67 | 2-(thiophen-3-yl)thiazol-4-yl | (S)-benzyl |
| C68 | 2-(3-chlorothiophen-2-yl)thiazol-4-yl | (S)-benzyl |
| C69 | 2-(3-methylthiophen-2-yl)thiazol-4-yl | (S)-benzyl |
| C70 | 2-(2-methylthiazol-4-yl)thiazol-4-yl | (S)-benzyl |
| C71 | 2-(furan-2-yl)thiazol-4-yl | (S)-benzyl |
| C72 | 2-(pyrazin-2-yl)thiazol-4-yl | (S)-benzyl |
| C73 | 2-[(2-methyl)pyridin-5-yl]thiazol-4-yl | (S)-benzyl |
| C74 | 2-(4-chlorobenzenesulfonylmethyl)thiazol-4-yl | (S)-benzyl |
| C75 | 2-(tert-butylsulfonylmethyl)thiazol-4-yl | (S)-benzyl |

The compounds encompassed within the second aspect of Category I of the present disclosure can be prepared by the procedure outlined in Scheme II and described in Example 2 herein below.

Scheme II
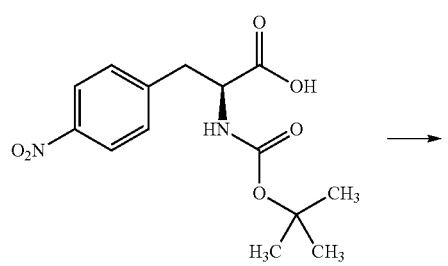
5
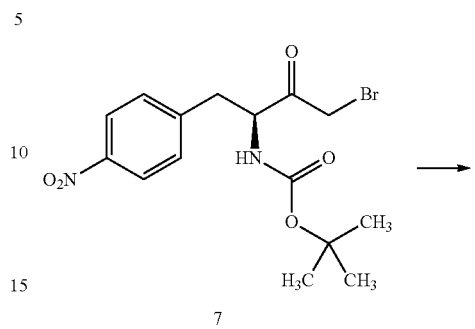
7
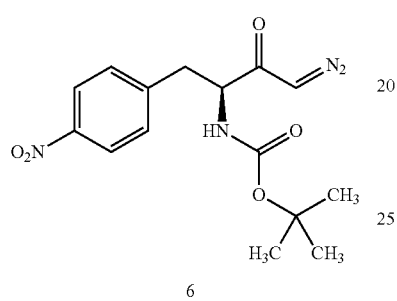
6
Reagents and Conditions: (a)(i) (Iso-Butyl)OCOCl, Et₃N, THF; 0° C., 20 Min
(ii) CH₂N₂; Room Temp for 3 Hours
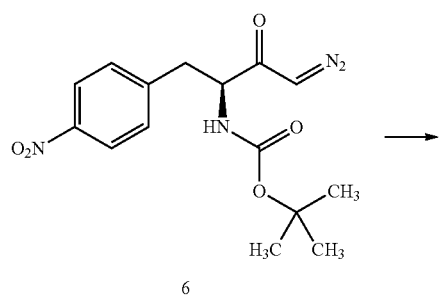
6
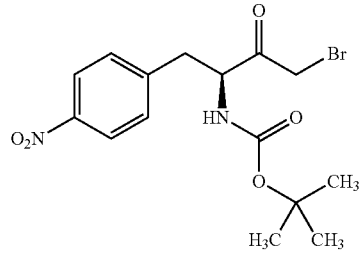
7
Reagents and Conditions: (b) 48% HBr, THF; 0° C., 1.5 hr
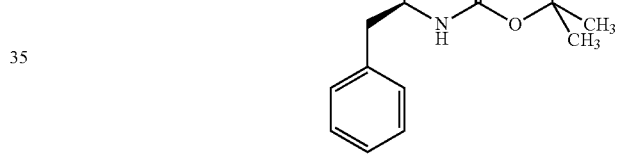
8
Reagents and Conditions: (c)(i) Thiobenzamide, CH₃CN; Reflux, 2 hr
(ii) Boc-Phe, HOBt, DIPEA, DMF; Rt, 18 hr
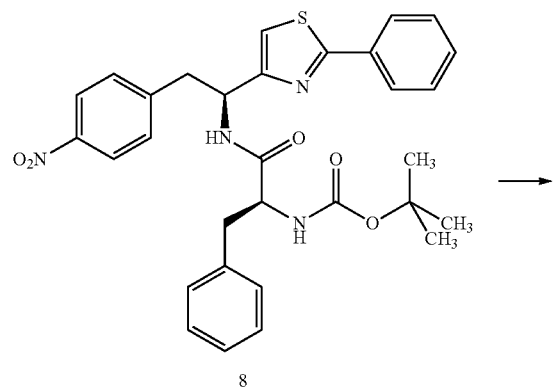
8

-continued

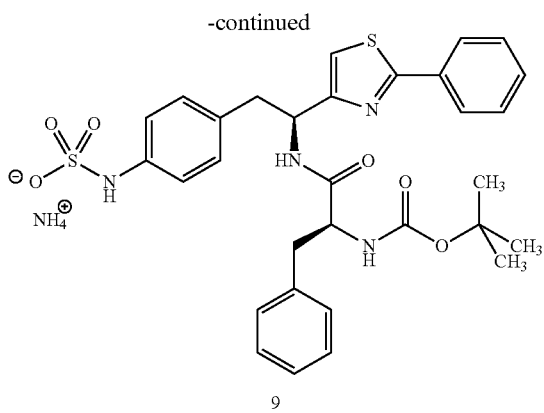

9

Reagents and Conditions: (d) (i) H₂:Pd/C, MeOH;
(ii) SO₃-Pyridine, NH₄OH; Rt, 12 hr

EXAMPLE 2

4-{(S)-2-(S)-2-(tert-Butoxycarbonylamino)-3-phenylpropanamido-2-(2-phenylthiazol-4-yl}phenylsulfamic Acid (9)

Preparation of (S)-[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes and filtered. The filtrate is treated with an ether solution of diazomethane (~16 mmol) at 0° C. The reaction mixture is stirred at room temperature for 3 hours then concentrated in vacuo. The resulting residue is dissolved in EtOAc and washed successively with water and brine, dried (Na₂SO₄), filtered and concentrated. The residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture is stirred at 0° C. for 1.5 hours then the reaction is quenched at 0° C. with sat. Na₂CO₃. The mixture is extracted with EtOAc (3×25 mL) and the combined organic extracts are washed with brine, dried (Na₂SO₄), filtered and concentrated to obtain 0.400 g of the product which is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of tert-butyl (S)-1-(S)-2-(4-nitrophenyl)-1-(2-phenylthiazole-4-yl)ethylamino-1-oxo-3-phenylpropan-2-ylcarbamate (8): A mixture of thiobenzamide (0.117 g, 0.85 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed 2 hours. The reaction mixture is cooled to room temperature and diethyl ether is added to precipitate the intermediate 2-(nitrophenyl)-(S)-1-(4-phenylthiazol-2-yl)ethylamine which is isolated by filtration as the hydrobromide salt. The hydrobromide salt is dissolved in DMF (3 mL) together with diisoproylethylamine (0.42 mL, 2.31 mmol), 1-hydroxybenzotriazole (0.118 g, 0.79 mmol) and (S)-(2-tert-butoxycarbonylamino)-3-phenylpropionic acid (0.212 g, 0.80 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.395 g (90% yield) of the desired product which is used without further purification. LC/MS ESI+ 573 (M+1).

Preparation of 4-{(S)-2-(S)-2-(tert-butoxycarbonyl)-3-phenylpropaneamido-2-(2-phenylthiazole-4-yl)}phenylsulfamic acid (9): tert-butyl (S)-1-(S)-2-(4-nitrophenyl)-1-(2-phenylthiazole-4-yl)ethylamino-1-oxo-3-phenylpropan-2-ylcarbamate, 8, (0.360 g) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO₃-pyridine (0.296 g). The reaction is stirred at room temperature for 5 minutes after which a 7% solution of NH₄OH (10 mL) is added. The mixture is then concentrated and the resulting residue is purified by reverse phase chromatography to afford 0.050 g of the desired product as the ammonium salt. ¹H NMR (300 MHz, MeOH-d₄) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The first aspect of Category II of the present disclosure relates to compounds wherein R is a substituted or unsubstituted thiazol-4-yl unit having the formula:

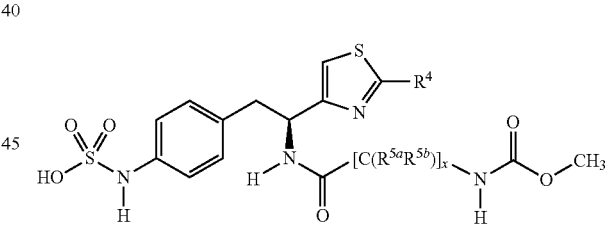

one embodiment of which relates to inhibitors having the formula:

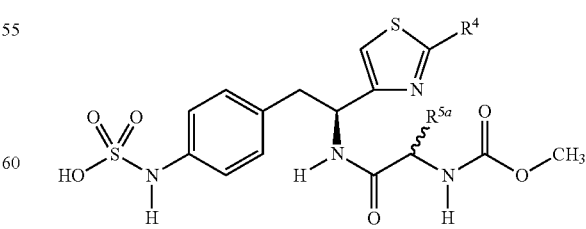

wherein R units are thiazol-4-yl units, that when substituted, are substituted with R⁴ units. R and R⁵ᵃ units are further described in Table IV.

TABLE IV

| No. | R | R⁵ᵃ |
|---|---|---|
| D76 | thiazol-4-yl | (S)-benzyl |
| D77 | 2-methylthiazol-4-yl | (S)-benzyl |
| D78 | 2-ethylthiazol-4-yl | (S)-benzyl |
| D79 | 2-propylthiazol-4-yl | (S)-benzyl |
| D80 | 2-iso-propylthiazol-4-yl | (S)-benzyl |
| D81 | 2-cyclopropylthiazol-4-yl | (S)-benzyl |
| D82 | 2-butylthiazol-4-yl | (S)-benzyl |
| D83 | 2-tert-butylthiazol-4-yl | (S)-benzyl |
| D84 | 2-cyclohexylthiazol-4-yl | (S)-benzyl |
| D85 | 2-(2,2,2-trifluoroethyl)thiazol-4-yl | (S)-benzyl |
| D86 | 2-(3,3,3-trifluoropropyl)thiazol-4-yl | (S)-benzyl |
| D87 | 2-(2,2-difluorocyclopropyl)thiazol-4-yl | (S)-benzyl |
| D88 | 2-phenylthiazol-4-yl | (S)-benzyl |
| D89 | 2-(4-chlorophenyl)thiazol-4-yl | (S)-benzyl |
| D90 | 2-(3,4-dimethylphenyl)thiazol-4-yl | (S)-benzyl |
| D91 | 2-(thiophen-2-yl)thiazol-4-yl | (S)-benzyl |
| D92 | 2-(thiophen-3-yl)thiazol-4-yl | (S)-benzyl |
| D93 | 2-(3-chlorothiophen-2-yl)thiazol-4-yl | (S)-benzyl |
| D94 | 2-(3-methylthiophen-2-yl)thiazol-4-yl | (S)-benzyl |
| D95 | 2-(2-methylthiazol-4-yl)thiazol-4-yl | (S)-benzyl |
| D96 | 2-(furan-2-yl)thiazol-4-yl | (S)-benzyl |
| D97 | 2-(pyrazin-2-yl)thiazol-4-yl | (S)-benzyl |
| D98 | 2-[(2-methyl)pyridin-5-yl]thiazol-4-yl | (S)-benzyl |
| D99 | 2-(4-chlorobenzenesulfonylmethyl)thiazol-4-yl | (S)-benzyl |
| D100 | 2-(tert-butylsulfonylmethyl)thiazol-4-yl | (S)-benzyl |

The compounds encompassed within the second aspect of Category II of the present disclosure can be prepared by the procedure outlined in Scheme III and described in Example 3 herein below.

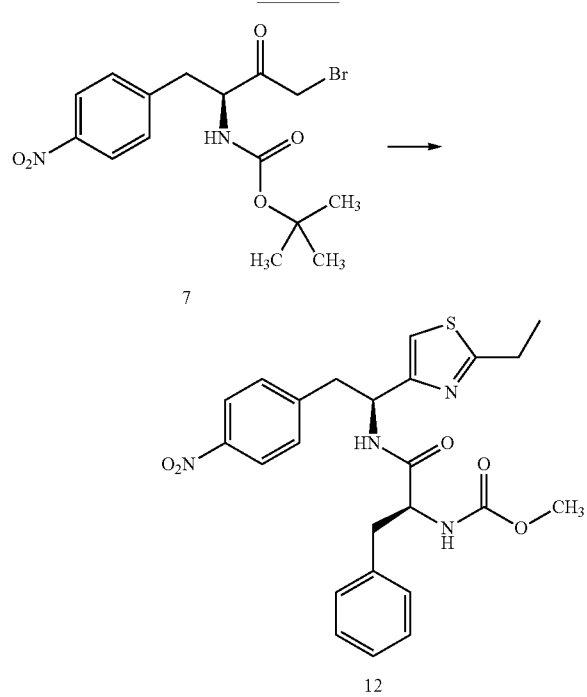

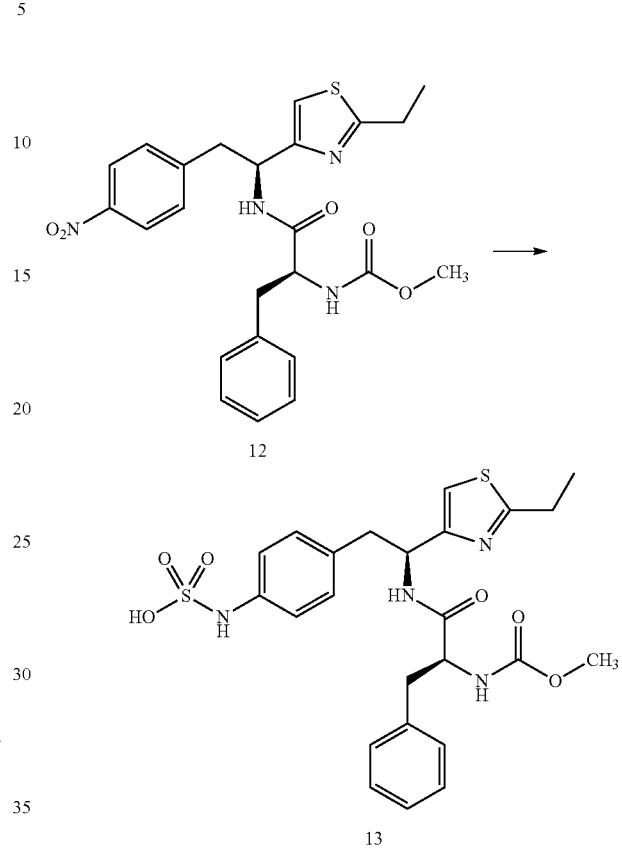

Reagents and Conditions: (a)(i) Propanethioamide, CH₃CN; Reflux, 2 hr (ii) Boc-Phe, HOBt, DIPEA, DMF; rt, 18 hr Reagents and Conditions: (b) (i) H₂:Pd/C, MeOH;
(ii) SO₃-Pyridine, NH₄OH; Rt, 18 hr

EXAMPLE 3

4-{(S)-2-[(S)-2-(Methoxycarbonylamino)-3-phenyl-propanamido]-2-(2-ethylthiazol-4-yl) ethyl}phenylsulfamic Acid (13)

Preparation of methyl (S)-1-[(S)-1-(2-ethylthiazole-4-yl)-2-(4-nitrophenyl)-ethyl]amino-1-oxo-3-phenylpropane-2-ylcarbamate (12): A mixture of propanethioamide (69 mg, 0.78 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed for 2 hours. The reaction mixture is cooled to room temperature and diethyl ether is added to precipitate the intermediate 2-(nitrophenyl)-(S)-1-(4-ethyl-thiazol-2-yl)ethylamine which is isolated by filtration as the hydrobromide salt. The hydrobromide salt is dissolved in DMF (8 mL) together with diisoproylethylamine (0.38 mL, 2.13 mmol), 1-hydroxybenzotriazole (107 mg, 0.71 mmol) and (S)-(2-methoxycarbonylamino)-3-phenylpropionic acid (175 mg, 0.78 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.300 g (81% yield) of the desired product which is used without further purification. LC/MS ESI+MS 483 (M+1).

Preparation of 4-((S)-2-((S)-2-(methoxycarbonylamino)-3-phenylpropanamido)-2-(2-ethylthiazol-4-yl) ethyl)phenylsulfamic acid ammonium salt (13): tert-Butyl (S)-1-(S)-2-(4-nitrophenyl)-1-(2-ethylthiazole-4-yl)ethylamino-1-oxo-3-phenylpropan-2-ylcarbamate, 12, (0.300 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (223 mg, 1.40 mmol). The reaction is stirred at room temperature for 5 minutes after which a 7% solution of NH$_4$OH (12 mL) is added. The mixture is then concentrated and the resulting residue is purified by reverse phase chromatography to afford 25 mg of the desired product as the ammonium salt. $^1$H NMR (300 MHz, MeOH-d$_4$) δ 7.14-7.24 (m, 6H), 6.97-7.0 (m, 4H), 6.62 (s, 1H), 5.10-5.30 (m, 1H), 4.36 (t, J=7.2 Hz, 1H), 3.63 (s, 3H), 3.14 (dd, J=13.5 and 6.3 Hz, 1H), 2.93-3.07 (m, 5H), 2.81 (dd, J=13.5 and 6.3 HZ, 1H), 1.39 (t, J=7.8 Hz, 3H).

In another iteration of the process of the present disclosure, compound 13, as well as the other analogs which comprise the present disclosure, can be isolated as the free acid by adapting the procedure described herein below.

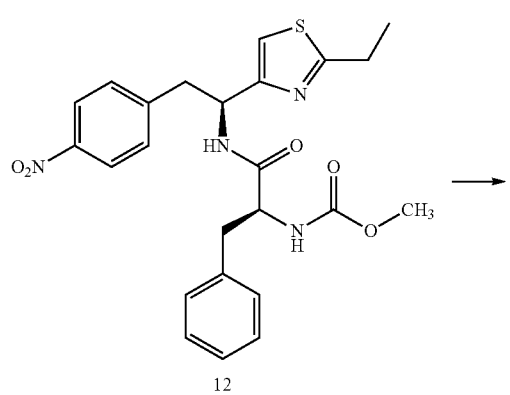

12

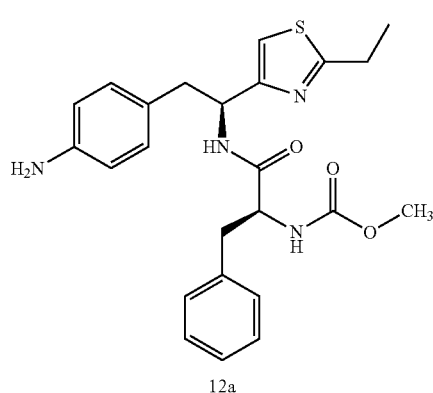

12a

Reagents and Conditions: (a) H$_2$:Pd/C, MeOH; Rt, 40 hr

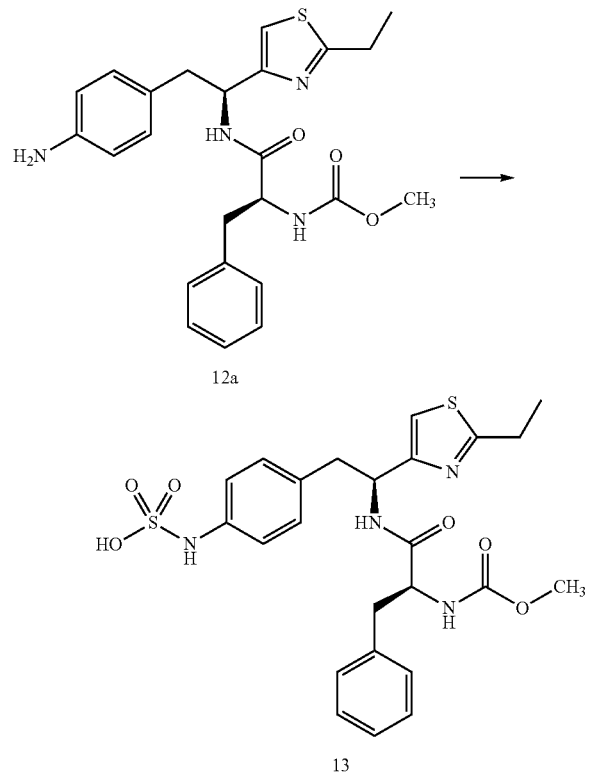

12a

13

Reagents and Conditions: (b) SO$_3$-Pyridine, CH$_3$CN; Heat, 45 Min

EXAMPLE 4

4-((S)-2-((S)-2-(Methoxycarbonylamino)-3-phenylpropanamido)-2-(2-ethylthiazol-4-yl) ethyl)phenylsulfamic Acid [Free Acid Form] (13)

Preparation of {1-[2-(S)-(4-(S)-aminophenyl)-1-(2-ethylthiazol-4-yl)ethyl-carbamoyl]-2-phenylethyl}-carbamic acid methyl ester (12a): A Parr hydrogenation vessel is charged with tert-butyl (S)-1-(S)-2-(4-nitrophenyl)-1-(2-ethylthiazole-4-yl)ethylamino-1-oxo-3-phenylpropan-2-yl-carbamate, 12, (18.05 g, 37.4 mmol, 1.0 eq) and Pd/C (10% Pd on C, 50% wet, Degussa-type E101 NE/W, 2.68 g, 15 wt %) as solids. MeOH (270 mL, 15 mL/g) is added to provide a suspension. The vessel is put on a Parr hydrogenation apparatus. The vessel is submitted to a fill/vacuum evacuate process with N$_2$ (3×20 psi) to inert, followed by the same procedure with H$_2$ (3×40 psi). The vessel is filled with H$_2$ and the vessel is shaken under 40 psi H$_2$ for ~40 hr. The vessel is evacuated and the atmosphere is purged with N$_2$ (5×20 psi). An aliquot is filtered and analyzed by HPLC to insure complete conversion. The suspension is filtered through a pad of celite to remove the catalyst, and the homogeneous yellow filtrate is concentrated by rotary evaporation to afford 16.06 g (95% yield) of the desired product as a tan solid, which is used without further purification.

Preparation of 4-((S)-2-((S)-2-(methoxycarbonyl)-3-phenylpropanamido)-2-(2-ethylthiazol-4-yl) ethyl)phenylsulfamic acid (13): A 100 mL RBF is charged with {1-[2-(S)-(4-(S)-aminophenyl)-1-(2-ethylthiazol-4-yl)ethyl-carbamoyl]-2-phenylethyl}-carbamic acid methyl ester, 12a, (10.36 g, 22.9 mmol, 1.0 eq.) prepared in the step described herein above. Acetonitrile (50 mL, 5 mL/g) is added and the yellow suspension is stirred at room temperature. A second 3-necked 500 mL RBF is charged with $SO_3 \cdot pyr$ (5.13 g, 32.2 mmol, 1.4 eq.) and acetonitrile (50 mL 5 mL/g) and the white suspension is stirred at room temperature. Both suspensions are gently heated until the reaction solution containing {1-[2-(S)-(4-(S)-aminophenyl)-1-(2-ethylthiazol-4-yl)ethyl-carbamoyl]-2-phenylethyl}-carbamic acid methyl ester becomes red-orange in color (typically for this example about 44° C.). This substrate containing solution is poured in one portion into the stirring suspension of $SO_3 \cdot pyr$ at 35° C. The resulting opaque mixture (39° C.) is stirred vigorously while allowed to slowly cool to room temperature. After stirring for 45 min, the reaction is determined to be complete by HPLC. $H_2O$ (200 mL, 20 mL/g) is added to the orange suspension to provide a yellow-orange homogeneous solution having a pH of approximately 2.4. Concentrated $H_3PO_4$ is added slowly over 12 minutes to lower the pH to approximately 1.4. During this pH adjustment, an off-white precipitate is formed and the solution is stirred at room temperature for 1 hr. The suspension is filtered and the filter cake is washed with the filtrate. The filter cake is air-dried on the filter overnight to afford 10.89 g (89% yield) of the desired product as a tan solid.

The following are further non-limiting examples of the second aspect of Category II of the present disclosure.

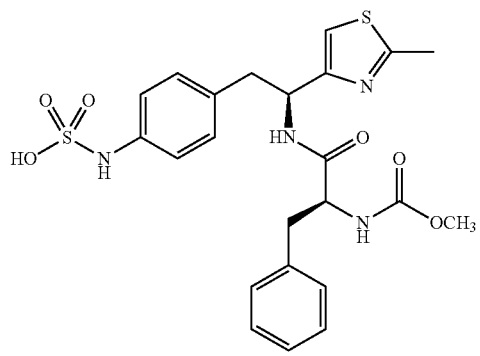 [SMILES: COC(=O)N[C@@H](Cc1ccccc1)C(=O)N[C@@H](Cc1ccc(NS(=O)(=O)O)cc1)c1csc(C)n1]

4-{(S)-2-[(S)-2-(Methoxycarbonylamino)-3-phenylpropanamido]-2-(2-methylthiazol-4-yl)ethyl}phenylsulfamic acid: $^1$H NMR (300 MHz, MeOH-$d_4$) δ 8.15 (d, J=8.4 Hz, 1H), 7.16-7.25 (m, 5H), 6.97-7.10 (m, 4H), 6.61 (s, 1H), 5.00-5.24 (m, 1H), 4.36 (t, J=7.2 Hz, 1H), 3.64 (s, 2H), 3.11-3.19 (s, 1H), 2.92-3.04 (s, 2H), 2.81 (dd, J=13.5 and 8.1 Hz, 1H), 2.75 (s, 3H).

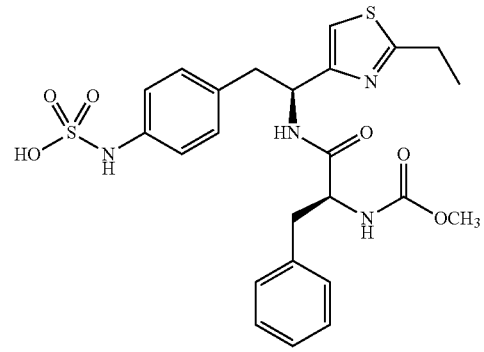 [SMILES: CCc1nc([C@H](Cc2ccc(NS(=O)(=O)O)cc2)NC(=O)[C@H](Cc2ccccc2)NC(=O)OC)cs1]

4-{(S)-2-(2-Ethylthiazole-4-yl)-2-[(S)-2-(methoxycarbonylamino)-3-phenylpropan-amido]ethyl}phenylsulfamic acid: $^1$H NMR (300 MHz, MeOH-$d_4$) δ 7.16-7.29 (m, 5H), 7.02-7.12 (m, 4H), 6.83 (s, 1H), 5.10-5.35 (m, 1H), 3.52-3.67 (m, 3H), 3.18-3.25 (m, 2H), 3.05 (q, J=7.5 Hz, 2H), 2.82-2.95 (m, 2H), 2.65 (s, 3H), 1.39 (t, J=7.5 Hz, 3H).

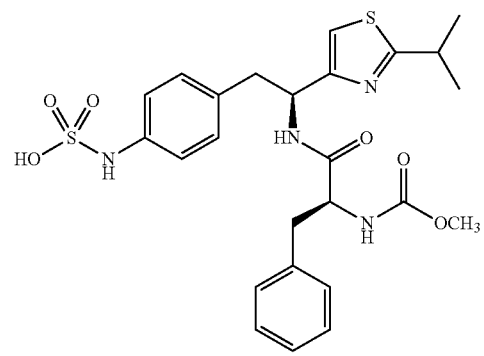 [SMILES: COC(=O)N[C@@H](Cc1ccccc1)C(=O)N[C@@H](Cc1ccc(NS(=O)(=O)O)cc1)c1csc(C(C)C)n1]

4-{(S)-2-(2-Isopropylthiazol-4-yl)-2-[(S)-2-(methoxycarbonylamino)-3-phenylpropan-amido]ethyl}phenylsulfamic acid: $^1$H NMR (CD$_3$OD) δ 8.16 (d, 1H, J=8.7 Hz), 7.22-7.13 (m, 3H), 7.07 (d, 1H, J=8.4 Hz), 6.96 (d, 1H, J=8.1 Hz), 6.62 (s, 1H), 5.19 (t, 1H, J=7.2 Hz), 4.36 (t, 1H, J=7.8 Hz), 3.63 (s, 3H), 3.08 (1H, A of ABX, J=3.6, 14.5 Hz), 2.99 (1H, B of ABX, J=7.2, 13.8 Hz), 2.85-2.78 (m, 1H), 1.41 (d, 6H, J=6.9 Hz).

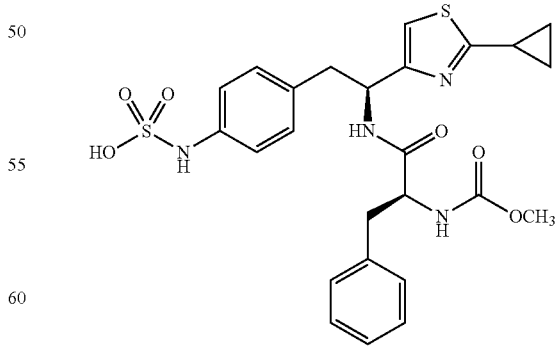

4-{(S)-2-(2-Cyclopropylthiazol-4-yl)-2-[(S)-2-(methoxycarbonylamino)-3-phenylpropanamido] ethyl}phenylsulfamic acid: $^1$H NMR (CD$_3$OD): δ 7.15-7.02 (m, 5H), 6.96-6.93 (d, 2H, J=8.4 Hz), 6.86-6.83 (d, 2H, J=8.3 Hz), 6.39 (s, 1H), 5.01 (t, 1H, J=5.0 Hz), 4.22 (t, 1H, J=7.4 Hz), 3.51 (s, 3H), 2.98-2.69 (m, 2H), 2.22-2.21 (m, 1H), 1.06-1.02 (m, 2H), 0.92-0.88 (m, 2H).

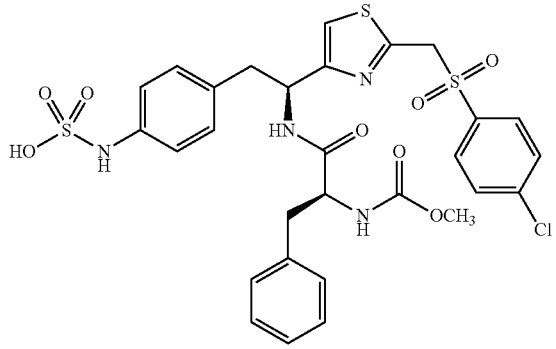 [SMILES: COC(=O)N[C@@H](Cc1ccccc1)C(=O)N[C@@H](Cc1ccc(NS(=O)(=O)O)cc1)c1csc(CS(=O)(=O)c2ccc(Cl)cc2)n1]

4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid: ¹H NMR (CD₃OD): δ 7.96-7.93 (d, 2H, J=8.6 Hz), 7.83-7.80 (d, 2H, J=8.6 Hz), 7.44-7.34 (m, 5H), 7.29-7.27 (d, 2H, J=8.4 Hz), 7.14-7.11 (d, 2H, J=8.4 Hz), 6.97 (s, 1H), 5.31 (t, 1H, J=6.8 Hz), 5.22-5.15 (m, 2H), 4.55 (t, 1H, J=7.3 Hz), 3.84 (s, 3H), 3.20-2.96 (m, 4H).

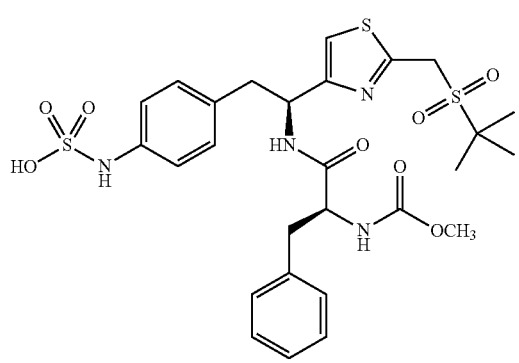 [SMILES: COC(=O)N[C@@H](Cc1ccccc1)C(=O)N[C@@H](Cc1ccc(NS(=O)(=O)O)cc1)c1csc(CS(=O)(=O)C(C)(C)C)n1]

4-{(S)-2-[2-(tert-Butylsulfonylmethyl)thiazol-4-yl]-2-[(S)-2-(methoxycarbonyl-amino)-3-phenylpropanamido]ethyl}phenylsulfamic acid: ¹H NMR (CD₃OD): δ 7.40-7.30 (m, 5H), 7.21-7.10 (m, 4H), 7.02 (s, 1H), 5.37 (t, 1H, J=6.9 Hz), 5.01-4.98 (m, 2H), 4.51 (t, 1H, J=7.1 Hz), 3.77 (s, 3H), 3.34-2.91 (m, 4H), 1.58 (s, 9H).

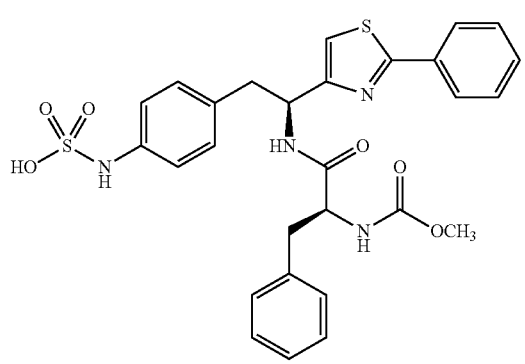 [SMILES: COC(=O)N[C@@H](Cc1ccccc1)C(=O)N[C@@H](Cc1ccc(NS(=O)(=O)O)cc1)c1csc(-c2ccccc2)n1]

4-{(S)-2-[(S)-2-(Methoxycarbonylamino)-3-phenylpropionamido]-2-(2-phenylthiazole-4-yl)ethyl}phenylsulfamic acid: ¹H NMR (300 MHz, DMSO-d₆) δ 7.96-7.99 (m, 2H), 7.51-7.56 (m, 3H), 7.13-7.38 (m, 6H), 6.92-6.95 (m, 4H), 5.11-5.16 (m, 1H), 4.32-4.35 (m, 1H), 3.51 (s, 3H), 3.39-3.40 (m, 2H), 3.09-3.19 (m, 1H), 2.92-3.02 (m, 2H), 2.75 (dd, J=10.5 Hz and 9.9 Hz, 1H).

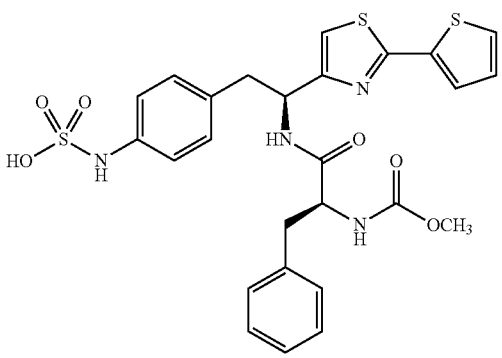 [SMILES: COC(=O)N[C@@H](Cc1ccccc1)C(=O)N[C@@H](Cc1ccc(NS(=O)(=O)O)cc1)c1csc(-c2cccs2)n1]

4-{(S)-2-[(S)-2-(Methoxycarbonylamino)-3-phenylpropanamido]-2-[2-(thiophen-2-yl)thiazol-4-yl]ethyl}phenylsulfamic acid: ¹H NMR (CD₃OD): δ 7.61-7.56 (m, 2H), 7.25-7.01 (m, 10H), 6.75 (s, 1H), 5.24-5.21 (q, 1H, J=7.2 Hz), 4.38 (t, 1H, J=7.2 Hz), 3.60 (s, 3H), 3.23-3.14 (m, 1H), 3.08-3.00 (m, 2H), 2.87-2.80 (m, 1H).

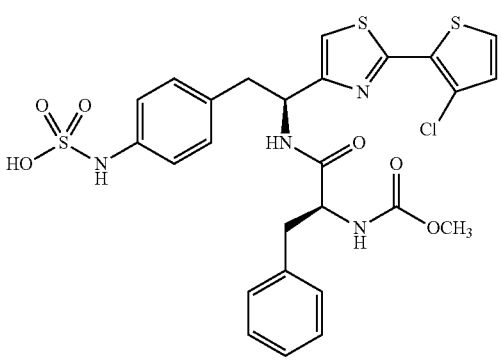 [SMILES: COC(=O)N[C@@H](Cc1ccccc1)C(=O)N[C@@H](Cc1ccc(NS(=O)(=O)O)cc1)c1csc(-c2sccc2Cl)n1]

4-{(S)-2-[2-(3-Chlorothiophen-2-yl)thiazol-4-yl]-2-[(S)-2-(methoxycarbonylamino)-3-phenylpropanamido]ethyl}phenylsulfamic acid: ¹H NMR (CD₃OD): δ 7.78-7.76 (d, 1H, J=5.4 Hz), 7.36-7.14 (m, 10H), 7.03 (s, 1H), 5.39 (t, 1H, J=6.9 Hz), 4.54 (t, 1H, J=7.3 Hz), 3.80 (s, 3H), 3.39-2.98 (m, 4H).

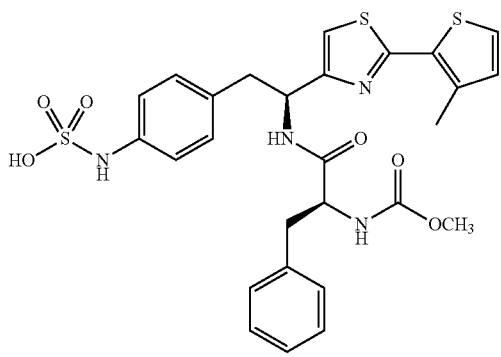 [SMILES: COC(=O)N[C@@H](Cc1ccccc1)C(=O)N[C@@H](Cc1ccc(NS(=O)(=O)O)cc1)c1csc(-c2sccc2C)n1]

4-{(S)-2-[(S)-2-(Methoxycarbonylamino)-3-phenylpropanamido]-2-[2-(3-methylthiophen-2-yl)thiazol-4-yl]ethyl}phenylsulfamic acid: $^1$H NMR (CD$_3$OD): δ 7.38 (d, 1H, J=5.1 Hz), 7.15-6.93 (m, 10H), 6.73 (s, 1H), 5.17 (t, 1H, J=6.9 Hz), 4.31 (t, 1H, J=7.3 Hz), 3.57 (s, 3H), 3.18-3.11 (m, 1H), 3.02-2.94 (m, 2H), 2.80-2.73 (m, 1H), 2.46 (s, 3H).

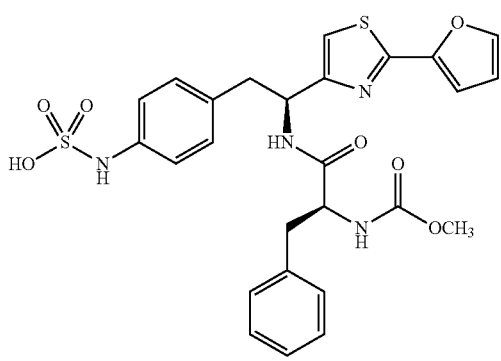 [SMILES: COC(=O)N[C@@H](Cc1ccccc1)C(=O)N[C@@H](Cc1ccc(NS(=O)(=O)O)cc1)c1csc(-c2ccco2)n1]

4-{[(S)-2-(2-(Furan-2-yl)thiazol-4-yl]-2-[(S)-2-(methoxycarbonylamino)-3-phenylpropanamido]ethyl}phenylsulfamic acid: $^1$H NMR (CD$_3$OD): δ 7.54-7.46 (m, 1H), 7.02-6.79 (m, 10H), 6.55-6.51 (m, 1H), 6.44-6.41 (m, 1H), 5.02-5.00 (q, 1H, J=6.4 Hz), 4.16-4.14 (q, 1H, J=7.1 Hz), 3.43 (s, 3H), 2.96-2.58 (m, 4H).

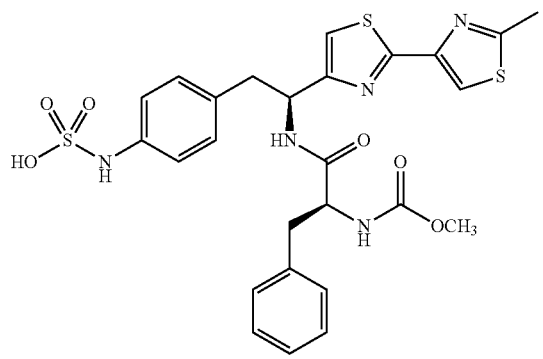 [SMILES: COC(=O)N[C@@H](Cc1ccccc1)C(=O)N[C@@H](Cc1ccc(NS(=O)(=O)O)cc1)c1csc(-c2csc(C)n2)n1]

4-{(S)-2-[(S)-2-(Methoxycarbonylamino)-3-phenylpropanamido]-2-[2-(2-methylthiazole-4-yl)thiazole-4-yl]ethyl}phenylsulfamic acid: $^1$H NMR (300 MHz, MeOH-d$_4$) δ 8.27 (d, J=5.4 Hz, 1H), 7.97 (s, 1H), 6.99-7.21 (m, 8H), 5.18-5.30 (m, 1H), 4.30-4.39 (m, 1H), 3.64 (s, 3H), 3.20 (dd, J=14.1 and 6.6 Hz, 1H), 2.98-3.08 (m, 2H), 2.84 (dd, J=14.1 and 6.6 Hz, 1H), 2.78 (s, 3H).

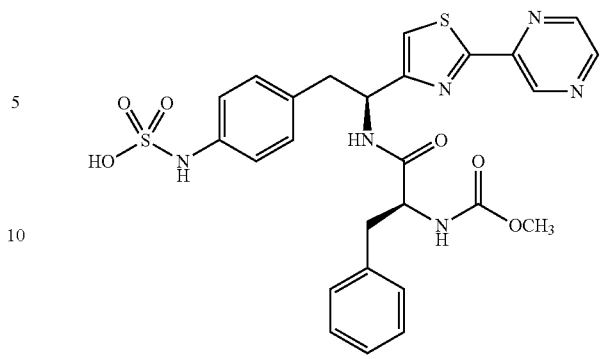

4-{(S)-2-[(S)-2-(Methoxycarbonylamino)-3-phenylpropanamido]-2-[(2-pyrazin-2-yl)thiazole-4-yl]ethyl}phenylsulfamic acid: $^1$H NMR (300 MHz, MeOH-d$_4$) δ 9.34 (s, 1H), 8.65 (s, 2H), 8.34 (d, J=8.1 Hz, 1H), 7.00-5.16 (m, 9H), 5.30 (q, J=7.2 Hz, 1H), 4.41 (t, J=7.2 Hz, 1H), 3.65 (s, 3H), 3.23 (dd, J=13.8 and 6.9 Hz, 1H), 2.98-3.13 (m, 2H), 2.85 (dd, J=13.8 and 6.9 Hz, 1H).

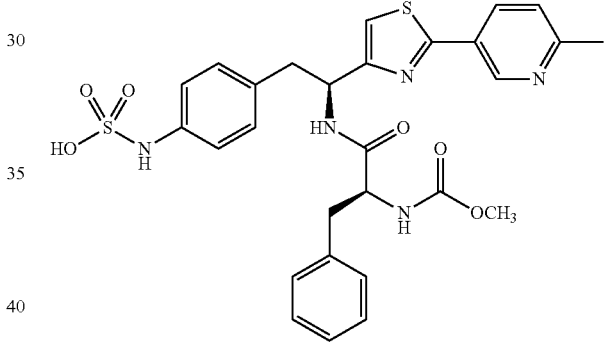

4-{(S)-2-[(S)-2-(Methoxycarbonylamino)-3-phenylpropanamido]-2-[2-(6-methylpyridin-3-yl)thiazol-4-yl]ethyl}phenylsulfamic acid: $^1$H NMR (CD$_3$OD): δ 8.90 (s, 1H), 8.19-8.13 (m, 1H), 7.39-7.36 (d, 1H, J=8.2 Hz), 7.07-6.88 (m, 9H), 6.79 (s, 1H), 5.17 (t, 1H, J=7.0 Hz), 4.29 (t, 1H, J=7.4 Hz), 3.54 (s, 3H), 3.10-2.73 (m, 4H), 2.53 (s, 3H).

Category III of the present disclosure relates to compounds wherein R is a substituted or unsubstituted thiazol-2-yl unit having the formula:

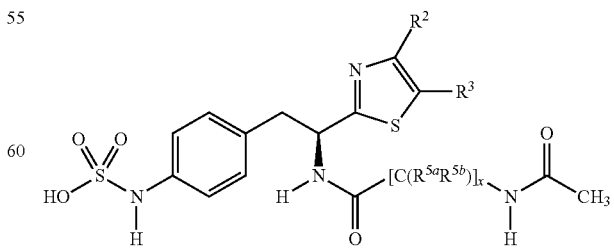

one embodiment of which relates to inhibitors having the formula:

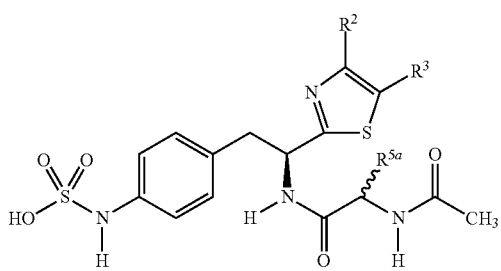

wherein R units are thiazol-2-yl units, that when substituted, are substituted with $R^2$ and $R^3$ units. R and $R^{5a}$ units are further described in Table V.

TABLE V

| No. | R | $R^{5a}$ |
|---|---|---|
| E101 | thiazol-2-yl | (S)-benzyl |
| E102 | 4-methylthiazol-2-yl | (S)-benzyl |
| E103 | 4-ethylthiazol-2-yl | (S)-benzyl |
| E104 | 4-propylthiazol-2-yl | (S)-benzyl |
| E105 | 4-iso-propylthiazol-2-yl | (S)-benzyl |
| E106 | 4-cyclopropylthiazol-2-yl | (S)-benzyl |
| E107 | 4-butylthiazol-2-yl | (S)-benzyl |
| E108 | 4-tert-butylthiazol-2-yl | (S)-benzyl |
| E109 | 4-cyclohexylthiazol-2-yl | (S)-benzyl |
| E110 | 4-(2,2,2-trifluoroethyl)thiazol-2-yl | (S)-benzyl |
| E111 | 4-(3,3,3-trifluoropropyl)thiazol-2-yl | (S)-benzyl |
| E112 | 4-(2,2-difluorocyclopropyl)thiazol-2-yl | (S)-benzyl |
| E113 | 4-(methoxymethyl)thiazol-2-yl | (S)-benzyl |
| E114 | 4-(carboxylic acid ethyl ester)thiazol-2-yl | (S)-benzyl |
| E115 | 4,5-dimethylthiazol-2-yl | (S)-benzyl |
| E116 | 4-methyl-5-ethylthiazol-2-yl | (S)-benzyl |
| E117 | 4-phenylthiazol-2-yl | (S)-benzyl |
| E118 | 4-(4-chlorophenyl)thiazol-2-yl | (S)-benzyl |
| E119 | 4-(3,4-dimethylphenyl)thiazol-2-yl | (S)-benzyl |
| E120 | 4-methyl-5-phenylthiazol-2-yl | (S)-benzyl |
| E121 | 4-(thiophen-2-yl)thiazol-2-yl | (S)-benzyl |
| E122 | 4-(thiophen-3-yl)thiazol-2-yl | (S)-benzyl |
| E123 | 4-(5-chlorothiophen-2-yl)thiazol-2-yl | (S)-benzyl |
| E124 | 5,6-dihydro-4H-cyclopenta[d]thiazol-2-yl | (S)-benzyl |
| E125 | 4,5,6,7-tetrahydrobenzo[d]thiazol-2-yl | (S)-benzyl |

The compounds encompassed within Category III of the present disclosure can be prepared by the procedure outlined in Scheme IV and described in Example 5 herein below.

Scheme IV

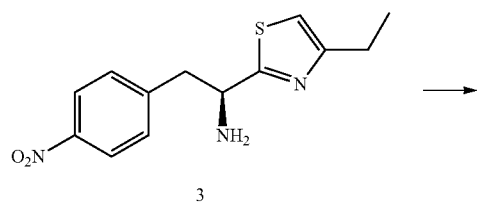

3

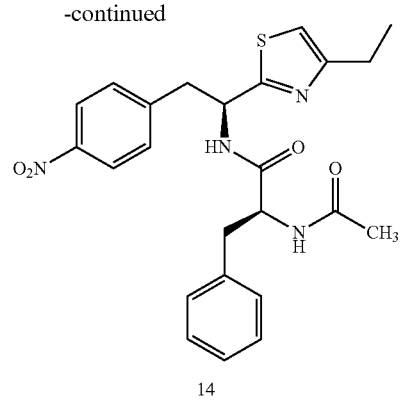

14

Reagents and Conditions: (a) Ac-Phe, EDCI, HOBt, DIPEA, DMF; Rt, 18 hr

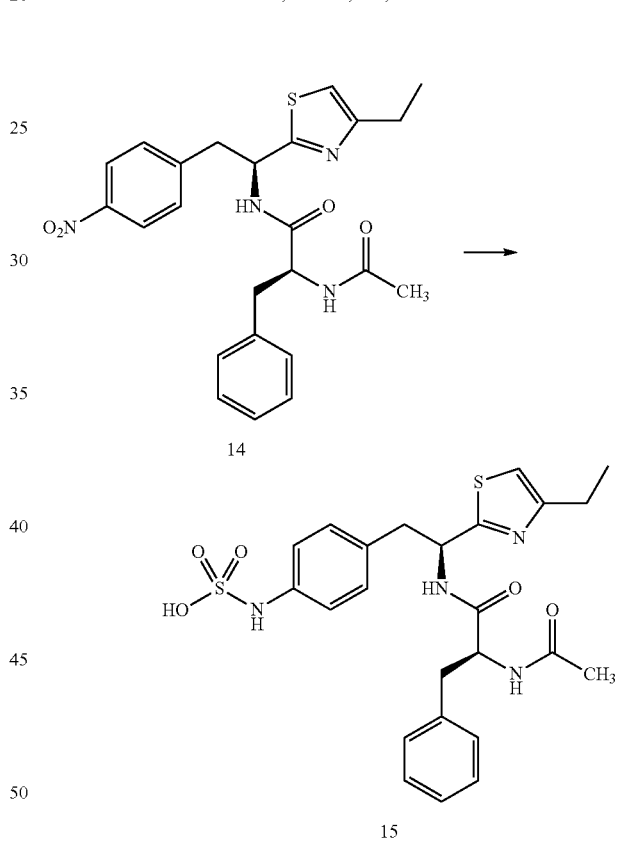

Reagents and Conditions: (b) (i) $H_2$:Pd/C, MeOH; (ii) $SO_3$-Pyridine, $NH_4OH$

EXAMPLE 5

4-[(S)-2-((S)-2-Acetamido-3-phenylpropanamido)-2-(4-ethylthiazol-2-yl)ethyl]phenylsulfamic Acid (15)

Preparation of (S)-2-acetamido-N—[(S)-1-(4-ethylthiazol-2-yl)-2-(4-nitrophenyl)-ethyl]-3-phenylpropanamide (14): To a solution of 1-(S)-(4-ethylthiazol-2-yl)-2-(4-nitrophenyl)ethyl amine hydrobromide, 3, (0.343 g, 0.957 mmol), N-acetyl-L-phenylalanine (0.218 g), 1-hydroxybenzotriazole (HOBt) (0.161 g), diisopropyl-ethylamine (0.26 g), in DMF (10 mL) at 0°, is added 1-(3-dimethylaminopropyl)-3-ethylcarbodiimide (EDCI) (0.201 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.313 g (70% yield) of the desired product which is used without further purification. LC/MS ESI+ 467 (M+1).

Preparation of 4-((S)-2-((S)-2-acetamido-3-phenylpropanamido)-2-(4-ethylthiazol-2-yl)ethyl)phenylsulfamic acid (15): (S)-2-Acetamido-N—[(S)-1-(4-ethylthiazol-2-yl)-2-(4-nitrophenyl)ethyl]-3-phenylpropanamide, 14, (0.313 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO$_3$-pyridine (0.320 g). The reaction is stirred at room temperature for 5 minutes after which a 7% solution of NH$_4$OH (30 mL) is added. The mixture is then concentrated and the resulting residue is purified by reverse phase chromatography to afford 0.215 g of the desired product as the ammonium salt. $^1$H NMR (CD$_3$OD): δ 7.23-6.98 (m, 10H), 5.37 (t, 1H), 4.64 (t, 1H, J=6.3 Hz), 3.26-2.74 (m, 6H), 1.91 (s, 3H), 1.29 (t, 3H, J=7.5 Hz).

The following are further non-limiting examples of compounds encompassed within Category III of the present disclosure.

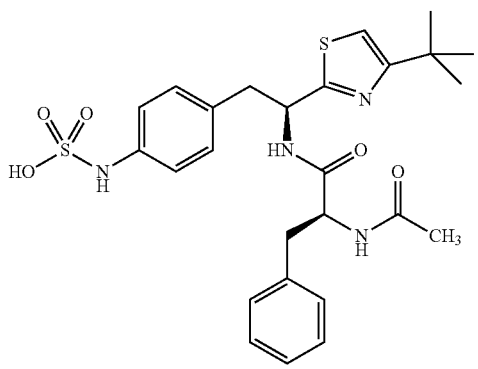 [SMILES: CC(=O)N[C@@H](Cc1ccccc1)C(=O)N[C@@H](Cc1ccc(NS(=O)(=O)O)cc1)c1nc(C(C)(C)C)cs1]

4-[(S)-2-((S)-2-Acetamido-3-phenylpropanamido)-2-(4-tert-butylthiazol-2-yl)ethyl]phenylsulfamic acid: $^1$H NMR (300 MHz, CD$_3$OD): δ 7.22-7.17 (m, 5H), 7.06 (dd, J=14.1, 8.4 Hz, 4H), 6.97 (d, J=0.9 Hz, 1H), 5.39 (dd, J=8.4, 6.0 Hz, 1H), 4.65 (t, J=7.2 Hz, 1H), 3.33-3.26 (m, 1H), 3.13-3.00 (m, 3H), 2.80 (dd, J=13.5, 8.7 Hz, 1H), 1.91 (s, 3H), 1.36 (s, 9H).

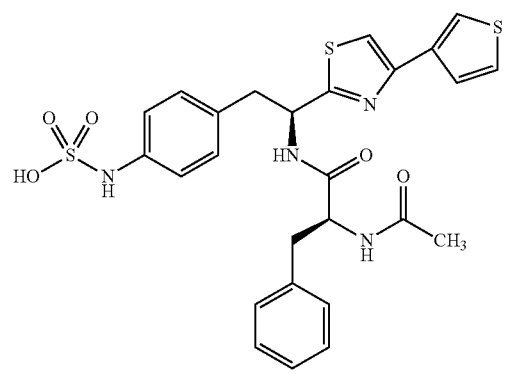 [SMILES: CC(=O)N[C@@H](Cc1ccccc1)C(=O)N[C@@H](Cc1ccc(NS(=O)(=O)O)cc1)c1nc(-c2ccsc2)cs1]

4-{(S)-2-((S)-2-Acetamido-3-phenylpropanamido)-2-[4-(thiophen-3-yl)thiazol-2-yl]ethyl)phenylsulfamic acid: $^1$H NMR (300 MHz, CD$_3$OD): δ 8.58 (d, J=8.1 Hz, 1H), 7.83-7.82 (m, 1H), 7.57-7.46 (m, 3H), 7.28-6.93 (m, 11H), 5.54-5.43 (m, 1H), 4.69-4.55 (m, 2H), 3.41-3.33 (m, 1H), 3.14-3.06 (3H), 2.86-2.79 (m, 1H), 1.93 (s, 3H).

The first aspect of Category IV of the present disclosure relates to compounds wherein R is a substituted or unsubstituted thiazol-2-yl unit having the formula:

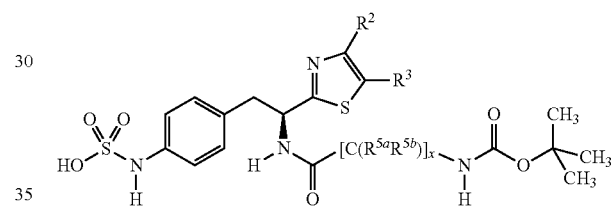

one embodiment of which relates to inhibitors having the formula:

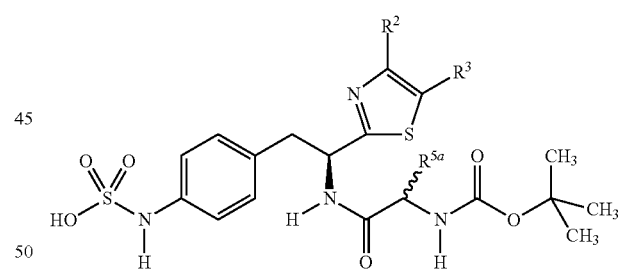

wherein R units and R$^{5a}$ units further described in Table VI.

TABLE VI

| No. | R | R$^{5a}$ |
|---|---|---|
| F126 | thiazol-2-yl | hydrogen |
| F127 | 4-methylthiazol-2-yl | hydrogen |
| F128 | 4-ethylthiazol-2-yl | hydrogen |
| F129 | 4-propylthiazol-2-yl | hydrogen |
| F130 | 4-iso-propylthiazol-2-yl | hydrogen |
| F131 | 4-cyclopropylthiazol-2-yl | hydrogen |
| F132 | 4-butylthiazol-2-yl | hydrogen |
| F133 | 4-tert-butylthiazol-2-yl | hydrogen |
| F134 | 4-cyclohexylthiazol-2-yl | hydrogen |
| F135 | 4,5-dimethylthiazol-2-yl | hydrogen |
| F136 | 4-methyl-5-ethylthiazol-2-yl | hydrogen |

TABLE VI-continued

| No. | R | R$^{5a}$ |
|---|---|---|
| F137 | 4-phenylthiazol-2-yl | hydrogen |
| F138 | thiazol-2-yl | (S)-iso-propyl |
| F139 | 4-methylthiazol-2-yl | (S)-iso-propyl |
| F140 | 4-ethylthiazol-2-yl | (S)-iso-propyl |
| F141 | 4-propylthiazol-2-yl | (S)-iso-propyl |
| F142 | 4-iso-propylthiazol-2-yl | (S)-iso-propyl |
| F143 | 4-cyclopropylthiazol-2-yl | (S)-iso-propyl |
| F144 | 4-butylthiazol-2-yl | (S)-iso-propyl |
| F145 | 4-tert-butylthiazol-2-yl | (S)-iso-propyl |
| F146 | 4-cyclohexylthiazol-2-yl | (S)-iso-propyl |
| F147 | 4,5-dimethylthiazol-2-yl | (S)-iso-propyl |
| F148 | 4-methyl-5-ethylthiazol-2-yl | (S)-iso-propyl |
| F149 | 4-phenylthiazol-2-yl | (S)-iso-propyl |
| F150 | 4-(thiophen-2-yl)thiazol-2-yl | (S)-iso-propyl |

The compounds encompassed within Category IV of the present disclosure can be prepared by the procedure outlined in Scheme V and described in Example 6 herein below.

Scheme V

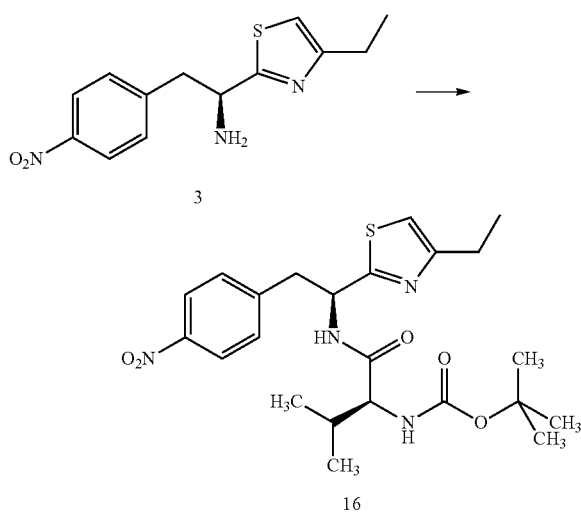

Reagents and Conditions: (a) Boc-Val; EDCI, HOBt, DIPEA, DMF; Rt, 18 hr

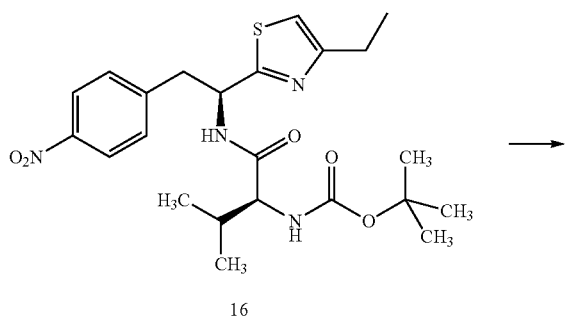

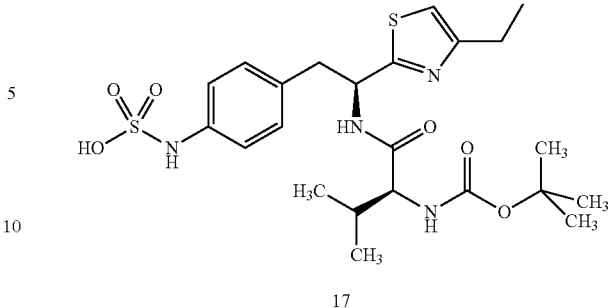

Reagents and Conditions: (b) (i) H$_2$:Pd/C, MeOH; (ii) SO$_3$-Pyridine, NH$_4$OH, Rt, 2 hr

EXAMPLE 6

4-{(S)-2-[(S)-2-(tert-Butoxycarbonylamino)-3-methylbutanamido]-2-(4-ethylthiazol-2-yl)ethyl}phenylsulfamic Acid (17)

Preparation of tert-butyl (S)-1-[(S)-(4-ethylthiazol-2-yl)-2-(4-nitrophenyl)ethylamino]-3-methyl-1-oxobutan-2-yl-carbamate (16): To a solution of 1-(S)-(4-ethylthiazol-2-yl)-2-(4-nitrophenyl)ethyl amine hydrobromide, 3, (0.200 g, 0.558 mmol), (S)-(2-tert-butoxycarbonylamino)-3-methyl-butyric acid (0.133 g) and 1-hydroxybenzo-triazole (HOBt) (0.094 g) in DMF (5 mL) at 0°, is added 1-(3-dimethylaminopropyl)-3-ethylcarbodiimide (EDCI) (0.118 g) followed by diisopropylamine (0.151 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.219 g (82% yield) of the desired product which is used without further purification. LC/MS ESI+ 477 (M+1).

Preparation of 4-{(S)-2-[(S)-2-(tert-butoxycarbonylamino)-3-methylbutanamido]-2-(4-ethylthiazol-2-yl)ethyl}phenylsulfamic acid (17): tert-Butyl (S)-1-[(S)-(4-ethylthiazol-2-yl)-2-(4-nitrophenyl)ethylamino]-3-methyl-1-oxobutan-2-ylcarbamate, 16, (0.219 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (5 mL) and treated with SO$_3$-pyridine (0.146 g). The reaction is stirred at room temperature for 5 minutes after which a 7% solution of NH$_4$OH (30 mL) is added. The mixture is then concentrated and the resulting residue is purified by reverse phase chromatography to afford 0.148 g of the desired product as the ammonium salt. $^1$H NMR (CD$_3$OD): δ 7.08 (s, 4H), 7.02 (s, 1H), 5.43 (s, 1H), 3.85 (s, 1H), 3.28-2.77 (m, 4H), 1.94 (s, 1H), 1.46 (s, 9H), 1.29 (s, 3H, J=7.3 Hz), 0.83 (s, 6H).

The following are further non-limiting examples of the second aspect of Category IV of the present disclosure.

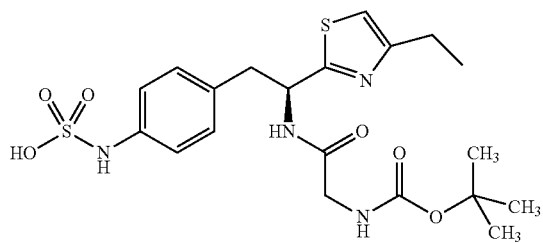 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonyl)acetamide]-2-(4-ethyl-thiazol-2-yl)ethyl}phenylsulfamic acid: ¹H NMR (CD₃OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

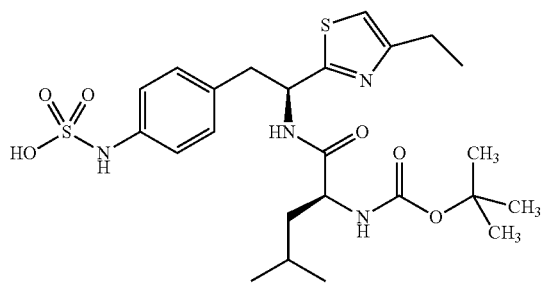 [SMILES: CCc1csc([C@H](Cc2ccc(NS(=O)(=O)O)cc2)NC(=O)[C@H](CC(C)C)NC(=O)OC(C)(C)C)n1]

4-{(S)-2-[(S)-2-(tert-Butoxycarbonylamino)-4-methyl-pentanamido]-2-(4-ethylthiazol-2-yl)ethyl}phenylsulfamic acid: ¹H NMR (CD₃OD) δ 7.19-7.00 (m, 4H), 5.50-5.40 (m, 1H), 4.13-4.06 (m, 1H), 3.32 (1H, A of ABX, J=7.5, 18 Hz), 3.12 (1H, B of ABX, J=8.1, 13.8 Hz), 2.79 (q, 2H, J=7.8, 14.7 Hz), 1.70-1.55 (m, 1H), 1.46 (s, 9H), 1.33 (t, 3H, J=2.7 Hz), 0.92 (q, 6H, J=6, 10.8 Hz).

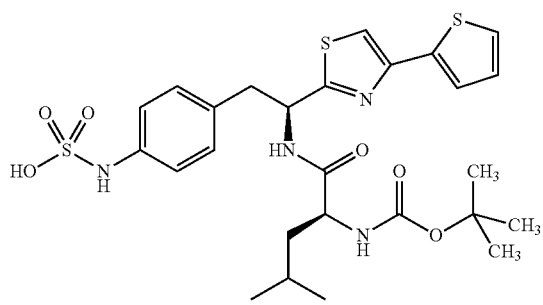 [SMILES: CC(C)C[C@H](NC(=O)OC(C)(C)C)C(=O)N[C@@H](Cc1ccc(NS(=O)(=O)O)cc1)c1nc(-c2cccs2)cs1]

4-{(S)-2-[(S)-2-(tert-Butoxycarbonylamino)-4-methyl-pentanamido]-2-[2-(thiophen-2-yl)thiazol-4-yl]ethyl}phenylsulfamic acid: ¹H NMR (CD3OD) δ 8.06 (d, 1H, J=8.4 Hz), 7.61-7.58 (m, 1H), 7.57 (s, 1H), 7.15 (t, 1H, J=0.6 Hz), 7.09-6.98 (m, 6H), 5.30-5.20 (m, 1H), 4.10-4.00 (m, 1H), 3.19-3.13 (m, 2H), 1.63-1.55 (m, 2H), 1.48-1.33 (m, 10H), 0.95-0.89 (m, 6H).

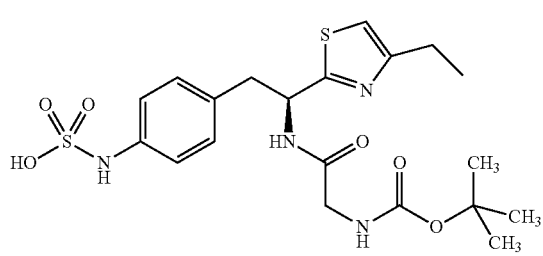 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonyl)acetamide]-2-(4-ethyl-thiazol-2-yl)ethyl}-phenylsulfamic acid: ¹H NMR (CD₃OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

A further embodiment of Category IV relates to inhibitors having the formula:

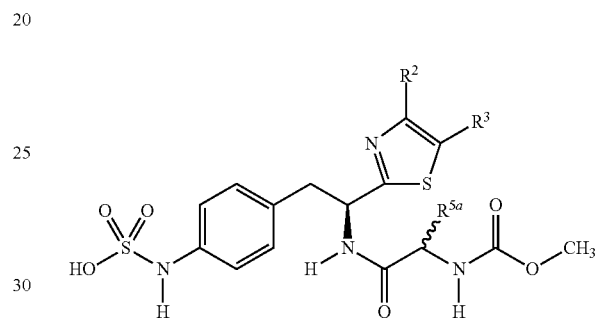

wherein R units and $R^{5a}$ units further described in Table VII.

TABLE VII

| No. | R | $R^{5a}$ |
|---|---|---|
| G151 | thiazol-2-yl | hydrogen |
| G152 | 4-methylthiazol-2-yl | hydrogen |
| G153 | 4-ethylthiazol-2-yl | hydrogen |
| G154 | 4-propylthiazol-2-yl | hydrogen |
| G155 | 4-iso-propylthiazol-2-yl | hydrogen |
| G156 | 4-cyclopropylthiazol-2-yl | hydrogen |
| G157 | 4-butylthiazol-2-yl | hydrogen |
| G158 | 4-tert-butylthiazol-2-yl | hydrogen |
| G159 | 4-cyclohexylthiazol-2-yl | hydrogen |
| G160 | 4,5-dimethylthiazol-2-yl | hydrogen |
| G161 | 4-methyl-5-ethylthiazol-2-yl | hydrogen |
| G162 | 4-phenylthiazol-2-yl | hydrogen |
| G163 | thiazol-2-yl | (S)-iso-propyl |
| G164 | 4-methylthiazol-2-yl | (S)-iso-propyl |
| G165 | 4-ethylthiazol-2-yl | (S)-iso-propyl |
| G166 | 4-propylthiazol-2-yl | (S)-iso-propyl |
| G167 | 4-iso-propylthiazol-2-yl | (S)-iso-propyl |
| G168 | 4-cyclopropylthiazol-2-yl | (S)-iso-propyl |
| G169 | 4-butylthiazol-2-yl | (S)-iso-propyl |
| G170 | 4-tert-butylthiazol-2-yl | (S)-iso-propyl |
| G171 | 4-cyclohexylthiazol-2-yl | (S)-iso-propyl |
| G172 | 4,5-dimethylthiazol-2-yl | (S)-iso-propyl |
| G173 | 4-methyl-5-ethylthiazol-2-yl | (S)-iso-propyl |
| G174 | 4-phenylthiazol-2-yl | (S)-iso-propyl |
| G175 | 4-(thiophen-2-yl)thiazol-2-yl | (S)-iso-propyl |

The compounds encompassed within this embodiment of Category IV can be made according to the procedure outlined in Scheme V and described in Example 6 by substituting the corresponding methylcarbamate for the Boc-protected reagent. The following are non-limiting examples of this embodiment.

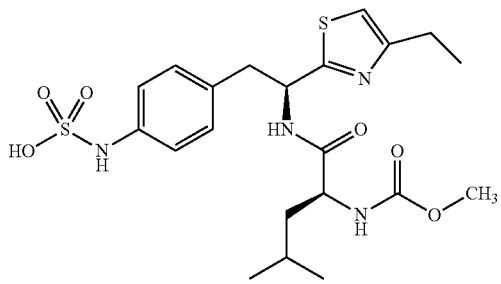 [SMILES: CCc1csc([C@H](Cc2ccc(NS(=O)(=O)O)cc2)NC(=O)[C@H](CC(C)C)NC(=O)OC)n1]

4-{(S)-2-(4-Ethylthiazol-2-yl)-2-[(S)-2-(methoxycarbonyl)-4-methylpentan-amido]ethyl}phenylsulfamic acid: $^1$H NMR (CD3OD) δ 7.12-7.03 (m, 5H), 6.84 (d, 1H, J=8.4 Hz), 5.40 (t, 1H, J=5.7 Hz), 4.16 (t, 1H, J=6.3 Hz), 3.69 (s, 3H), 3.61-3.55 (m, 1H), 3.29-3.27 (m, 1H), 3.14-3.07 (m, 1H), 2.81 (q, 2H, J=3.9, 11.2 Hz), 1.66-1.59 (m, 1H), 1.48-1.43 (m, 2H), 1.31 (t, 3H, J=4.5 Hz), 0.96-0.90 (m, 6H).

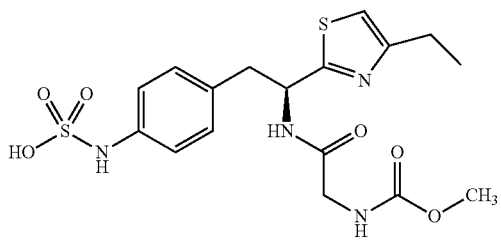 [SMILES: CCc1csc([C@H](Cc2ccc(NS(=O)(=O)O)cc2)NC(=O)CNC(=O)OC)n1]

(S)-4-{2-(4-Ethylthiazol-2-yl)-2-[2-(methoxycarbonyl)acetamido]ethyl}-phenylsulfamic acid: $^1$H NMR (CD$_3$OD): δ 7.12-7.07 (m, 4H), 7.03 (s, 1H), 5.42 (t, 1H, J=5.7 Hz), 3.83-3.68 (q, 2H, J=11.4 Hz), 3.68 (s, 3H), 3.34-3.04 (m, 2H), 2.83-2.76 (q, 2H, J=7.8 Hz), 1.31 (t, 3H, J=7.5 Hz).

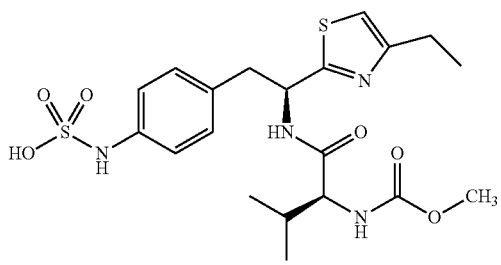 [SMILES: CCc1csc([C@H](Cc2ccc(NS(=O)(=O)O)cc2)NC(=O)[C@@H](NC(=O)OC)C(C)C)n1]

4-{(S)-2-(4-Ethylthiazol-2-yl)-2-[(S)-2-(methoxycarbonyl)-3-methylbutanamido]-ethyl}phenylsulfamic acid: $^1$H NMR (CD$_3$OD) δ 8.56 (d, 1H, J=7.8 Hz), 7.09 (s, 4H), 7.03 (s, 1H), 5.26-5.20 (m, 1H), 3.90 (d, 1H, J=7.8 Hz), 3.70 (s, 3H), 3.30 (1H, A of ABX, obscured by solvent), 3.08 (1H, B of ABX, J=9.9, 9 Hz), 2.79 (q, 2H, J=11.1, 7.2 Hz), 2.05-1.97 (m, 1H), 1.31 (t, 3H, J=7.5 Hz), 0.88 (s, 3H), 0.85 (s, 3H), 0.79-0.75 (m, 1H).

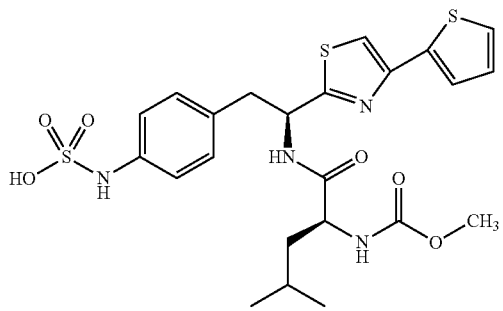 [SMILES: COC(=O)N[C@@H](CC(C)C)C(=O)N[C@@H](Cc1ccc(NS(=O)(=O)O)cc1)c1nc(-c2cccs2)cs1]

4-{(S)-2-[(S)-2-(Methoxycarbonyl)-4-methylpentanamido]-2-[2-(thiophen-2-yl)thiazol-4-yl]ethyl}phenylsulfamic acid: $^1$H NMR (CD$_3$OD) δ 8.22 (d, 1H, J=9 Hz), 7.62-7.57 (m, H), 7.15 (t, 1H, J=0.6 Hz), 7.10-6.97 (m, 4H), 5.30-5.20 (m, 1H), 4.16-4.11 (m, 1H), 3.67 (s, 2H), 3.22 (1H, A of ABX, J=6.9, 13.5 Hz), 3.11 (1H, B of ABX, J=7.8, 13.6 Hz), 1.65-1.58 (m, 1H), 1.50-1.45 (m, 2H), 0.95-0.88 (m, 6H).

Category IV of the present disclosure relates to compounds having the formula:

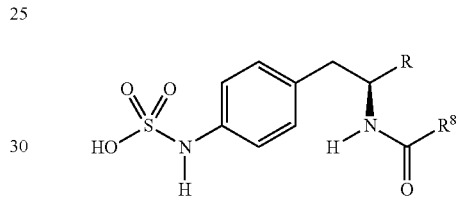

wherein R is a substituted or unsubstituted thiophen-2-yl or thiophen-4-yl unit and non-limiting examples of $R^2$ are further described in Table VIII.

TABLE VIII

| No. | R | $R^8$ |
|---|---|---|
| H176 | thiazol-2-yl | —OC(CH$_3$)$_3$ |
| H177 | 4-methylthiazol-2-yl | —OC(CH$_3$)$_3$ |
| H178 | 4-ethylthiazol-2-yl | —OC(CH$_3$)$_3$ |
| H179 | 4-cyclopropylthiazol-2-yl | —OC(CH$_3$)$_3$ |
| H180 | 4-tert-butylthiazol-2-yl | —OC(CH$_3$)$_3$ |
| H181 | 4-cyclohexylthiazol-2-yl | —OC(CH$_3$)$_3$ |
| H182 | 4-(2,2,2-trifluoroethyl)thiazol-2-yl | —OC(CH$_3$)$_3$ |
| H183 | 4-(3,3,3-trifluoropropyl)thiazol-2-yl | —OC(CH$_3$)$_3$ |
| H184 | 4-(2,2-difluorocyclopropyl)thiazol-2-yl | —OC(CH$_3$)$_3$ |
| H185 | 4,5-dimethylthiazol-2-yl | —OC(CH$_3$)$_3$ |
| H186 | 4-methyl-5-ethylthiazol-2-yl | —OC(CH$_3$)$_3$ |
| H187 | 4-phenylthiazol-2-yl | —OC(CH$_3$)$_3$ |
| H188 | 4-(4-chlorophenyl)thiazol-2-yl | —OC(CH$_3$)$_3$ |
| H189 | 4-(3,4-dimethylphenyl)thiazol-2-yl | —OC(CH$_3$)$_3$ |
| H190 | 4-methyl-5-phenylthiazol-2-yl | —OC(CH$_3$)$_3$ |
| H191 | 4-(thiophen-2-yl)thiazol-2-yl | —OC(CH$_3$)$_3$ |
| H192 | thiazol-4-yl | —OC(CH$_3$)$_3$ |
| H193 | 4-methylthiazol-4-yl | —OC(CH$_3$)$_3$ |
| H194 | 4-ethylthiazol-4-yl | —OC(CH$_3$)$_3$ |
| H195 | 4-cyclopropylthiazol-4-yl | —OC(CH$_3$)$_3$ |
| H196 | 4-tert-butylthiazol-4-yl | —OC(CH$_3$)$_3$ |
| H197 | 4-cyclohexylthiazol-4-yl | —OC(CH$_3$)$_3$ |
| H198 | 4-(2,2,2-trifluoroethyl)thiazol-4-yl | —OC(CH$_3$)$_3$ |
| H199 | 4-(3,3,3-trifluoropropyl)thiazol-4-yl | —OC(CH$_3$)$_3$ |
| H200 | 4-(2,2-difluorocyclopropyl)thiazol-4-yl | —OC(CH$_3$)$_3$ |
| H201 | 4,5-dimethylthiazol-4-yl | —OC(CH$_3$)$_3$ |
| H202 | 4-methyl-5-ethylthiazol-4-yl | —OC(CH$_3$)$_3$ |
| H203 | 4-phenylthiazol-4-yl | —OC(CH$_3$)$_3$ |
| H204 | 4-(4-chlorophenyl)thiazol-4-yl | —OC(CH$_3$)$_3$ |
| H205 | 4-(3,4-dimethylphenyl)thiazol-4-yl | —OC(CH$_3$)$_3$ |
| H206 | 4-methyl-5-phenylthiazol-4-yl | —OC(CH$_3$)$_3$ |
| H207 | 4-(thiophen-2-yl)thiazol-4-yl | —OC(CH$_3$)$_3$ |

TABLE VIII-continued

| No. | R | R⁸ |
|---|---|---|
| H208 | thiazol-2-yl | —OCH₃ |
| H209 | 4-methylthiazol-2-yl | —OCH₃ |
| H210 | 4-ethylthiazol-2-yl | —OCH₃ |
| H211 | 4-cyclopropylthiazol-2-yl | —OCH₃ |
| H212 | 4-tert-butylthiazol-2-yl | —OCH₃ |
| H213 | 4-cyclohexylthiazol-2-yl | —OCH₃ |
| H214 | 4-(2,2,2-trifluoroethyl)thiazol-2-yl | —OCH₃ |
| H215 | 4-(3,3,3-trifluoropropyl)thiazol-2-yl | —OCH₃ |
| H216 | 4-(2,2-difluorocyclopropyl)thiazol-2-yl | —OCH₃ |
| H217 | 4,5-dimethylthiazol-2-yl | —OCH₃ |
| H218 | 4-methyl-5-ethylthiazol-2-yl | —OCH₃ |
| H219 | 4-phenylthiazol-2-yl | —OCH₃ |
| H220 | 4-(4-chlorophenyl)thiazol-2-yl | —OCH₃ |
| H221 | 4-(3,4-dimethylphenyl)thiazol-2-yl | —OCH₃ |
| H222 | 4-methyl-5-phenylthiazol-2-yl | —OCH₃ |
| H223 | 4-(thiophen-2-yl)thiazol-2-yl | —OCH₃ |
| H224 | thiazol-4-yl | —OCH₃ |
| H225 | 4-methylthiazol-4-yl | —OCH₃ |
| H226 | 4-ethylthiazol-4-yl | —OCH₃ |
| H227 | 4-cyclopropylthiazol-4-yl | —OCH₃ |
| H228 | 4-tert-butylthiazol-4-yl | —OCH₃ |
| H229 | 4-cyclohexylthiazol-4-yl | —OCH₃ |
| H230 | 4-(2,2,2-trifluoroethyl)thiazol-4-yl | —OCH₃ |
| H231 | 4-(3,3,3-trifluoropropyl)thiazol-4-yl | —OCH₃ |
| H232 | 4-(2,2-difluorocyclopropyl)thiazol-4-yl | —OCH₃ |
| H233 | 4,5-dimethylthiazol-4-yl | —OCH₃ |
| H234 | 4-methyl-5-ethylthiazol-4-yl | —OCH₃ |
| H235 | 4-phenylthiazol-4-yl | —OCH₃ |
| H236 | 4-(4-chlorophenyl)thiazol-4-yl | —OCH₃ |
| H237 | 4-(3,4-dimethylphenyl)thiazol-4-yl | —OCH₃ |
| H238 | 4-methyl-5-phenylthiazol-4-yl | —OCH₃ |
| H239 | 4-(thiophen-2-yl)thiazol-4-yl | —OCH₃ |
| H240 | thiazol-2-yl | —CH₃ |
| H241 | 4-methylthiazol-2-yl | —CH₃ |
| H242 | 4-ethylthiazol-2-yl | —CH₃ |
| H243 | 4-cyclopropylthiazol-2-yl | —CH₃ |
| H244 | 4-tert-butylthiazol-2-yl | —CH₃ |
| H245 | 4-cyclohexylthiazol-2-yl | —CH₃ |
| H246 | 4-(2,2,2-trifluoroethyl)thiazol-2-yl | —CH₃ |
| H247 | 4-(3,3,3-trifluoropropyl)thiazol-2-yl | —CH₃ |
| H248 | 4-(2,2-difluorocyclopropyl)thiazol-2-yl | —CH₃ |
| H249 | 4,5-dimethylthiazol-2-yl | —CH₃ |
| H250 | 4-methyl-5-ethylthiazol-2-yl | —CH₃ |
| H251 | 4-phenylthiazol-2-yl | —CH₃ |
| H252 | 4-(4-chlorophenyl)thiazol-2-yl | —CH₃ |
| H253 | 4-(3,4-dimethylphenyl)thiazol-2-yl | —CH₃ |
| H254 | 4-methyl-5-phenylthiazol-2-yl | —CH₃ |
| H255 | 4-(thiophen-2-yl)thiazol-2-yl | —CH₃ |
| H256 | thiazol-4-yl | —CH₃ |
| H257 | 4-methylthiazol-4-yl | —CH₃ |
| H258 | 4-ethylthiazol-4-yl | —CH₃ |
| H259 | 4-cyclopropylthiazol-4-yl | —CH₃ |
| H260 | 4-tert-butylthiazol-4-yl | —CH₃ |
| H261 | 4-cyclohexylthiazol-4-yl | —CH₃ |
| H262 | 4-(2,2,2-trifluoroethyl)thiazol-4-yl | —CH₃ |
| H263 | 4-(3,3,3-trifluoropropyl)thiazol-4-yl | —CH₃ |
| H264 | 4-(2,2-difluorocyclopropyl)thiazol-4-yl | —CH₃ |
| H265 | 4,5-dimethylthiazol-4-yl | —CH₃ |
| H266 | 4-methyl-5-ethylthiazol-4-yl | —CH₃ |
| H267 | 4-phenylthiazol-4-yl | —CH₃ |
| H268 | 4-(4-chlorophenyl)thiazol-4-yl | —CH₃ |
| H269 | 4-(3,4-dimethylphenyl)thiazol-4-yl | —CH₃ |
| H270 | 4-methyl-5-phenylthiazol-4-yl | —CH₃ |
| H271 | 4-(thiophen-2-yl)thiazol-4-yl | —CH₃ |

The compounds encompassed within Category IV of the present disclosure can be prepared by the procedure outlined in VI and described in Example 7 herein below.

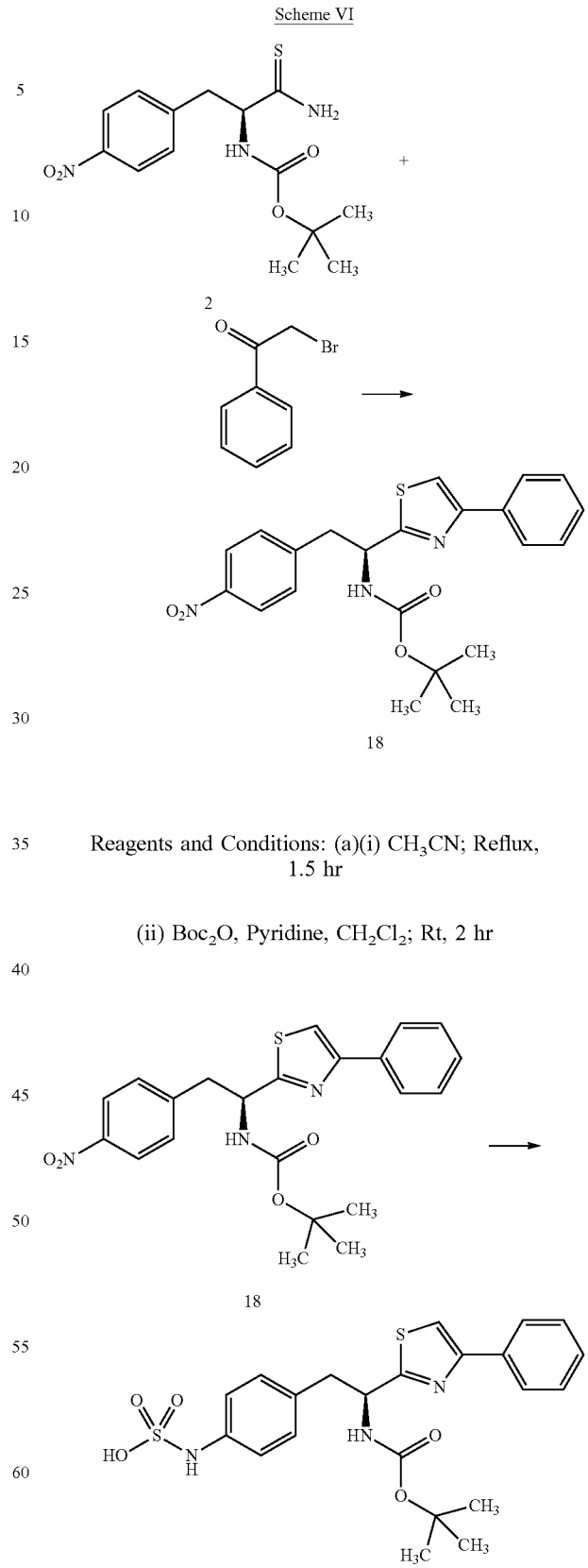

Scheme VI

Reagents and Conditions: (a)(i) CH₃CN; Reflux, 1.5 hr (ii) Boc₂O, Pyridine, CH₂Cl₂; Rt, 2 hr Reagents and Conditions: (b)(i) H₂:Pd/C, MeOH; Reflux (ii) SO₃-pyridine, NH₄OH; rt, 12 hr

EXAMPLE 7

[1-(S)-(Phenylthiazol-2-yl)-2-(4-sulfoaminophenyp-ethyl]-carbamic Acid tert-butyl Ester (19)

Preparation of [2-(4-nitrophenyl)-1-(S)-(4-phenylthiazol-2-yl)ethyl]-carbamic acid tert-butyl ester (18): A mixture of [2-(4-nitrophenyl)-1-(S)-thiocarbamoylethyl]-carbamic acid tert-butyl ester, 2, (0.343 g, 1.05 mmol), 2-bromoacetophenone (0.231 g, 1.15 mmol), in CH₃CN (5 mL) is refluxed 1.5 hour. The solvent is removed under reduced pressure and the residue re-dissolved in CH₂Cl₂ then pyridine (0.24 mL, 3.0 mmol) and Boc₂O (0.24 mL, 1.1 mmol) are added. The reaction is stirred for 2 hours and diethyl ether is added to the solution and the precipitate which forms is removed by filtration. The organic layer is dried (Na₂SO₄), filtered, and concentrated to a residue which is purified over silica to afford 0.176 g (39%) of the desired product ESI+ MS 426 (M+1).

Preparation of [1-(S)-(phenylthiazol-2-yl)-2-(4-sulfoaminophenyl)ethyl]-carbamic acid tert-butyl ester (19): [2-(4-nitrophenyl)-1-(S)-(4-phenylthiazol-2-yl)ethyl]-carbamic acid tert-butyl ester, 18, (0.176 g, 0.41 mmol) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO₃-pyridine (0.195 g, 1.23 mmol). The reaction is stirred at room temperature for 5 minutes after which a 7% solution of NH₄OH (10 mL) is added. The mixture is then concentrated and the resulting residue is purified by reverse phase chromatography to afford 0.080 g of the desired product as the ammonium salt. ¹H NMR (300 MHz, MeOH-d₄) δ 7.93 (d, J=6.0 Hz, 2H), 7.68 (s, 1H), 7.46-7.42 (m, 3H), 7.37-7.32 (m, 1H), 7.14-7.18 (m, 3H), 5.13-5.18 (m, 1H), 3.40 (dd, J=4.5 and 15.0 Hz, 1H), 3.04 (dd, J=9.6 and 14.1 Hz, 1H), 1.43 (s, 9H).

The following are further non-limiting examples of Category IV of the present disclosure.

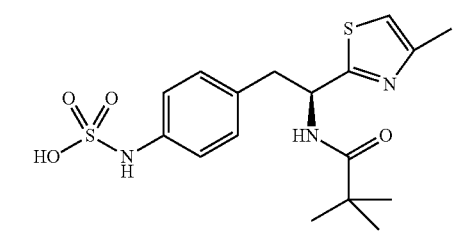 [SMILES: Cc1csc([C@H](Cc2ccc(NS(=O)(=O)O)cc2)NC(=O)C(C)(C)C)n1]

(S)-4-(2-(4-Methylthiazol-2-yl)-2-pivalamidoethyl)phenylsulfamic acid: ¹H NMR(CD₃OD): δ 7.31 (s, 4H), 7.20 (s, 1H), 5.61-5.56 (m, 1H), 3.57-3.22 (m, 2H), 2.62 (s, 3H), 1.31 (s, 3H).

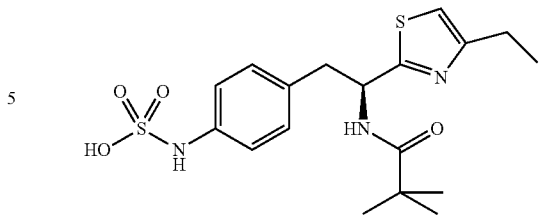

(S)-4-(2-(4-Ethylthiazol-2-yl)-2-pivalamidoethyl)phenylsulfamic acid: ¹H NMR (300 MHz, MeOH-d₄) δ 7.92 (d, J=8.1 Hz, 1H), 7.12-7.14 (m, 4H), 7.03 (s, 1H), 5.38-5.46 (m, 1H), 3.3-3.4 (m, 1H), 3.08 (dd, J=10.2 and 13.8 Hz, 1H), 2.79 (q, J=7.2 Hz, 2H), 1.30 (t, J=7.2 Hz, 3H), 1.13 (s, 9H).

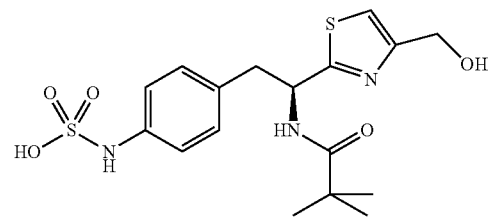 [SMILES: CC(C)(C)C(=O)N[C@@H](Cc1ccc(NS(=O)(=O)O)cc1)c1nc(CO)cs1]

(S)-4-(2-(4-(Hydroxymethyl)thiazol-2-yl)-2-pivalamidoethyl)phenylsulfamic acid: ¹H NMR (300 MHz, MeOH-d₄) δ 7.92 (d, J=8.1 Hz, 1H), 7.24 (s, 1H), 7.08 (d, J=8.7 Hz, 2H), 7.00 (d, J=8.7 Hz, 2H), 5.29-5.37 (m, 1H), 4.55 (s, 2H), 3.30 (dd, J=4.8 and 13.5 Hz, 1H), 2.99 (dd, J=10.5 and 13.5 Hz, 1H), 0.93 (s, 9H).

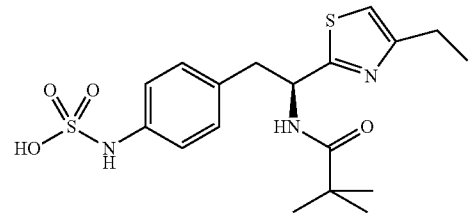 [SMILES: CCc1csc([C@H](Cc2ccc(NS(=O)(=O)O)cc2)NC(=O)C(C)(C)C)n1]

(S)-4-(2-(4-(Ethoxycarbonyl)thiazol-2-yl)-2-pivalamidoethyl)phenylsulfamic acid: ¹H NMR (300 MHz, MeOH-d₄) δ 8.30 (s, 1H), 8.04 (d, J=8.1 Hz, 1H), 7.13 (s, 4H), 5.41-5.49 (m, 1H), 4.41 (q, J=7.2 Hz, 2H), 3.43 (dd, J=5.1 and 13.8 Hz, 1H), 3.14 (dd, J=5.7 and 9.9 Hz, 1H), 1.42 (t, J=7.2 Hz, 3H), 1.14 (s, 9H).

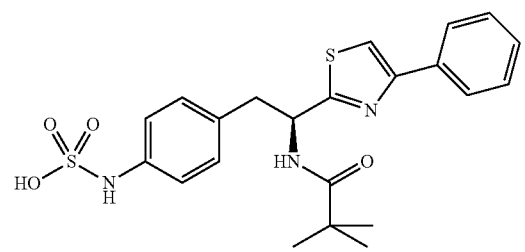 [SMILES: CC(C)(C)C(=O)N[C@@H](Cc1ccc(NS(=O)(=O)O)cc1)c1nc(-c2ccccc2)cs1]

(S)-4-(2-(4-Phenylthiazol-2-yl)-2-pivalamidoethyl)phenylsulfamic acid: ¹H NMR (300 MHz, MeOH-d₄) δ 7.94-8.01 (m, 3H), 7.70 (s, 1H), 7.42-7.47 (m, 2H), 7.32-7.47 (m, 1H), 7.13-7.20 (m, 3H), 5.48-5.55 (m, 1H), 3.50 (dd, J=5.1 and 14.1 Hz, 1H), 3.18 (dd, J=10.2 and 14.1 Hz, 1H), 1.17 (s, 9H).

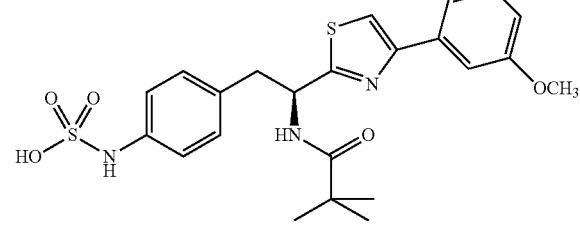

4-((S)-2-(4-(3-Methoxyphenyl)thiazol-2-yl)-2-pivalamidoethyl)phenylsulfamic acid: $^1$H NMR (CD$_3$OD): δ 7.96-7.93 (d, 1H, J=8.1 Hz), 7.69 (s, 1H), 7.51-7.49 (d, 2H, J=7.9 Hz), 7.33 (t, 1H, J=8.0 Hz), 7.14 (s, 4H), 6.92-6.90 (d, 1H, J=7.8 Hz), 5.50 (t, 1H, J=5.1 Hz), 3.87 (s, 3H), 3.50-3.13 (m, 2H), 1.15 (s, 9H).

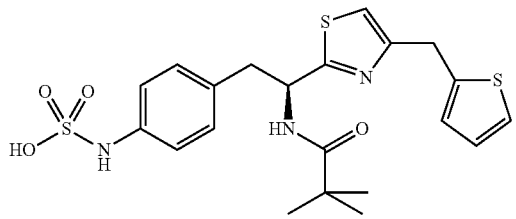 [SMILES: CC(C)(C)C(=O)N[C@@H](Cc1ccc(NS(=O)(=O)O)cc1)c1nc(Cc2cccs2)cs1]

4-((S)-2-(4-(2,4-Dimethoxyphenyl)thiazol-2-yl)-2-pivalamidoethyl)phenylsulfamic acid: $^1$H NMR (CD$_3$OD): δ 8.11-8.09 (d, 1H, J=7.8 Hz), 7.96-7.93 (d, 1H, J=8.4 Hz), 7.74 (s, 1H), 7.18-7.16 (m, 4H), 6.67-6.64 (d, 2H, J=9.0 Hz), 5.55-5.47 (m, 1H), 3.95 (s, 3H), 3.87 (s, 3H), 3.52-3.13 (m, 2H), 1.17 (s, 9H).

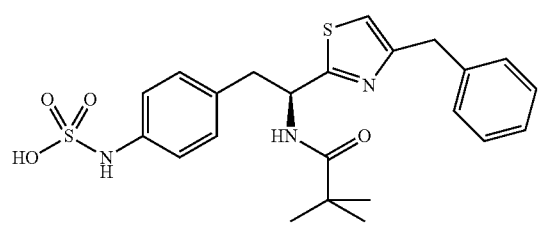 [SMILES: CC(C)(C)C(=O)N[C@@H](Cc1ccc(NS(=O)(=O)O)cc1)c1nc(Cc2ccccc2)cs1]

(S)-4-(2-(4-Benzylthiazol-2-yl)-2-pivalamidoethyl)phenylsulfamic acid: $^1$H NMR (CD$_3$OD) δ 7.85 (d, 1H, J=8.4 Hz), 7.38-7.20 (m, 4H), 7.11-7.02 (m, 1H), 7.00 (s, 1H), 5.42-5.37 (m, 1H), 4.13 (s, 2H), 3.13-3.08 (m, 2H), 1.13 (s, 9H).

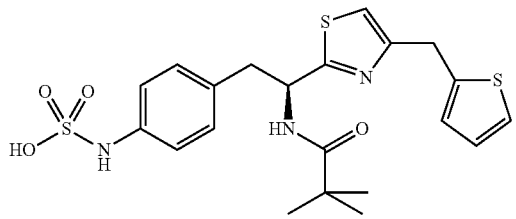 [SMILES: CC(C)(C)C(=O)N[C@@H](Cc1ccc(NS(=O)(=O)O)cc1)c1nc(Cc2cccs2)cs1]

(S)-4-(2-Pivalamido-2-(4-(thiophen-2-ylmethyl)thiazol-2-yl)ethyl)phenylsulfamic acid: $^1$H NMR (CD$_3$OD) δ 7.88-7.85 (d, 1H), 7.38-7.35 (m, 1H), 7.10-7.01 (m, 4H), 7.02 (s, 1H), 5.45-5.38 (m, 1H), 4.13 (s, 2H), 3.13-3.05 (m, 2H), 1.13 (2, 9H).

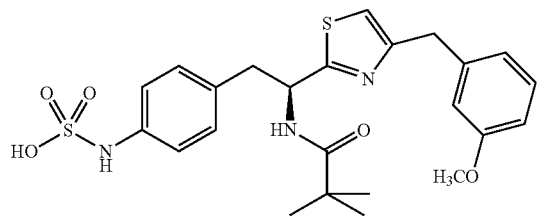 [SMILES: COc1cccc(Cc2csc([C@H](Cc3ccc(NS(=O)(=O)O)cc3)NC(=O)C(C)(C)C)n2)c1]

(S)-4-(2-(4-(3-Methoxybenzyl)thiazol-2-yl)-2-pivalamidoethyl)phenylsulfamic acid: $^1$H NMR (CD$_3$OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

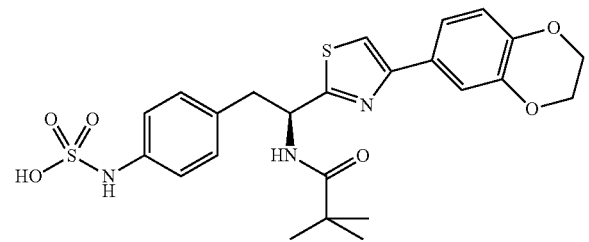 [SMILES: CC(C)(C)C(=O)N[C@@H](Cc1ccc(NS(=O)(=O)O)cc1)c1nc(-c2ccc3c(c2)OCCO3)cs1]

4-((S)-2-(4-(2,3-Dihydrobenzo[b][1,4]dioxin-6-yl)thiazol-2-yl)-2-pivalamidoethyl)-phenylsulfamic acid: $^1$H NMR (CD$_3$OD): δ 7.53 (s, 1H), 7.45 (s, 1H), 7.42-7.40 (d, 1H, J=8.4 Hz), 7.19-7.15 (m, 4H), 6.91-6.88 (d, 2H, J=8.4 Hz), 5.51-5.46 (m, 1H), 4.30 (s, 4H), 3.51-3.12 (m, 2H), 1.16 (s, 9H).

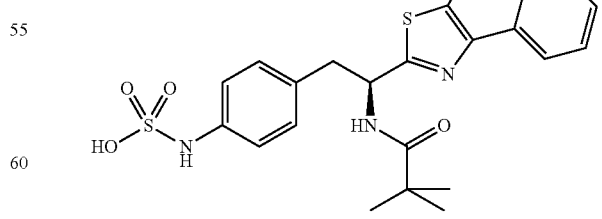

(S)-4-(2-(5-Methyl-4-phenylthiazol-2-yl)-2-pivalamidoethyl)phenylsulfamic acid: $^1$H NMR (CD$_3$OD): δ 7.63-7.60 (d, 2H, J=7.1 Hz), 7.49-7.35 (m, 3H), 7.14 (s, 4H), 5.43-5.38 (m, 1H), 3.42-3.09 (m, 2H), 2.49 (s, 3H), 1.14 (s, 9H).

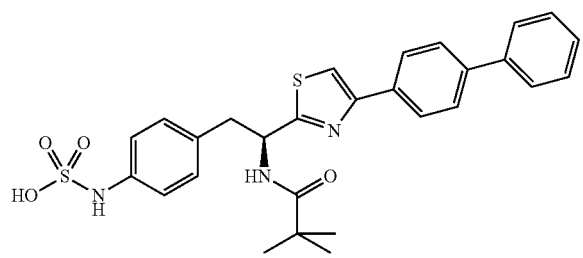 [SMILES: CC(C)(C)C(=O)N[C@@H](Cc1ccc(NS(=O)(=O)O)cc1)c1nc(-c2ccc(-c3ccccc3)cc2)cs1]

(S)-4-(2-(4-(Biphen-4-yl)thiazol-2-yl)-2-pivalamido-ethyl)phenylsulfamic acid: ¹H NMR (CD₃OD): δ 8.04-8.01 (m, 2H), 7.72-7.66 (m, 5H), 7.48-7.35 (m, 3H), 7.15 (s, 4H), 5.50 (t, 1H, J=5.0 Hz), 3.57-3.15 (d, 2H), 1.16 (s, 9H).

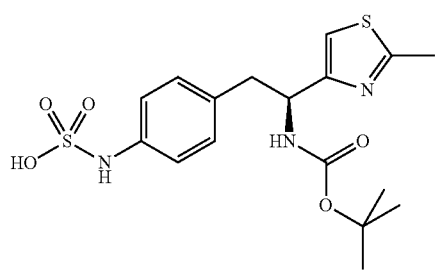 [SMILES: Cc1nc([C@H](Cc2ccc(NS(=O)(=O)O)cc2)NC(=O)OC(C)(C)C)cs1]

(S)-4-(2-tert-Butoxycarbonyl-2-(2-methylthaizol-4-yl)-phenylsulfamic acid ¹H NMR (300 MHz, D₂O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

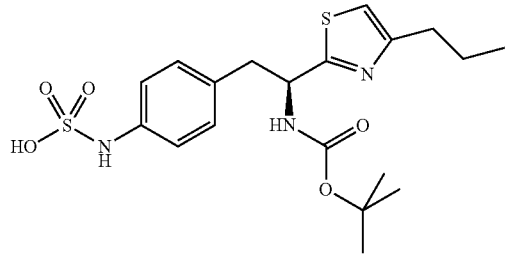 [SMILES: CCCc1csc([C@H](Cc2ccc(NS(=O)(=O)O)cc2)NC(=O)OC(C)(C)C)n1]

(S)-4-(2-(tert-Butoxycarbonyl)-2-(4-propylthiazol-2-yl) ethyl)-phenyl sulfamic acid: ¹H NMR (300 MHz, CD₃OD): δ 7.18-7.02 (m, 5H), 5.06-5.03 (m, 1H), 3.26 (dd, J=13.8, 4.8 Hz, 1H), 2.95 (dd, J=13.8, 9.3 Hz, 1H), 2.74 (dd, J=15.0, 7.2 Hz, 2H), 1.81-1.71 (m, 2H), 1.40 (s, 7H), 1.33 (bs, 2H), 0.988 (t, J=7.5 Hz 3H).

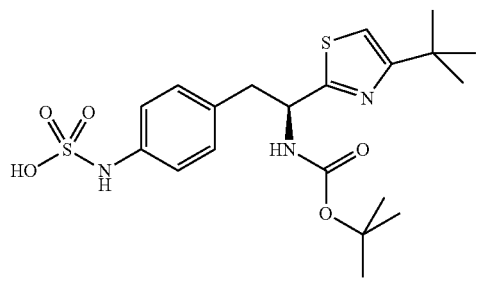 [SMILES: CC(C)(C)OC(=O)N[C@@H](Cc1ccc(NS(=O)(=O)O)cc1)c1nc(C(C)(C)C)cs1]

(S)-4-(2-(tert-Butoxycarbonyl)-2-(4-tert-butylthiazol-2-yl)ethyl)-phenyl sulfamic acid: ¹H NMR (300 MHz, CD₃OD): δ 7.12 (s, 4H), 7.01 (s, 1H), 5.11-5.06 (m, 1H), 3.32-3.25 (m, 1H), 2.96 (m, 1H), 1.42 (s, 8H), 1.38 (s, 9H), 1.32 (s, 1H).

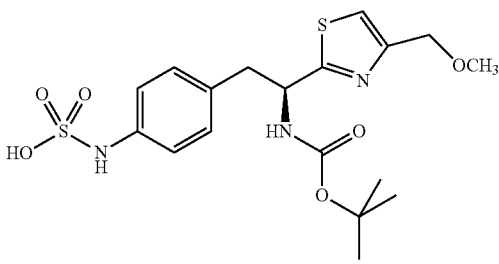 [SMILES: COCc1csc([C@H](Cc2ccc(NS(=O)(=O)O)cc2)NC(=O)OC(C)(C)C)n1]

(S)-4-(2-(tert-Butoxycarbonylamino)-2-(4-(methoxymethyl)thiazol-2-yl)ethyl)-phenyl sulfamic acid: ¹H NMR (300 MHz, CD₃OD): δ 7.36 (s, 1H), 7.14-7.05 (m, 4H), 5.06 (dd, J=9.0, 5.1 Hz, 1H), 4.55 (s, 2H), 3.42 (s, 3H), 3.31-3.24 (m, 1H), 2.97 (dd, J=13.8, 9.9 Hz, 1H), 1.47-1.31 (m, 9H).

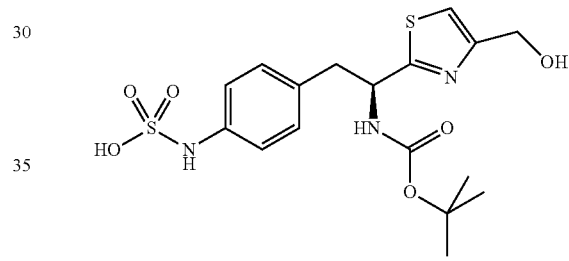

(S)-4-(2-tert-Butoxycarbonylamino)-2-(4-(2-hydroxymethyl)thiazol-2-yl)ethyl)phenylsulfamic acid: ¹H NMR (300 MHz, MeOH-d₄) δ 7.22-7.25 (m, 1H), 7.09-7.15 (m, 4H), 5.00-5.09 (m, 1H), 4.32-4.35 (m, 1H), 3.87 (t, J=6.6 Hz, 2H), 3.23-3.29 (m, 1H), 3.09-3.18 (m, 1H), 2.98 (t, J=6.6 Hz, 2H), 1.41 (s, 9H).

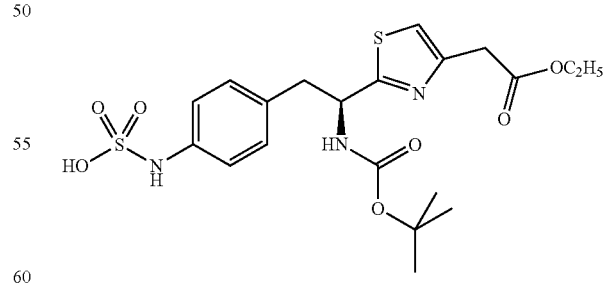

(S)-4-(2-tert-Butoxycarbonylamino)-2-(4-(2-ethoxy-2-oxoethyl)-thiazole-2-yl)-ethyl)phenylsulfamic acid: ¹H NMR (300 MHz, MeOH-d₄) δ 7.29 (s, 1H), 7.09-7.16 (m, 4H), 5.04-5.09 (m, 1H), 4.20 (q, J=6.9 Hz, 2H), 3.84 (s, 2H), 3.30 (dd, J=4.8 and 14.1 HZ, 1H), 2.97 (dd, J=9.6 Hz and 13.8 Hz, 1H), 1.41 (s, 9H), 1.29 (t, J=7.2 Hz, 3H).

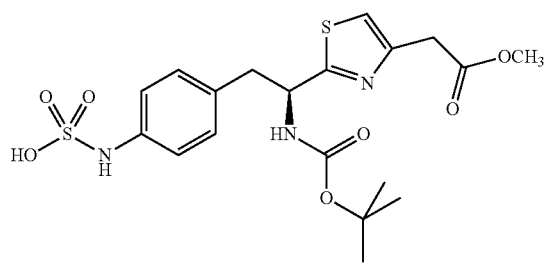 [SMILES: COC(=O)Cc1csc([C@H](Cc2ccc(NS(=O)(=O)O)cc2)NC(=O)OC(C)(C)C)n1]

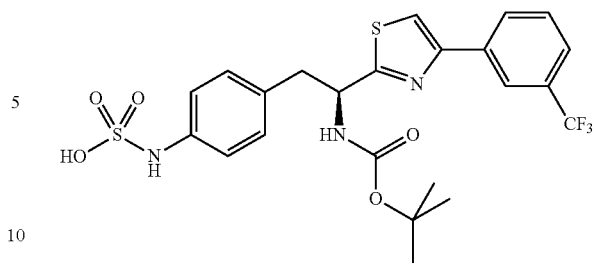

(S)-4-(2-(tert-Butoxycarbonylamino)-2-(4-(2-methoxy-2-oxoethyl)thiazol-2-yl)ethyl)phenylsulfamic acid: $^1$H NMR (300 MHz, MeOH-d$_4$) δ 7.31 (s, 1H), 7.01-7.16 (m, 4H), 5.04-5.09 (m, 1H), 4.01 (s, 2H), 3.78 (s, 2H), 3.74 (s, 3H), 3.29 (dd, J=5.1 and 13.8 Hz, 1H), 2.99 (dd, J=9.3 and 13.8 Hz, 1H), 1.41 (s, 9H).

4-((S)-2-(tert-Butoxycarbonylamino)-2-(4-(3-(trifluoromethyl)phenyl)thiazol-2-yl)ethyl)phenyl sulfamic acid: $^1$H NMR (300 MHz, CD$_3$OD): δ 8.28 (s, 1H), 8.22-8.19 (m, 1H), 7.89 (s, 1H), 7.65 (d, J=5.1 Hz, 2H), 7.45 (d, J=8.1 Hz, 1H), 7.15 (s, 4H), 5.17-5.14 (m, 1H), 3.43-3.32 (m, 1H), 3.05 (dd, J=14.1, 9.6 Hz, 1H), 1.42 (s, 9H).

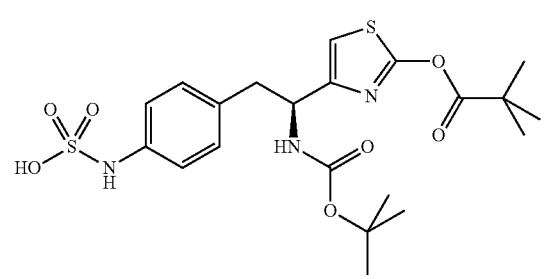 [SMILES: CC(C)(C)OC(=O)N[C@@H](Cc1ccc(NS(=O)(=O)O)cc1)c1csc(OC(=O)C(C)(C)C)n1]

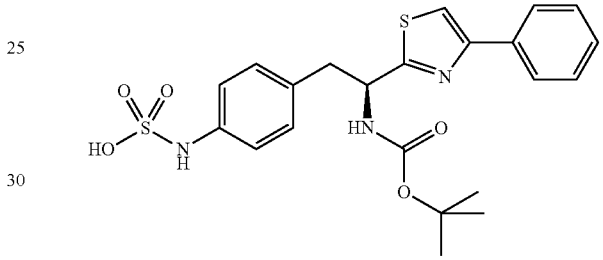

(S)-4-(2-(tert-Butoxycarbonylamino)-2-(2-(pivaloyloxy)thiazol-4-yl)ethyl)-phenylsulfamic acid: $^1$H NMR (300 MHz, D$_2$O) δ 6.95 (s, 4H), 6.63 (s, 1H), 2.94 (dd, J=13.5 and 4.8 Hz, 1H), 2.75 (dd, J=13.5 and 4.8 Hz, 1H), 1.16 (s, 9H), 1.13 (s, 9H).

(S)-4-(2-(tert-Butoxycarbonylamino)-2-(4-phenylthiazol-2-yl)ethyl)-phenyl sulfamic acid: $^1$H NMR (300 MHz, CD$_3$OD): δ 7.98 (s, 1H), 7.94 (d, J=7.2 Hz, 2H), 7.46-7.35 (m, 4H), 7.14 (s, 4H), 5.09 (bs, 1H), 3.07-2.99 (m, 2H), 1.43 (s, 9H).

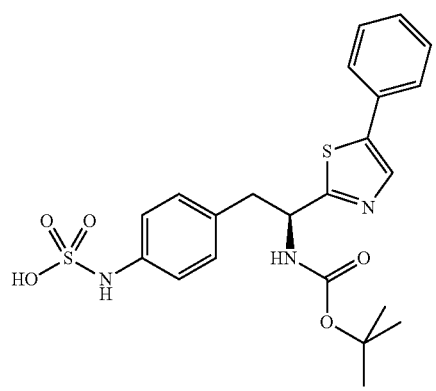 [SMILES: CC(C)(C)OC(=O)N[C@@H](Cc1ccc(NS(=O)(=O)O)cc1)c1ncc(-c2ccccc2)s1]

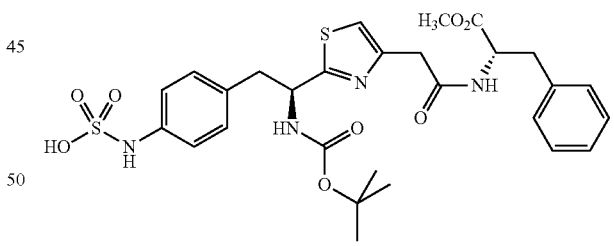

(S,S)-2-(2-{2-[2-tert-Butoxycarbonylamino-2-(4-sulfoaminophenyl)ethyl]thiazol-4-yl}acetylamido)-3-phenyl-propionic acid methyl ester: $^1$H NMR (300 MHz, MeOH-d$_4$) δ 6.85-6.94 (m, 9H), 6.64 (s, 1H), 4.83 (s, 1H), 4.54-4.58 (m, 1H), 3.49 (s, 3H), 3.39 (s, 2H), 2.80-2.97 (m, 1H), 2.64-2.78 (m, 1H), 1.12 (s, 9H).

(S)-4-(2-(tert-Butoxycarbonylamino)-2-(5-phenylthiazol-2-yl)ethyl)-phenyl sulfamic acid: $^1$H NMR (300 MHz, CD$_3$OD): δ 7.98 (s, 1H), 7.62 (d, J=7.2 Hz, 2H), 7.46-7.35 (m, 4H), 7.14 (s, 4H), 5.09 (bs, 1H), 3.07-2.99 (m, 2H), 1.43 (s, 9H).

(S)-[1-{1-Oxo-4-[2-(1-phenyl-1H-tetrazol-5-sulfonyl)ethyl]-1H-1λ$^4$-thiazol-2-yl}-2-(4-sulfamino-phenyl)-ethyl]-carbamic acid tert-butyl ester: $^1$H NMR (300 MHz, MeOH-d$_4$) δ 7.22-7.75 (m, 2H), 7.62-7.69 (m, 2H), 7.55 (s, 1H), 7.10-7.20 (m, 5H), 5.25 (m, 1H), 4.27-4.36 (m, 1H), 4.11-4.21 (m, 1H), 3.33-3.44 (m, 4H), 2.84-2.90 (m, 1H), 1.33 (s, 9H).

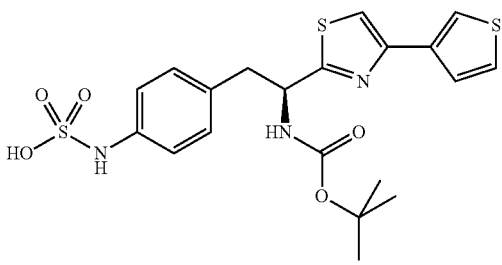 [SMILES: CC(C)(C)OC(=O)N[C@@H](Cc1ccc(NS(=O)(=O)O)cc1)c1nc(-c2ccsc2)cs1]

4-((S)-2-(tert-Butoxycarbonylamino)-2-(4-(thiophen-3-yl)thiazol-2-yl)ethyl)phenyl sulfamic acid: $^1$H NMR (300 MHz, CD$_3$OD): δ 7.84 (dd, J=3.0, 1.5 Hz, 1H), 7.57-7.55 (m, 2H), 7.47 (dd, J=4.8, 3.0 Hz, 1H), 7.15 (s, 4H), 5.15-5.10 (m, 1H), 3.39-3.34 (m, 1H), 3.01 (dd, J=14.1, 9.6 Hz, 1H), 1.42 (s, 8H), 1.32 (s, 1H).

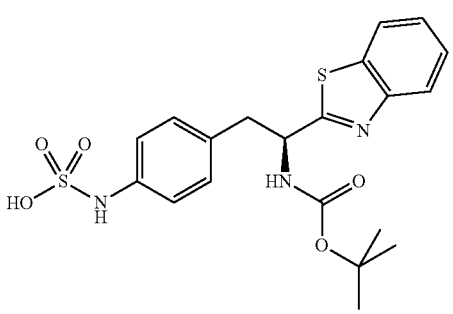 [SMILES: CC(C)(C)OC(=O)N[C@@H](Cc1ccc(NS(=O)(=O)O)cc1)c1nc2ccccc2s1]

(S)-4-(2-(Benzo[d]thiazol-2-ylamino)-2-(tert-butoxycarbonyl)ethyl)phenylsulfamic acid: $^1$H NMR (CD$_3$OD) δ 7.86-7.82 (m, 2H), 7.42 (t, 2H, J=7.1 Hz), 7.33 (t, 1H, J=8.2 Hz), 7.02 (s, 4H), 5.10-5.05 (m, 1H), 2.99-2.91 (m, 2H), 1.29 (s, 9H).

(S)-4-(2-tert-Butoxycarbonylamino)-2-(2-methylthiazol-4-yl)-phenylsulfamic acid $^1$H NMR (300 MHz, D$_2$O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

The first aspect of Category V of the present disclosure relates to 2-(thiazol-2-yl) compounds having the formula:

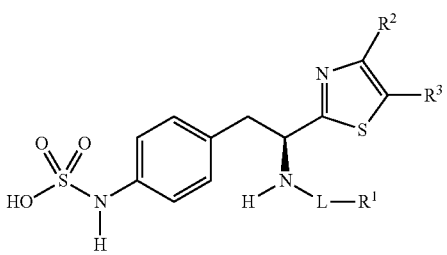

wherein R$^1$, R$^2$, R$^3$, and L are further defined herein in Table IX herein below.

TABLE IX

| No. | L | R$^1$ | R$^2$ | R$^3$ |
|---|---|---|---|---|
| I272 | —C(O)CH$_2$— | phenyl | —CH$_3$ | —H |
| I273 | —C(O)CH$_2$— | 2-fluorophenyl | —CH$_3$ | —H |

TABLE IX-continued

| No. | L | R$^1$ | R$^2$ | R$^3$ |
|---|---|---|---|---|
| I274 | —C(O)CH$_2$— | 3-fluorophenyl | —CH$_3$ | —H |
| I275 | —C(O)CH$_2$— | 4-fluorophenyl | —CH$_3$ | —H |
| I276 | —C(O)CH$_2$— | 2,3-difluorophenyl | —CH$_3$ | —H |
| I277 | —C(O)CH$_2$— | 3,4-difluorophenyl | —CH$_3$ | —H |
| I278 | —C(O)CH$_2$— | 3,5-difluorophenyl | —CH$_3$ | —H |
| I279 | —C(O)CH$_2$— | 2-chlorophenyl | —CH$_3$ | —H |
| I280 | —C(O)CH$_2$— | 3-chlorophenyl | —CH$_3$ | —H |
| I281 | —C(O)CH$_2$— | 4-chlorophenyl | —CH$_3$ | —H |
| I282 | —C(O)CH$_2$— | 2,3-dichlorophenyl | —CH$_3$ | —H |
| I283 | —C(O)CH$_2$— | 3,4-dichlorophenyl | —CH$_3$ | —H |
| I284 | —C(O)CH$_2$— | 3,5-dichlorophenyl | —CH$_3$ | —H |
| I285 | —C(O)CH$_2$— | 2-hydroxyphenyl | —CH$_3$ | —H |
| I286 | —C(O)CH$_2$— | 3-hydroxyphenyl | —CH$_3$ | —H |
| I287 | —C(O)CH$_2$— | 4-hydroxyphenyl | —CH$_3$ | —H |
| I288 | —C(O)CH$_2$— | 2-methoxyphenyl | —CH$_3$ | —H |
| I289 | —C(O)CH$_2$— | 3-methoxyphenyl | —CH$_3$ | —H |
| I290 | —C(O)CH$_2$— | 4-methoxyphenyl | —CH$_3$ | —H |
| I291 | —C(O)CH$_2$— | 2,3-dimethoxyphenyl | —CH$_3$ | —H |
| I292 | —C(O)CH$_2$— | 3,4-dimethoxyphenyl | —CH$_3$ | —H |
| I293 | —C(O)CH$_2$— | 3,5-dimethoxyphenyl | —CH$_3$ | —H |
| I294 | —C(O)CH$_2$— | phenyl | —CH$_2$CH$_3$ | —H |
| I295 | —C(O)CH$_2$— | 2-fluorophenyl | —CH$_2$CH$_3$ | —H |
| I296 | —C(O)CH$_2$— | 3-fluorophenyl | —CH$_2$CH$_3$ | —H |
| I297 | —C(O)CH$_2$— | 4-fluorophenyl | —CH$_2$CH$_3$ | —H |
| I298 | —C(O)CH$_2$— | 2,3-difluorophenyl | —CH$_2$CH$_3$ | —H |
| I299 | —C(O)CH$_2$— | 3,4-difluorophenyl | —CH$_2$CH$_3$ | —H |
| I300 | —C(O)CH$_2$— | 3,5-difluorophenyl | —CH$_2$CH$_3$ | —H |
| I301 | —C(O)CH$_2$— | 2-chlorophenyl | —CH$_2$CH$_3$ | —H |
| I302 | —C(O)CH$_2$— | 3-chlorophenyl | —CH$_2$CH$_3$ | —H |
| I303 | —C(O)CH$_2$— | 4-chlorophenyl | —CH$_2$CH$_3$ | —H |
| I304 | —C(O)CH$_2$— | 2,3-dichlorophenyl | —CH$_2$CH$_3$ | —H |
| I305 | —C(O)CH$_2$— | 3,4-dichlorophenyl | —CH$_2$CH$_3$ | —H |
| I306 | —C(O)CH$_2$— | 3,5-dichlorophenyl | —CH$_2$CH$_3$ | —H |
| I307 | —C(O)CH$_2$— | 2-hydroxyphenyl | —CH$_2$CH$_3$ | —H |
| I308 | —C(O)CH$_2$— | 3-hydroxyphenyl | —CH$_2$CH$_3$ | —H |
| I309 | —C(O)CH$_2$— | 4-hydroxyphenyl | —CH$_2$CH$_3$ | —H |
| I310 | —C(O)CH$_2$— | 2-methoxyphenyl | —CH$_2$CH$_3$ | —H |
| I311 | —C(O)CH$_2$— | 3-methoxyphenyl | —CH$_2$CH$_3$ | —H |
| I312 | —C(O)CH$_2$— | 4-methoxyphenyl | —CH$_2$CH$_3$ | —H |
| I313 | —C(O)CH$_2$— | 2,3-dimethoxyphenyl | —CH$_2$CH$_3$ | —H |
| I314 | —C(O)CH$_2$— | 3,4-dimethoxyphenyl | —CH$_2$CH$_3$ | —H |
| I315 | —C(O)CH$_2$— | 3,5-dimethoxyphenyl | —CH$_2$CH$_3$ | —H |
| I316 | —C(O)CH$_2$CH$_2$— | phenyl | —CH$_3$ | —H |
| I317 | —C(O)CH$_2$CH$_2$— | 2-fluorophenyl | —CH$_3$ | —H |
| I318 | —C(O)CH$_2$CH$_2$— | 3-fluorophenyl | —CH$_3$ | —H |
| I319 | —C(O)CH$_2$CH$_2$— | 4-fluorophenyl | —CH$_3$ | —H |
| I320 | —C(O)CH$_2$CH$_2$— | 2,3-difluorophenyl | —CH$_3$ | —H |
| I321 | —C(O)CH$_2$CH$_2$— | 3,4-difluorophenyl | —CH$_3$ | —H |
| I322 | —C(O)CH$_2$CH$_2$— | 3,5-difluorophenyl | —CH$_3$ | —H |
| I323 | —C(O)CH$_2$CH$_2$— | 2-chlorophenyl | —CH$_3$ | —H |
| I324 | —C(O)CH$_2$CH$_2$— | 3-chlorophenyl | —CH$_3$ | —H |
| I325 | —C(O)CH$_2$CH$_2$— | 4-chlorophenyl | —CH$_3$ | —H |
| I326 | —C(O)CH$_2$CH$_2$— | 2,3-dichlorophenyl | —CH$_3$ | —H |
| I327 | —C(O)CH$_2$CH$_2$— | 3,4-dichlorophenyl | —CH$_3$ | —H |
| I328 | —C(O)CH$_2$CH$_2$— | 3,5-dichlorophenyl | —CH$_3$ | —H |
| I329 | —C(O)CH$_2$CH$_2$— | 2-hydroxyphenyl | —CH$_3$ | —H |
| I330 | —C(O)CH$_2$CH$_2$— | 3-hydroxyphenyl | —CH$_3$ | —H |
| I331 | —C(O)CH$_2$CH$_2$— | 4-hydroxyphenyl | —CH$_3$ | —H |
| I332 | —C(O)CH$_2$CH$_2$— | 2-methoxyphenyl | —CH$_3$ | —H |
| I333 | —C(O)CH$_2$CH$_2$— | 3-methoxyphenyl | —CH$_3$ | —H |
| I334 | —C(O)CH$_2$CH$_2$— | 4-methoxyphenyl | —CH$_3$ | —H |
| I335 | —C(O)CH$_2$CH$_2$— | 2,3-dimethoxyphenyl | —CH$_3$ | —H |
| I336 | —C(O)CH$_2$CH$_2$— | 3,4-dimethoxyphenyl | —CH$_3$ | —H |
| I337 | —C(O)CH$_2$CH$_2$— | 3,5-dimethoxyphenyl | —CH$_3$ | —H |
| I338 | —C(O)CH$_2$CH$_2$— | phenyl | —CH$_2$CH$_3$ | —H |
| I339 | —C(O)CH$_2$CH$_2$— | 2-fluorophenyl | —CH$_2$CH$_3$ | —H |
| I340 | —C(O)CH$_2$CH$_2$— | 3-fluorophenyl | —CH$_2$CH$_3$ | —H |
| I341 | —C(O)CH$_2$CH$_2$— | 4-fluorophenyl | —CH$_2$CH$_3$ | —H |
| I342 | —C(O)CH$_2$CH$_2$— | 2,3-difluorophenyl | —CH$_2$CH$_3$ | —H |
| I343 | —C(O)CH$_2$CH$_2$— | 3,4-difluorophenyl | —CH$_2$CH$_3$ | —H |
| I344 | —C(O)CH$_2$CH$_2$— | 3,5-difluorophenyl | —CH$_2$CH$_3$ | —H |
| I345 | —C(O)CH$_2$CH$_2$— | 2-chlorophenyl | —CH$_2$CH$_3$ | —H |
| I346 | —C(O)CH$_2$CH$_2$— | 3-chlorophenyl | —CH$_2$CH$_3$ | —H |
| I347 | —C(O)CH$_2$CH$_2$— | 4-chlorophenyl | —CH$_2$CH$_3$ | —H |
| I348 | —C(O)CH$_2$CH$_2$— | 2,3-dichlorophenyl | —CH$_2$CH$_3$ | —H |
| I349 | —C(O)CH$_2$CH$_2$— | 3,4-dichlorophenyl | —CH$_2$CH$_3$ | —H |
| I350 | —C(O)CH$_2$CH$_2$— | 3,5-dichlorophenyl | —CH$_2$CH$_3$ | —H |
| I351 | —C(O)CH$_2$CH$_2$— | 2-hydroxyphenyl | —CH$_2$CH$_3$ | —H |

TABLE IX-continued

| No. | L | R¹ | R² | R³ |
|---|---|---|---|---|
| I352 | —C(O)CH₂CH₂— | 3-hydroxyphenyl | —CH₂CH₃ | —H |
| I353 | —C(O)CH₂CH₂— | 4-hydroxyphenyl | —CH₂CH₃ | —H |
| I354 | —C(O)CH₂CH₂— | 2-methoxyphenyl | —CH₂CH₃ | —H |
| I355 | —C(O)CH₂CH₂— | 3-methoxyphenyl | —CH₂CH₃ | —H |
| I356 | —C(O)CH₂CH₂— | 4-methoxyphenyl | —CH₂CH₃ | —H |
| I357 | —C(O)CH₂CH₂— | 2,3-dimethoxyphenyl | —CH₂CH₃ | —H |
| I358 | —C(O)CH₂CH₂— | 3,4-dimethoxyphenyl | —CH₂CH₃ | —H |
| I359 | —C(O)CH₂CH₂— | 3,5-dimethoxyphenyl | —CH₂CH₃ | —H |

The compounds encompassed within the first aspect of Category V of the present disclosure can be prepared by the procedure outlined in Scheme VII and described in Example 8 herein below.

Scheme VII

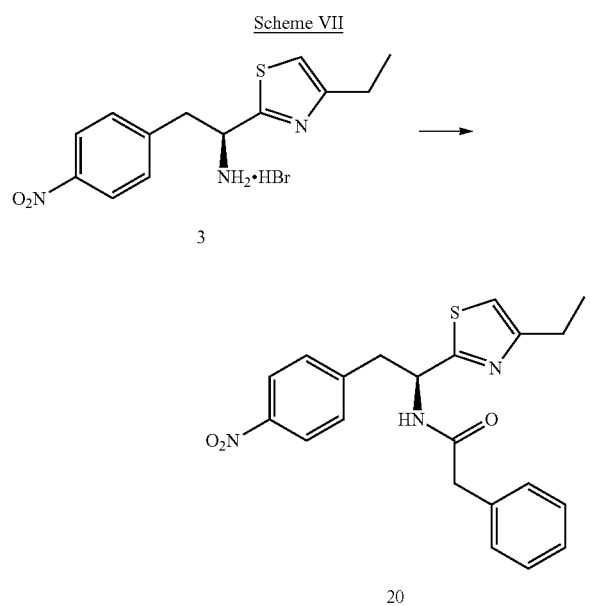

Reagents and Conditions: (a) C₆H₄CO₂H, EDCI, HOBt, DIPEA, DMF; rt, 18 hr

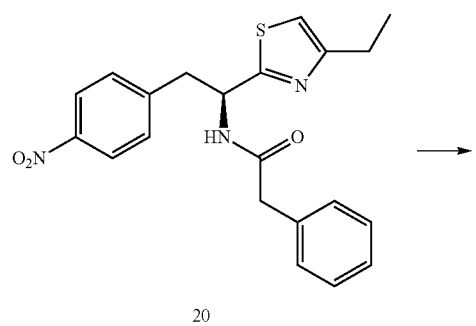

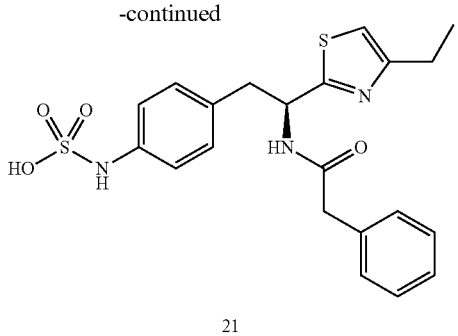

Reagents and Conditions: (b) (i) H₂:Pd/C, MeOH; (ii) SO₃-pyridine, NH₄OH, rt, 18 hr

EXAMPLE 8

{4-[2-(S)-(4-Ethylthiazol-2-yl)-2-(2-phenylacetylamido)ethyl]phenyl}sulfamic Acid (21)

Preparation of N-[1-(4-ethylthiazol-2-yl)-2-(4-nitrophenyl)ethyl]-2-phenyl-acetamide (20): To a solution of 1-(S)-(4-ethylthiazol-2-yl)-2-(4-nitrophenyl)ethyl amine hydrobromide, 3, (0.393 g, 1.1 mmol), phenylacetic acid (0.190 g, 1.4 mmol) and 1-hydroxybenzotriazole (HOBt) (0.094 g, 0.70 mmol) in DMF (10 mL) at 0°, is added 1-(3-dimethylaminopropyl)-3-ethylcarbodiimide (EDCI) (0.268 g, 1.4 mmol) followed by triethylamine (0.60 mL, 4.2 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.260 g (60% yield) of the desired product which is used without further purification. ESI+ MS 396 (M+1).

Preparation of {4-[2-(S)-(4-ethylthiazol-2-yl)-2-(2-phenylacetylamido)ethyl]-phenyl}sulfamic acid (21): N-[1-(4-ethylthiazol-2-yl)-2-(4-nitrophenyl)ethyl]-2-phenyl-acetamide, 20, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.177 g, 1.23). The reaction is stirred at room temperature for 5 minutes after which a 7% solution of NH₄OH (10 mL) is added. The mixture is then concentrated and the resulting residue is purified by reverse phase chromatography to afford 0.136 g of the desired product as the ammonium salt. ¹H NMR (CD₃OD) δ 8.60 (d, 1H, J=8.1 Hz), 7.33-7.23 (m, 3H), 7.16-7.00 (m, 6H), 5.44-5.41 (m, 1H), 3.28 (1H, A of ABX, obscured by solvent), 3.03 (1H, B of ABX, J=14.1, 9.6 Hz), 2.80 (q, 2H, J=10.5, 7.8 Hz) 1.31 (t, 3H, J=4.6 Hz).

The following are non-limiting examples of the first aspect of Category V of the present disclosure.

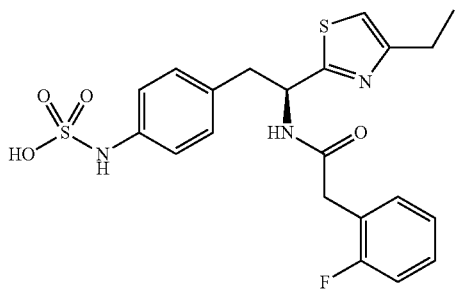

(S)-4-(2-(4-Ethylthiazol-2-yl)-2-(2-(2-fluorophenyl)acetamido)ethyl)phenylsulfamic acid: ¹H NMR (CD₃OD) δ 8.65 (d, 1H, J=8.4 Hz), 7.29-7.15 (m, 1H), 7.13-7.03 (m, 7H), 5.46-5.42 (m, 1H), 3.64-3.51 (m, 2H), 3.29 (1H), 3.04 (1H, B of ABX, J=13.8, 9.6 Hz), 2.81 (q, 2H, J=15.6, 3.9 Hz), 1.31 (t, 3H, J=7.8 Hz). ¹⁹F NMR (CD₃OD) δ 43.64.

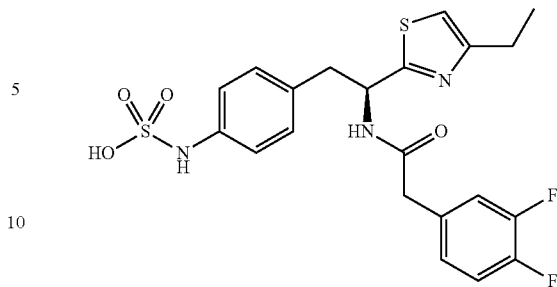

(S)-4-(2-(2-(3,4-Difluorophenyl)acetamido)-2-(4-ethylthiazol-2-yl)ethyl)-phenylsulfamic acid: ¹H NMR (CD₃OD) δ 8.75 (d, 1H, J=7.8 Hz), 7.23-7.04 (m, 6H), 6.88-6.84 (m, 1H), 5.44-5.40 (m, 1H), 3.49 (s, 2H), 3.34 (1H), 3.02 (1H, B of ABX, J=14.1, 9.9 Hz), 2.80 (q, 2H, J=15.1, 7.8 Hz), 1.31 (t, 1H, J=7.5 Hz). 19F NMR (CD3OD) δ 22.18, 19.45.

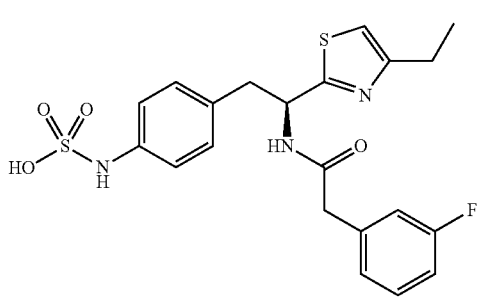 [SMILES: CCc1csc([C@H](Cc2ccc(NS(=O)(=O)O)cc2)NC(=O)Cc2cccc(F)c2)n1]

(S)-4-(2-(4-Ethylthiazol-2-yl)-2-(2-(3-fluorophenyl)acetamido)ethyl)phenylsulfamic acid: ¹H NMR (CD3OD) δ 8.74 (d, 1H, J=8.4 Hz), 7.32 (q, 1H, J=6.6, 14.2 Hz), 7.10-6.91 (m, 8H), 5.47-5.40 (m, 1H), 3.53 (s, 2H), 3.30 (1H), 3.11 (1H, B of ABX, J=9.6, 14.1 Hz), 2.80 (q, 2H, J=6.6, 15.1 Hz), 1.31 (t, 3H, J=7.8 Hz). 19F NMR δ 47.42.

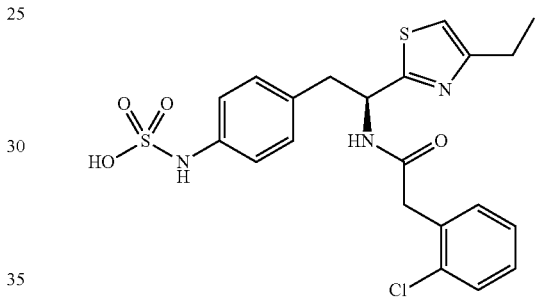

(S)-4-(2-(2-(2-Chlorophenyl)acetamido)-2-(4-ethylthiazol-2-yl)ethyl)phenylsulfamic acid: ¹H NMR (CD3OD) δ 7.39-7.36 (m, 1H), 7.27-7.21 (m, 2H), 7.15-6.98 (m, 5H), 5.49-5.44 (m, 1H), 3.69 (d, 2H, J=11.7 Hz), 3.32 (1H), 3.04 (1H, B of ABX, J=9.3, 13.9 Hz), 2.80 (q, 2H, J=7.8, 15.3 Hz), 1.31 (t, 3H, J=7.5 Hz).

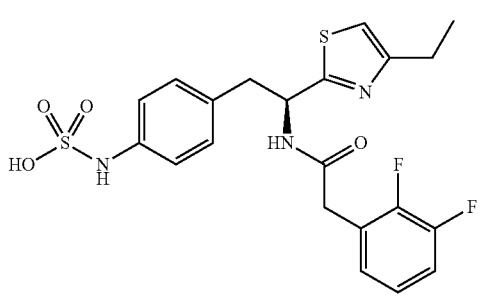 [SMILES: CCc1csc([C@H](Cc2ccc(NS(=O)(=O)O)cc2)NC(=O)Cc2cccc(F)c2F)n1]

(S)-4-(2-(2-(2,3-Difluorophenyl)acetamido)-2-(4-ethylthiazol-2-yl)ethyl)-phenylsulfamic acid: ¹H NMR (CD₃OD) δ 7.16-7.05 (m, 5H), 6.85-6.80 (m, 1H), 5.48-5.43 (m, 1H), 3.63 (s, 2H), 3.38 (1H, A of ABX, obscured by solvent), 3.03 (1H), 2.80 (q, H, J=15.1, 7.8 Hz), 1.31 (t, 3H, J=7.5 Hz).

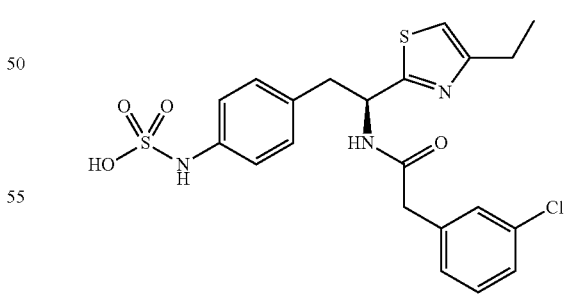

(S)-4-(2-(2-(3-Chlorophenyl)acetamido)-2-(4-ethylthiazol-2-yl)ethyl)phenylsulfamic acid: ¹H NMR (CD3OD) δ 7.33-7.23 (m, 3H), 7.13-7.03 (m, 5H), 5.43 (q, 1H, J=5.1, 9.6 Hz), 3.51 (s, 2H), 3.29 (1H), 3.03 (1H, B of ABX, J=9.9, 14.1 Hz), 2.80 (q, 2H, J=7.5, 15 Hz), 1.31 (t, 3H, J=7.8 Hz).

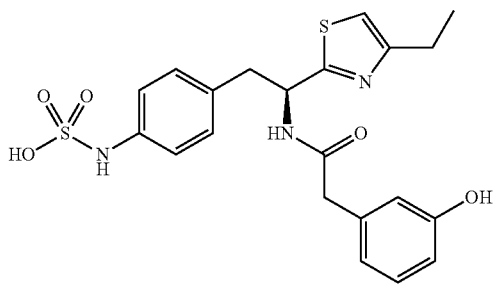 [SMILES: CCc1csc([C@H](Cc2ccc(NS(=O)(=O)O)cc2)NC(=O)Cc2cccc(O)c2)n1]

(S)-4-(2-(4-Ethylthiazol-2-yl)-2-(2-(3-hydroxyphenyl)acetamido)ethyl)-phenylsulfamic acid: $^1$H NMR (CD$_3$OD) δ 7.16-7.08 (m, 3H), 7.03-7.00 (m, 3H), 6.70-6.63 (m, 2H), 5.42-5.40 (m, 1H), 3.44 (s, 2H), 3.28 (1H, A of ABX, obscured by solvent), 3.04 (B of ABX, J=14.1, 9.6 Hz), 2.89 (q, 2H, J=15, 7.5 Hz), 1.31 (t, 3H, J=7.5 Hz).

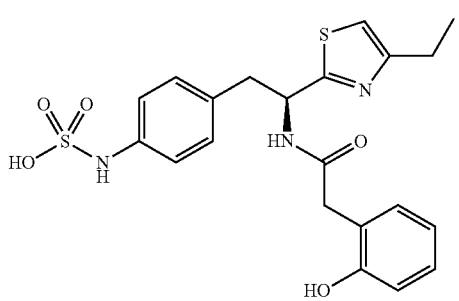

(S)-4-(2-(4-Ethylthiazol-2-yl)-2-(2-(2-methoxyphenyl)acetamido)ethyl)-phenylsulfamic acid: $^1$H NMR (CD$_3$OD) δ 8.00 (d, 1H, J=7.8 Hz), 7.26 (t, 1H, J=13.2 Hz), 7.09-7.05 (m, 4H), 7.01 (s, 1H), 6.91-6.89 (m, 4H), 5.44-5.39 (m, 1H), 3.71 (s, 3H), 3.52 (s, 2H), 3.26 (1H, A of ABX, J=14.1, 5.1 Hz), 3.06 (1H B of ABX, J=13.8, 8.4 Hz), 2.80 (q, 2H, J=8.1, 15.6 Hz), 1.31 (t, 3H, J=1.2 Hz).

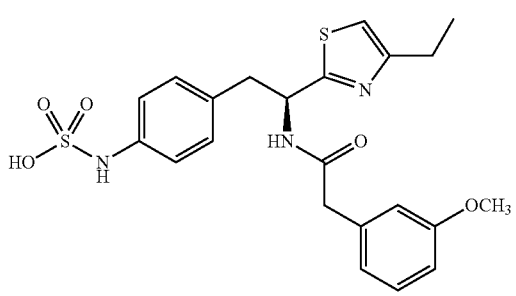 [SMILES: CCc1csc([C@H](Cc2ccc(NS(=O)(=O)O)cc2)NC(=O)Cc2cccc(OC)c2)n1]

(S)-4-{2-(4-Ethylthiazol-2-yl)-2-[2-(3-methoxyphenyl)acetamido]ethyl}-phenylsulfamic acid: $^1$H NMR (CD$_3$OD) δ 8.58 (d, 1H, J=8.1 Hz), 7.21 (t, 1H, J=7.8 Hz), 7.12-7.02 (m, 4H), 6.81 (s, 2H), 6.72 (d, 1H, J=7.5 Hz), 5.45-5.40 (m, 1H), 3.79 (s, 3H), 3.50 (s, 2H), 3.29 (1H, A of ABX, obscured by solvent), 3.08 (1H, B of ABX, J=11.8, 5.1 Hz), 2.80 (q, 2H, J=15, 7.5 Hz), 1.31 (t, 3H, J=6.6 Hz).

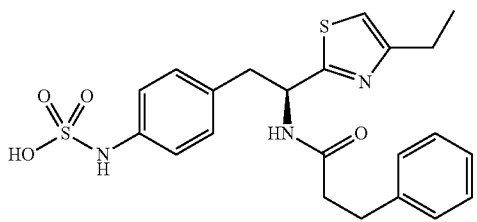 [SMILES: CCc1csc([C@H](Cc2ccc(NS(=O)(=O)O)cc2)NC(=O)CCc2ccccc2)n1]

(S)-4-(2-(4-Ethylthiazol-2-yl)-2-(3-phenylpropanamido)ethyl)phenylsulfamic acid: $^1$H NMR (CD$_3$OD) δ 8.56 (d, 1H, J=8.4 Hz), 7.25-6.98 (m, 9H), 5.43-5.38 (m, 1H), 3.26 (1H, A of ABX, J=14.1, 9.6 Hz), 2.97 (1H, B of ABX, J=10.9, 3 Hz), 2.58-2.76 (m, 3H), 2.98 (q, 2H, J=13.8, 7.2 Hz), 1.29 (t, 3H, J=8.7 Hz).

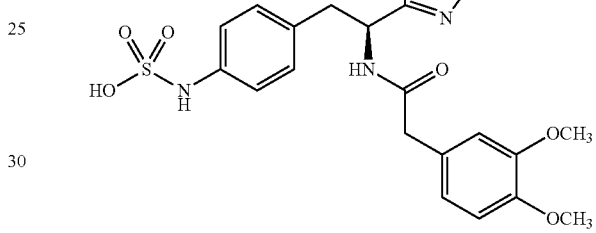

(S)-4-(2-(2-(3,4-Dimethoxyphenyl)acetamido)-2-(4-ethylthiazol-2-yl)ethyl)-phenylsulfamic acid: $^1$H NMR (CD$_3$OD) δ 7.12-7.03 (m, 3H), 6.91 (d, 1H, J=8.4 Hz), 6.82 (s, 1H), 6.66 (d, 1H, J=2.1 Hz), 6.63 (d, 1H, J=2.1 Hz), 5.43 (m, 1H), 3.84 (s, 3H), 3.80 (s, 3H), 3.45 (s, 2H), 3.30 (1H), 3.03 (1H, B of ABX, J=14.1, 9.6 Hz), 2.79 (q, 2H, J=15.1, 7.2 Hz), 1.30 (t, 3H, J=7.2 Hz).

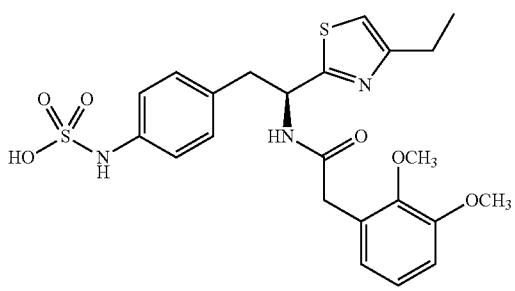 [SMILES: CCc1csc([C@H](Cc2ccc(NS(=O)(=O)O)cc2)NC(=O)Cc2cccc(OC)c2OC)n1]

(S)-4-(2-(2-(2,3-Dimethoxyphenyl)acetamido)-2-(4-ethylthiazol-2-yl)ethyl)-phenylsulfamic acid: $^1$H NMR (CD$_3$OD) δ 8.31 (d, 1H, J=7.8 Hz), 7.11-6.93 (m, 6H), 6.68 (d, 1H, J=7.5 Hz), 5.49-5.40 (m, 1H), 3.87 (s, 3H), 3.70 (s, 3H), 3.55 (s, 2H), 3.26 (1H, A of ABX, obscured by solvent), 3.06 (1H, B of ABX, J=13.9, 9 Hz), 2.80 (q, 2H, J=14.8, 7.5 Hz), 1.31 (t, 3H, J=7.5 Hz).

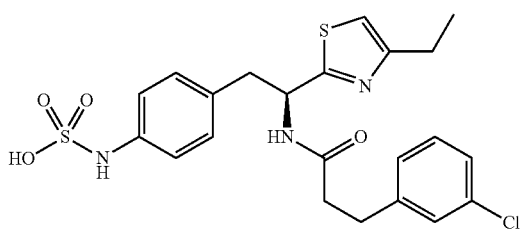 [SMILES: CCc1csc([C@H](Cc2ccc(NS(=O)(=O)O)cc2)NC(=O)CCc2cccc(Cl)c2)n1]

(S)-4-(2-(3-(3-Chlorophenyl)propanamido)-2-(4-ethyl-thiazol-2-yl)ethyl)phenylsulfamic acid: ¹H NMR (CD3OD) δ 7.27-7.18 (m, 3H), 7.13-7.08 (m, 5H), 7.01 (s, 1H), 5.39 (q, 1H, J=5.1, 9.4 Hz), 3.28 (1H, A of ABX, J=5.1, 14.1 Hz), 2.97 (1H, B of ABX, J=9.3, 13.9 Hz), 2.88-2.76 (m, 4H), 2.50 (t, 2H, J=8.1 Hz), 1.31 (t, 3H, J=7.8 Hz).

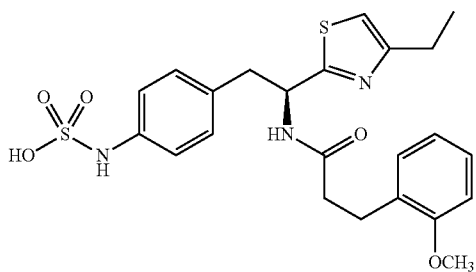 [SMILES: CCc1csc([C@H](Cc2ccc(NS(=O)(=O)O)cc2)NC(=O)CCc2ccccc2OC)n1]

(S)-4-(2-(4-Ethylthiazol-2-yl)-2-(3-(2-methoxyphenyl)propanamido)ethyl)-phenylsulfamic acid: ¹H NMR (CD₃OD) δ 7.18-7.08 (m, 6H), 6.92 (d, 1H, J=8.1 Hz), 6.82 (t, 1H, J=7.5 Hz), 5.40-5.35 (m, 1H), 3.25 (1H, A of ABX, J=15, 5.4 Hz), 3.00 (1H, B of ABX, J=10.5, 7.5 Hz), 2.88-2.76 (m, 4H), 2.47 (q, 2H, J=9.1, 6 Hz), 1.31 (t, 3H, J=7.8 Hz).

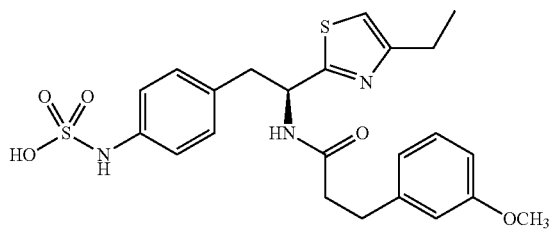 [SMILES: CCc1csc([C@H](Cc2ccc(NS(=O)(=O)O)cc2)NC(=O)CCc2cccc(OC)c2)n1]

(S)-4-(2-(4-Ethylthiazol-2-yl)-2-(3-(3-methoxyphenyl)propanamido)ethyl)-phenylsulfamic acid: ¹H NMR (CD₃OD) δ 7.19-7.00 (m, 5H), 6.75 (s, 1H), 6.73 (s, 1H), 5.42-5.37 (m, 1H), 3.76 (s, 3H), 3.25 (1H, A of ABX, J=13.9, 5.4 Hz), 2.98 (1H, B of ABX, J=14.1, 9.6 Hz), 2.86-2.75 (m, 4H), 2.48 (q, 2H, J=11.7, 1.2 Hz), 1.31 (t, 3H, J=7.5 Hz).

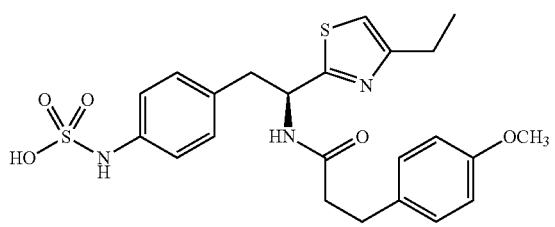 [SMILES: CCc1csc([C@H](Cc2ccc(NS(=O)(=O)O)cc2)NC(=O)CCc2ccc(OC)cc2)n1]

(S)-4-(2-(4-Ethylthiazol-2-yl)-2-(3-(4-methoxyphenyl)propanamido)ethyl)-phenylsulfamic acid: ¹H NMR (CD₃OD) δ 7.13-6.99 (m, 7H), 6.82-6.78 (m, 2H), 5.42-5.37 (m, 1H), 3.33 (s, 3H), 3.23 (1H), 2.97 (1H, B of ABX, J=13.3, 11.4 Hz), 2.83-2.75 (m, 4H), 2.49 (q, 2H, J=6.4, 3.3 Hz), 1.31 (t, 3H, J=7.5 Hz).

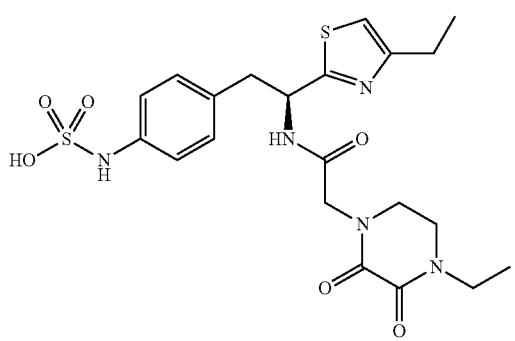 [SMILES: CCc1csc([C@H](Cc2ccc(NS(=O)(=O)O)cc2)NC(=O)CN2CCN(CC)C(=O)C2=O)n1]

(S)-4-{2-[2-(4-Ethyl-2,3-dioxopiperazin-1-yl)acet-amido]-2-(4-ethylthiazol-2-yl)ethyl}phenylsulfamic acid: ¹H NMR (CD₃OD) δ 7.14 (s, 4H), 7.08 (s, 1H), 5.56-5.51 (m, 1H), 4.34 (d, 2H, J=16.2 Hz), 3.88 (d, 2H, J=17.6 Hz), 3.59-3.40 (m, 3H), 3.26-3.14 (m, 3H), 2.98 (1H, B of ABX, J=10.8, 13.9 Hz), 2.82 (q, 2H, J=6.9, 15 Hz), 1.32 (t, 3H, J=7.5 Hz), 1.21 (t, 3H, J=7.2 Hz).

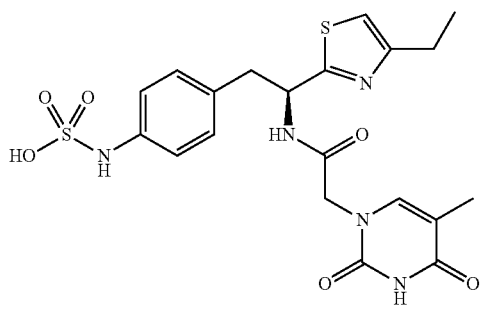 [SMILES: CCc1csc([C@H](Cc2ccc(NS(=O)(=O)O)cc2)NC(=O)Cn2cc(C)c(=O)[nH]c2=O)n1]

(S)-4-{2-(4-Ethylthiazol-2-yl)-2-[2-(5-methyl-2,4-dioxo-3,4-dihydropyrimidin-1(2H)-yl)acetamido]ethyl}phenylsulfamic acid: ¹H NMR (CD₃OD): δ 7.13 (s, 1H), 7.06-7.02 (m, 4H), 6.95 (s, 1H), 5.42-5.31 (m, 1H), 4.43-4.18 (dd, 2H, J=16.5 Hz), 3.24-2.93 (m, 2H), 2.74-2.69 (q, 2H, J=7.3 Hz), 1.79 (s, 3H), 1.22 (t, 3H, J=7.5 Hz).

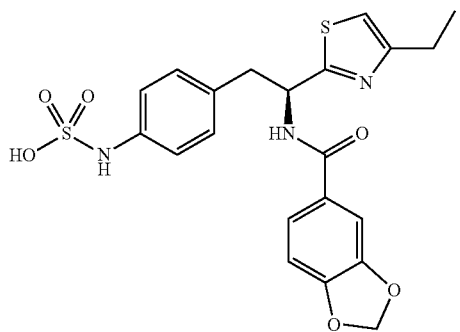 [SMILES: CCc1csc([C@H](Cc2ccc(NS(=O)(=O)O)cc2)NC(=O)c2ccc3c(c2)OCO3)n1]

(S)-4-[2-(benzo[d][1,3]dioxole-5-carboxamido)-2-(4-ethylthiazol-2-yl)ethyl]-phenylsulfamic acid: ¹H NMR (CD₃OD) δ 7.25 (d, 1H, J=6.5 Hz), 7.13 (s, 1H), 7.06 (d, 2H, J=8.5 Hz), 7.00 (d, 2H, J=8.5 Hz), 6.91 (s, 1H), 6.76 (d, 1H, J=8.1 Hz), 5.90 (s, 2H), 5.48 (q, 1H, J=5.0 Hz), 3.32-3.24 (m, 2H), 3.07-2.99 (m, 2H), 2.72 (q, 2H, J=7.5 Hz), 1.21 (t, 3H, J=7.5 HZ).

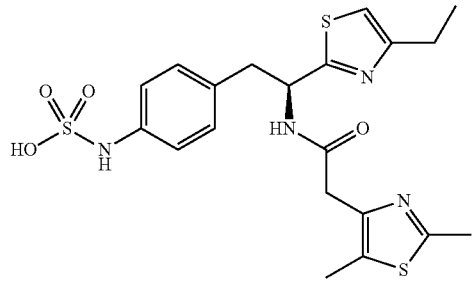 [SMILES: CCc1csc([C@H](Cc2ccc(NS(=O)(=O)O)cc2)NC(=O)Cc2nc(C)sc2C)n1]

(S)-4-{2-[2-(2,5-Dimethylthiazol-4-yl)acetamido]-2-(4-ethylthiazol-2-yl)ethyl}-phenylsulfamic acid: ¹H NMR (CD₃OD): δ 7.10-7.01 (m, 5H), 5.41 (t, 1H, J=6.9 Hz), 3.58 (s, 2H), 3.33-3.01 (m, 2H), 2.82-2.75 (q, 2H, J=7.5 Hz), 2.59 (s, 3H), 2.23 (s, 3H), 1.30 (t, 3H, J=7.5 Hz).

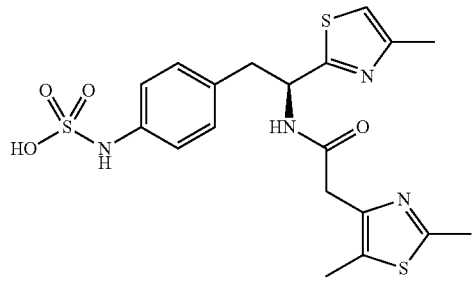 [SMILES: Cc1csc([C@H](Cc2ccc(NS(=O)(=O)O)cc2)NC(=O)Cc2nc(C)sc2C)n1]

(S)-4-{2-[2-(2,4-Dimethylthiazol-5-yl)acetamido]-2-(4-methylthiazol-2-yl)ethyl}-phenylsulfamic acid: ¹H NMR (CD₃OD): δ 8.71-8.68 (d, 1H, J=8.4 Hz), 7.10-7.03 (m, 4H), 7.01 (s, 1H), 5.41 (m, 1H), 3.59 (s, 1H), 3.34-2.96 (m, 2H), 2.59 (s, 3H), 2.40 (s, 3H), 2.23 (s, 3H).

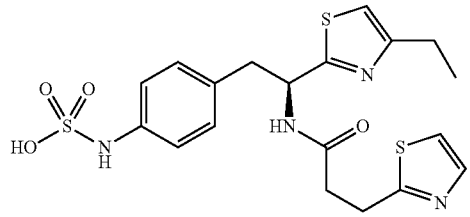 [SMILES: CCc1csc([C@H](Cc2ccc(NS(=O)(=O)O)cc2)NC(=O)CCc2nccs2)n1]

(S)-4-{2-(4-Ethylthiazol-2-yl)-2-[3-(thiazol-2-yl)propanamido]ethyl}phenylsulfamic acid: ¹H NMR (CD₃OD): δ 7.67-7.65 (m, 1H), 7.49-7.47 (m, 1H), 7.14-7.08 (m, 4H), 7.04 (s, 1H), 5.46-5.41 (q, 1H, J=5.1 Hz), 3.58 (s, 2H), 3.30-3.25 (m, 3H), 3.02-2.67 (m, 5H), 1.31 (t, 3H, J=7.5 Hz).

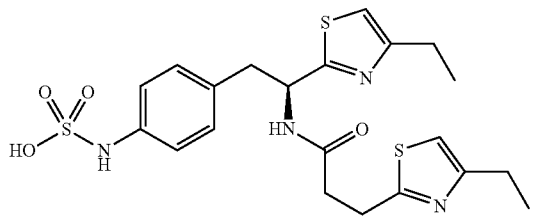 [SMILES: CCc1csc(CCC(=O)N[C@@H](Cc2ccc(NS(=O)(=O)O)cc2)c2nc(CC)cs2)n1]

(S)-4-{2-(4-Ethylthiazol-2-yl)-2-[2-(4-ethylthiazol-2-yl)acetamido]ethyl}-phenylsulfamic acid: ¹H NMR (CD₃OD): δ 7.04-6.91 (m, 6H), 5.32 (t, 1H, J=5.4 Hz), 3.25-2.90 (m, 2H), 2.71-2.61 (m, 4H) 1.93 (s, 2H) 1.22-1.14 (m, 6H).

The second aspect of Category V of the present disclosure relates to 2-(thiazol-4-yl) compounds having the formula:

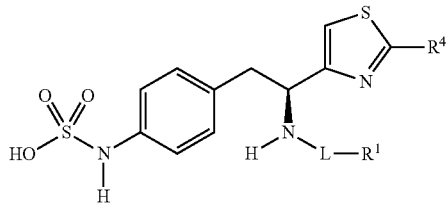

wherein R¹, R⁴, and L are further defined in Table X herein below.

TABLE X

| No. | L | R¹ | R⁴ |
|---|---|---|---|
| J360 | —C(O)CH₂— | phenyl | methyl |
| J361 | —C(O)CH₂— | phenyl | ethyl |
| J362 | —C(O)CH₂— | phenyl | phenyl |
| J363 | —C(O)CH₂— | phenyl | thiophen-2-yl |
| J364 | —C(O)CH₂— | phenyl | thiazol-2-yl |
| J365 | —C(O)CH₂— | phenyl | oxazol-2-yl |
| J366 | —C(O)CH₂— | phenyl | isoxazol-3-yl |
| J367 | —C(O)CH₂— | 3-chlorophenyl | methyl |
| J368 | —C(O)CH₂— | 3-chlorophenyl | ethyl |
| J369 | —C(O)CH₂— | 3-chlorophenyl | phenyl |
| J370 | —C(O)CH₂— | 3-chlorophenyl | thiophen-2-yl |
| J371 | —C(O)CH₂— | 3-chlorophenyl | thiazol-2-yl |
| J372 | —C(O)CH₂— | 3-chlorophenyl | oxazol-2-yl |
| J373 | —C(O)CH₂— | 3-chlorophenyl | isoxazol-3-yl |
| J374 | —C(O)CH₂— | 3-methoxyphenyl | methyl |
| J375 | —C(O)CH₂— | 3-methoxyphenyl | ethyl |
| J376 | —C(O)CH₂— | 3-methoxyphenyl | phenyl |
| J377 | —C(O)CH₂— | 3-methoxyphenyl | thiophen-2-yl |
| J378 | —C(O)CH₂— | 3-methoxyphenyl | thiazol-2-yl |
| J379 | —C(O)CH₂— | 3-methoxyphenyl | oxazol-2-yl |
| J380 | —C(O)CH₂— | 3-methoxyphenyl | isoxazol-3-yl |
| J381 | —C(O)CH₂— | 3-fluorophenyl | methyl |
| J382 | —C(O)CH₂— | 3-fluorophenyl | ethyl |
| J383 | —C(O)CH₂— | 3-fluorophenyl | phenyl |
| J384 | —C(O)CH₂— | 3-fluorophenyl | thiophen-2-yl |
| J385 | —C(O)CH₂— | 3-fluorophenyl | thiazol-2-yl |
| J386 | —C(O)CH₂— | 3-fluorophenyl | oxazol-2-yl |
| J387 | —C(O)CH₂— | 3-fluorophenyl | isoxazol-3-yl |
| J388 | —C(O)CH₂— | 2,5-dimethylthiazol-4-yl | methyl |
| J389 | —C(O)CH₂— | 2,5-dimethylthiazol-4-yl | ethyl |
| J390 | —C(O)CH₂— | 2,5-dimethylthiazol-4-yl | phenyl |
| J391 | —C(O)CH₂— | 2,5-dimethylthiazol-4-yl | thiophen-2-yl |
| J392 | —C(O)CH₂— | 2,5-dimethylthiazol-4-yl | thiazol-2-yl |
| J393 | —C(O)CH₂— | 2,5-dimethylthiazol-4-yl | oxazol-2-yl |
| J394 | —C(O)CH₂— | 2,5-dimethylthiazol-4-yl | isoxazol-3-yl |
| J395 | —C(O)CH₂— | 2,4-dimethylthiazol-5-yl | methyl |
| J396 | —C(O)CH₂— | 2,4-dimethylthiazol-5-yl | ethyl |
| J397 | —C(O)CH₂— | 2,4-dimethylthiazol-5-yl | phenyl |
| J398 | —C(O)CH₂— | 2,4-dimethylthiazol-5-yl | thiophen-2-yl |
| J399 | —C(O)CH₂— | 2,4-dimethylthiazol-5-yl | thiazol-2-yl |

TABLE X-continued

| No. | L | R¹ | R⁴ |
|---|---|---|---|
| J400 | —C(O)CH₂— | 2,4-dimethylthiazol-5-yl | oxazol-2-yl |
| J401 | —C(O)CH₂— | 2,4-dimethylthiazol-5-yl | isoxazol-3-yl |
| J402 | —C(O)CH₂— | 4-ethylthiazol-2-yl | methyl |
| J403 | —C(O)CH₂— | 4-ethylthiazol-2-yl | ethyl |
| J404 | —C(O)CH₂— | 4-ethylthiazol-2-yl | phenyl |
| J405 | —C(O)CH₂— | 4-ethylthiazol-2-yl | thiophen-2-yl |
| J406 | —C(O)CH₂— | 4-ethylthiazol-2-yl | thiazol-2-yl |
| J407 | —C(O)CH₂— | 4-ethylthiazol-2-yl | oxazol-2-yl |
| J408 | —C(O)CH₂— | 4-ethylthiazol-2-yl | isoxazol-3-yl |
| J409 | —C(O)CH₂— | 3-methyl-1,2,4-oxadiazol-5-yl | methyl |
| J410 | —C(O)CH₂— | 3-methyl-1,2,4-oxadiazol-5-yl | ethyl |
| J411 | —C(O)CH₂— | 3-methyl-1,2,4-oxadiazol-5-yl | phenyl |
| J412 | —C(O)CH₂— | 3-methyl-1,2,4-oxadiazol-5-yl | thiophen-2-yl |
| J413 | —C(O)CH₂— | 3-methyl-1,2,4-oxadiazol-5-yl | thiazol-2-yl |
| J414 | —C(O)CH₂— | 3-methyl-1,2,4-oxadiazol-5-yl | oxazol-2-yl |
| J415 | —C(O)CH₂— | 3-methyl-1,2,4-oxadiazol-5-yl | isoxazol-3-yl |
| J416 | —C(O)CH₂CH₂— | phenyl | methyl |
| J417 | —C(O)CH₂CH₂— | phenyl | ethyl |
| J418 | —C(O)CH₂CH₂— | phenyl | phenyl |
| J419 | —C(O)CH₂CH₂— | phenyl | thiophen-2-yl |
| J420 | —C(O)CH₂CH₂— | phenyl | thiazol-2-yl |
| J421 | —C(O)CH₂CH₂— | phenyl | oxazol-2-yl |
| J422 | —C(O)CH₂CH₂— | phenyl | isoxazol-3-yl |
| J423 | —C(O)CH₂CH₂— | 3-chlorophenyl | methyl |
| J424 | —C(O)CH₂CH₂— | 3-chlorophenyl | ethyl |
| J425 | —C(O)CH₂CH₂— | 3-chlorophenyl | phenyl |
| J426 | —C(O)CH₂CH₂— | 3-chlorophenyl | thiophen-2-yl |
| J427 | —C(O)CH₂CH₂— | 3-chlorophenyl | thiazol-2-yl |
| J428 | —C(O)CH₂CH₂— | 3-chlorophenyl | oxazol-2-yl |
| J429 | —C(O)CH₂CH₂— | 3-chlorophenyl | isoxazol-3-yl |
| J430 | —C(O)CH₂CH₂— | 3-methoxyphenyl | methyl |
| J431 | —C(O)CH₂CH₂— | 3-methoxyphenyl | ethyl |
| J432 | —C(O)CH₂CH₂— | 3-methoxyphenyl | phenyl |
| J433 | —C(O)CH₂CH₂— | 3-methoxyphenyl | thiophen-2-yl |
| J434 | —C(O)CH₂CH₂— | 3-methoxyphenyl | thiazol-2-yl |
| J435 | —C(O)CH₂CH₂— | 3-methoxyphenyl | oxazol-2-yl |
| J436 | —C(O)CH₂CH₂— | 3-methoxyphenyl | isoxazol-3-yl |
| J437 | —C(O)CH₂CH₂— | 3-fluorophenyl | methyl |
| J438 | —C(O)CH₂CH₂— | 3-fluorophenyl | ethyl |
| J439 | —C(O)CH₂CH₂— | 3-fluorophenyl | phenyl |
| J440 | —C(O)CH₂CH₂— | 3-fluorophenyl | thiophen-2-yl |
| J441 | —C(O)CH₂CH₂— | 3-fluorophenyl | thiazol-2-yl |
| J442 | —C(O)CH₂CH₂— | 3-fluorophenyl | oxazol-2-yl |
| J443 | —C(O)CH₂CH₂— | 3-fluorophenyl | isoxazol-3-yl |
| J444 | —C(O)CH₂CH₂— | 2,5-dimethylthiazol-4-yl | methyl |
| J445 | —C(O)CH₂CH₂— | 2,5-dimethylthiazol-4-yl | ethyl |
| J446 | —C(O)CH₂CH₂— | 2,5-dimethylthiazol-4-yl | phenyl |
| J447 | —C(O)CH₂CH₂— | 2,5-dimethylthiazol-4-yl | thiophen-2-yl |
| J448 | —C(O)CH₂CH₂— | 2,5-dimethylthiazol-4-yl | thiazol-2-yl |
| J449 | —C(O)CH₂CH₂— | 2,5-dimethylthiazol-4-yl | oxazol-2-yl |
| J450 | —C(O)CH₂CH₂— | 2,5-dimethylthiazol-4-yl | isoxazol-3-yl |
| J451 | —C(O)CH₂CH₂— | 2,4-dimethylthiazol-5-yl | methyl |
| J452 | —C(O)CH₂CH₂— | 2,4-dimethylthiazol-5-yl | ethyl |
| J453 | —C(O)CH₂CH₂— | 2,4-dimethylthiazol-5-yl | phenyl |
| J454 | —C(O)CH₂CH₂— | 2,4-dimethylthiazol-5-yl | thiophen-2-yl |
| J455 | —C(O)CH₂CH₂— | 2,4-dimethylthiazol-5-yl | thiazol-2-yl |
| J456 | —C(O)CH₂CH₂— | 2,4-dimethylthiazol-5-yl | oxazol-2-yl |
| J457 | —C(O)CH₂CH₂— | 2,4-dimethylthiazol-5-yl | isoxazol-3-yl |
| J458 | —C(O)CH₂CH₂— | 4-ethylthiazol-2-yl | methyl |
| J459 | —C(O)CH₂CH₂— | 4-ethylthiazol-2-yl | ethyl |
| J460 | —C(O)CH₂CH₂— | 4-ethylthiazol-2-yl | phenyl |
| J461 | —C(O)CH₂CH₂— | 4-ethylthiazol-2-yl | thiophen-2-yl |
| J462 | —C(O)CH₂CH₂— | 4-ethylthiazol-2-yl | thiazol-2-yl |
| J463 | —C(O)CH₂CH₂— | 4-ethylthiazol-2-yl | oxazol-2-yl |
| J464 | —C(O)CH₂CH₂— | 4-ethylthiazol-2-yl | isoxazol-3-yl |
| J465 | —C(O)CH₂CH₂— | 3-methyl-1,2,4-oxadiazol-5-yl | methyl |
| J466 | —C(O)CH₂CH₂— | 3-methyl-1,2,4-oxadiazol-5-yl | ethyl |
| J467 | —C(O)CH₂CH₂— | 3-methyl-1,2,4-oxadiazol-5-yl | phenyl |
| J468 | —C(O)CH₂CH₂— | 3-methyl-1,2,4-oxadiazol-5-yl | thiophen-2-yl |
| J469 | —C(O)CH₂CH₂— | 3-methyl-1,2,4-oxadiazol-5-yl | thiazol-2-yl |
| J470 | —C(O)CH₂CH₂— | 3-methyl-1,2,4-oxadiazol-5-yl | oxazol-2-yl |
| J471 | —C(O)CH₂CH₂— | 3-methyl-1,2,4-oxadiazol-5-yl | isoxazol-3-yl |

The compounds encompassed within the second aspect of Category I of the present disclosure can be prepared by the procedure outlined in Scheme II and described in Example 9 herein below.

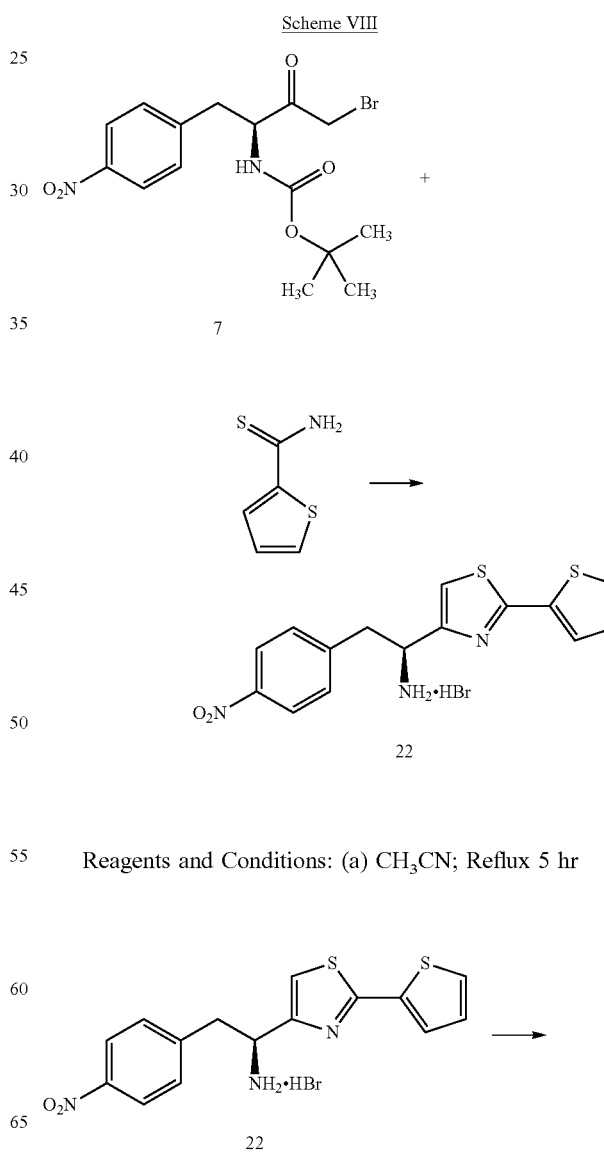

Scheme VIII

Reagents and Conditions: (a) CH₃CN; Reflux 5 hr

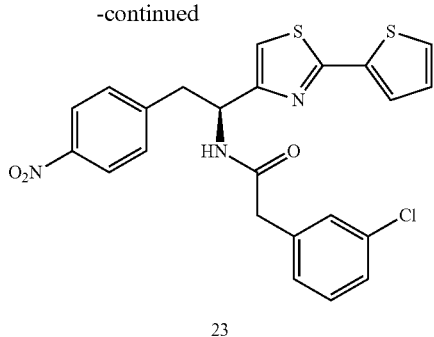

23

Reagents and Conditions: (b) (3-Cl)C$_6$H$_4$CO$_2$H, EDCI, HOBt, DIPEA, DMF; rt, 18 hr

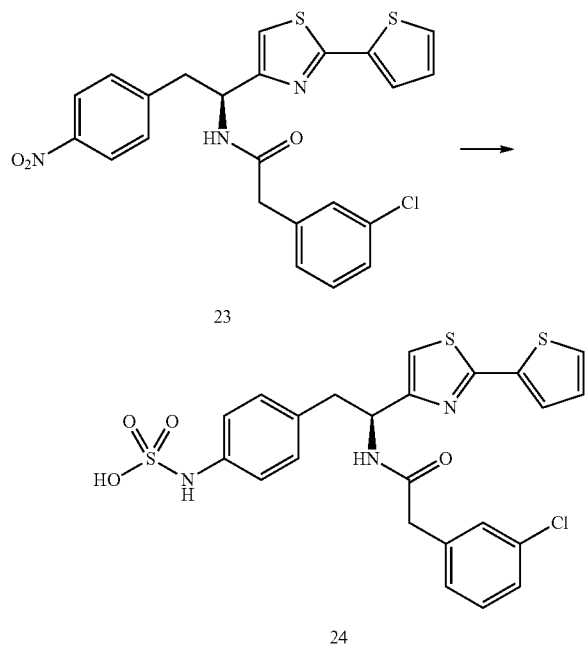

Reagents and Conditions: (c) (i) H$_2$:Pd/C, MeOH; (ii) SO$_3$-pyridine, NH$_4$OH, rt, 18 hr

EXAMPLE 9

44(S)-2-(2-(3-chlorophenyl)acetamido)-2-(2-(thiophen-2-yl)thiazol-4-yl)ethyl)phenylsulfamic acid (24)

Preparation of (S)-2-(4-nitrophenyl)-1-[(thiophen-2-yl)thiazol-4-yl]ethanamine hydrobromide salt (22): A mixture of (S)-tert-butyl 4-bromo-1-(4-nitrophenyl)-3-oxobutan-2-ylcarbamate, 7, (7.74 g, 20 mmol), and thiophen-2-carbothioic acid amide (3.14 g, 22 mmol) in CH$_3$CN (200 mL) is refluxed for 5 hours. The reaction mixture is cooled to room temperature and diethyl ether (50 mL) is added to the solution. The precipitate which forms is collected by filtration. The solid is dried under vacuum to afford 7.14 g (87% yield) of the desired product. ESI+ MS 332 (M+1).

Preparation of 2-(3-chlorophenyl)-N—{(S)-2-(4-nitrophenyl)-1-[2-(thiophen-2-yl)thiazol-4-yl]ethyl}acetamide (23): To a solution of 2-(4-nitrophenyl)-1-(2-thiophene2-ylthiazol-4-yl)ethylamine, 22, (0.41 g, 1 mmol) 3-chlorophenylacetic acid (0.170 g, 1 mmol) and 1-hydroxybenzotriazole (HOBt) (0.070 g, 0.50 mmol) in DMF (5 mL) at 0° C., is added 1-(3-dimethylaminopropyl)-3-ethylcarbodiimide (EDCI) (0.190 g, 1 mmol) followed by triethylamine (0.42 mL, 3 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.290 g (60% yield) of the desired product which is used without further purification. ESI– MS 482 (M–1).

Preparation of {4-[2-(3-chlorophenyl)acetylamino]-2-(2-thiophen-2-ylthiazol-4-yl)ethyl]phenyl}sulfamic acid (24): 2-(3-chlorophenyl)-N—{(S)-2-(4-nitrophenyl)-1-[2-(thiophene2-yl)thiazol-4-yl]ethyl}acetamide, 23, (0.290 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.157 g). The reaction is stirred at room temperature for 5 minutes after which a 7% solution of NH$_4$OH is added. The mixture is then concentrated and the resulting residue is purified by reverse phase chromatography to afford 0.078 g of the desired product as the ammonium salt. $^1$H NMR (CD3OD) δ 7.61 (d, 1H, J=3.6 Hz), 7.58 (d, 1H, J=5.1 Hz), 7.41-7.35 (m, 1H), 7.28-7.22 (m, 2H), 7.18-6.98 (m, 6H), 5.33 (t, 1H, J=6.6 Hz), 3.70 (d, 2H, J=3.9 Hz), 3.23 (1H, A of ABX, J=6.6, 13.8 Hz), 3.07 (1H, B of ABX, J=8.1, 13.5 Hz).

The following are non-limiting examples of compounds encompassed within the second aspect of Category V of the present disclosure.

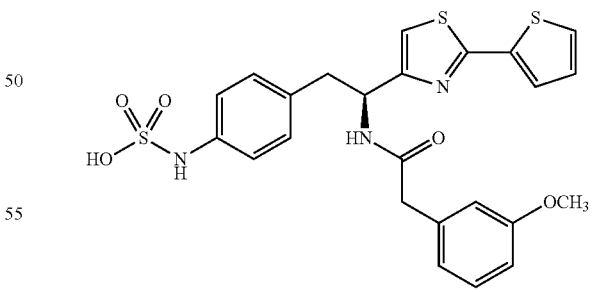

4-((S)-2-(2-(3-Methoxyphenyl)acetamido)-2-(2-(thiophene2-yl)thiazol-4-yl)ethyl)-phenylsulfamic acid: $^1$H NMR (CD3OD) δ 8.35 (d, 1H, J=8.7 Hz), 7.61-7.57 (m, 2H), 7.25-7.20 (m, 2H), 7.25-7.20 (m, 2H), 7.09 (s, 1H), 7.05 (d, 2H, J=4.2 Hz), 6.99 (d, 1H, J=8.7 Hz), 6.81 (d, 1H, J=7.8 Hz), 6.77 (s, 1H), 5.30-5.28 (m, 1H), 3.76 (s, 3H), 3.51 (s, 2H), 3.20 (1H, A of ABX, J=6.3, 13.6 Hz), 3.06 (1H, B of ABX, J=8.1, 13.8 Hz).

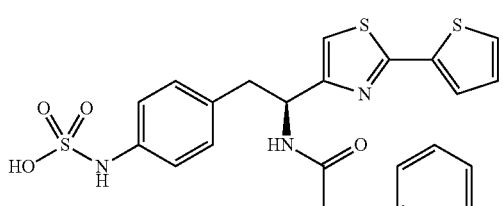

4-{(S)-2-(3-Phenylpropanamido)-2-[2-(thiophene2-yl)thiazol-4-yl]ethyl}-phenylsulfamic acid: $^1$H NMR (CD3OD) δ 8.30 (d, 1H, J=9 Hz), 7.61-7.56 (m, 2H), 7.26-7.14 (m, 7H), 7.12 (d, 1H, J=1.5 Hz), 7.09 (d, 1H, J=2.1 Hz), 6.89 (s, 1H), 5.28-5.26 (m, 1H), 3.18 (1H, A of ABX, J=6.2, 13.8 Hz), 2.96 (1H, B of ABX, J=8.4, 13.6 Hz).

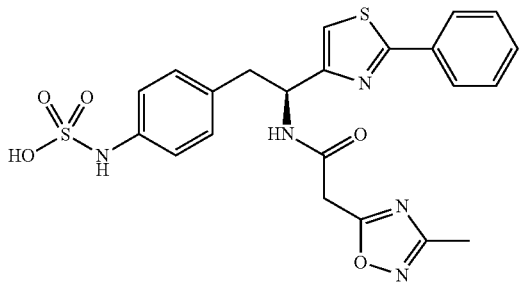

(S)-4-{2-[2-(3-Methyl-1,2,4-oxadiazol-5-yl)acetamido]-2-(2-phenylthiazol-4-yl)ethyl}phenylsulfamic acid: $^1$H NMR (CD$_3$OD): δ 7.98-7.95 (m, 2H), 7.48-7.46 (m, 3H), 7.23 (s, 1H), 7.09-7.05 (m, 4H), 5.33 (t, 1H, J=7.2 Hz), 3.33-3.06 (m, 2H), 2.35 (s, 3H).

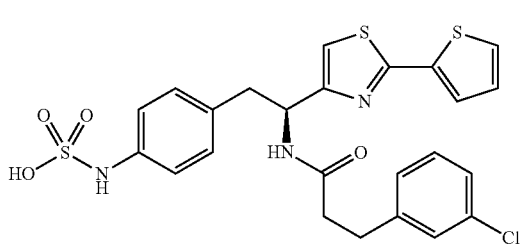 [SMILES: O=C(CCc1cccc(Cl)c1)N[C@@H](Cc1ccc(NS(=O)(=O)O)cc1)c1csc(-c2cccs2)n1]

4-{(S)-2-(3-(3-Chlorophenyl)propanamido)-2-[2-(thiophene2-yl)thiazol-4-yl]ethyl}phenylsulfamic acid: $^1$H NMR (CD$_3$OD) δ 7.61-7.56 (m, 3H), 7.22-7.14 (m, 6H), 7.08 (d, 1H), 7.00 (d, 1H, J=77.5 Hz), 6.870 (s, 1H), 5.25 (t, 1H, J=7.8 Hz), 3.18 (1H, A of ABX, J=6.6, 13.8 Hz), 2.97 (1H, B of ABX, J=7.8, 13.8 Hz), 2.87 (t, 2H, J=7.5 Hz), 2.51 (t, 2H, J=7.2 Hz).

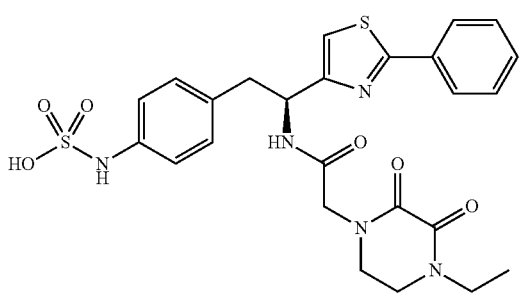 [SMILES: CCN1CCN(CC(=O)N[C@@H](Cc2ccc(NS(=O)(=O)O)cc2)c2csc(-c3ccccc3)n2)C(=O)C1=O]

4-{(S)-2-[2-(4-ethyl-2,3-dioxopiperazin-1-yl)acetamido]-2-[2-(thiophen-2-yl)thiazol-4-yl]ethyl}phenylsulfamic acid: $^1$H NMR (CD$_3$OD) δ 7.62 (d, 1H, J=3 Hz), 7.58 (d, 1H, J=15.6 Hz), 7.27 (s, 1H), 7.16 (t, 1H, J=1.5 Hz), 5.42-5.32 (m, 1H), 4.31 (d, 1H, J=15.6 Hz), 3.91 (d, 1H, J=15.9 Hz), 3.60-3.50 (m, 4H), 3.30-3.23 (m, 2H), 2.98 (1H, B of ABX, J=9.9, 13.8 Hz), 1.21 (t, 3H, J=6.9 Hz).

The third aspect of Category V of the present disclosure relates to compounds having the formula:

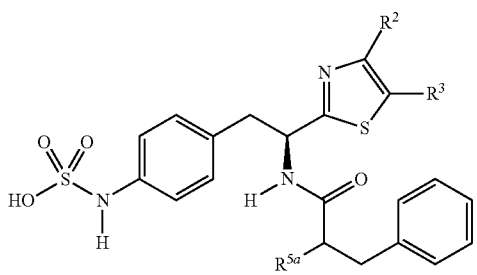

wherein the linking unit L comprises a phenyl unit, said linking group having the formula:

$R^1$ is hydrogen, $R^{6a}$ is phenyl, $R^{5a}$ is phenyl or substituted phenyl and non-limiting examples of the units $R^2$, $R^3$, and $R^{5a}$ are further exemplified herein below in Table XI.

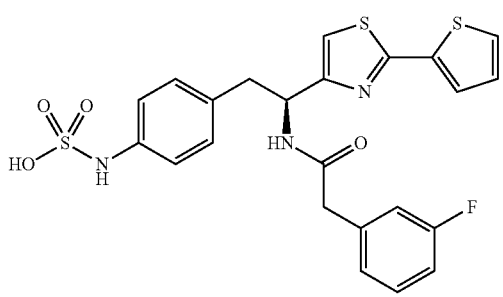

4-{(S)-2-[2-(3-Fluorophenyl)acetamido]-2-[2-(thiophen-2-yl)thiazol-4-yl]ethyl}phenylsulfamic acid: $^1$H NMR (CD$_3$OD) δ 7.61-7.57 (m, 2H), 7.32-7.28 (m, 1H), 7.19-7.16 (m, 2H), 7.08 (t, 1H, J=4.5 Hz), 7.02-6.95 (m, 6H), 5.29 (t, 1H, J=8.1 Hz), 3.53 (s, 2H), 3.22 (1H, A of ABX, J=6.6, 13.9 Hz), 3.06 (1H, B of ABX, J=8.4, 13.6 Hz).

TABLE XI

| No. | R² | R³ | R⁵ᵃ |
|---|---|---|---|
| K472 | methyl | hydrogen | phenyl |
| K473 | methyl | hydrogen | 2-fluorophenyl |
| K474 | methyl | hydrogen | 3-fluorophenyl |
| K475 | methyl | hydrogen | 4-fluorophenyl |
| K476 | methyl | hydrogen | 3,4-difluorophenyl |
| K477 | methyl | hydrogen | 2-chlorophenyl |
| K478 | methyl | hydrogen | 3-chlorophenyl |
| K479 | methyl | hydrogen | 4-chlorophenyl |
| K480 | methyl | hydrogen | 3,4-dichlorophenyl |
| K481 | methyl | hydrogen | 2-methoxyphenyl |
| K482 | methyl | hydrogen | 3-methoxyphenyl |
| K483 | methyl | hydrogen | 4-methoxyphenyl |
| K484 | ethyl | hydrogen | phenyl |
| K485 | ethyl | hydrogen | 2-fluorophenyl |
| K486 | ethyl | hydrogen | 3-fluorophenyl |
| K487 | ethyl | hydrogen | 4-fluorophenyl |
| K488 | ethyl | hydrogen | 3,4-difluorophenyl |
| K489 | ethyl | hydrogen | 2-chlorophenyl |
| K490 | ethyl | hydrogen | 3-chlorophenyl |
| K491 | ethyl | hydrogen | 4-chlorophenyl |
| K492 | ethyl | hydrogen | 3,4-dichlorophenyl |
| K493 | ethyl | hydrogen | 2-methoxyphenyl |
| K494 | ethyl | hydrogen | 3-methoxyphenyl |
| K495 | ethyl | hydrogen | 4-methoxyphenyl |

The compounds encompassed within the third aspect of Category V of the present disclosure can be prepared by the procedure outlined in Scheme IX and described in Example 10 herein below.

Scheme IX

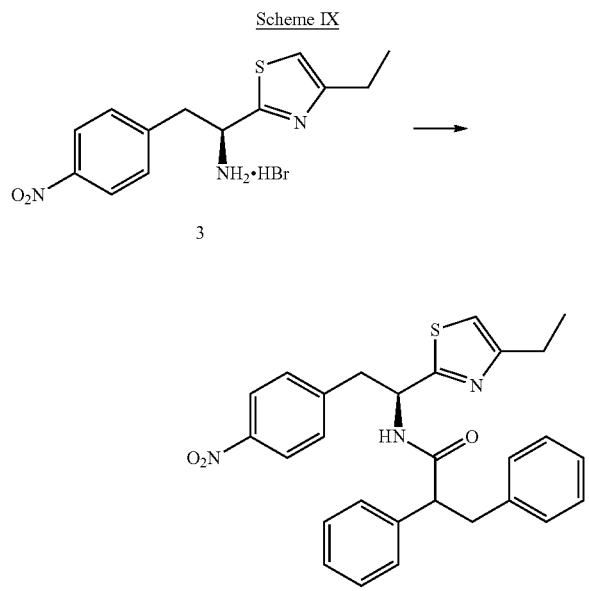

Reagents and Conditions: (a) Diphenylpropionic Acid, EDCI, HOBt, TEA, DMF; 0° C. to rt, 18 hr

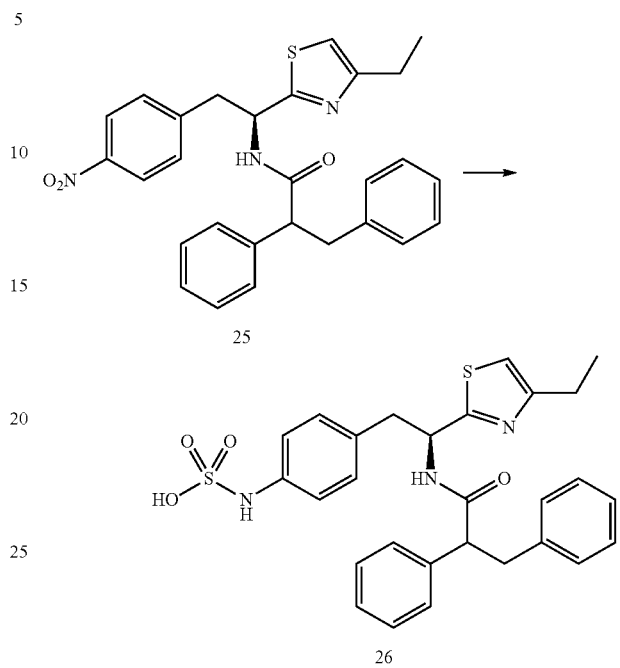

Reagents and Conditions: (b) (i) $H_2$:Pd/C, MeOH; (ii) $SO_3$-pyridine, $NH_4OH$; rt, 18 hr

EXAMPLE 10

(S)-4-(2-(2,3-Diphenylpropanamido)-2-(4-ethylthiazol-2-yl)ethyl)-phenylsulfamic acid (26)

Preparation of (S)—N-[1-(4-ethylthiazol-2-yl)-2-(4-nitrophenyl)ethyl]-2,3-diphenyl-propanamide (25): To a solution of 1-(S)-(4-ethylthiazol-2-yl)-2-(4-nitrophenyl)ethyl amine hydrobromide, 3, (0.95 g, 2.65 mmol), diphenylpropionic acid (0.60 g, 2.65 mmol) and 1-hydroxybenzotriazole (HOBt) (0.180 g, 1.33 mmol) in DMF (10 mL) at 0°, is added 1-(3-dimethylaminopropyl)-3-ethylcarbodiimide (EDCI) (0.502 g, 2.62 mmol) followed by triethylamine (1.1 mL, 7.95 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.903 g (70% yield) of the desired product which is used without further purification.

Preparation of (S)-4-(2-(2,3-diphenylpropanamido)-2-(4-ethylthiazol-2-yl)ethyl)phenylsulfamic acid (26) (S)—N-[1-(4-ethylthiazol-2-yl)-2-(4-nitrophenyl)ethyl]-2,3-diphenyl-propanamide, 25, (0.903 g) is dissolved in MeOH (10 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (30 mL) and treated with $SO_3$-pyridine (0.621 g). The reaction is stirred at room temperature for 5 minutes after which a 7% solution of NH₄OH is added. The mixture is then concentrated and the resulting residue is purified by reverse phase chromatography to afford 0.415 g of the desired product as the ammonium salt. ¹H NMR (CD₃OD) δ 8.59-8.52 (m, 1H), 7.37-7.04 (m, 9H), 6.97-6.93 (m, 1H), 6.89-6.85 (m, 2H), 5.36-5.32 (m, 1H), 3.91-3.83 (m, 1H), 3.29 (1H, A of ABX, obscured by solvent), 3.15 (1H, B of ABX, J=5.4, 33.8 Hz), 2.99-2.88 (m, 2H), 2.81-2.69 (m, 2H), 1.32-1.25 (m, 3H).

The precursors of many of the Z units which comprise the third aspect of Category V are not readily available. The following procedure illustrates an example of the procedure which can be used to provide different $R^{5a}$ units according to the present disclosure. Using the procedure outlined in Scheme X and described in Example 11 the artisan can make modifications without undue experimentation to achieve the $R^{5a}$ units encompassed by the present disclosure.

Scheme X

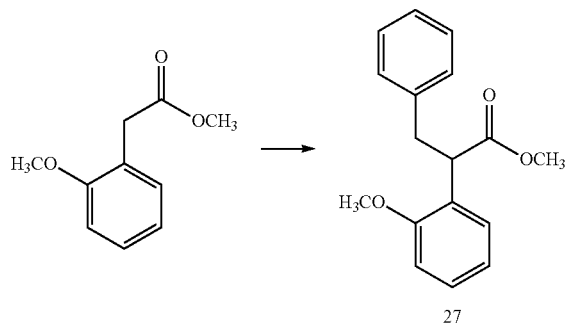

27

Reagents and Conditions: (a) Benzyl Bromide, LDA, THF; 0° C. to rt 18 hr

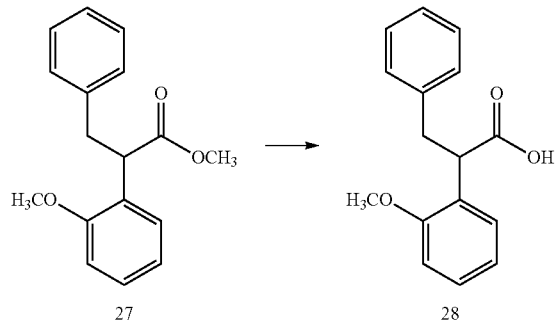 [SMILES: COC(=O)C(Cc1ccccc1)c1ccccc1OC ; COc1ccccc1C(Cc1ccccc1)C(=O)O]

27              28

Reagents and Conditions: (b) NaOH, THF/MeOH; rt, 18 hr

EXAMPLE 11

2-(2-Methoxyphenyl)-3-phenylpropanoic Acid (28)

Preparation of methyl 2-(2-methoxyphenyl)-3-phenylpropanoate (27): A 500 mL round-bottom flask is charged with methyl 2-(2-methoxyphenyl)acetate (8.496 g, 47 mmol, 1 eq) and THF (200 mL). The homogeneous mixture is cooled to 0° C. in an ice bath. Lithium diisopropyl amide (23.5 mL of a 2.0M solution in heptane/THF) is added, maintaining a temperature less than 3° C. The reaction is stirred 45 minutes at this reduced temperature. Benzyl bromide (5.6 mL, 47 mmol, 1 eq) is added dropwise. The reaction is allowed to gradually warm to room temperature and is stirred for 18 hours. The reaction is quenched with 1N HCl and extracted 3 times with equal portions of EtOAc. The combined extracts are washed with H₂O and brine, dried over Na₂SO₄, filtered, and concentrated. The residue is purified over silica to afford 4.433 g (35%) of the desired compound. ESI+ MS 293 (M+Na).

Preparation of 2-(2-methoxyphenyl)-3-phenylpropanoic acid (28): Methyl 2-(2-methoxyphenyl)-3-phenylpropanoate (4.433 g, 16 mmol, 1 eq) is dissolved in 100 mL of a 1:1 (v:v) mixture of THF and methanol. Sodium hydroxide (3.28 g, 82 mmol, 5 eq) is added and the reaction mixture is stirred 18 hours at room temperature. The reaction is then poured into H₂O and the pH is adjusted to 2 via addition of 1N HCl. A white precipitate forms which is removed by filtration. The resulting solution is extracted with 3 portion of diethyl ether. The extracts are pooled, washed with H₂O and brine, dried over Na₂SO₄, filtered, and concentrated in vacuo. The resulting residue is purified over silica to afford 2.107 g (51%) of the desired compound. ESI– MS 255 (M–1), 211 (M–CO₂H).

Intermediate 28 can be carried forward according to the procedure outlined in Scheme IX and described in Example 10 to produce the following compound according to the third aspect of Category V.

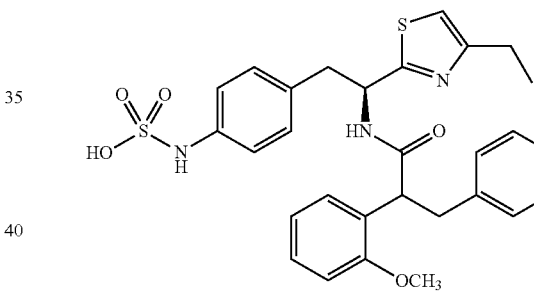

(S)-4-[2-(4-Ethylthiazol-2-yl)-2-{2-(2-methoxyphenyl)-3-phenylpropanamido]-ethyl}phenylsulfamic acid: ¹H NMR (CD₃OD) δ 7.32-7.12 (m, 7H), 7.05-7.02 (m, 1H), 6.99-6.83 (m, 4H), 6.80-6.75 (m, 2H), 5.35-5.31 (m, 1H), 4.31-4.26 (m, 1H), 3.75 (s, 3H), 3.20-2.90 (m, 4H), 2.79-2.74 (m, 2H), 1.32-1.25 (m, 3H).

The following are further non-limiting examples of compounds according to the third aspect of Category I of the present disclosure.

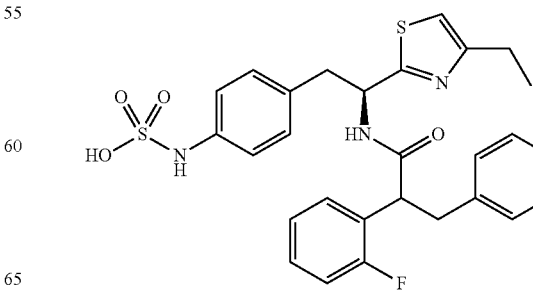

(S)-4-{2-(4-Ethylthiazol-2-yl)-2-[2-(3-fluorophenyl)-3-phenylpropanamido]-ethyl}phenylsulfamic acid: $^1$H NMR (CD$_3$OD) δ 7.33-6.87 (m, 14H), 5.39-5.25 (m, 1H), 3.95-3.83 (m, 1H), 3.31-3.10 (m, 1H), 3.05-2.88 (m, 2H), 2.80-2.70 (m, 2H), 1.32-1.23 (m, 3H). $^{19}$F NMR δ 47.59.

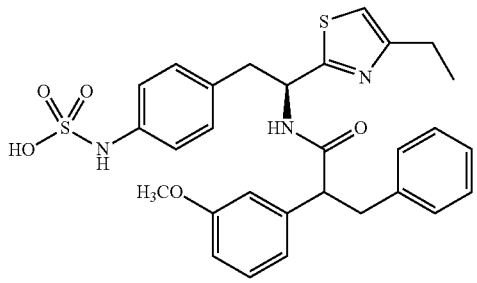 [SMILES: CCc1csc([C@H](Cc2ccc(NS(=O)(=O)O)cc2)NC(=O)C(Cc2ccccc2)c2cccc(OC)c2)n1]

(S)-4-{2-(4-Ethylthiazol-2-yl)-2-[2-(3-methoxyphenyl)-3-phenylpropanamido]-ethyl}phenylsulfamic acid: $^1$H NMR (CD$_3$OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

The fourth aspect of Category V of the present disclosure relates to compounds having the formula:

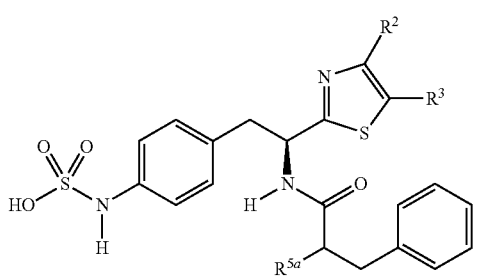

wherein the linking unit L comprises a phenyl unit, said linking group having the formula:

—C(O)[(CR$^{5a}$H)][(CR$^{6a}$H)]—

R$^1$ is hydrogen, R$^{6a}$ is phenyl, R$^{5a}$ is substituted or unsubstituted heteroaryl and the units R$^2$, R$^3$, and R$^{5a}$ are further exemplified herein below in Table XII.

TABLE XII

| No. | R$^2$ | R$^3$ | R$^{5a}$ |
|---|---|---|---|
| L496 | methyl | hydrogen | 3-methyl-1,2,4-oxadiazol-5-yl |
| L497 | methyl | hydrogen | thiophen-2-yl |
| L498 | methyl | hydrogen | thiazol-2-yl |
| L499 | methyl | hydrogen | oxazol-2-yl |
| L500 | methyl | hydrogen | isoxazol-3-yl |
| L501 | ethyl | hydrogen | 3-methyl-1,2,4-oxadiazol-5-yl |
| L502 | ethyl | hydrogen | thiophen-2-yl |
| L503 | ethyl | hydrogen | thiazol-2-yl |
| L504 | ethyl | hydrogen | oxazol-2-yl |
| L505 | ethyl | hydrogen | isoxazol-3-yl |
| L506 | ethyl | methyl | 3-methyl-1,2,4-oxadiazol-5-yl |
| L507 | ethyl | methyl | thiophen-2-yl |
| L508 | ethyl | methyl | thiazol-2-yl |
| L509 | ethyl | methyl | oxazol-2-yl |
| L510 | ethyl | methyl | isoxazol-3-yl |
| L511 | thiophen-2-yl | hydrogen | 3-methyl-1,2,4-oxadiazol-5-yl |
| L512 | thiophen-2-yl | hydrogen | thiophen-2-yl |
| L513 | thiophen-2-yl | hydrogen | thiazol-2-yl |
| L514 | thiophen-2-yl | hydrogen | oxazol-2-yl |
| L515 | thiophen-2-yl | hydrogen | isoxazol-3-yl |
| L516 | isoxazol-3-yl | hydrogen | 3-methyl-1,2,4-oxadiazol-5-yl |
| L517 | isoxazol-3-yl | hydrogen | thiophen-2-yl |
| L518 | isoxazol-3-yl | hydrogen | thiazol-2-yl |
| L519 | isoxazol-3-yl | hydrogen | oxazol-2-yl |
| L520 | isoxazol-3-yl | hydrogen | isoxazol-3-yl |

The compounds encompassed within the fourth aspect of Category V of the present disclosure can be prepared by the procedure outlined in Scheme V and described in Example 5 herein below.

Scheme XI

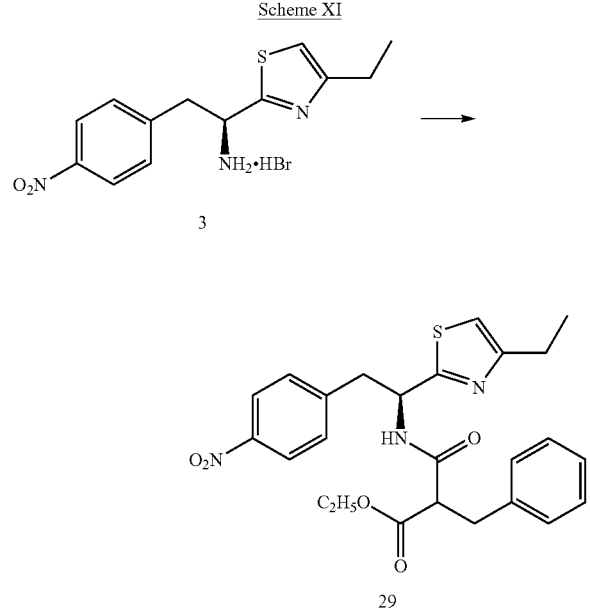

Reagents and Conditions: (a) 2-benzyl-3-ethoxy-3-oxopropanoic Acid, EDCI, HOBt, DIPEA, DMF; rt, 18 hr

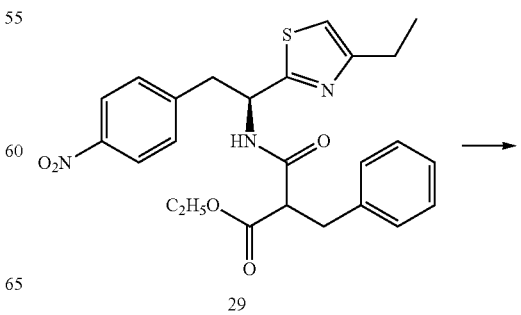

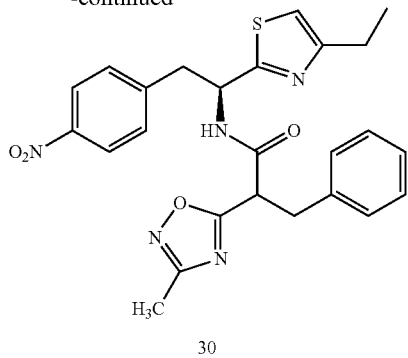

30

Reagents and Conditions: (b) CH₃C(=NOH)NH₂, K₂CO₃, Toluene; Reflux, 18 hr

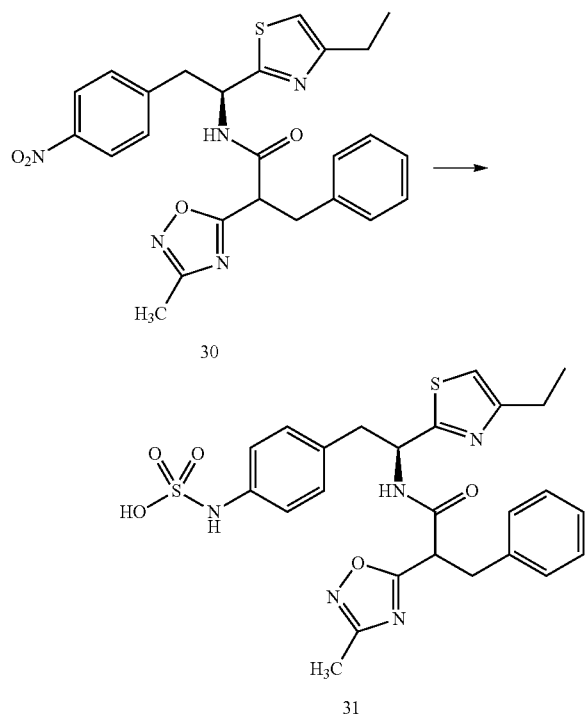

Reagents and Conditions: (c) (i) tin (II) chloride, EtOH; (ii) SO₃-pyridine, NH₄OH; rt, 18 hr

EXAMPLE 12

4-{(S)-2-(4-Ethylthiazol-2-yl)-2-[2-(3-methyl-1,2,4-oxadiazol-5-yl)-3-phenylpropanamido]ethyl}phenylsulfamic acid (31)

Preparation of ethyl-2-benzyl-3-[(S)-1-(4-ethylthiazol-2-yl)-2-(4-nitrophenyl)-ethylamino]-3-oxopropanoate (29): To a solution of 1-(S)-(4-ethylthiazol-2-yl)-2-(4-nitrophenyl)ethyl amine hydrobromide, 3, (0.406 g, 1.13 mmol), 2-benzyl-3-ethoxy-3-oxopropanoic acid (0.277 g) and 1-hydroxybenzotriazole (HOBt) (0.191 g, 1.41 mmol) in DMF (10 mL) at 0°, is added 1-(3-dimethylaminopropyl)-3-ethylcarbodiimide (EDCI) (0.240 g, 1.25 mmol) followed by diisopropylethylamine (DIPEA) (0.306 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.169 g (31% yield) of the desired product which is used without further purification.

Preparation of N—[(S)-1-(4-ethylthiazol-2-yl)-2-(4-nitrophenyl)ethyl]-2-(3-methyl-1,2,4-oxadiazol-5-yl)-3-phenylpropanamide (30): Ethyl 2-benzyl-3-((S)-1-(4-ethylthiazol-2-yl)-2-(4-nitrophenyl)ethylamino)-3-oxopropanoate is dissolved in toluene (5 mL) and heated to reflux. Potassium carbonate (80 mg) and acetamide oxime (43 mg) are added. and treated with 80 mg potassium carbonate and 43 mg acetamide oxime at reflux. The reaction mixture is cooled to room temperature, filtered and concentrated. The residue is chromatographed over silica to afford 0.221 g (94%) of the desired product as a yellow oil.

Preparation of 4-{(S)-2-(4-ethylthiazol-2-yl)-2-[2-(3-methyl-1,2,4-oxadiazol-5-yl)-3-phenylpropanamido]ethyl}phenylsulfamic acid (31): N—[(S)-1-(4-ethylthiazol-2-yl)-2-(4-nitrophenyl)ethyl]-2-(3-methyl-1,2,4-oxadiazol-5-yl)-3-phenylpropanamide, 30, (0.221 g) and tin (II) chloride (507 mg, 2.2 mmol) are dissolved in EtOH (25 mL) and the solution is brought to reflux 4 hours. The solvent is removed in vacuo and the resulting residue is dissolved in EtOAc. A saturated solution of NaHCO₃ (50 mL) is added and the solution is stirred 1 hour. The organic layer is separated and the aqueous layer extracted twice with EtOAc. The combined organic layers are dried (Na₂SO₄), filtered and concentrated to a residue which is dissolved in pyridine (0.143 g) and treated with SO₃-pyridine (0.143 g). The reaction is stirred at room temperature for 5 minutes after which a 7% solution of NH₄OH is added. The mixture is then concentrated and the resulting residue is purified by reverse phase chromatography to afford 0.071 g of the desired product as the ammonium salt. ¹H NMR (CD₃OD): δ 7.29-6.87 (m, 10H), 5.38-5.30 (m, 1H), 4.37-4.30 (m, 1H), 3.42-2.74 (m, 6H), 2.38-2.33 (m, 3H), 1.34-1.28 (m, 3H).

Category VI of the present disclosure relates to 2-(thiazol-2-yl) compounds having the formula:

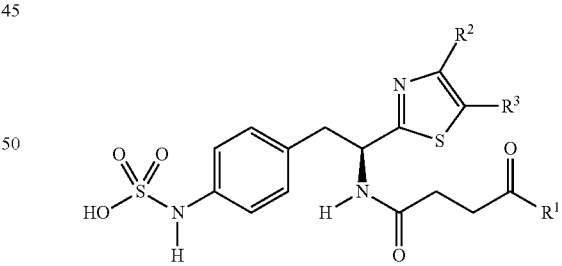

wherein R¹, R², R³, and L are further defined herein in Table XIII herein below.

TABLE XIII

| No. | R² | R³ | R¹ |
| --- | --- | --- | --- |
| M521 | ethyl | hydrogen | thiophen-2-yl |
| M522 | ethyl | hydrogen | thiazol-2-yl |
| M523 | ethyl | hydrogen | oxazol-2-yl |
| M524 | ethyl | hydrogen | isoxazol-3-yl |
| M525 | ethyl | hydrogen | imidazol-2-yl |

TABLE XIII-continued

| No. | R² | R³ | R¹ |
|---|---|---|---|
| M526 | ethyl | hydrogen | isoxazol-3-yl |
| M527 | ethyl | hydrogen | oxazol-4-yl |
| M528 | ethyl | hydrogen | isoxazol-4-yl |
| M529 | ethyl | hydrogen | thiophen-4-yl |
| M530 | ethyl | hydrogen | thiazol-4-yl |
| M531 | ethyl | methyl | methyl |
| M532 | ethyl | methyl | ethyl |
| M533 | ethyl | methyl | propyl |
| M534 | ethyl | methyl | iso-propyl |
| M535 | ethyl | methyl | butyl |
| M536 | ethyl | methyl | phenyl |
| M537 | ethyl | methyl | benzyl |
| M538 | ethyl | methyl | 2-fluorophenyl |
| M539 | ethyl | methyl | 3-fluorophenyl |
| M540 | ethyl | methyl | 4-fluorophenyl |
| M541 | phenyl | hydrogen | methyl |
| M542 | phenyl | hydrogen | ethyl |
| M543 | phenyl | hydrogen | propyl |
| M544 | phenyl | hydrogen | iso-propyl |
| M545 | phenyl | hydrogen | butyl |
| M546 | phenyl | hydrogen | phenyl |
| M547 | phenyl | hydrogen | benzyl |
| M548 | phenyl | hydrogen | 2-fluorophenyl |
| M549 | phenyl | hydrogen | 3-fluorophenyl |
| M550 | phenyl | hydrogen | 4-fluorophenyl |
| M551 | thiophen-2-yl | hydrogen | methyl |
| M552 | thiophen-2-yl | hydrogen | ethyl |
| M553 | thiophen-2-yl | hydrogen | propyl |
| M554 | thiophen-2-yl | hydrogen | iso-propyl |
| M555 | thiophen-2-yl | hydrogen | butyl |
| M556 | thiophen-2-yl | hydrogen | phenyl |
| M557 | thiophen-2-yl | hydrogen | benzyl |
| M558 | thiophen-2-yl | hydrogen | 2-fluorophenyl |
| M559 | thiophen-2-yl | hydrogen | 3-fluorophenyl |
| M560 | thiophen-2-yl | hydrogen | 4-fluorophenyl |

The compounds encompassed within Category VI of the present disclosure can be prepared by the procedure outlined in Scheme XII and described in Example 13 herein below.

Scheme VI

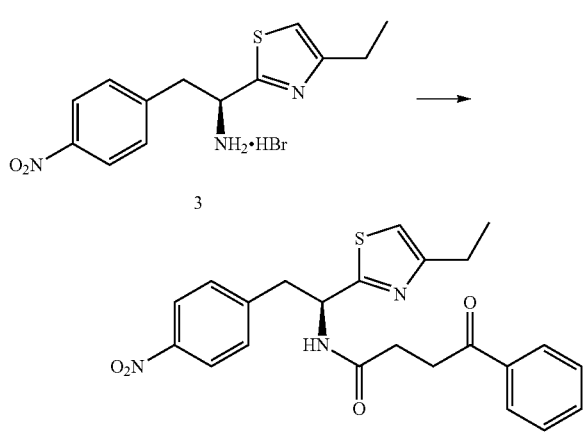

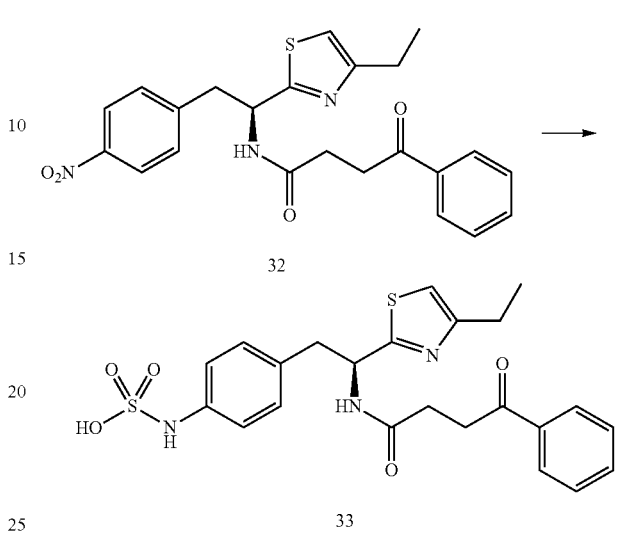

Reagents and Conditions: (a) 3-benzoylpropionic Acid, SOCl₂, N-methyl imidazole, CH₂Cl₂; rt, 18 hr Reagents and Conditions: (b) (i) H₂:Pd/C, MeOH; (ii) SO₃-pyridine, NH₄OH

EXAMPLE 13

(S)-4-[2-(4-Ethylthiazol-2-yl)-2-(4-oxo-4-phenylbutanamido)ethyl]-phenylsulfamic acid (33)

Preparation of (S)—N-[1-(4-ethylthiazol-2-yl)-2-(4-nitrophenyl)ethyl]-4-oxo-4-phenylbutanamide (32): 3-Benzoylpropionic acid (0.250 g) is dissolved in CH₂Cl₂ (5 mL), N-methyl imidazole (0.333 mL) is added and the resulting solution is cooled to 0° C. after which a solution of thionyl chloride (0.320 g) in CH₂Cl₂ (2 mL) is added dropwise. After 0.5 hours (S)-1-(4-ethylthiazol-2-yl)-2-(4-nitrophenyl)ethanamine, 3, (0.388 g) is added. The reaction is stirred for 18 hours at room temperature and then concentrated in vacuo. The resulting residue is dissolved in EtOAc and washed with 1N HCl and brine. The solution is dried over Na₂SO₄, filtered, and concentrated and the crude material purified over silica to afford 0.415 g of the desired product.

Preparation of (S)-4-[2-(4-ethylthiazol-2-yl)-2-(4-oxo-4-phenylbutanamido)-ethyl]phenylsulfamic acid (33): (S)—N-[1-(4-ethylthiazol-2-yl)-2-(4-nitrophenyl)ethyl]-2,3-diphenyl-propanamide, 32, (0.2 g) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (5 mL) and treated with SO₃-pyridine (0.153 g). The reaction is stirred at room temperature for 5 minutes after which a 7% solution of NH₄OH is added. The mixture is then concentrated and the resulting residue is purified by reverse phase chromatography to afford 0.090 g of the desired product as the ammonium salt. $^1$H NMR (CD₃OD) δ 8.68 (d, 1H, J=8.2 Hz), 8.00 (d, 2H, J=7.2 Hz), 7.80-7.50 (m, 3H), 7.12 (s, 4H), 7.03 (s, 1H), 5.46-5.38 (m, 1H), 3.29-3.14 (m, 2H), 3.06-2.99 (m, 2H), 2.83 (q, 2H, J=7.5 Hz), 2.69-2.54 (m, 2H), 1.33 (t, 3H, J=7.5 Hz).

The following are non-limiting examples of compounds encompassed within Category II of the present disclosure. The intermediate nitro compounds of the following can be prepared by coupling the appropriate 4-oxo-carboxcylic acid with intermediate 3 under the conditions described herein above for the formation of intermediate 4 of scheme I.

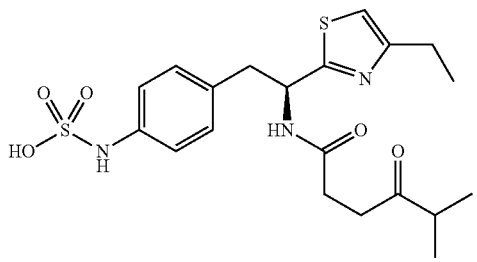 [SMILES: CCc1csc([C@H](Cc2ccc(NS(=O)(=O)O)cc2)NC(=O)CCC(=O)C(C)C)n1]

(S)-4-(2-(4-Ethylthiazol-2-yl)-2-(5-methyl-4-oxohexanamido)ethyl)phenylsulfamic acid: ¹H NMR (CD₃OD) δ 8.59 (d, 1H, J=8.1 Hz), 7.14 (s, 4H), 7.08 (t, 1H, J=13.0 Hz), 5.40-5.35 (m, 1H), 3.37-3.27 (m, 2H), 3.04-2.97 (m, 1H), 2.83-2.61 (m, 4H), 2.54-2.36 (m, 3H), 1.33 (t, 2H, J=7.3 Hz), 1.09 (dd, 6H, J=7.0, 2.2 Hz).

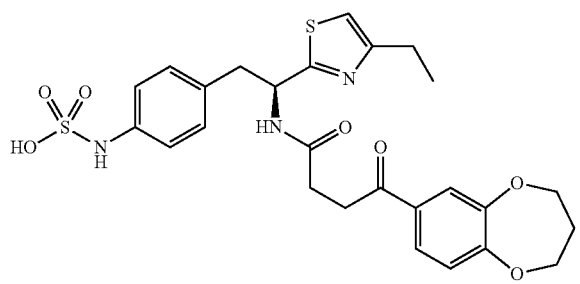 [SMILES: CCc1csc([C@H](Cc2ccc(NS(=O)(=O)O)cc2)NC(=O)CCC(=O)c2ccc3c(c2)OCCCO3)n1]

(S)-4-{2-[4-(3,4-Dihydro-2H-benzo[b][1,4]dioxepin-7-yl)-4-oxobutanamido]-2-(4-ethylthiazol-2-yl)ethyl}phenylsulfamic acid: ¹H NMR (CD₃OD) δ 8.64 (d, 1H, J=8.4 Hz), 7.60 (d, 2H, J=10.6 Hz), 7.11 (s, 3H), 7.04 (d, 2H, J=5.5 Hz), 5.42-5.40 (m, 1H), 4.30-4.22 (m, 4H), 3.20-2.98 (m, 4H), 2.82 (q, 2H, J=7.3 Hz), 2.67-2.48 (m, 2H), 2.23 (t, 2H, J=5.5 Hz), 1.32 (t, 3H, J=7.3 Hz).

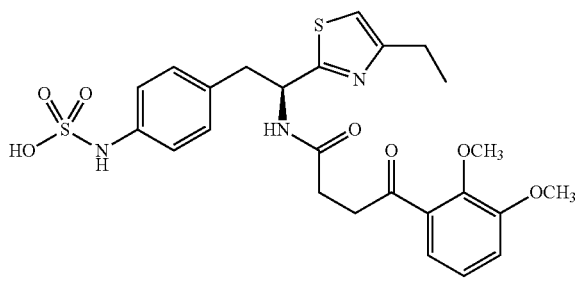 [SMILES: CCc1csc([C@H](Cc2ccc(NS(=O)(=O)O)cc2)NC(=O)CCC(=O)c2cccc(OC)c2OC)n1]

(S)-4-{2-[4-(2,3-Dimethoxyphenyl)-4-oxobutanamido]-2-(4-ethylthiazol-2-yl)ethyl}phenylsulfamic acid: ¹H NMR (CD₃OD), δ 8.64 (d, 1H, J=8.1 Hz), 7.21-7.11 (m, 7H), 7.02 (s, 1H), 5.42 (q, 1H, J=5.9 Hz), 3.90 (d, 3H, J=3.3 Hz), 3.88 (d, 3H, J=2.9 Hz), 3.22-3.18 (m, 2H), 3.07-2.99 (m, 2H), 2.83 (q, 2H, J=7.3 Hz), 2.63-2.54 (m, 2H), 1.34 (t, 3H, J=7.69 Hz).

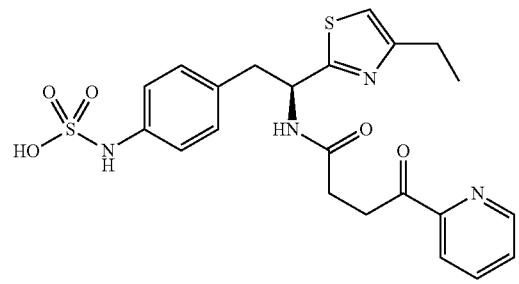 [SMILES: CCc1csc([C@H](Cc2ccc(NS(=O)(=O)O)cc2)NC(=O)CCC(=O)c2ccccn2)n1]

(S)-4-{2-(4-Ethylthiazol-2-yl)-2-[4-oxo-4-(pyridin-2-yl)butanamido]ethyl}-phenylsulfamic acid: ¹H NMR (CD₃OD) δ 8.60 (d, 1H, J=12.8 Hz), 7.91-7.81 (m, 2H), 7.48-7.44 (m, 1H), 7.22-7.21 (m, 1H), 6.99 (s, 3H), 6.91 (s, 1H), 5.30 (q, 1H, J=5.4 Hz), 3.36 (q, 2H, J=7.0 Hz), 3.21-3.15 (m, 1H), 2.91-2.85 (m, 1H), 2.74 (q, 2H, J=10.4 Hz), 2.57-2.50 (m, 2H), 1.20 (t, 3H, J=7.5 Hz).

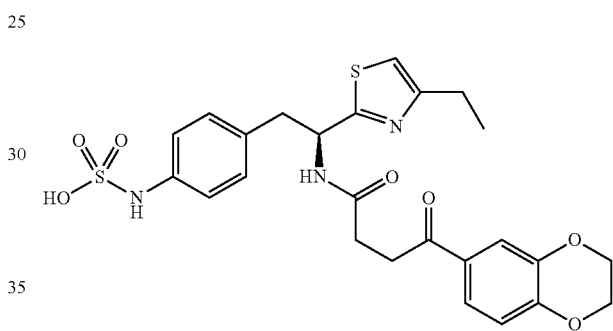

(S)-4-{2-[4-(2,3-dihydrobenzo[b][1,4]dioxin-6-yl)-4-oxobutanamido]-2-(4-ethylthiazol-2-yl)ethyl}phenylsulfamic acid: ¹H NMR (CD₃OD) δ 7.52-7.47 (m, 2H), 7.11 (s, 4H), 7.03 (s, 1H), 6.95 (d, 1H, J=8.4 Hz), 5.41 (q, 1H, J=3.7 Hz), 4.31 (d, 4H, J=5.5 Hz), 3.24-3.12 (m, 2H), 3.06-2.98 (m, 2H), 2.83 (q, 2H, J=7.3 Hz), 2.62-2.53 (m, 2H), 1.33 (t, 3H, J=7.3 Hz).

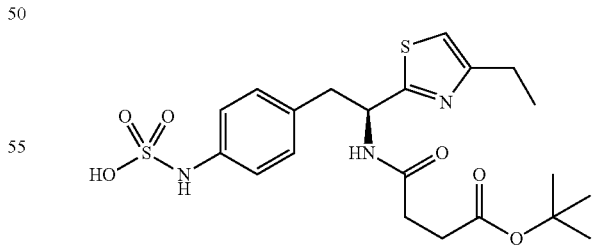

(S)-4-[2-(4-tert-butoxy-4-oxobutanamido)-2-(4-ethylthiazol-2-yl)ethyl]phenylsulfamic acid: ¹H NMR (CD₃OD), δ 7.10 (s 4H), 7.02 (s, 1H), 5.41 (q, 1H, J=3.7 Hz), 3.30-3.25 (m, 1H), 3.06-2.99 (m, 1H), 2.83 (q, 2H, J=7.3 Hz), 2.52-2.40 (m, 4H), 1.42 (s, 9H), 1.33 (t, 3H, J=7.3 Hz).

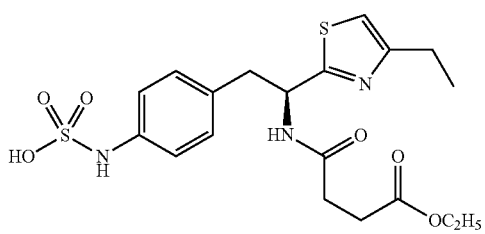 [SMILES: CCOC(=O)CCC(=O)N[C@@H](Cc1ccc(NS(=O)(=O)O)cc1)c1nc(CC)cs1]

(S)-4-[2-(4-ethoxy-4-oxobutanamido)-2-(4-ethylthiazol-2-yl)ethyl]phenylsulfamic acid: $^1$H NMR (CD$_3$OD) δ 8.62 (d, 1H, J=8.4 Hz), 7.10 (s, 4H), 7.02 (s, 1H), 5.40 (q, 1H, 3.7 Hz), 4.15 (q, 2H, J=7.3 Hz), 3.28-3.25 (m, 1H), 3.05-3.02 (m, 1H), 2.82 (q, 2H, J=4.4 Hz), 2.54-2.48 (m, 2H), 1.33 (t, 3H, J=7.3 Hz), 1.24 (t, 3H, J=7.0 Hz).

The first aspect of Category VII of the present disclosure relates to 2-(thiazol-2-yl) compounds having the formula:

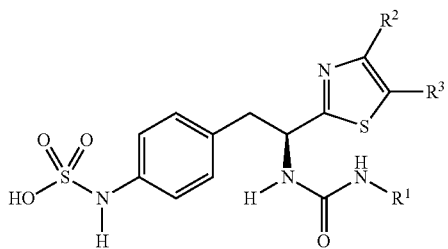

wherein non-limiting examples of $R^1$, $R^2$, and $R^3$ are further described herein below in Table XIV.

TABLE XIV

| No. | $R^2$ | $R^3$ | $R^1$ |
|---|---|---|---|
| N561 | methyl | hydrogen | phenyl |
| N562 | methyl | hydrogen | benzyl |
| N563 | methyl | hydrogen | 2-fluorophenyl |
| N564 | methyl | hydrogen | 3-fluorophenyl |
| N565 | methyl | hydrogen | 4-fluorophenyl |
| N566 | methyl | hydrogen | 2-chlorophenyl |
| N567 | methyl | hydrogen | 3-chlorophenyl |
| N568 | methyl | hydrogen | 4-chlorophenyl |
| N569 | ethyl | hydrogen | phenyl |
| N570 | ethyl | hydrogen | benzyl |
| N571 | ethyl | hydrogen | 2-fluorophenyl |
| N572 | ethyl | hydrogen | 3-fluorophenyl |
| N573 | ethyl | hydrogen | 4-fluorophenyl |
| N574 | ethyl | hydrogen | 2-chlorophenyl |
| N575 | ethyl | hydrogen | 3-chlorophenyl |
| N576 | ethyl | hydrogen | 4-chlorophenyl |
| N577 | thiene-2-yl | hydrogen | phenyl |
| N578 | thiene-2-yl | hydrogen | benzyl |
| N579 | thiene-2-yl | hydrogen | 2-fluorophenyl |
| N580 | thiene-2-yl | hydrogen | 3-fluorophenyl |
| N581 | thiene-2-yl | hydrogen | 4-fluorophenyl |
| N582 | thiene-2-yl | hydrogen | 2-chlorophenyl |
| N583 | thiene-2-yl | hydrogen | 3-chlorophenyl |
| N584 | thiene-2-yl | hydrogen | 4-chlorophenyl |

The compounds encompassed within Category VII of the present disclosure can be prepared by the procedure outlined in Scheme XIII and described in Example 14 herein below.

Scheme XIII

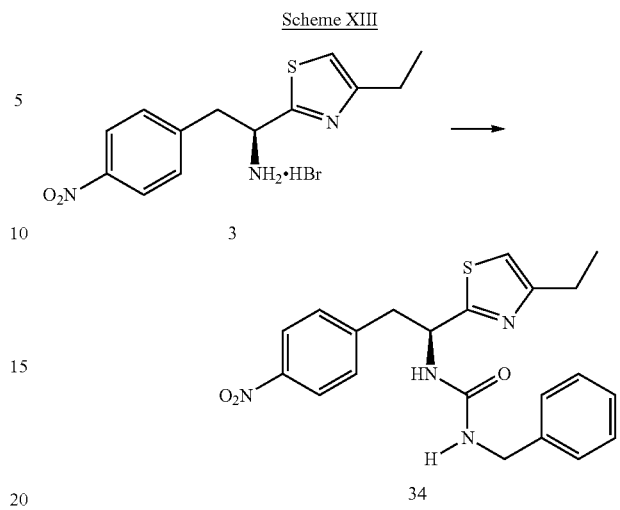

Reagents and Conditions: (a) Benzyl Isocyanate, TEA, CH$_2$Cl$_2$; Rt, 18 hr

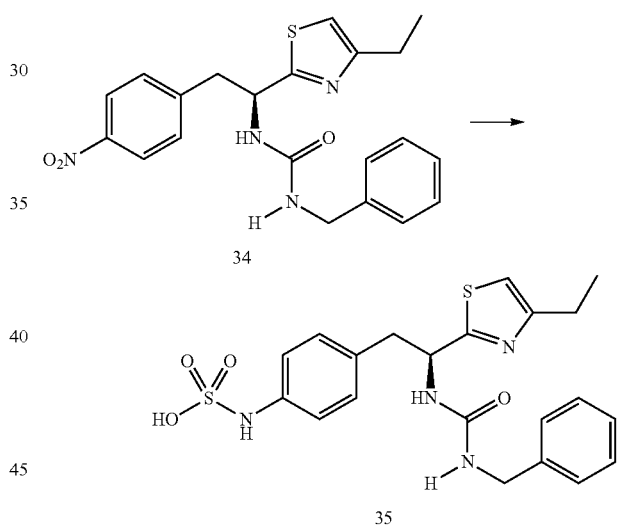

Reagents and Conditions: (b) (i) H$_2$:Pd/C, MeOH; (ii) SO$_3$-Pyridine, NH$_4$OH

EXAMPLE 14

(S)-4-(2-(3-Benzylureido)-2-(4-ethylthiazol-2-yl)ethyl)phenylsulfamic Acid (35)

Preparation of (S)-1-benzyl-3-[1-(4-ethylthiazol-2-yl)-2-(4-nitrophenyl)ethyl]urea (34): To a solution of 1-(S)-(4-ethylthiazol-2-yl)-2-(4-nitrophenyl)ethyl amine hydrobromide, 3, (0.360 g, 1 mmol) and Et$_3$N (0.42 mL, 3 mmol) in 10 mL CH$_2$Cl$_2$ is added benzyl isocyanate (0.12 mL, 1 mmol). The mixture is stirred at room temperature for 18 hours. The product is isolated by filtration to afford 0.425 g (96% yield) of the desired product which is used without further purification.

Preparation of (S)-4-(2-(3-benzylureido)-2-(4-ethylthiazol-2-yl)ethyl)phenylsulfamic acid (35): (S)-1-benzyl-3-[1-(4-ethylthiazol-2-yl)-2-(4-nitrophenyl)ethyl]urea, 34, (0.425 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.220 g). The reaction is stirred at room temperature for 5 minutes after which a 7% solution of NH$_4$OH is added. The mixture is then concentrated and the resulting residue is purified by reverse phase chromatography to afford 0.143 g of the desired product as the ammonium salt. $^1$H NMR (CD$_3$OD) δ 7.32-7.30 (m, 2H), 7.29-7.22 (m, 3H), 7.12-7.00 (m, 4H), 6.84 (d, 1H, J=8.1 Hz), 5.35-5.30 (m, 1H), 4.29 (s, 2H), 3.27-3.22 (m, 3H), 3.11-3.04 (m, 3H), 2.81 (q, 2H, J=10.2, 13.0 Hz), 1.31 (t, 3H, J=4.5 Hz).

The following is a non-limiting examples of compounds encompassed within the first aspect of Category VII of the present disclosure.

4-{[(S)-2-(2-Ethylthiazol-4-yl)-2-(3-(R)-methoxy-1-oxo-3-phenylpropan-2-yl)ureido]ethyl}phenylsulfamic acid: $^1$H NMR (CD$_3$OD) δ 7.36-7.26 (m, 3H), 7.19-7.17 (m, 2H), 7.10-7.06 (m, 2H), 6.90-6.86 (m, 3H), 5.12-5.06 (m, 1H), 4.60-4.55 (m, 1H), 3.69 (s, 3H) 3.12-2.98 (m, 6H), 1.44-1.38 (m, 3H).

The second aspect of Category VII of the present disclosure relates to 2-(thiazol-4-yl) compounds having the formula:

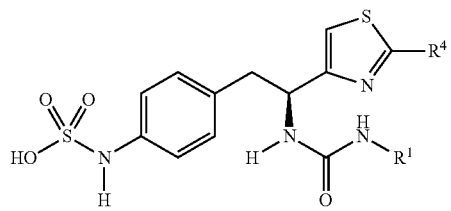

wherein non-limiting examples of R$^1$ and R$^4$ are further described herein below in Table XV.

TABLE XV

| No. | R$^1$ | R$^4$ |
|---|---|---|
| O585 | methyl | methyl |
| O586 | ethyl | methyl |
| O587 | n-propyl | methyl |
| O588 | iso-propyl | methyl |
| O589 | phenyl | methyl |
| O590 | benzyl | methyl |
| O591 | 2-fluorophenyl | methyl |
| O592 | 2-chlorophenyl | methyl |
| O593 | thiophen-2-yl | methyl |
| O594 | thiazol-2-yl | methyl |
| O595 | oxazol-2-yl | methyl |
| O596 | isoxazol-3-yl | methyl |
| O597 | methyl | ethyl |
| O598 | ethyl | ethyl |
| O599 | n-propyl | ethyl |
| O600 | iso-propyl | ethyl |
| O601 | phenyl | ethyl |
| O602 | benzyl | ethyl |
| O603 | 2-fluorophenyl | ethyl |
| O604 | 2-chlorophenyl | ethyl |
| O605 | thiophen-2-yl | ethyl |
| O606 | thiazol-2-yl | ethyl |
| O607 | oxazol-2-yl | ethyl |

TABLE XV-continued

| No. | R$^1$ | R$^4$ |
|---|---|---|
| O608 | isoxazol-3-yl | ethyl |
| O609 | methyl | thiophen-2-yl |
| O610 | ethyl | thiophen-2-yl |
| O611 | n-propyl | thiophen-2-yl |
| O612 | iso-propyl | thiophen-2-yl |
| O613 | phenyl | thiophen-2-yl |
| O614 | benzyl | thiophen-2-yl |
| O615 | 2-fluorophenyl | thiophen-2-yl |
| O616 | 2-chlorophenyl | thiophen-2-yl |
| O617 | thiophen-2-yl | thiophen-2-yl |
| O618 | thiazol-2-yl | thiophen-2-yl |
| O619 | oxazol-2-yl | thiophen-2-yl |
| O620 | isoxazol-3-yl | thiophen-2-yl |
| O621 | methyl | thiazol-2-yl |
| O622 | ethyl | thiazol-2-yl |
| O623 | n-propyl | thiazol-2-yl |
| O624 | iso-propyl | thiazol-2-yl |
| O625 | phenyl | thiazol-2-yl |
| O626 | benzyl | thiazol-2-yl |
| O627 | 2-fluorophenyl | thiazol-2-yl |
| O628 | 2-chlorophenyl | thiazol-2-yl |
| O629 | thiophen-2-yl | thiazol-2-yl |
| O630 | thiazol-2-yl | thiazol-2-yl |
| O631 | oxazol-2-yl | thiazol-2-yl |
| O632 | isoxazol-3-yl | thiazol-2-yl |
| O633 | methyl | oxazol-2-yl |
| O634 | ethyl | oxazol-2-yl |
| O635 | n-propyl | oxazol-2-yl |
| O636 | iso-propyl | oxazol-2-yl |
| O637 | phenyl | oxazol-2-yl |
| O638 | benzyl | oxazol-2-yl |
| O639 | 2-fluorophenyl | oxazol-2-yl |
| O640 | 2-chlorophenyl | oxazol-2-yl |
| O641 | thiophen-2-yl | oxazol-2-yl |
| O642 | thiazol-2-yl | oxazol-2-yl |
| O643 | oxazol-2-yl | oxazol-2-yl |
| O644 | isoxazol-3-yl | oxazol-2-yl |

The compounds encompassed within the second aspect of Category VII of the present disclosure can be prepared by the procedure outlined in Scheme XIV and described in Example 14 herein below.

Scheme XIV

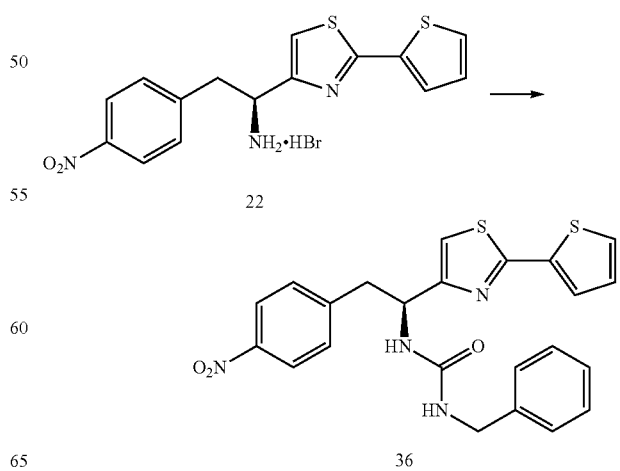

Reagents and Conditions (a) Benzyl Isocyanate, TEA, CH$_2$Cl$_2$; Rt, 18 hr

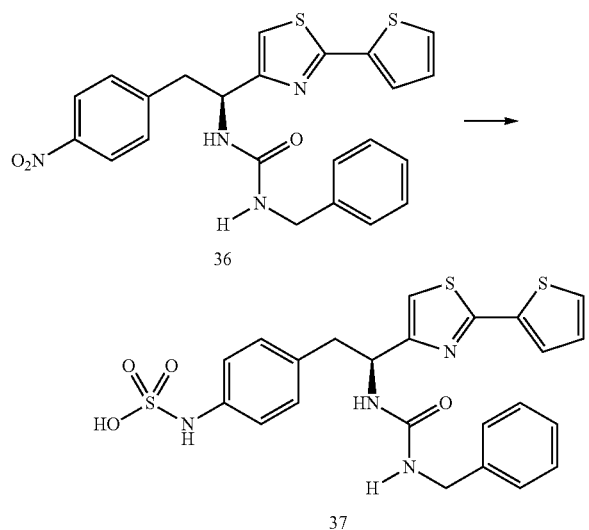

Reagents and Conditions: (b) (i) H$_2$:Pd/C, MeOH; (ii) SO$_3$-Pyridine, NH$_4$OH

EXAMPLE 15

4-{(S)-2-(3-Benzylureido)-2-[2-(thiophen-2-yl)thiazol-4-yl]ethyl}-phenylsulfamic acid (37)

Preparation of 1-benzyl-3-{(S)-2-(4-nitrophenyl)-1-[2-(thiophen-2-yl)thiazol-4-yl]ethyl}urea (36): To a solution of (S)-2-(4-nitrophenyl)-1-[(2-thiophen-2-yl)thiazol-4-yl)ethan-amine hydrobromide salt, 8, and Et$_3$N (0.42 mL, 3 mmol) in 10 mL DCM is added benzyl isocyanate (0.12 mL, 1 mmol). The mixture is stirred at room temperature for 18 hours. The product is isolated by filtration to afford 0.445 g (96% yield) of the desired product which is used without further purification.

Preparation of 4-{(S)-2-(3-benzylureido)-2-[2-(thiophen-2-yl)thiazol-4-yl]ethyl}phenylsulfamic acid (37): 1-Benzyl-3-{(S)-2-(4-nitrophenyl)-1-[2-(thiophen-2-yl)thiazol-4-yl]ethyl}urea, 36, (0.445 g) is dissolved in MeOH (10 mL) and CH$_2$Cl$_2$ (5 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.110 g). The reaction is stirred at room temperature for 5 minutes after which a 7% solution of NH$_4$OH is added. The mixture is then concentrated and the resulting residue is purified by reverse phase chromatography to afford 0.080 g of the desired product as the ammonium salt. $^1$H NMR (CD$_3$OD) δ 7.61 (d, 1H, J=2.1 Hz), 7.58 (d, 1H, J=6 Hz), 7.33-7.22 (m, 4H), 7.17-7.14 (m, 1H), 7.09-6.94 (m, 6H), 5.16 (t, 1H, J=6.6 Hz), 4.13 (s, 2H), 3.14-3.11 (m, 2H).

Category VIII of the present disclosure relates to 2-(thiazol-4-yl) compounds having the formula:

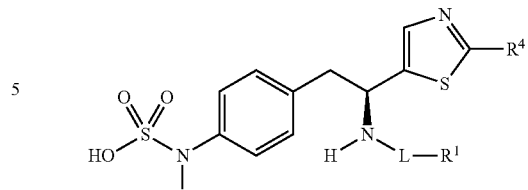

wherein R$^1$, R$^4$, and L are further defined herein in Table XVI herein below.

TABLE XVI

| No. | R$^4$ | L | R$^1$ |
|---|---|---|---|
| P645 | methyl | —SO$_2$— | methyl |
| P646 | ethyl | —SO$_2$— | methyl |
| P647 | phenyl | —SO$_2$— | methyl |
| P648 | thiophen-2-yl | —SO$_2$— | methyl |
| P649 | methyl | —SO$_2$— | trifluoromethyl |
| P650 | ethyl | —SO$_2$— | trifluoromethyl |
| P651 | phenyl | —SO$_2$— | trifluoromethyl |
| P652 | thiophen-2-yl | —SO$_2$— | trifluoromethyl |
| P653 | methyl | —SO$_2$— | ethyl |
| P654 | ethyl | —SO$_2$— | ethyl |
| P655 | phenyl | —SO$_2$— | ethyl |
| P656 | thiophen-2-yl | —SO$_2$— | ethyl |
| P657 | methyl | —SO$_2$— | 2,2,2-trifluoroethyl |
| P658 | ethyl | —SO$_2$— | 2,2,2-trifluoroethyl |
| P659 | phenyl | —SO$_2$— | 2,2,2-trifluoroethyl |
| P660 | thiophen-2-yl | —SO$_2$— | 2,2,2-trifluoroethyl |
| P661 | methyl | —SO$_2$— | phenyl |
| P662 | ethyl | —SO$_2$— | phenyl |
| P663 | phenyl | —SO$_2$— | phenyl |
| P664 | thiophen-2-yl | —SO$_2$— | phenyl |
| P665 | methyl | —SO$_2$— | 4-fluorophenyl |
| P666 | ethyl | —SO$_2$— | 4-fluorophenyl |
| P667 | phenyl | —SO$_2$— | 4-fluorophenyl |
| P668 | thiophen-2-yl | —SO$_2$— | 4-fluorophenyl |
| P669 | methyl | —SO$_2$— | 3,4-dihydro-2H-benzo[b][1,4]oxazin-7-yl |
| P670 | ethyl | —SO$_2$— | 3,4-dihydro-2H-benzo[b][1,4]oxazin-7-yl |
| P671 | phenyl | —SO$_2$— | 3,4-dihydro-2H-benzo[b][1,4]oxazin-7-yl |
| P672 | thiophen-2-yl | —SO$_2$— | 3,4-dihydro-2H-benzo[b][1,4]oxazin-7-yl |
| P673 | methyl | —SO$_2$— | 1-methyl-1H-imidazol-4-yl |
| P674 | ethyl | —SO$_2$— | 1-methyl-1H-imidazol-4-yl |
| P675 | phenyl | —SO$_2$— | 1-methyl-1H-imidazol-4-yl |
| P676 | thiophen-2-yl | —SO$_2$— | 1-methyl-1H-imidazol-4-yl |
| P678 | methyl | —SO$_2$— | 4-acetamidophenyl |
| P679 | ethyl | —SO$_2$— | 4-acetamidophenyl |
| P680 | phenyl | —SO$_2$— | 4-acetamidophenyl |
| P681 | thiophen-2-yl | —SO$_2$— | 4-acetamidophenyl |
| P682 | methyl | —SO$_2$CH$_2$— | phenyl |
| P683 | ethyl | —SO$_2$CH$_2$— | phenyl |
| P684 | phenyl | —SO$_2$CH$_2$— | phenyl |
| P685 | thiophen-2-yl | —SO$_2$CH$_2$— | phenyl |
| P686 | methyl | —SO$_2$CH$_2$— | (4-methylcarboxyphenyl)methyl |
| P687 | ethyl | —SO$_2$CH$_2$— | (4-methylcarboxyphenyl)methyl |
| P688 | phenyl | —SO$_2$CH$_2$— | (4-methylcarboxyphenyl)methyl |
| P689 | thiophen-2-yl | —SO$_2$CH$_2$— | (4-methylcarboxyphenyl)methyl |

TABLE XVI-continued

| No. | R⁴ | L | R¹ |
|---|---|---|---|
| P690 | methyl | —SO₂CH₂— | (2-methylthiazol-4-yl)methyl |
| P691 | ethyl | —SO₂CH₂— | (2-methylthiazol-4-yl)methyl |
| P692 | phenyl | —SO₂CH₂— | (2-methylthiazol-4-yl)methyl |
| P693 | thiophen-2-yl | —SO₂CH₂— | (2-methylthiazol-4-yl)methyl |
| P694 | methyl | —SO₂CH₂CH₂— | phenyl |
| P695 | ethyl | —SO₂CH₂CH₂— | phenyl |
| P696 | phenyl | —SO₂CH₂CH₂— | phenyl |
| P697 | thiophen-2-yl | —SO₂CH₂CH₂— | phenyl |

The compounds encompassed within Category VIII of the present disclosure can be prepared by the procedure outlined in Scheme XV and described in Example 16 herein below.

Scheme XV

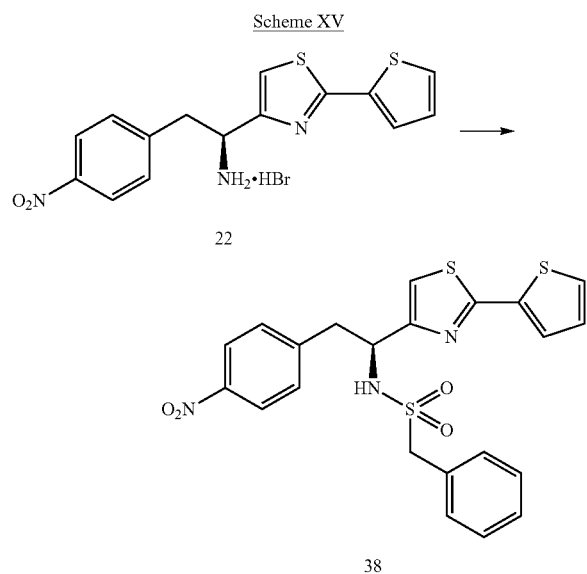

Reagents and Conditions: (a) C₆H₄CH₂SO₂Cl, DIPEA, CH₂Cl₂; 0° C. to rt, 14 hr

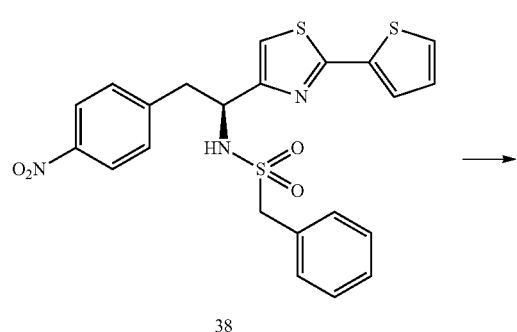

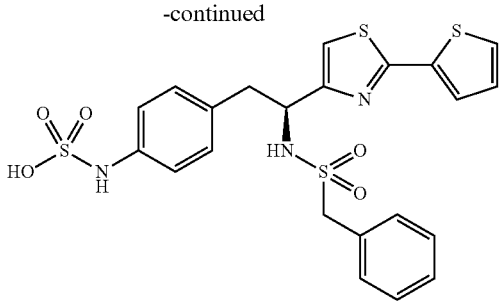

Reagents and Conditions: (b) (i) H₂:Pd/C, MeOH; (ii) SO₃-Pyridine, NH₄OH

EXAMPLE 16

{4-(S)-[2-Phenylmethanesulfonylamino-2-(2-thiophen-2-ylthiazol-4-yl)ethyl]phenyl}sulfamic acid (39)

Preparation of (S)—N-{2-(4-nitrophenyl)-1-[2-(thiophen-2-yl)thiazol-4-yl]ethyl}-1-phenylmethanesulfonamide (38): To a suspension of 2-(4-nitrophenyl)-1-(2-thiophene2-ylthiazol-4-yl)ethylamine, 8, (330 mg, 0.80 mmol) in CH₂Cl₂ (6 mL) at 0° C. is added diisopropylethylamine (0.30 mL, 1.6 mmol) followed by phenylmethanesulfonyl chloride (167 mg, 0.88 mmol). The reaction mixture is stirred at room temperature for 14 hours. The mixture is diluted with CH₂Cl₂ and washed with sat. NaHCO₃ followed by brine, dried (Na₂SO₄), filtered and concentrated in vacuo. The resulting residue is purified over silica to afford 210 mg of the desired product as a white solid.

Preparation of {4-(S)-[2-phenylmethanesulfonylamino-2-(2-thiophen-2-ylthiazol-4-yl)ethyl]phenyl}sulfamic acid (39): (S)—N-{2-(4-nitrophenyl)-1-[2-(thiophen-2-yl)thiazol-4-yl]ethyl}-1-phenylmethanesulfonamide, 38, (210 mg, 0.41 mmol) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (197 mg, 1.23 mmol). The reaction is stirred at room temperature for 5 minutes after which a 7% solution of NH₄OH is added. The mixture is then concentrated and the resulting residue is purified by reverse phase chromatography to afford 0.060 g of the desired product as the ammonium salt. ¹H NMR (300 MHz, MeOH-d₄) δ 7.52-7.63 (m, 6.70-7.28 (m, 11H), 4.75 (t, J=7.2 Hz, 1H), 3.95-4.09 (m, 2H), 3.20 (dd, J=13.5 and 7.8 Hz, 1H), 3.05 (dd, J=13.5 and 7.8 Hz, 1H). 1013770

Intermediates for use in Step (a) of Scheme XV can be conveniently prepared by the procedure outlined herein below in Scheme XVI and described in Example 17.

Scheme XVI

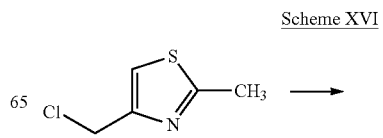

-continued

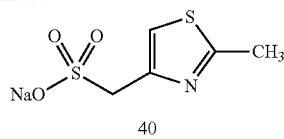

Reagents and Conditions: (a) Na$_2$SO$_3$, H$_2$O; Microwave @200° C., 20 Min

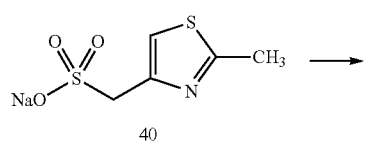

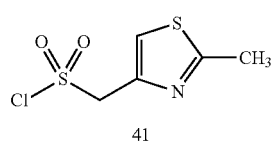

Reagents and Conditions: (b) PCl$_5$, POCl$_3$; 50° C., 3 Hrs

EXAMPLE 17

(2-Methylthiazol-4-yl)methanesulfonyl chloride (41)

Preparation of sodium (2-methylthiazol-4-yl)methanesulfonate (40): 4-Chloromethyl-2-methylthiazole (250 mg, 1.69 mmol) is dissolved in H$_2$O (2 mL) and treated with sodium sulfite (224 mg, 1.78 mmol). The reaction mixture is subjected to microwave irradiation for 20 minutes at 200° C. The reaction mixture is diluted with H$_2$O (30 mL) and washed with EtOAc (2×25 mL). The aqueous layer is concentrated to afford 0.368 g of the desired product as a yellow solid. LC/MS ESI+ 194 (M+1, free acid).

Preparation of (2-methylthiazol-4-yl)methanesulfonyl chloride (41): Sodium (2-methylthiazol-4-yl)methanesulfonate, 40, (357 mg, 1.66 mmol) is dissolved in phosphorous oxychloride (6 mL) and is treated with phosphorous pentachloride (345 mg, 1.66 mmol). The reaction mixture is stirred at 50° C. for 3 hours, then allowed to cool to room temperature. The solvent is removed under reduced pressure and the residue is re-dissolved in CH$_2$Cl$_2$ (40 mL) and is washed with sat. NaHCO$_3$ and brine. The organic layer is dried over MgSO$_4$, filtered, and the solvent removed in vacuo to afford 0.095 g of the desired product as a brown oil. LC/MS ESI+ 211 (M+1). Intermediates are obtained in sufficient purity to be carried forward according to Scheme IX without the need for further purification.

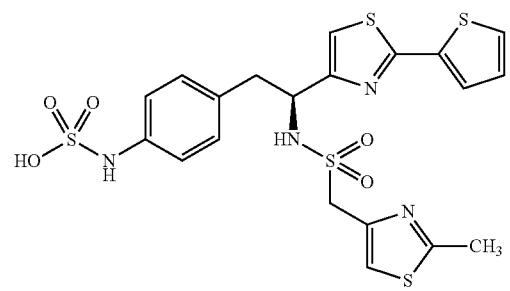 [SMILES: Cc1nc(CS(=O)(=O)N[C@@H](Cc2ccc(NS(=O)(=O)O)cc2)c2csc(-c3cccs3)n2)cs1]

4-{(S)-2-[(2-methylthiazol-4-yl)methylsulfonamido]-2-[2-(thiophen-2-yl)thiazol-4-yl]ethyl}phenylsulfamic acid: $^1$H NMR (CD$_3$OD): δ 7.71-7.66 (m, 2H), 7.27-7.10 (m, 7H), 4.87 (t, 1H, J=7.3 Hz), 4.30-4.16 (q, 2H, J=13.2 Hz), 3.34-3.13 (m, 2H), 2.70 (s, 3H).

The following are non-limiting examples of compounds encompassed within Category VIII of the present disclosure.

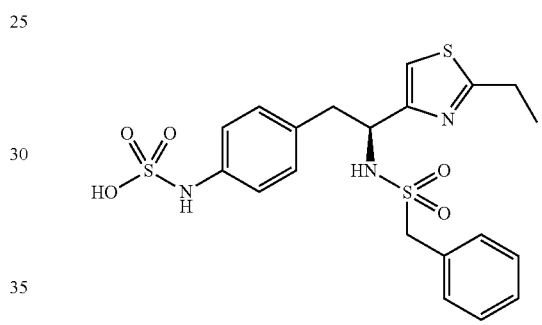

{4-(S)-[2-Phenylmethanesulfonylamino-2-(2-ethylthiazol-4-yl)ethyl]phenyl}-sulfamic acid: $^1$H NMR (300 MHz, MeOH-d$_4$) δ 7.27-7.32 (m, 3H), 7.16-7.20 (m, 3H), 7.05-7.6 (m, 2H), 6.96 (d, J=8.4 Hz, 2H), 4.70 (t, J=9.0 Hz, 1H), 3.91-4.02 (m, 2H), 2.95-3.18 (m, 4H), 1.41 (t, J=7.5 Hz, 3H).

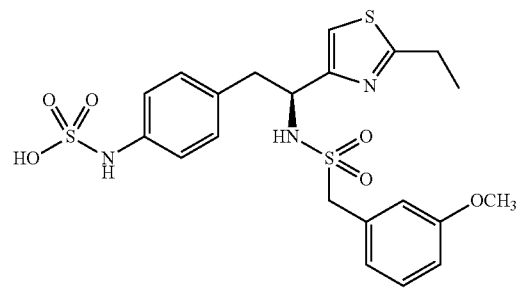 [SMILES: CCc1nc([C@H](Cc2ccc(NS(=O)(=O)O)cc2)NS(=O)(=O)Cc2cccc(OC)c2)cs1]

{4-(S)-[2-(3-Methoxyphenyl)methanesulfonylamino-2-(2-ethylthiazol-4-yl)ethyl]phenyl}sulfamic acid: $^1$H NMR (300 MHz, MeOH-d$_4$) δ 7.20 (t, J=8.1 Hz. 1H), 6.94-7.08 (m, 4H), 6.88-6.94 (m, 3H), 6.75-6.80 (m, 1H), 4.67 (t, J=7.2 Hz, 1H), 3.90-4.0 (m, 2H), 3.76 (s, 3H), 2.95-3.16 (m, 4H), 1.40 (t, J=7.5 HZ, 3H).

113

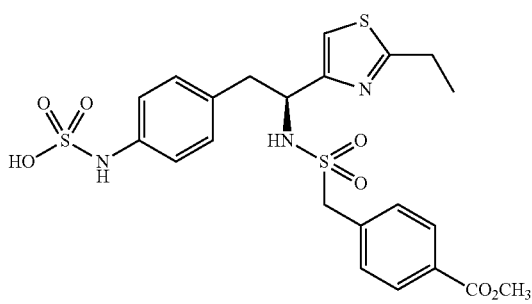 [SMILES: CCc1nc([C@H](Cc2ccc(NS(=O)(=O)O)cc2)NS(=O)(=O)Cc2ccc(C(=O)OC)cc2)cs1]

(S)-4-{[1-(2-Ethylthiazol-4-yl)-2-(4-sulfoaminophenyl) ethylsulfamoyl]methyl}-benzoic acid methyl ester: $^1$H NMR (300 MHz, MeOH-d$_4$) δ 7.90-7.94 (m, 2H), 7.27-7.30 (m, 2H), 7.06-7.11 (m, 3H), 6.97-7.00 (m, 2H), 4.71 (t, J=7.2 Hz, 1H), 3.95-4.08 (4, 2H), 3.92 (s, 3H), 2.80-3.50 (m, 4H), 1.38-1.44 (m, 3H).

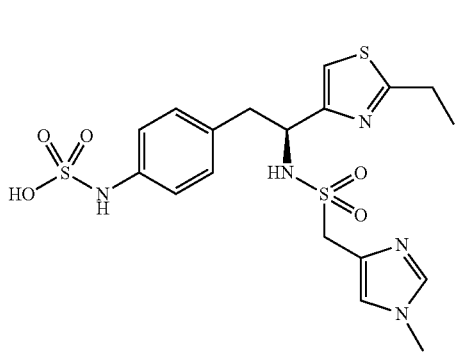 [SMILES: CCc1nc([C@H](Cc2ccc(NS(=O)(=O)O)cc2)NS(=O)(=O)Cc2cn(C)cn2)cs1]

(S)-4-[2-(2-Ethylthiazol-4-yl)-2-(1-methyl-1H-imidazol-4-sulfonamido)ethyl]-phenylsulfamic acid: $^1$H NMR (300 MHz, MeOH-d$_4$) δ 7.54 (s, 1H, 7.20 (s, 1H), 7.09 (s, 1H), 6.92-7.00 (m, 4H), 4.62 (t, J=5.4 Hz, 1H), 3.70 (s, 3H), 2.98-3.14 (m, 3H), 2.79 (dd, J=9.3 and 15.0 Hz, 1H), 1.39 (q, J=7.5 Hz, 3H).

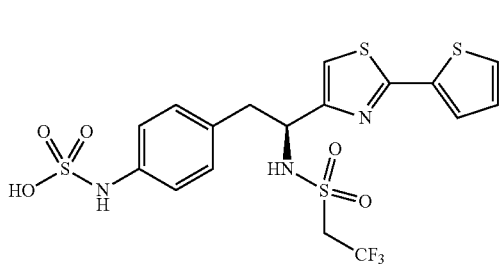 [SMILES: O=S(=O)(O)Nc1ccc(C[C@H](NS(=O)(=O)CC(F)(F)F)c2csc(-c3cccs3)n2)cc1]

4-{(S)-2-[2-(Thiophen-2-yl)thiazol-4-yl]-2-(2,2,2-trifluoroethylsulfonamido)-ethyl}phenylsulfamic acid: $^1$H NMR (CD$_3$OD): δ 7.62-7.56 (m, 2H), 7.22 (s, 1H), 7.16-7.06 (m, 5H), 4.84 (t, 1H, J=7.6 Hz), 3.71-3.62 (m, 2H), 3.32-3.03 (m, 2H).

114

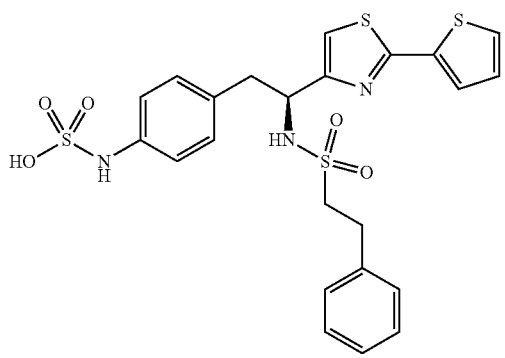 [SMILES: O=S(=O)(O)Nc1ccc(C[C@H](NS(=O)(=O)CCc2ccccc2)c2csc(-c3cccs3)n2)cc1]

{4-(S)-[2-(Phenylethanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 7.04-7.19 (m, 9H), 6.94-6.97 (m, 2H), 4.78 (t, J=7.8 Hz, 1H), 3.22-3.30 (m, 2H)), 3.11 (dd, J=13.5 and 7.8 Hz, 1H), 2.78-2.87 (m, 4H).

{4-(S)-[3-(Phenylpropanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 6.99-7.17 (m, 10H), 4.72 (t, J=7.8 Hz, 1H), 3.21 (dd, J=13.5 and 7.2 Hz, 1H), 3.02 (dd, J=13.5 and 7.2 Hz, 1H), 2.39-2.64 (m, 4H), 1.65-1.86 (m, 2H).

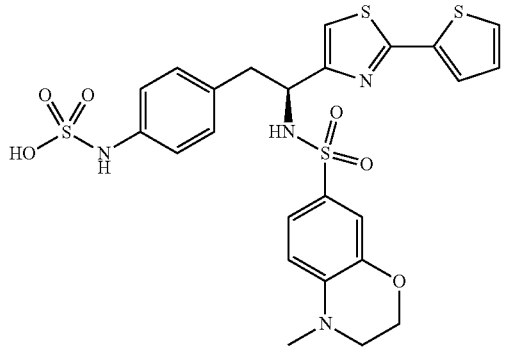 [SMILES: CN1CCOc2cc(S(=O)(=O)N[C@@H](Cc3ccc(NS(=O)(=O)O)cc3)c3csc(-c4cccs4)n3)ccc21]

(S)-{4-[2-(4-Methyl-3,4-dihydro-2H-benzo[1,4]oxazine-7-sulfonylamino)-2-(2-thiophen-2-ylthiazol-4-yl)ethyl] phenyl}sulfamic acid: $^1$H NMR (300 MHz, MeOH-d$_4$) δ 7.53 (d, J=5.1 Hz, 1H) 7.48 (d, J=5.1 Hz, 1H), 7.13-7.10 (m, 1H), 7.04 (d, J=8.4 Hz, 2H), 6.93-6.88 (m, 3H), 6.75 (d, J=8.1 Hz, 1H), 6.54 (d, J=8.1 Hz, 1H), 4.61 (t, J=7.5 Hz, 1H), 4.20-4.08 (m, 2H), 3.14-3.00 (m, 4H), 2.69 (s, 3H).

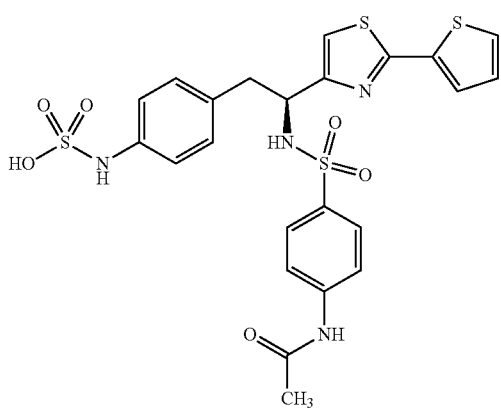 [SMILES: CC(=O)Nc1ccc(S(=O)(=O)N[C@@H](Cc2ccc(NS(=O)(=O)O)cc2)c2csc(-c3cccs3)n2)cc1]

4-{(S)-2-(4-acetamidophenylsulfonamido)-2-[2-(thiophen-2-yl)thiazol-4-yl]ethyl}phenylsulfamic acid: $^1$H NMR (CD$_3$OD): δ 7.67-7.52 (m, 6H), 7.24-7.23 (m, 1H), 7.12-7.09 (m, 3H), 7.02-6.99 (m, 2H), 4.70 (t, 1H, J=7.3 Hz), 3.25-3.00 (m, 2H), 2.24 (s, 3H).

The first aspect of Category IX of the present disclosure relates to compounds having the formula:

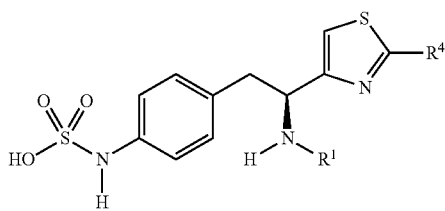

wherein R$^1$ is a substituted or unsubstituted heteroaryl and R$^4$ is C$_1$-C$_6$ linear, branched, or cyclic alkyl as further described herein below in Table XVII.

TABLE XVII

| No. | R$^4$ | R$^1$ |
|---|---|---|
| Q698 | —CH$_3$ | 4-(methoxycarbonyl)thiazol-5-yl |
| Q699 | —CH$_3$ | 4-[(2-methoxy-2-oxoethyl)carbamoyl]thiazol-5-yl |
| Q700 | —CH$_3$ | 5-[1-N-(2-methoxy-2-oxoethyl)-1-H-indol-3-yl]oxazol-2-yl |
| Q701 | —CH$_3$ | 5-(2-methoxyphenyl)oxazol-2-yl |
| Q702 | —CH$_3$ | 5-[(S)-1-(tert-butoxycarbonyl)-2-phenylethyl]oxazol-2-yl |
| Q703 | —CH$_3$ | 5-[4-(methylcarboxy)phenyl]oxazol-2-yl |
| Q704 | —CH$_3$ | 5-(3-methoxybenzyl)oxazol-2-yl |
| Q705 | —CH$_3$ | 5-(4-phenyl)oxazol-2-yl |
| Q706 | —CH$_3$ | 5-(2-methoxyphenyl)thiazol-2-yl |
| Q707 | —CH$_3$ | 5-(3-methoxyphenyl)thiazol-2-yl |
| Q708 | —CH$_3$ | 5-(4-fluorophenyl)thiazol-2-yl |
| Q709 | —CH$_3$ | 5-(2,4-difluorophenyl)thiazol-2-yl |
| Q710 | —CH$_3$ | 5-(3-methoxybenzyl)thiazol-2-yl |
| Q711 | —CH$_3$ | 4-(3-methoxyphenyl)thiazol-2-yl |
| Q712 | —CH$_3$ | 4-(4-fluorophenyl)thiazol-2-yl |
| Q713 | —CH$_2$CH$_3$ | 4-(methoxycarbonyl)thiazol-5-yl |
| Q714 | —CH$_2$CH$_3$ | 4-[(2-methoxy-2-oxoethyl)carbamoyl]thiazol-5-yl |
| Q715 | —CH$_2$CH$_3$ | 5-[1-N-(2-methoxy-2-oxoethyl)-1-H-indol-3-yl]oxazol-2-yl |
| Q716 | —CH$_2$CH$_3$ | 5-(2-methoxyphenyl)oxazol-2-yl |
| Q717 | —CH$_2$CH$_3$ | 5-[(S)-1-(tert-butoxycarbonyl)-2-phenylethyl]oxazol-2-yl |
| Q718 | —CH$_2$CH$_3$ | 5-[4-(methylcarboxy)phenyl]oxazol-2-yl |
| Q719 | —CH$_2$CH$_3$ | 5-(3-methoxybenzyl)oxazol-2-yl |

TABLE XVII-continued

| No. | R$^4$ | R$^1$ |
|---|---|---|
| Q720 | —CH$_2$CH$_3$ | 5-(4-phenyl)oxazol-2-yl |
| Q721 | —CH$_2$CH$_3$ | 5-(2-methoxyphenyl)thiazol-2-yl |
| Q722 | —CH$_2$CH$_3$ | 5-(3-methoxyphenyl)thiazol-2-yl |
| Q723 | —CH$_2$CH$_3$ | 5-(4-fluorophenyl)thiazol-2-yl |
| Q724 | —CH$_2$CH$_3$ | 5-(2,4-difluorophenyl)thiazol-2-yl |
| Q725 | —CH$_2$CH$_3$ | 5-(3-methoxybenzyl)thiazol-2-yl |
| Q726 | —CH$_2$CH$_3$ | 4-(3-methoxyphenyl)thiazol-2-yl |
| Q727 | —CH$_2$CH$_3$ | 4-(4-fluorophenyl)thiazol-2-yl |
| Q728 | cyclopropyl | 4-(methoxycarbonyl)thiazol-5-yl |
| Q729 | cyclopropyl | 4-[(2-methoxy-2-oxoethyl)carbamoyl]thiazol-5-yl |
| Q730 | cyclopropyl | 5-[1-N-(2-methoxy-2-oxoethyl)-1-H-indol-3-yl]oxazol-2-yl |
| Q731 | cyclopropyl | 5-(2-methoxyphenyl)oxazol-2-yl |
| Q732 | cyclopropyl | 5-[(S)-1-(tert-butoxycarbonyl)-2-phenylethyl]oxazol-2-yl |
| Q733 | cyclopropyl | 5-[4-(methylcarboxy)phenyl]oxazol-2-yl |
| Q734 | cyclopropyl | 5-(3-methoxybenzyl)oxazol-2-yl |
| Q735 | cyclopropyl | 5-(4-phenyl)oxazol-2-yl |
| Q736 | cyclopropyl | 5-(2-methoxyphenyl)thiazol-2-yl |
| Q737 | cyclopropyl | 5-(3-methoxyphenyl)thiazol-2-yl |
| Q738 | cyclopropyl | 5-(4-fluorophenyl)thiazol-2-yl |
| Q739 | cyclopropyl | 5-(2,4-difluorophenyl)thiazol-2-yl |
| Q740 | cyclopropyl | 5-(3-methoxybenzyl)thiazol-2-yl |
| Q741 | cyclopropyl | 4-(3-methoxyphenyl)thiazol-2-yl |
| Q742 | cyclopropyl | 4-(4-fluorophenyl)thiazol-2-yl |

Compounds according to the first aspect of Category IX which comprise a substituted or unsubstituted thiazol-4-yl unit for R$^1$ can be prepared by the procedure outlined in Scheme XVII and described herein below in Example 18.

Scheme XVII

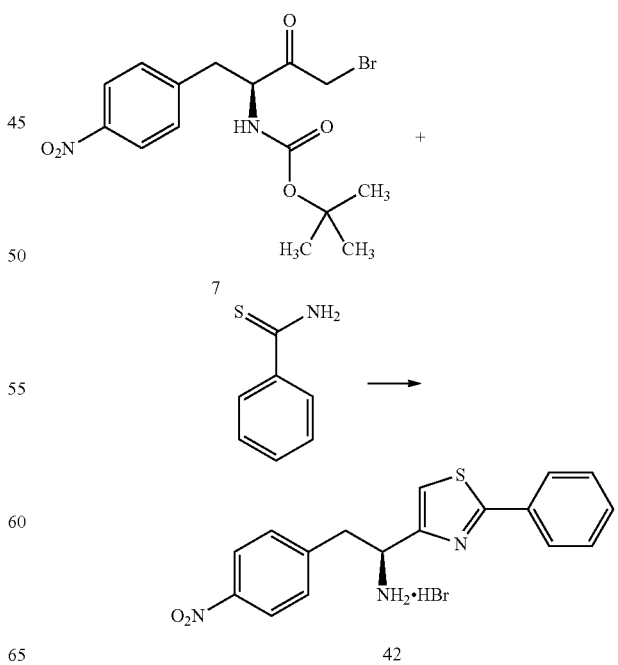

Reagents and Conditions: (a) CH₃CN, Reflux; 24 hr

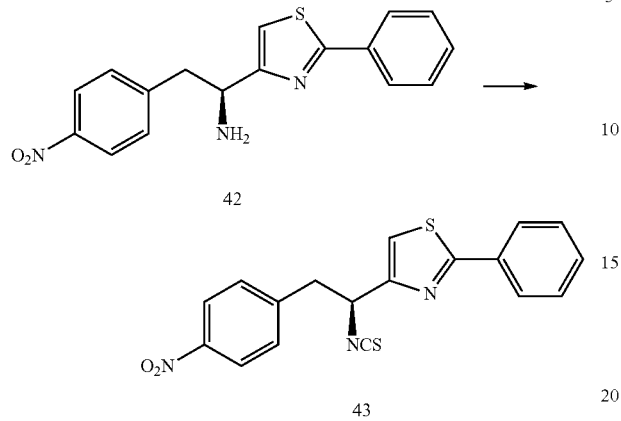

42

43

Reagents and Conditions: (b) Thiophosgene, CaCO₃, CCl₄, H₂O; Rt, 18 hr

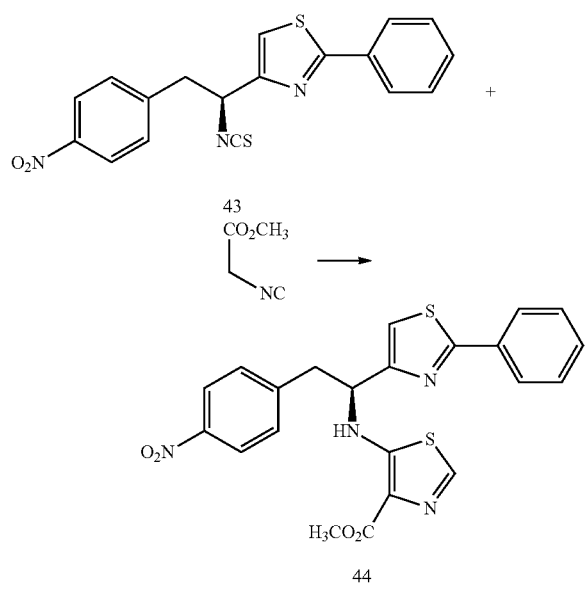

43

44

Reagents and Conditions: (c) KOtBu, THF; rt, 2 hr

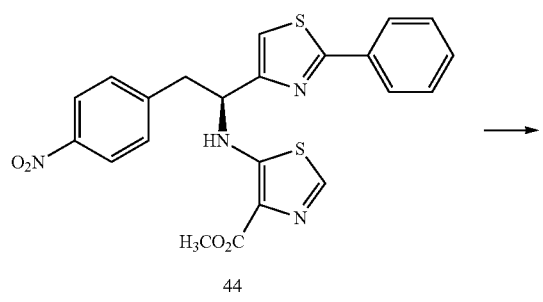

44

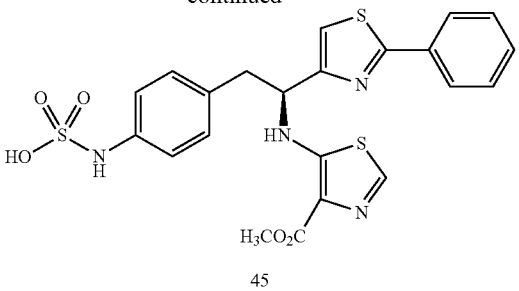

45

Reagents and Conditions: (d) (i) SnCl₂—2H₂O, EtOH; Reflux, 4 Hours (ii) SO₃-Pyridine, NH₄OH

EXAMPLE 18

(S)-4-(2-(2-Phenylthiazol-4-yl)2-(4-(methoxycarbonyl)thiazole-5-ylamino)ethyl)phenylsulfamic Acid (45)

Preparation of (S)-2-(4-nitrophenyl)-1-(2-phenylthiazol-4-yl)ethanamine hydrobromide salt (42): A mixture of (S)-tert-butyl 4-bromo-1-(4-nitrophenyl)-3-oxobutan-2-ylcarbamate, 7, (1.62 g, 4.17 mmol) and thiobenzamide (0.63 g, 4.60 mmol) in CH₃CN (5 mL) is refluxed for 24 hours. The reaction mixture is cooled to room temperature and diethyl ether (50 mL) is added to the solution. The precipitate which forms is collected by filtration. The solid is dried under vacuum to afford 1.2 g (67% yield) of the desired product. LC/MS ESI+ 326 (M+1).

Preparation of (S)-4-(1-isothiocyanato-2-(4-nitrophenyl)ethyl)-2-phenylthiazole (43): To a solution of (S)-2-(4-nitrophenyl)-1-(2-phenylthiazol-4-yl)ethanamine hydrobromide salt, 42, (726 mg, 1.79 mmol) and CaCO₃ (716 mg, 7.16 mmol) in H₂O (2 mL) is added CCl₄ (3 mL) followed by thiophosgene (0.28 mL, 3.58 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is purified over silica (CH₂Cl₂) to afford 480 mg (73%) of the desired product as a yellow solid. ¹H NMR (300 MHz, CDCl₃) δ 8.15 (d, J=8.7 Hz, 2H), 7.97-7.99 (m, 2H), 7.43-7.50 (m, 3H), 7.34 (d, J=8.7 Hz, 2H), 7.15 (d, J=0.9 Hz, 1H), 5.40-5.95 (m, 1H), 3.60 (dd, J=13.8 and 6.0 Hz, 1H), 3.46 (dd, J=13.8 and 6.0 Hz).

Preparation of (S)-methyl 5-[1-(2-phenylthiazol-4-yl)-2-(4-nitrophenyl)-ethylamino]thiazole-4-carboxylate (44): To a suspension of potassium tert-butoxide (89 mg, 0.75 mmol) in THF (3 mL) is added methyl isocyanoacetate (65 µL, 0.68 mmol) followed by (S)-2-phenyl-4-(1-isothiocyanato-2-(4-nitrophenyl)ethyl)thiazole, 43, (250 mg, 0.68 mmol). The reaction mixture is stirred at room temperature for 2 hours then poured into sat. NaHCO₃. The mixture is extracted with EtOAc (3×25 mL) and the combined organic layers are washed with brine and dried (Na₂SO₄) and concentrated in vacuo. The crude residue is purified over silica to afford 323 mg (~100% yield) of the desired product as a slightly yellow solid. ¹H NMR (300 MHz, CDCl₃) δ 8.09-8.13 (m, 2H), 7.95-7.98 (m, 3H), 7.84 (d, J=1.2 Hz, 1H), 7.44-7.50 (m, 3H), 7.28-7.31 (m, 2H), 7.96 (d, J=0.6 Hz, 1H), 4.71-4.78 (m, 1H), 3.92 (s, 3H), 3.60 (dd, J=13.8 and 6.0 Hz, 1H), 3.45 (dd, J=13.8 and 6.0 Hz, 1H).

Preparation of (S)-4-(2-(2-phenylthiazol-4-yl)2-(4-(methoxycarbonyl)thiazole-5-ylamino)ethyl)phenylsulfamic acid (45): (S)-methyl 5-[1-(2-phenylthiazol-4-yl)-2-(4-nitrophenyl)-ethylamino]thiazole-4-carboxylate, 44, (323 mg, 0.68 mmol) and tin (II) chloride (612 mg, 2.72 mmol) are dissolved in EtOH and the solution is brought to reflux. The solvent is removed in vacuo and the resulting residue is dissolved in EtOAc. A saturated solution of NaHCO$_3$ is added and the solution is stirred 1 hour. The organic layer is separated and the aqueous layer extracted twice with EtOAc. The combined organic layers are dried (Na$_2$SO$_4$), filtered and concentrated to a residue which is dissolved in pyridine (10 mL) and treated with SO$_3$-pyridine (130 mg, 0.82 mmol). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

Compounds according to the first aspect of Category IX which comprise a substituted or unsubstituted thiazol-2-yl unit for R$^1$ can be prepared by the procedure outlined in Scheme XVIII and described herein below in Example 19. Intermediate 46 can be prepared according to Scheme II and Example 2 by substituting cyclopropane-carbothioic acid amide for thiophen-2-carbothioic acid amide.

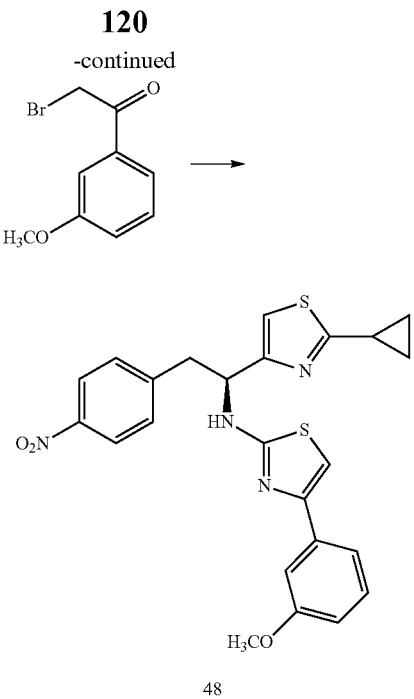

Reagents and Conditions: (b) CH$_3$CN, Reflux, 24 hr

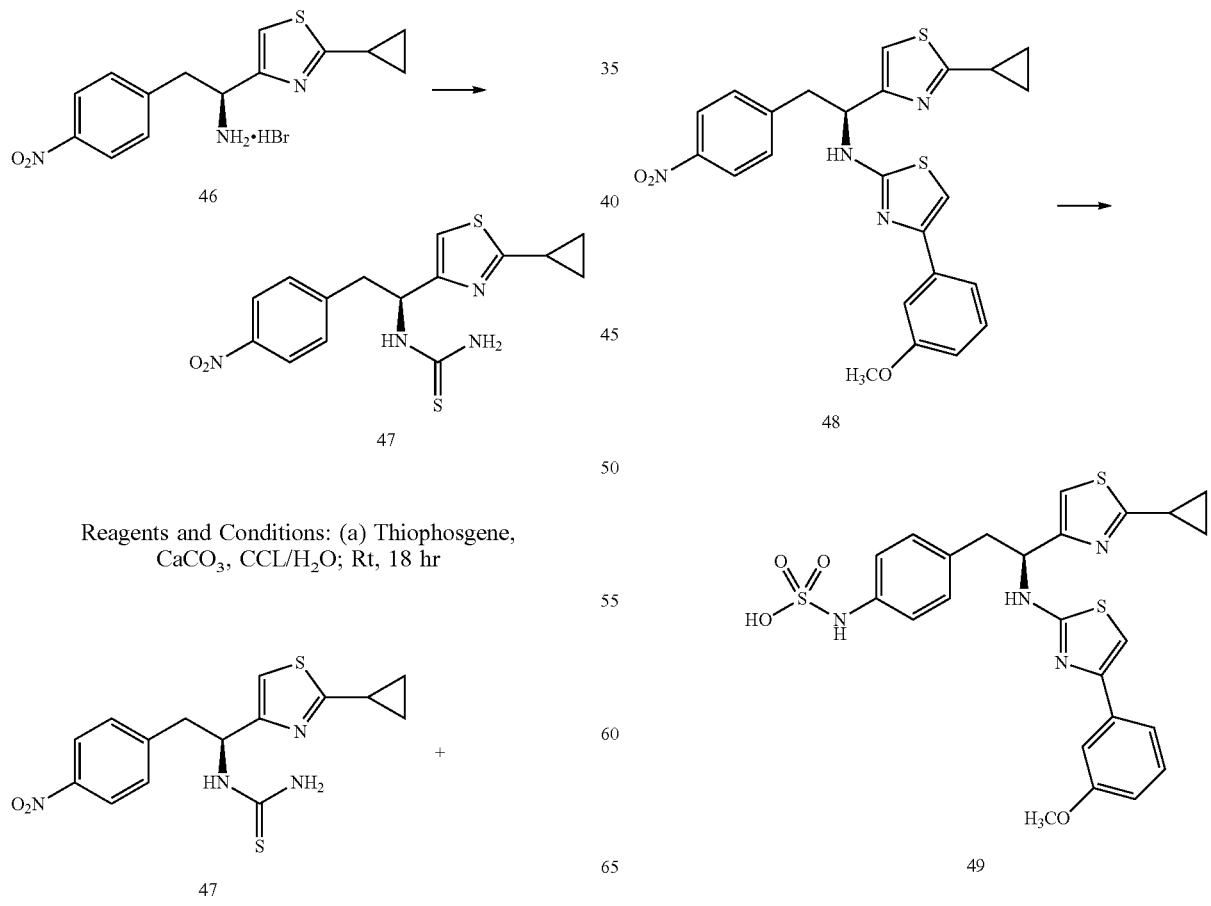

Scheme XVIII

Reagents and Conditions: (a) Thiophosgene, CaCO$_3$, CCL/H$_2$O; Rt, 18 hr

Reagents and Conditions: (c) (i) H₂:Pd/C, MeOH; (ii) SO₃-Pyridine, NH₄OH

EXAMPLE 19

4-{(S)-2-(2-Cyclopropylthiazol-4-yl)-2-[4-(3-methoxyphenyl)thiazol-2-ylamino]ethyl}phenylsulfamic Acid (50)

Preparation of (S)-1-(1-(2-cyclopropylthiazol-4-yl)-2-(4-nitrophenyl)ethyl)-thiourea (47): To a solution of (S)-1-(2-cyclopropylthiazol-4-yl)-2-(4-nitrophenyl)ethan-amine hydrobromide hydrobromide salt, 32, (4.04 g, 10.9 mmol) and CaCO₃ (2.18 g, 21.8 mmol) in CCL/water (25 mL/20 mL) is added thiophosgene (1.5 g, 13.1 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is subsequently treated with ammonia (0.5M in 1,4-dioxane, 120 mL) which is purified over silica to afford 2.90 g of the desired product as a red-brown solid. LC/MS ESI– 347 (M–1).

Preparation of (S)-4-(3-methoxybenzyl)-N-(1-(2-cyclopropylthiazol-4-yl)-2-(4-nitrophenyl)ethyl)thiazol-2-amine (48): (S)-1-(1-(2-Cyclopropylthiazol-4-yl)-2-(4-nitrophenyl)ethyl)-thiourea, 47, (350 mg, 1.00 mmol) and 2-bromo-3'-methoxy-acetophenone (253 mg, 1.10 mmol) are combined in 3 mL CH₃CN and heated to reflux for 24 hours. The mixture is concentrated and chromatographed to afford 0.172 g of the product as a yellow solid. LC/MS ESI+ 479 (M+1).

Preparation of 4-{(S)-2-(2-cyclopropylthiazol-4-yl)-2-[4-(3-methoxyphenyl)-thiazol-2-ylamino]ethyl}phenylsulfamic acid (49): (S)-4-(3-methoxybenzyl)-N-(1-(2-cyclopropylthiazol-4-yl)-2-(4-nitrophenyl)ethyl)thiazol-2-amine, 48, (0.172 g) is dissolved in 10 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 5 mL pyridine and treated with SO₃-pyridine (114 mg). The reaction is stirred at room temperature for 5 minutes after which 10 mL of a 7% solution of NH₄OH is added. The mixture is then concentrated and the resulting residue is purified by reverse-phase chromatography to afford 0.033 g of the desired product as the ammonium salt. ¹H NMR (CD₃OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

The following are non-limiting examples of compounds encompassed within the first aspect of Category IX.

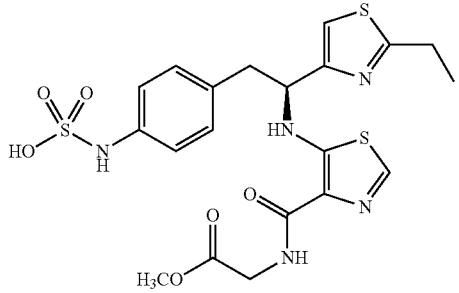 [SMILES: CCc1nc([C@H](Cc2ccc(NS(=O)(=O)O)cc2)Nc2scnc2C(=O)NCC(=O)OC)cs1]

(S)-4-(2-(4-((2-Methoxy-2-oxoethyl)carbamoyl)thiazole-5-ylamino)2-(2-ethylthiazole-4-yl)ethyl)phenylsulfamic acid: ¹H NMR (300 MHz, MeOH-d₄) δ 7.91 (s, 1H), 7.08-7.10 (m, 3H), 6.99 (d, J=8.7 Hz, 2H), 4.58 (t, J=6.9 Hz, 1H), 4.11 (d, J=2.7 Hz, 2H), 3.78 (s, 3H), 3.14-3.28 (m, 2H), 3.06 (q, J=7.5 Hz, 2H), 1.41 (t, J=7.5 Hz, 3H).

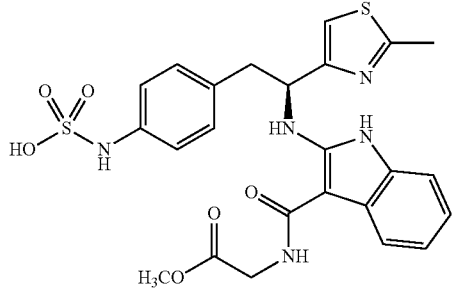 [SMILES: COC(=O)CNC(=O)c1c(N[C@@H](Cc2ccc(NS(=O)(=O)O)cc2)c2csc(C)n2)[nH]c2ccccc12]

(S)-4-(2-{5-[1-N-(2-Methoxy-2-oxoethylcarbamoyl)-1-H-indol-3-yl]oxazol-2-ylamino}-2-(2-methylthiazol-4-yl)ethyl)phenylsulfamic acid: ¹H NMR (300 MHz, MeOH-d₄) δ 7.63 (d, J=7.8 Hz, 1H), 7.37 (s, 1H), 7.18-7.29 (m, 4H), 7.02-7.16 (m, 4H), 6.85 (s, 1H), 5.04-5.09 (m, 1H), 4.85 (s, 3H), 3.27 (dd, J=13.5 and 8.1 Hz, 1H), 3.10 (m, J=13.5 and 8.1 Hz, 1H), 2.69 (s, 3H).

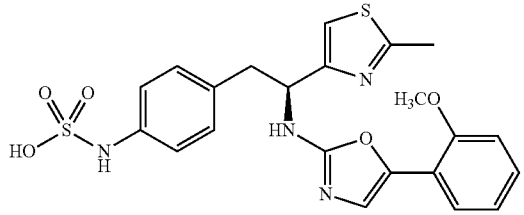 [SMILES: COc1ccccc1-c1cnc(N[C@@H](Cc2ccc(NS(=O)(=O)O)cc2)c2csc(C)n2)o1]

4-((S)-2-(5-(2-Methoxyphenyl)oxazol-2-ylamino)-2-(2-methylthiazol-4-yl)ethyl)phenylsulfamic acid: ¹H NMR (300 MHz, MeOH-d₄) δ 7.52 (dd, J=7.5 and 1.2 Hz, 1H), 6.95-7.24 (m, 10H), 5.04-5.09 (m, 1H), 3.92 (s, 3H), 3.26 (dd, J=13.8 and 8.4 Hz, 1H), 3.10 (dd, J=13.8 and 8.4 Hz, 1H), 2.72 (s, 3H).

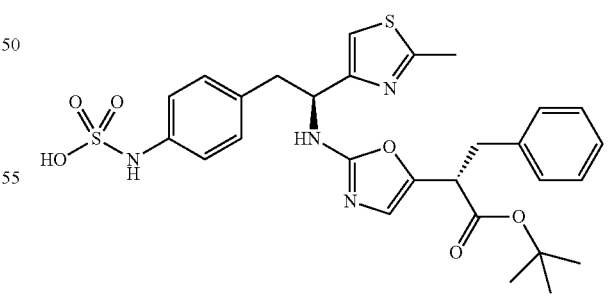

4-((S)-2-(5-((S)-1-(tert-Butoxycarbonyl)-2-phenylethyl)oxazole-2-ylamino)-2-(2-methylthiazol-4-yl)ethyl)phenylsulfamic acid: ¹H NMR (300 MHz, MeOH-d₄) δ 7.03-7.27 (m, 10H), 6.50 (s, 1H), 4.95-5.00 (m, 1H), 4.76 (t, J=6.9 Hz, 1H), 3.22 (dd, J=14.1 and 6.9 Hz, 1H), 3.00-3.10 (m, 2H), 2.90 (dd, J=14.1 and 6.9 Hz, 1H), 2.72 (s, 3H), 1.37 (s, 9H).

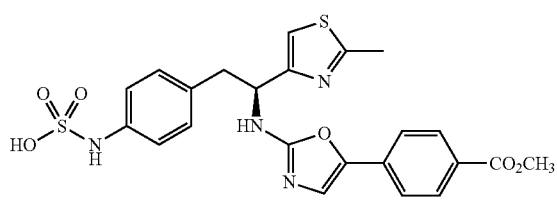 [SMILES: COC(=O)c1ccc(-c2cnc(N[C@@H](Cc3ccc(NS(=O)(=O)O)cc3)c3csc(C)n3)o2)cc1]

(S)-{4-[2-[5-(4-Methoxycarbonyl)phenyl]oxazol-2-ylamino}-2-(2-methylthiazol-4-yl)ethyl]phenylsulfamic acid: $^1$H NMR (300 MHz, MeOH-$d_4$) δ 7.99 (d, J=7.5 Hz, 2H), 7.56-7.59 (m, 2H), 7.23-7.24 (m, 1H), 7.08-7.14 (m, 4H), 6.83 (d, J=10.2 Hz, 1H), 5.08 (t, J=6.0 Hz, 1H), 3.91 (s, 3H), 3.25-3.35 (m, 1H), 3.09-3.13 (m, 1H), 2.73 (s, 3H).

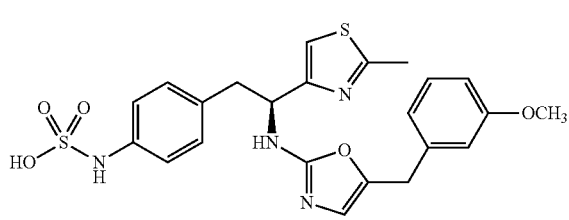 [SMILES: COc1cccc(Cc2cnc(N[C@@H](Cc3ccc(NS(=O)(=O)O)cc3)c3csc(C)n3)o2)c1]

(S)-4-(2-(5-(3-Methoxybenzyl)oxazole-2-ylamino)-2-(2-methylthiazole-4-yl)ethyl)phenylsulfamic acid: $^1$H NMR (300 MHz, MeOH-$d_4$) δ 7.03-7.28 (m, 8H), 6.79-6.83 (m, 1H), 5.70 (s, 1H), 4.99-5.06 (m, 2H), 4.41 (d, J=2.1 Hz, 2H), 3.80 (s, 3H), 3.27-3.37 (m, 1H), 3.03-3.15 (m, 1H), 2.71 (s, 3H).

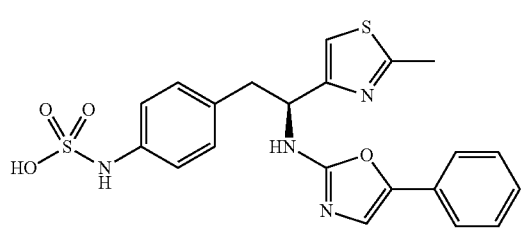 [SMILES: Cc1nc([C@H](Cc2ccc(NS(=O)(=O)O)cc2)Nc2ncc(-c3ccccc3)o2)cs1]

(S)-4-(2-(2-Methylthiazole-4-yl)2-(5-phenyloxazole-2-ylamino)ethyl)phenyl-sulfamic acid: $^1$H NMR (300 MHz, MeOH-$d_4$) δ 7.45 (d, J=8.7 Hz, 2H), 7.33 (t, J=7.8 Hz, 2H), 7.18-7.22 (m, 1H), 7.10-7.14 (m, 6H), 7.04 (s, 1H), 5.04-5.09 (m, 1H), 3.26 (dd, J=13.8 and 6.3 Hz, 1H), 3.10 (dd, J=13.8 and 6.3 Hz, 1H), 2.70 (s, 3H).

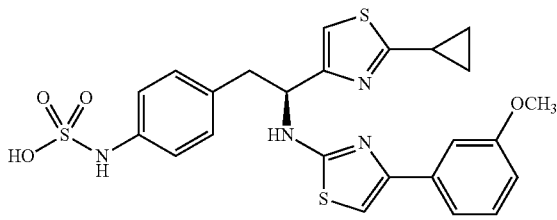 [SMILES: COc1cccc(-c2csc(N[C@@H](Cc3ccc(NS(=O)(=O)O)cc3)c3csc(C4CC4)n3)n2)c1]

4-((S)-2-(2-Cyclopropylthiazol-4-yl)-2-(4-(3-methoxyphenyl)thiazol-2-ylamino)-ethyl)phenylsulfamic acid: $^1$H NMR (CD$_3$OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

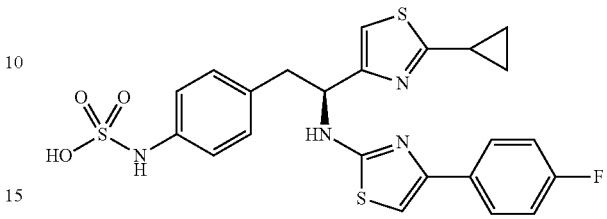

(S)-4-(2-(2-cyclopropylthiazol-4-yl)-2-(4-(4-fluorophenyl)thiazol-2-ylamino)ethyl)-phenylsulfamic acid: $^1$H NMR (CD$_3$OD): δ 7.79-7.74 (m, 2H), 7.14-7.03 (m, 7H), 7.21 (s, 1H), 6.79 (s, 1H), 5.08 (t, 1H, J=6.6 Hz), 3.29-3.12 (m, 2H), 2.40 (q, 2.40, J=5.1 Hz), 1.23-1.18 (m, 2H), 1.08-1.02 (m, 2H).

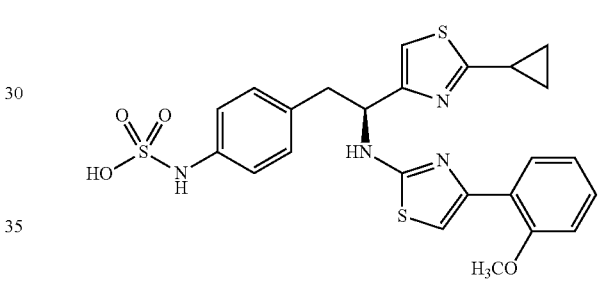

4-((S)-2-(2-cyclopropylthiazol-4-yl)-2-(4-(2-methoxyphenyl)thiazol-2-ylamino)-ethyl)phenylsulfamic acid: $^1$H NMR (CD$_3$OD): δ 7.89-7.87 (d, 1H, J=7.6 Hz), 7.28 (t, 1H, J=7.0 Hz), 7.10-6.96 (m, 8H), 5.03 (t, 1H, J=6.9 Hz), 3.90 (s, 1H), 3.19 (q, 2H, J=6.6 Hz), 2.38 (q, 1H, J=4.8 Hz), 1.21-1.14 (m, 2H), 1.06-1.00 (m, 2H).

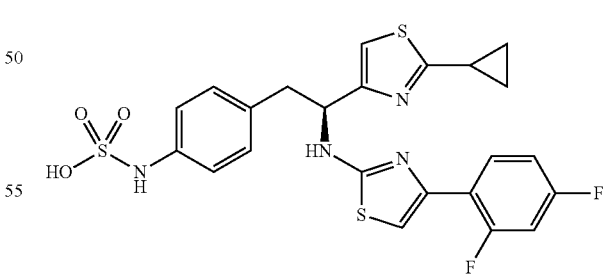

4-((S)-2-(2-cyclopropylthiazol-4-yl)-2-(4-(2,4-difluorophenyl)thiazol-2-ylamino)-ethyl)phenylsulfamic acid: $^1$H NMR (CD$_3$OD): δ 8.06-8.02 (q, 2H, J=6.9 Hz), 7.12-6.95 (m, 7H), 6.88 (s, 1H), 5.11 (t, 1H, J=6.9 Hz), 3.22-3.15 (m, 2H), 2.38 (q, 1H, J=4.8 Hz), 1.22-1.15 (m, 2H), 1.06-1.02 (m, 2H)

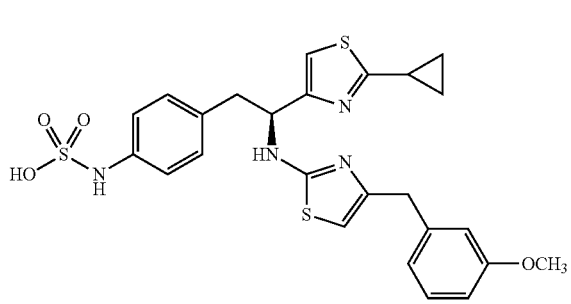 [SMILES: COc1cccc(Cc2csc(N[C@@H](Cc3ccc(NS(=O)(=O)O)cc3)c3csc(C4CC4)n3)n2)c1]

(S)-4-(2-(4-(3-methoxybenzyl)thiazol-2-ylamino)-2-(2-cyclopropylthiazol-4-yl)ethyl)phenylsulfamic acid: $^1$H NMR (CD$_3$OD): δ 7.22-7.17 (m, 3H), 7.09-6.97 (m, 5H), 6.78-6.66 (m, 3H), 3.77 (s, 2H), 3.75 (s, 3H), 3.20-3.07 (m, 2H), 2.35 (q, 1H, J=4.8 Hz), 1.19-1.13 (m, 2H), 1.03-1.00 (m, 2H).

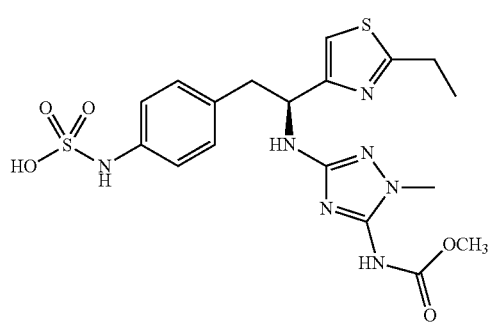 [SMILES: CCc1nc([C@H](Cc2ccc(NS(=O)(=O)O)cc2)Nc2nc(NC(=O)OC)n(C)n2)cs1]

(S)-{5-[1-(2-Ethylthiazol-4-yl)-2-(4-sulfoaminophenyl)ethylamino]-2-methyl-2H-[1,2,4]triazol-3-yl}carbamic acid methyl ester: $^1$H NMR (300 MHz, MeOH-d$_4$) δ 6.97-7.08 (m, 5H), 3.71 (s, 3H), 3.51 (s, 3H), 3.15 (dd, J=13.5 and 6.3 Hz, 1H), 3.02-3.07 (m, 3H), 1.40 (t, J=6.6 Hz, 3H).

The second aspect of Category V of the present disclosure relates to compounds having the formula:

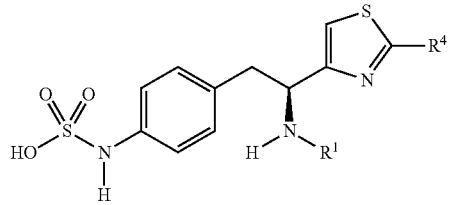

wherein $R^1$ is a substituted or unsubstituted heteroaryl and $R^4$ is substituted or unsubstituted phenyl and substituted or unsubstituted heteroaryl as further described herein below in Table XVIII.

TABLE XVIII

| No. | $R^4$ | $R^1$ |
|---|---|---|
| R743 | phenyl | 4-(methoxycarbonyl)thiazol-5-yl |
| R744 | phenyl | 4-[(2-methoxy-2-oxoethyl)carbamoyl]thiazol-5-yl |
| R745 | phenyl | 5-[1-N-(2-methoxy-2-oxoethyl)-1-H-indol-3-yl]oxazol-2-yl |
| R746 | phenyl | 5-(2-methoxyphenyl)oxazol-2-yl |

TABLE XVIII-continued

| No. | $R^4$ | $R^1$ |
|---|---|---|
| R747 | phenyl | 5-[(S)-1-(tert-butoxycarbonyl)-2-phenylethyl]oxazol-2-yl |
| R748 | phenyl | 5-[4-(methylcarboxy)phenyl]oxazol-2-yl |
| R749 | phenyl | 5-(3-methoxybenzyl)oxazol-2-yl |
| R750 | phenyl | 5-(4-phenyl)oxazol-2-yl |
| R751 | phenyl | 5-(2-methoxyphenyl)thiazol-2-yl |
| R752 | phenyl | 5-(3-methoxyphenyl)thiazol-2-yl |
| R753 | phenyl | 5-(4-fluorophenyl)thiazol-2-yl |
| R754 | phenyl | 5-(2,4-difluorophenyl)thiazol-2-yl |
| R755 | phenyl | 5-(3-methoxybenzyl)thiazol-2-yl |
| R756 | phenyl | 4-(3-methoxyphenyl)thiazol-2-yl |
| R757 | phenyl | 4-(4-fluorophenyl)thiazol-2-yl |
| R758 | thiophen-2-yl | 4-(methoxycarbonyl)thiazol-5-yl |
| R759 | thiophen-2-yl | 4-[(2-methoxy-2-oxoethyl)carbamoyl]thiazol-5-yl |
| R760 | thiophen-2-yl | 5-[1-N-(2-methoxy-2-oxoethyl)-1-H-indol-3-yl]oxazol-2-yl |
| R761 | thiophen-2-yl | 5-(2-methoxyphenyl)oxazol-2-yl |
| R762 | thiophen-2-yl | 5-[(S)-1-(tert-butoxycarbonyl)-2-phenylethyl]oxazol-2-yl |
| R763 | thiophen-2-yl | 5-[4-(methylcarboxy)phenyl]oxazol-2-yl |
| R764 | thiophen-2-yl | 5-(3-methoxybenzyl)oxazol-2-yl |
| R765 | thiophen-2-yl | 5-(4-phenyl)oxazol-2-yl |
| R766 | thiophen-2-yl | 5-(2-methoxyphenyl)thiazol-2-yl |
| R767 | thiophen-2-yl | 5-(3-methoxyphenyl)thiazol-2-yl |
| R768 | thiophen-2-yl | 5-(4-fluorophenyl)thiazol-2-yl |
| R769 | thiophen-2-yl | 5-(2,4-difluorophenyl)thiazol-2-yl |
| R770 | thiophen-2-yl | 5-(3-methoxybenzyl)thiazol-2-yl |
| R771 | thiophen-2-yl | 4-(3-methoxyphenyl)thiazol-2-yl |
| R772 | thiophen-2-yl | 4-(4-fluorophenyl)thiazol-2-yl |
| R773 | cyclopropyl | 4-(methoxycarbonyl)thiazol-5-yl |
| R774 | cyclopropyl | 4-[(2-methoxy-2-oxoethyl)carbamoyl]thiazol-5-yl |
| R775 | cyclopropyl | 5-[1-N-(2-methoxy-2-oxoethyl)-1-H-indol-3-yl]oxazol-2-yl |
| R776 | cyclopropyl | 5-(2-methoxyphenyl)oxazol-2-yl |
| R777 | cyclopropyl | 5-[(S)-1-(tert-butoxycarbonyl)-2-phenylethyl]oxazol-2-yl |
| R778 | cyclopropyl | 5-[4-(methylcarboxy)phenyl]oxazol-2-yl |
| R779 | cyclopropyl | 5-(3-methoxybenzyl)oxazol-2-yl |
| R780 | cyclopropyl | 5-(4-phenyl)oxazol-2-yl |
| R781 | cyclopropyl | 5-(2-methoxyphenyl)thiazol-2-yl |
| R782 | cyclopropyl | 5-(3-methoxyphenyl)thiazol-2-yl |
| R783 | cyclopropyl | 5-(4-fluorophenyl)thiazol-2-yl |
| R784 | cyclopropyl | 5-(2,4-difluorophenyl)thiazol-2-yl |
| R785 | cyclopropyl | 5-(3-methoxybenzyl)thiazol-2-yl |
| R786 | cyclopropyl | 4-(3-methoxyphenyl)thiazol-2-yl |
| R787 | cyclopropyl | 4-(4-fluorophenyl)thiazol-2-yl |

Compounds according to the second aspect of Category IX which comprise a substituted or unsubstituted thiazol-4-yl unit for $R^1$ can be prepared by the procedure outlined in Schemes XIX, XX, and XXI and described herein below in Examples 20, 21, and 22.

Scheme XIX

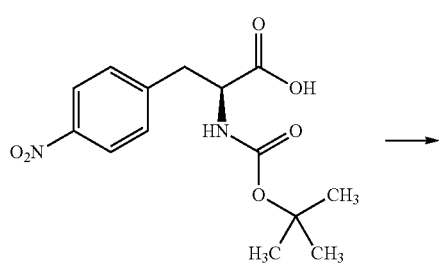

-continued
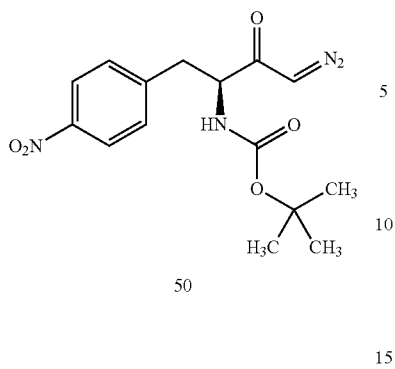
50
Reagents and Conditions: (a)(i) (Iso-Butyl)OCOCl, Et₃N, THF; 0° C., 20 Min
(ii) CH₂N₂; 0° C. to Room Temp for 3 Hours
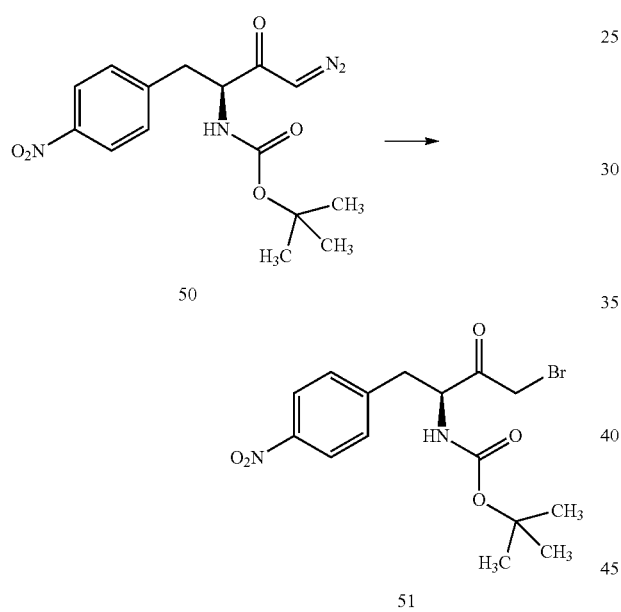
Reagents and Conditions: (b) 48% HBr, THF; 0° C., 1.5 hr
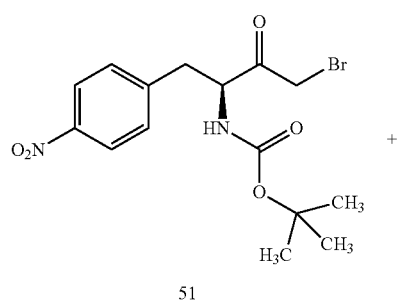
-continued
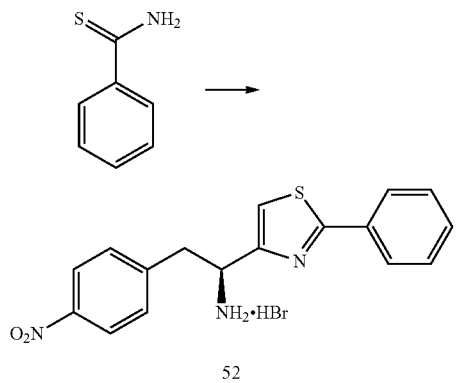
Reagents and Conditions: (c) CH₃CN; Reflux 2 hr
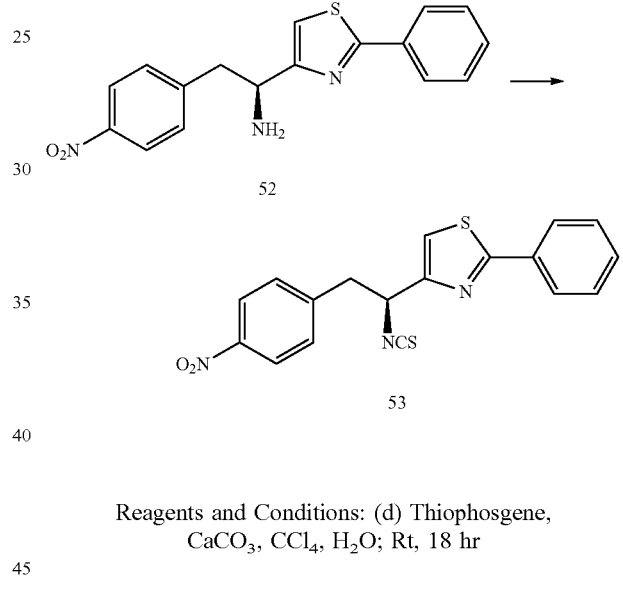
Reagents and Conditions: (d) Thiophosgene, CaCO₃, CCl₄, H₂O; Rt, 18 hr
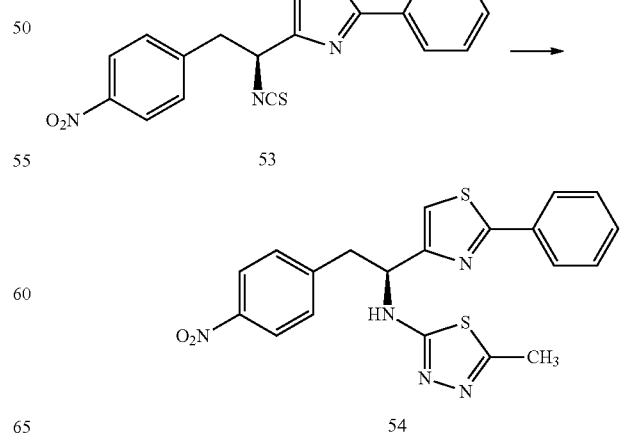

Reagents and Conditions: (e)(i) CH₃C(O)NHNH₂, EtOH; Reflux, 2 hr (ii) POCl₃, Rt 18 hr; 50° C. 2 hr

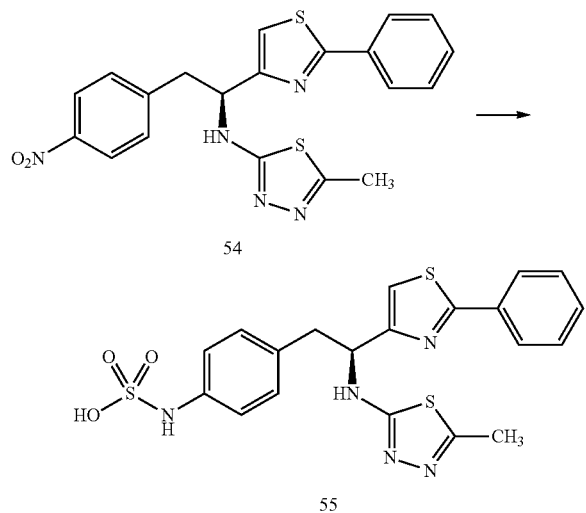

Reagents and Conditions: (f) (i) H₂:Pd/C, MeOH; (ii) SO₃-Pyridine, NH₄OH

EXAMPLE 20

(S)-4-(2-(5-Methyl-1,3,4-thiadiazol-2-ylamino)-2-(2-phenylthiazol-4-yl)ethyl)phenylsulfamic Acid (55)

Preparation of [3-diazo-1-(4-nitrobenzyl)-2-oxo-propyl]-carbamic acid tert-butyl ester (50): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes then filtered. The filtrate is treated with an ether solution of diazomethane (~16 mmol) at 0° C. The reaction mixture is stirred at room temperature for 3 hours and concentrated. The residue is dissolved in EtOAc and washed successively with water and brine, dried (Na₂SO₄), filtered and concentrated in vacuo. The resulting residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of [3-bromo-1-(4-nitro-benzyl)-2-oxo-propyl]carbamic acid tert-butyl ester (51): To a 0° C. solution of [3-diazo-1-(4-nitrobenzyl)-2-oxo-propyl]-carbamic acid tert-butyl ester, 50, (0.350 g, 1.04 mmol) in THF (5 mL) is added dropwise 48% aq. HBr (0.14 mL, 1.25 mmol). The reaction mixture is stirred at 0° C. for 1.5 hours and quenched at 0° C. with saturated aqueous Na₂CO₃. The mixture is extracted with EtOAc (3×25 mL) and the combined organic extracts are washed with brine, dried (Na₂SO₄), filtered and concentrated in vacuo to afford 0.400 g of the desired product that is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-(2-phenylthiazol-4-yl)ethanamine hydrobromide salt (52): A mixture of [3-bromo-1-(4-nitro-benzyl)-2-oxo-propyl]-carbamic acid tert-butyl ester, 51, (1.62 g, 4.17 mmol) and benzothioamide (0.630 g, 4.59 mmol), in CH₃CN (5 mL) is refluxed for 24 hours. The reaction mixture is cooled to room temperature and diethyl ether (50 mL) is added to the solution and the precipitate that forms is collected by filtration. The solid is dried under vacuum to afford 1.059 g (63%) of the desired product. ESI+MS 326 (M+1).

Preparation of (S)-4-[1-isothiocyanato-2-(4-nitrophenyl)-ethyl]-2-phenylthiazole (53): To a solution of (S)-2-(4-nitrophenyl)-1-(2-phenylthiazol-4-yl)ethanamine hydrobromide salt, 52, (2.03 g, 5 mmol) and CaCO₃ (1 g, 10 mmol) in CCl₄/water (10:7.5 mL) is added thiophosgene (0.46 mL, 6 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue that is purified over silica (CH₂Cl₂) to afford 1.71 g (93% yield) of the desired product. ESI+ MS 368 (M+1).

Preparation of (S)-5-methyl-N-[2-(4-nitrophenyl)-1-(2-phenylthiazol-4-yl)ethyl]-1,3,4-thiadiazol-2-amine (54): A solution of (S)-4-[1-isothiocyanato-2-(4-nitrophenyl)-ethyl]-2-phenylthiazole, 53, (332 mg, 0.876 mmol) and acetic hydrazide (65 mg, 0.876 mmol) in EtOH (5 mL) is refluxed for 2 hours. The solvent is removed under reduced pressure, the residue is dissolved in POCl₃ (3 mL) and the resulting solution is stirred at room temperature for 18 hours after which the solution is heated to 50° C. for 2 hours. The solvent is removed in vacuo and the residue is dissolved in EtOAc (40 mL) and the resulting solution is treated with 1N NaOH until the pH remains approximately 8. The solution is extracted with EtOAc. The combined aqueous layers are washed with EtOAc, the organic layers combined, washed with brine, dried over MgSO₄, filtered, and concentrated in vacuo to afford 0.345 g (93% yield) of the desired product as a yellow solid. ¹H NMR (CDCl₃) 8.09 (d, J=8.4 Hz, 2H), 7.91 (m, 2H), 7.46 (m, 4H), 7.44 (s, 1H), 5.23 (m, 1H), 3.59 (m, 2H), 2.49 (s, 3H). ESI+ MS 424 (M+1).

Preparation of (S)-4-[2-(5-methyl-1,3,4-thiadiazol-2-ylamino)-2-(2-phenylthiazol-4-yl)ethyl]phenylsulfamic acid (55): (S)-5-Methyl-N-[2-(4-nitrophenyl)-1-(2-phenylthiazol-4-yl)ethyl]-1,3,4-thiadiazol-2-amine, 54, (0.404 g, 0.954 mmol) is dissolved in MeOH (5 mL). Pd/C (50 mg, 10% w/w) is added and the mixture is stirred under a hydrogen atmosphere until the reaction is judged to be complete. The reaction mixture is filtered through a bed of CELITE™ and the solvent removed under reduced pressure. The crude product is dissolved in pyridine (4 mL) and treated with SO₃-pyridine (0.304 g, 1.91 mmol). The reaction is stirred at room temperature for 5 minutes after which a 7% solution of NH₄OH (50 mL) is added. The mixture is then concentrated and the resulting residue is purified by reverse phase preparative HPLC to afford 0.052 g (11% yield) of the desired product as the ammonium salt. ¹H NMR (CD₃OD): δ 8.00-7.97 (m, 2H), 7.51-7.47 (m, 3H), 7.23 (s, 1H), 7.11-7.04 (q, 4H, J=9.0 Hz), 5.18 (t, 1H, J=7.2 Hz), 3.34-3.22 (m, 2H), 2.50 (s, 3H). ESI– MS 472 (M–1).

Scheme XX

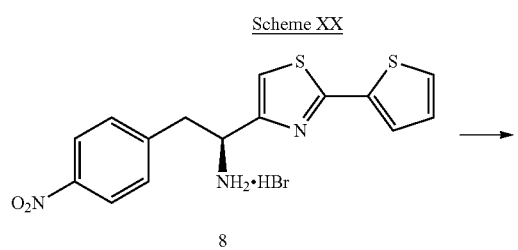

Reagents and Conditions: (a) Thiophosgene, CaCO₃, CCL/H₂O; Rt, 18 hr

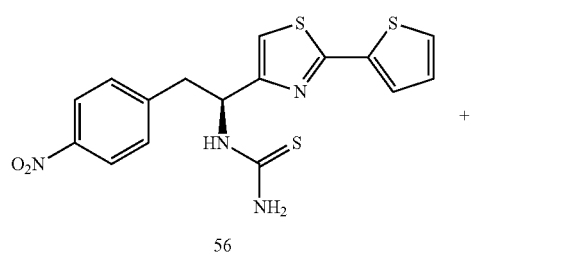

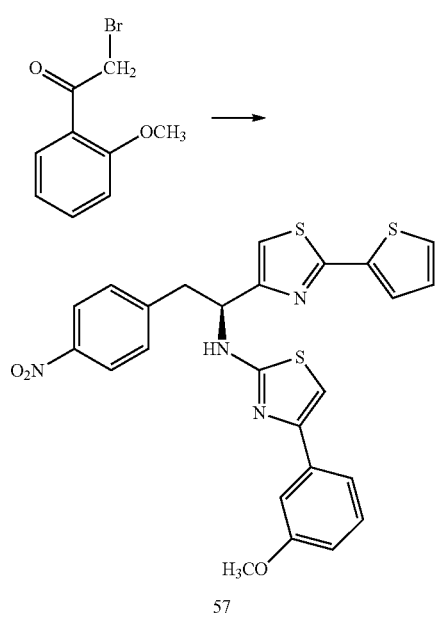

Reagents and Conditions: (b) CH₃CN, Reflux, 5 Hours

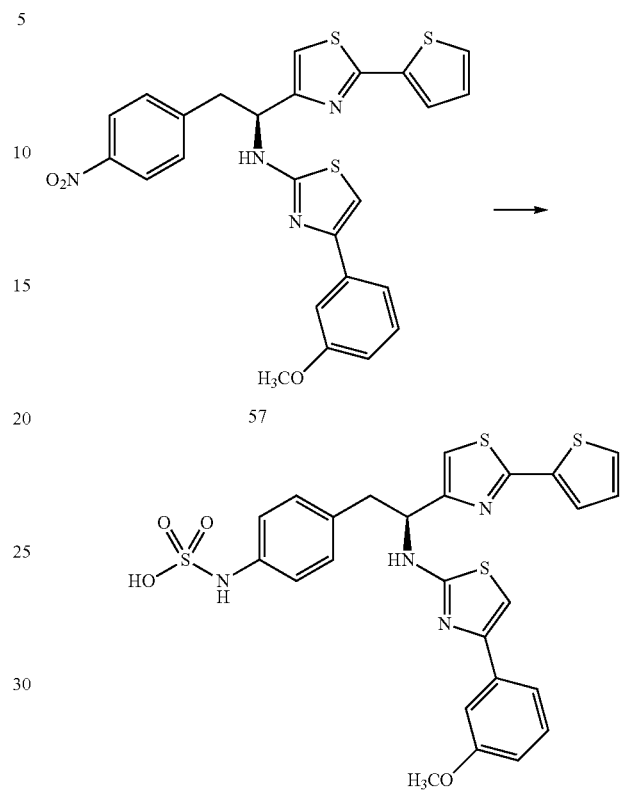

Reagents and Conditions: (c) (i) H₂:Pd/C, MeOH; (ii) SO₃-Pyridine, NH₄OH; Rt, 18 hr

EXAMPLE 21

4-{(S)-2-[4-(2-Methoxyphenyl)thiazol-2-ylamino)-2-[2-(thiophen-2-yl)thiazol-4-yl] ethyl}phenylsulfamic Acid (58)

Preparation of (S)-1-[1-(thiophen-2-ylthiazol-4-yl)-2-(4-nitrophenyl)ethyl]-thiourea (56): To a solution of (S)-2-(4-nitrophenyl)-1-(thiophen-2-ylthiazol-4-yl)ethanamine hydrobromide salt, 8, (1.23 g, 2.98 mmol) and CaCO₃ (0.597 g, 5.96 mmol) in CCl₄/water (10 mL/5 mL) is added thiophosgene (0.412 g, 3.58 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is subsequently treated with ammonia (0.5M in 1,4-dioxane, 29.4 mL, 14.7 mmol) which is purified over silica to afford 0.490 g of the desired product as a red-brown solid. ESI+ MS 399 (M+1).

Preparation of 4-(2-methoxyphenyl)-N—{(S)-2-(4-nitrophenyl)-1-[2-(thiophen-2-yl)thiazol-4-yl]ethyl}thiazol-2-amine (57): (S)-1-[1-(thiophen-2-ylthiazol-4-yl)-2-(4-nitrophenyl)ethyl]-thiourea, 56, (265 mg, 0.679 mmol) is treated with bromo-2'-methoxyacetophenone (171 mg, 0.746 mmol) to afford 0.221 g of the product as a yellow solid. ESI+ MS 521 (M+1).

Preparation on 4-{(S)-2-[4-(2-methoxyphenyl)thiazol-2-ylamino)-2-[2-(thiophen-2-yl)thiazol-4-yl]ethyl}phenylsulfamic acid (58): 4-(2-methoxyphenyl)-N—{(S)-2-(4-nitrophenyl)-1-[2-(thiophen-2-yl)thiazol-4-yl]ethyl}thiazol-2-amine, 57, (0.229 g) is dissolved in 12 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 6 mL pyridine and treated with $SO_3$-pyridine (140 mg). The reaction is stirred at room temperature for 5 minutes after which 10 mL of a 7% solution of $NH_4OH$ is added. The mixture is then concentrated and the resulting residue is purified by reverse-phase chromatography to afford 0.033 g of the desired product as the ammonium salt. $^1H$ NMR ($CD_3OD$): δ 7.96-7.93 (m, 1H), 7.60-7.55 (m, 2H), 7.29-7.23 (m, 1H), 7.18-6.95 (m, 9H), 5.15 (t, 1H, J=6.9 Hz), 3.90 (s, 3H), 3.35-3.24 (m, 2H).

Compounds according to the second aspect of Category IX which comprise a substituted or unsubstituted oxazol-2-yl unit for $R^1$ can be prepared by the procedure outlined in Scheme XXI and described herein below in Example 22. Intermediate 39 can be prepared according to Scheme XVII and Example 18.

Reagents and Conditions: (a)
1-Azido-1-(3-Methoxyphenyl)Ethanone, $PPh_3$, Dioxane, 90° C. 20 Minutes

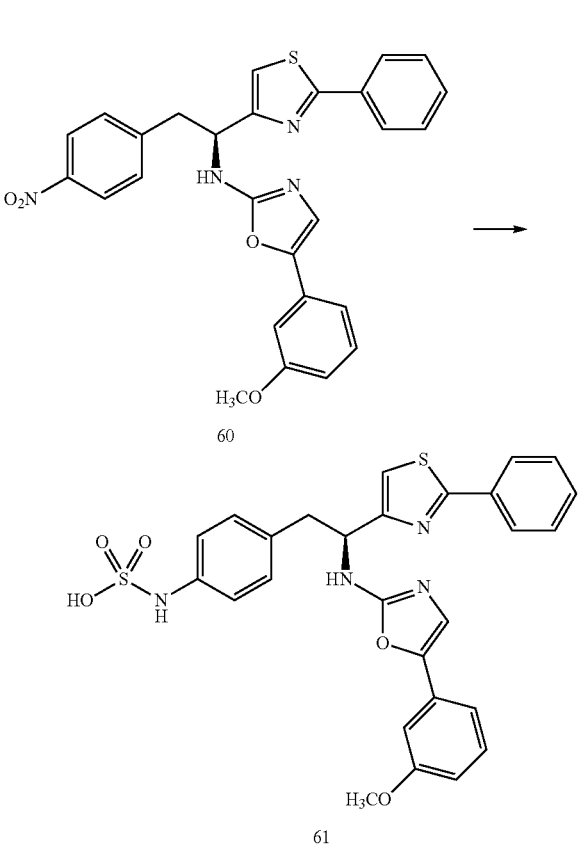

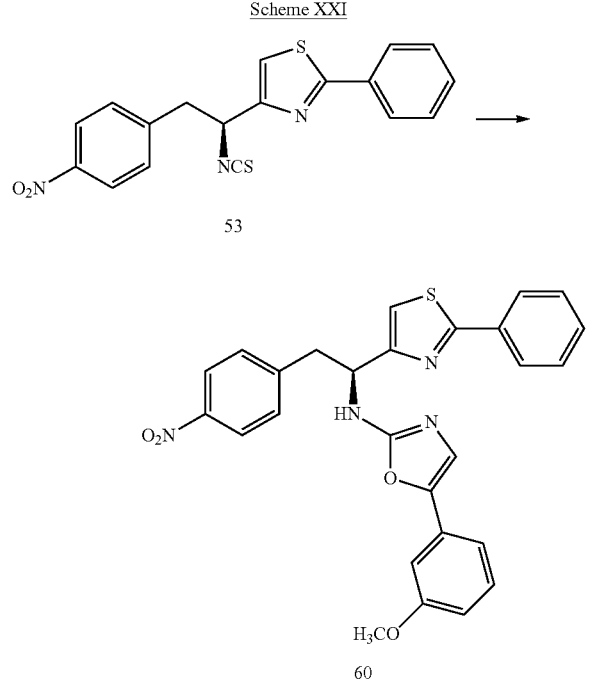

Reagents and Conditions: (b) (i) $H_2$:Pd/C, MeOH; (ii) $SO_3$-Pyridine, $NH_4OH$; Rt, 18 hr

EXAMPLE 22

4-{(S)-2-[5-(3-Methoxyphenyl)oxazole-2-ylamino]-2-(2-phenylthiazole-4-yl)ethyl}phenylsulfamic Acid (61)

Preparation of [5-(3-methoxyphenyl)oxazol-2-yl]-[2-(4-nitrophenyl)-1-(2-phenylthiazole-4-yl) ethyl]amine (60): A mixture of (S)-4-(isothiocyanato-2-(4-nitrophenyl)ethyl)-2-phenylthiazole, 53, (300 mg, 0.81 mmol), 1-azido-1-(3-methoxyphenyl)ethanone (382 mg, 2.0 mmol) and $PPh_3$ (0.8 g, polymer bound, ~3 mmol/g) in dioxane (6 mL) is heated at 90° C. for 20 minutes. The reaction solution is cooled to room temperature and the solvent removed in vacuo and the resulting residue is purified over silica to afford 300 mg (74% yield) of the desired product as a yellow solid. $^1H$ NMR (300 MHz, MeOH-$d_4$) δ 8.02 (d, J=7.2 Hz, 2H), 7.92-7.99 (m, 2H), 7.42-7.47 (m, 3H), 7.22-7.27 (m, 3H), 6.69-7.03 (m, 4H), 6.75-6.78 (m, 1H), 5.26 (t, J=6.3 Hz, 1H), 3.83 (s, 4H), 3.42-3.45 (m, 2H).

Preparation of 4-{(S)-2-[5-(3-methoxyphenyl)oxazole-2-ylamino]-2-(2-phenylthiazole-4-yl)ethyl}phenylsulfamic acid (61): [5-(3-methoxyphenyl)oxazol-2-yl]-[2-(4-nitrophenyl)-1-(2-phenylthiazole-4-yl) ethyl]amine, 60, (300 mg, 0.60 mmol) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (10 mL) and treated with SO₃-pyridine (190 mg, 1.2 mmol). The reaction is stirred at room temperature for 5 minutes after which a 7% solution of NH₄OH is added. The mixture is then concentrated and the resulting residue is purified by reverse-phase chromatography to afford 0.042 g of the desired product as the ammonium salt. ¹H NMR (300 MHz, MeOH-d₄) δ 7.99 (d, J=7.5 Hz, 2H), 7.46-7.50 (m, 3H), 7.23-7.29 (m, 3H), 7.04-7.12 (m, 6H), 6.78 (dd, J=8.4 and 2.4 Hz, 1H), 5.16 (t, J=6.6 Hz, 1H), 3.81 (s, 3H), 3.29-3.39 (m, 1H), 3.17 (dd, J=13.8 and 8.1 Hz, 1H).

The following are non-limiting examples of the second aspect of Category IX of the present disclosure.

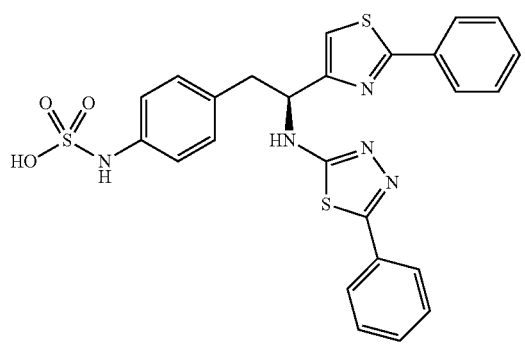 [SMILES: O=S(=O)(O)Nc1ccc(C[C@H](Nc2nnc(-c3ccccc3)s2)c2csc(-c3ccccc3)n2)cc1]

(S)-4-(2-(5-Phenyl-1,3,4-thiadiazol-2-ylamino)-2-(2-phenylthiazol-4-yl)ethyl)-phenylsulfamic acid: ¹H NMR (CD₃OD): δ 7.97-7.94 (m, 2H), 7.73-7.70 (m, 2H), 7.44-7.39 (m, 6H), 7.25 (s, 1H), 7.12 (s, 4H), 5.29 (t, 1H, J=6.9 Hz), 3.35-3.26 (m, 2H).

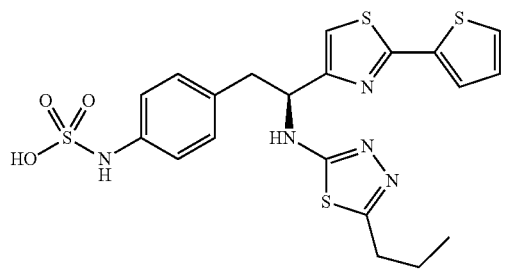 [SMILES: CCCc1nnc(N[C@@H](Cc2ccc(NS(=O)(=O)O)cc2)c2csc(-c3cccs3)n2)s1]

4-((S)-2-(5-Propyl-1,3,4-thiadiazol-2-ylamino)-2-(2-(thiophen-2-yl)thiazol-4-yl)ethyl)phenylsulfamic acid: ¹H NMR (CD₃OD): δ 7.59-7.54 (m, 2H), 7.17-7.03 (m, 6H), 5.13 (t, 1H, J=7.2 Hz), 3.32-3.13 (m, 2H), 2.81 (t, 2H, J=7.4 Hz), 1.76-1.63 (h, 6H, J=7.4 Hz), 0.97 (t, 3H, J=7.3 Hz).

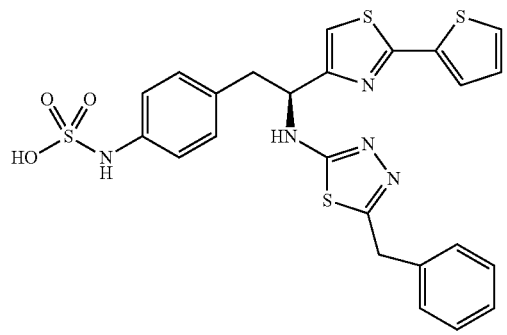 [SMILES: O=S(=O)(O)Nc1ccc(C[C@H](Nc2nnc(Cc3ccccc3)s2)c2csc(-c3cccs3)n2)cc1]

4-((S)-2-(5-Benzyl-1,3,4-thiadiazol-2-ylamino)-2-(2-(thiophen-2-yl)thiazol-4-yl)ethyl)phenylsulfamic acid: ¹H NMR (CD₃OD): δ (m, 2H), 7.49-7.45 (m, 2H), 7.26-7.16 (m, 5H), 7.05-6.94 (m, 6H), 5.04 (t, 1H, J=7.1 Hz), 4.07 (s, 2H), 3.22-3.04 (m, 2H).

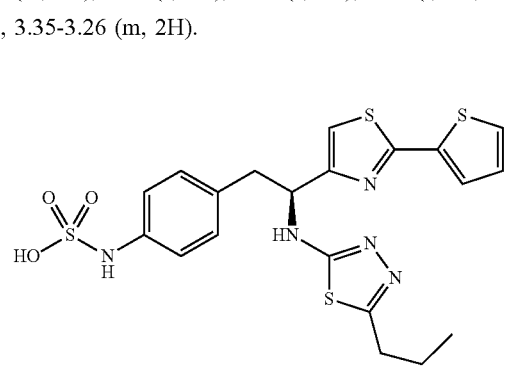

4-((S)-2-(5-(Naphthalen-1-ylmethyl)-1,3,4-thiadiazol-2-ylamino)-2-(2-(thiophen-2-yl)thiazol-4-yl)ethyl)phenylsulfamic acid: ¹H NMR (CD₃OD): δ 8.08-8.05 (m, 1H), 7.89-7.80 (m, 2H), 7.55-7.43 (m, 6H), 7.11-7.00 (m, 6H), 5.08 (t, 1H, J=7.1 Hz), 4.63 (s, 2H), 3.26-3.08 (m, 2H).

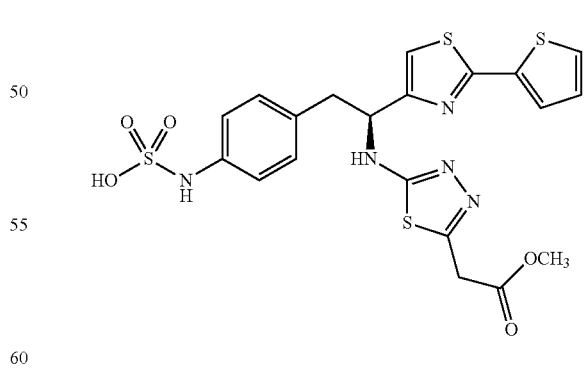

4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid: ¹H NMR (CD₃OD): δ 7.48-7.44 (m, 2H), 7.03-6.92 (m, 6H), 5.02 (t, 1H, J=7.2 Hz), 4.30 (s, 2H), 3.55 (s, 3H), 3.22-3.02 (m, 2H).

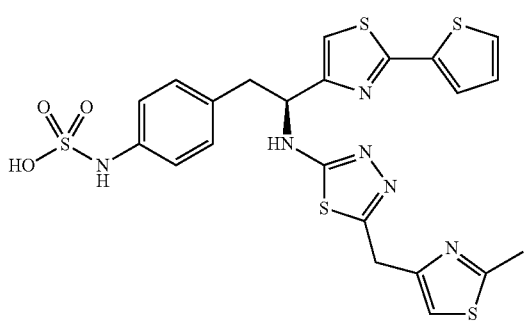 [SMILES: Cc1nc(Cc2nnc(N[C@@H](Cc3ccc(NS(=O)(=O)O)cc3)c3csc(-c4cccs4)n3)s2)cs1]

4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid: $^1$H NMR (CD$_3$OD): δ 7.60-7.56 (m, 2H), 7.19 (s, 1H), 7.15-7.12 (m, 2H), 7.09-7.03 (q, 4H, J=8.7 Hz), 5.14 (t, 1H, J=7.2 Hz), 4.28 (s, 2H), 3.33-3.14 (m, 2H), 2.67 (s, 3H).

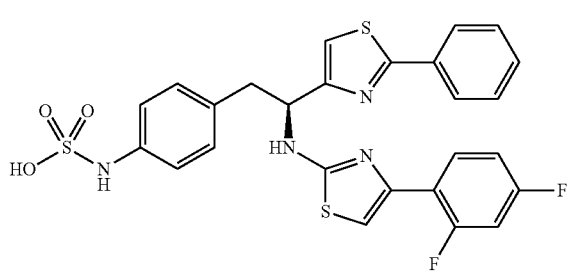 [SMILES: O=S(=O)(O)Nc1ccc(C[C@H](Nc2nc(-c3ccc(F)cc3F)cs2)c2csc(-c3ccccc3)n2)cc1]

4-{(S)-2-[4-(2,4-Difluorophenyl)thiazol-2-ylamino]-2-[2-(thiophen-2-yl)thiazol-4-yl]ethyl}phenylsulfamic acid: $^1$H NMR (CD$_3$OD): δ 8.06-8.02 (q, 1H, J=6.8 Hz), 7.59-7.54 (m, 2H), 7.16-7.08 (m, 6H), 7.01-6.88 (m, 4H), 5.20 (t, 1H, J=7.0 Hz), 3.36-3.17 (m, 2H).

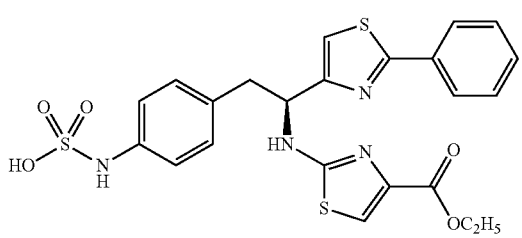 [SMILES: CCOC(=O)c1csc(N[C@@H](Cc2ccc(NS(=O)(=O)O)cc2)c2csc(-c3ccccc3)n2)n1]

(S)-4-{2-[4-(Ethoxycarbonyl)thiazol-2-ylamino]-2-(2-phenylthiazol-4-yl)ethyl}phenylsulfamic acid: $^1$H NMR (CD$_3$OD): δ 8.02-7.99 (m, 2H), 7.54-7.45 (m, 4H), 7.26 (s, 1H), 7.08 (s, 4H), 5.26 (t, 1H, J=6.9 Hz), 4.35-4.28 (q, 2H, J=6.9 Hz), 3.38-3.18 (m, 2H), 1.36 (t, 3H, J=7.2 Hz).

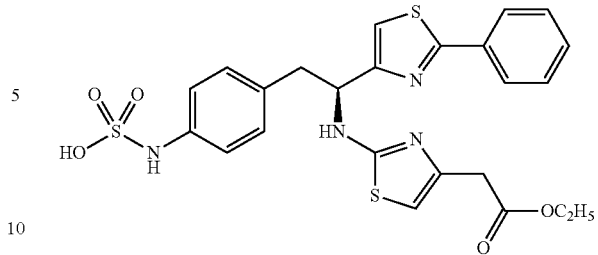

(S)-4-{2-[4-(2-Ethoxy-2-oxoethyl)thiazol-2-ylamino]-2-(2-phenylthiazol-4-yl)ethyl}phenylsulfamic acid: $^1$H NMR (CD$_3$OD): δ 7.96 (m, 2H), 7.50-7.46 (m, 3H), 7.21 (s, 1H), 7.10-7.04 (m, 4H), 6.37 (s, 1H), 5.09 (t, 1H, J=6.9 Hz), 4.17-4.10 (q, 2H, J=7.1 Hz), 3.54 (s, 2H), 3.35-3.14 (m, 2H), 1.22 (t, 3H, J=7.1 Hz).

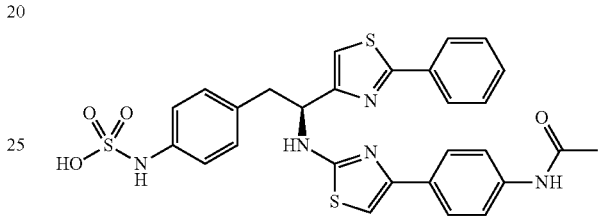

(S)-4-{2-[4-(4-acetamidophenyl)thiazol-2-ylamino]-2-(2-phenylthiazol-4-yl)ethyl}phenylsulfamic acid: $^1$H NMR (CD$_3$OD): δ 8.11 (m, 2H), 7.82-7.80 (m, 2H), 7.71-7.61 (m, 6H), 7.40 (s, 1H), 7.23 (s, 4H), 5.32 (t, 1H, J=7.0 Hz), 3.51-3.35 (m, 2H), 2.28 (s, 3H).

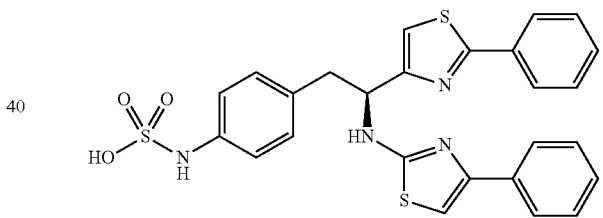

(S)-4-[2-(4-phenylthiazol-2-ylamino)-2-(2-phenylthiazol-4-yl)ethyl]phenylsulfamic acid: $^1$H NMR (CD$_3$OD): δ 8.03-7.99 (m, 2H), 7.75-7.72 (d, 2H, J=8.4 Hz), 7.53-7.48 (m, 3H), 7.42 (m, 4H), 7.12 (s, 4H), 6.86 (s, 1H), 5.23 (t, 1H, J=7.2 Hz), 3.40-3.27 (m, 2H).

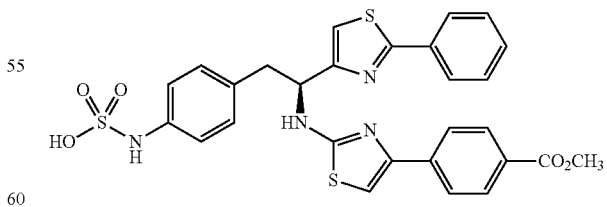

(S)-4-{2-[4-(4-(methoxycarbonyl)phenyl)thiazol-2-ylamino]-2-(2-phenylthiazol-4-yl)ethyl}phenylsulfamic acid: $^1$H NMR (CD$_3$OD): δ 8.04-8.00 (m, 4H), 7.92-7.89 (d, 2H, J=9.0 Hz), 7.53-7.49 (m, 3H), 7.30 (s, 1H), 7.15 (s, 4H), 7.05 (s, 1H), 5.28 (t, 1H, J=6.9 Hz), 3.93 (s, 3H), 3.35-3.24 (m, 2H).

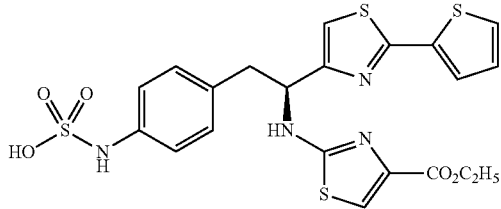 [SMILES: CCOC(=O)c1csc(N[C@@H](Cc2ccc(NS(=O)(=O)O)cc2)c2csc(-c3cccs3)n2)n1]

4-{(S)-2-[4-(Ethoxycarbonyl)thiazol-2-ylamino]-2-[2-(thiophen-2-yl)thiazol-4-yl]ethyl}phenylsulfamic acid: $^1$H NMR (CD$_3$OD): δ 7.43-7.38 (m, 2H), 7.26 (s, 1H), 7.00-6.94 (m, 3H), 6.89 (s, 4H), 5.02 (t, 1H, J=7.0 Hz), 4.16-4.09 (q, 2H, J=7.1 Hz), 3.14-2.94 (m, 2H), 1.17 (t, 3H, J=7.1 Hz).

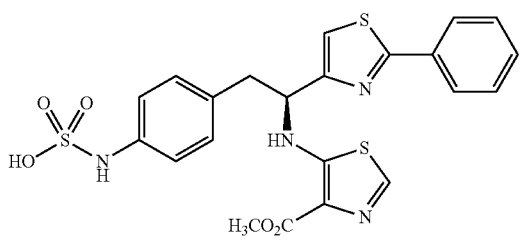 [SMILES: COC(=O)c1ncsc1N[C@@H](Cc1ccc(NS(=O)(=O)O)cc1)c1csc(-c2ccccc2)n1]

(S)-4-[2-(4-(Methoxycarbonyl)thiazol-5-ylamino)-2-(2-phenylthiazole-4-yl)ethyl]phenylsulfamic acid: $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

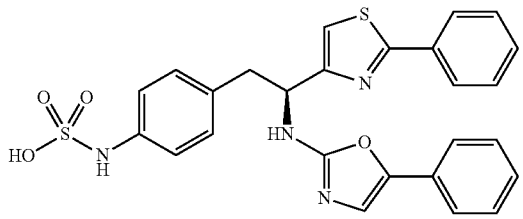 [SMILES: O=S(=O)(O)Nc1ccc(C[C@H](Nc2ncc(-c3ccccc3)o2)c2csc(-c3ccccc3)n2)cc1]

(S)-4-[2-(5-Phenyloxazol-2-ylamino)-2-(2-phenylthiazol-4-yl)ethyl]-phenylsulfamic acid: $^1$H NMR (300 MHz, MeOH-d$_4$) δ 7.94-7.96 (m, 2H), 7.45-7.49 (m, 5H), 7.32 (t, J=7.8 Hz, 2H), 7.12 (s, 1H), 7.19 (t, J=7.2 Hz, 1H), 7.12 (s, 4H), 7.05 (s, 1H), 5.15 (t, J=6.4 Hz, 1H), 3.34 (dd, J=14.1 and 8.4 Hz, 1H), 3.18 (dd, J=14.1 and 8.4 Hz, 1H).

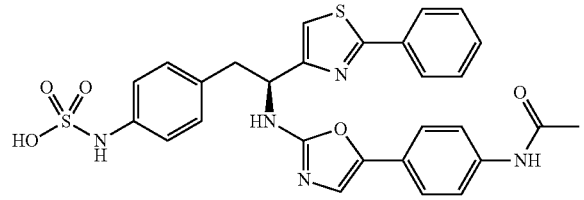 [SMILES: CC(=O)Nc1ccc(-c2cnc(N[C@@H](Cc3ccc(NS(=O)(=O)O)cc3)c3csc(-c4ccccc4)n3)o2)cc1]

(S)-4-{2-[5-(4-Acetamidophenyl)oxazol-2-ylamino]-2-(2-phenylthiazol-4-yl)ethyl}phenylsulfamic acid: $^1$H NMR (300 MHz, MeOH-d$_4$) δ 7.92-7.94 (m, 2H), 7.55-7.58 (m, 2H), 7.39-7.50 (m, 5H), 7.26 (s, 1H), 7.12 (s, 4H), 7.02 (s, 1H0), 5.14 (t, J=7.8 Hz, 1H), 3.13-3.38 (m, 2H), 2.11 (s, 3H).

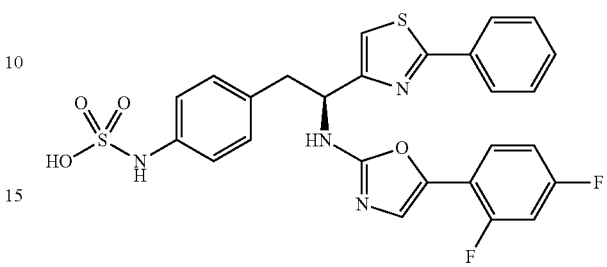

4-((S)-2-(5-(2,4-Difluorophenyl)oxazole-2-ylamino)-2-(2-phenylthiazole-4-yl)ethyl)phenylsulfamic acid: $^1$H NMR (300 MHz, MeOH-d$_4$) δ 7.97-7.99 (m, 2H), 7.54-7.62 (m, 1H), 7.45-7.50 (m, 3H), 7.28 (s, 1H), 7.12 (s, 4H), 6.97-7.06 (m, 3H), 5.15-5.20 (m, 1H), 3.28-3.40 (m, 1H), 3.20 (dd, J=13.8 and 8.4 Hz, 1H).

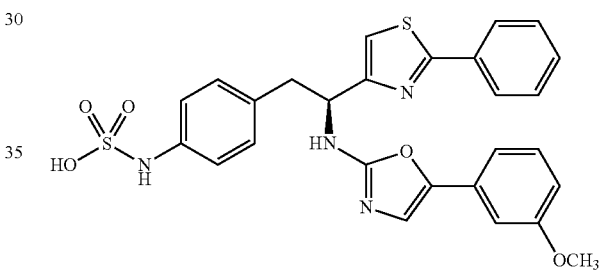

4-{(S)-2-[5-(3-Methoxyphenyl)oxazol-2-ylamino]-2-[(2-thiophen-2-yl)thiazole-4-yl]ethyl}phenylsulfamic acid: $^1$H NMR (300 MHz, MeOH-d$_4$) δ 7.55-7.60 (m, 2H), 7.26 (t, J=8.1 Hz, 1H), 7.21 (s, 1H), 7.04-7.15 (m, 8H), 6.77-6.81 (m, 1H), 5.10 (t, J=6.3 Hz, 1H), 3.81 (s, 3H), 3.29-3.36 (m, 1H), 3.15 (dd, J=14.1 and 8.4 Hz, 1H).

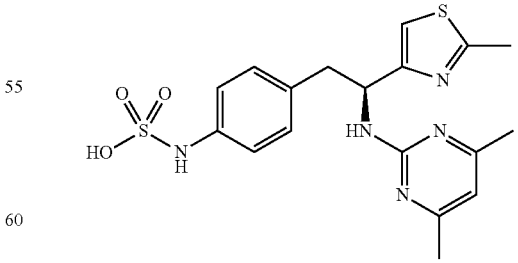

(S)-4-[2-(4,6-Dimethylpyrimidin-2-ylamino)-2-(2-methylthiazole-4-yl)ethyl]phenylsulfamic acid: $^1$H NMR (300 MHz, MeOH-d$_4$) δ 7.00-7.10 (m, 5H), 6.44 (s, 1H), 5.50 (t, J=7.2 Hz, 1H), 3.04-3.22 (m, 2H), 2.73 (s, 3H), 2.27 (s, 6H).

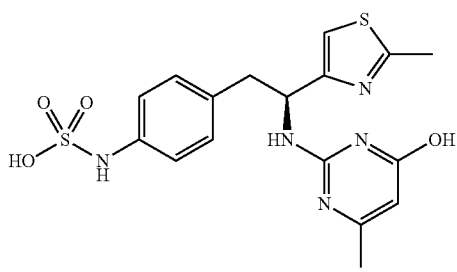 [SMILES: Cc1cc(O)nc(N[C@@H](Cc2ccc(NS(=O)(=O)O)cc2)c2csc(C)n2)n1]

(S)-4-[2-(4-Hydroxy-6-methylpyrimidine-2-ylamino)-2-(2-methylthiazole-4-yl)ethyl]phenylsulfamic acid: $^1$H NMR (300 MHz, MeOH-d4) δ 7.44 (d, J=8.4 Hz, 2H), 6.97-7.10 (m, 4H), 5.61 (s, 1H), 5.40-5.49 (m, 1H), 3.10-3.22 (m, 2H), 2.73 (s, 3H), 2.13 (s, 3H).

The first aspect of Category X of the present disclosure relates to compounds having the formula:

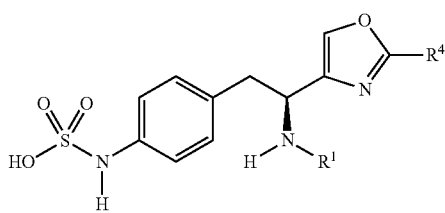

wherein $R^1$ is heteroaryl and $R^4$ is further described herein below in Table XIX.

TABLE XIX

| No. | $R^4$ | $R^1$ |
|---|---|---|
| S788 | phenyl | 4-(methoxycarbonyl)thiazol-5-yl |
| S789 | phenyl | 4-[(2-methoxy-2-oxoethyl)carbamoyl]thiazol-5-yl |
| S790 | phenyl | 5-[1-N-(2-methoxy-2-oxoethyl)-1-H-indol-3-yl]oxazol-2-yl |
| S791 | phenyl | 5-(2-methoxyphenyl)oxazol-2-yl |
| S792 | phenyl | 5-[(S)-1-(tert-butoxycarbonyl)-2-phenylethyl]oxazol-2-yl |
| S793 | phenyl | 5-[4-(methylcarboxy)phenyl]oxazol-2-yl |
| S794 | phenyl | 5-(3-methoxybenzyl)oxazol-2-yl |
| S795 | phenyl | 5-(4-phenyl)oxazol-2-yl |
| S796 | phenyl | 5-(2-methoxyphenyl)thiazol-2-yl |
| S797 | phenyl | 5-(3-methoxyphenyl)thiazol-2-yl |
| S798 | phenyl | 5-(4-fluorophenyl)thiazol-2-yl |
| S799 | phenyl | 5-(2,4-difluorophenyl)thiazol-2-yl |
| S800 | phenyl | 5-(3-methoxybenzyl)thiazol-2-yl |
| S801 | phenyl | 4-(3-methoxyphenyl)thiazol-2-yl |
| S802 | phenyl | 4-(4-fluorophenyl)thiazol-2-yl |
| S803 | thiophen-2-yl | 4-(methoxycarbonyl)thiazol-5-yl |
| S804 | thiophen-2-yl | 4-[(2-methoxy-2-oxoethyl)carbamoyl]thiazol-5-yl |
| S805 | thiophen-2-yl | 5-[1-N-(2-methoxy-2-oxoethyl)-1-H-indol-3-yl]oxazol-2-yl |
| S806 | thiophen-2-yl | 5-(2-methoxyphenyl)oxazol-2-yl |
| S807 | thiophen-2-yl | 5-[(S)-1-(tert-butoxycarbonyl)-2-phenylethyl]oxazol-2-yl |
| S808 | thiophen-2-yl | 5-[4-(methylcarboxy)phenyl]oxazol-2-yl |
| S809 | thiophen-2-yl | 5-(3-methoxybenzyl)oxazol-2-yl |
| S810 | thiophen-2-yl | 5-(4-phenyl)oxazol-2-yl |
| S811 | thiophen-2-yl | 5-(2-methoxyphenyl)thiazol-2-yl |
| S812 | thiophen-2-yl | 5-(3-methoxyphenyl)thiazol-2-yl |
| S813 | thiophen-2-yl | 5-(4-fluorophenyl)thiazol-2-yl |
| S814 | thiophen-2-yl | 5-(2,4-difluorophenyl)thiazol-2-yl |
| S815 | thiophen-2-yl | 5-(3-methoxybenzyl)thiazol-2-yl |
| S816 | thiophen-2-yl | 4-(3-methoxyphenyl)thiazol-2-yl |
| S817 | thiophen-2-yl | 4-(4-fluorophenyl)thiazol-2-yl |

TABLE XIX-continued

| No. | $R^4$ | $R^1$ |
|---|---|---|
| S818 | cyclopropyl | 4-(methoxycarbonyl)thiazol-5-yl |
| S819 | cyclopropyl | 4-[(2-methoxy-2-oxoethyl)carbamoyl]thiazol-5-yl |
| S820 | cyclopropyl | 5-[1-N-(2-methoxy-2-oxoethyl)-1-H-indol-3-yl]oxazol-2-yl |
| S821 | cyclopropyl | 5-(2-methoxyphenyl)oxazol-2-yl |
| S822 | cyclopropyl | 5-[(S)-1-(tert-butoxycarbonyl)-2-phenylethyl]oxazol-2-yl |
| S823 | cyclopropyl | 5-[4-(methylcarboxy)phenyl]oxazol-2-yl |
| S824 | cyclopropyl | 5-(3-methoxybenzyl)oxazol-2-yl |
| S825 | cyclopropyl | 5-(4-phenyl)oxazol-2-yl |
| S826 | cyclopropyl | 5-(2-methoxyphenyl)thiazol-2-yl |
| S827 | cyclopropyl | 5-(3-methoxyphenyl)thiazol-2-yl |
| S828 | cyclopropyl | 5-(4-fluorophenyl)thiazol-2-yl |
| S829 | cyclopropyl | 5-(2,4-difluorophenyl)thiazol-2-yl |
| S830 | cyclopropyl | 5-(3-methoxybenzyl)thiazol-2-yl |
| S831 | cyclopropyl | 4-(3-methoxyphenyl)thiazol-2-yl |
| S832 | cyclopropyl | 4-(4-fluorophenyl)thiazol-2-yl |

Compounds according to the first aspect of Category X can be prepared by the procedure outlined in Scheme XXII and described herein below in Example 23.

Scheme XXII

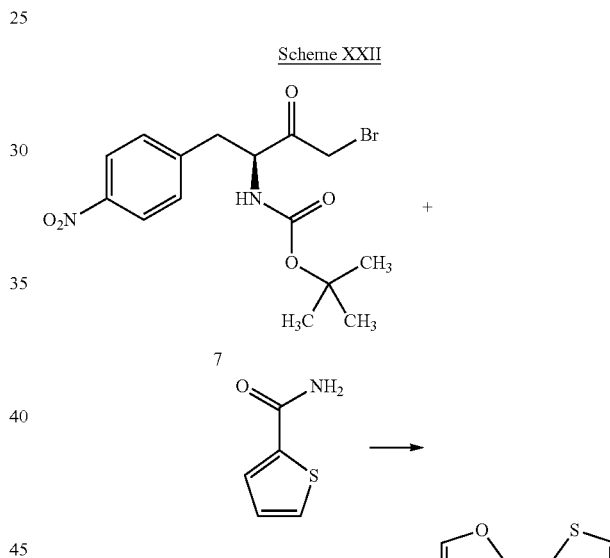

Reagents and Conditions: (a) CH$_3$CN; Reflux 2 hr

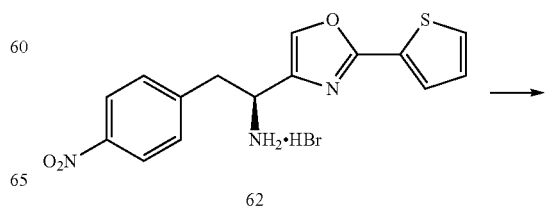

143
-continued

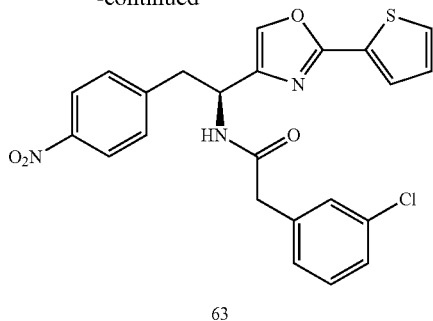

63

Reagents and Conditions: (b) (3-Cl)C₆H₄CO₂H, EDCI, HOBt, DIPEA, DMF; Rt, 18 hr

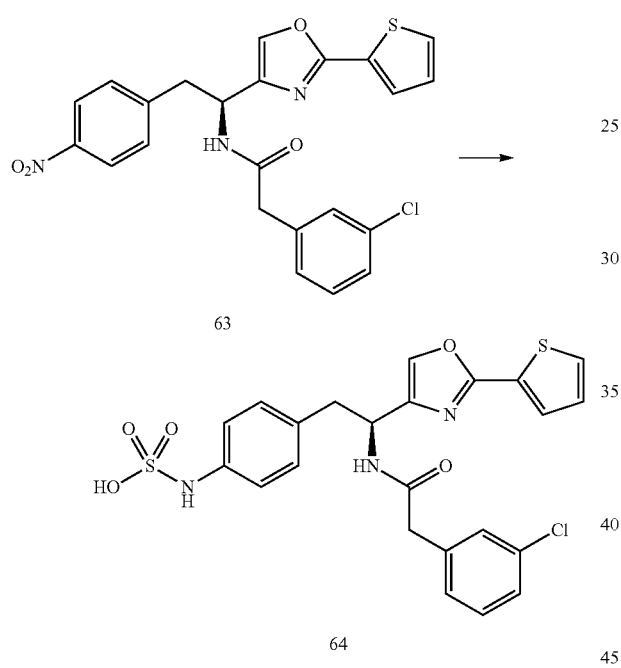

Reagents and Conditions: (c) (i) H₂:Pd/C, MeOH; (ii) SO₃-Pyridine, NH₄OH, Rt, 18 hr

EXAMPLE 23

4-((S)-2-(2-(3-Chlorophenyl)acetamido)-2-(2-(thiophen-2-yl)oxazol-4-yl)ethyl)phenylsulfamic Acid (64)

Preparation of (S)-2-(4-nitrophenyl)-1-[(thiophen-2-yl)oxazol-4-yl]ethanamine hydrobromide salt (62): A mixture of (S)-tert-butyl 4-bromo-1-(4-nitrophenyl)-3-oxobutan-2-ylcarbamate, 7, (38.7 g, 100 mmol), and thiophen-2-carboxamide (14 g, 110 mmol) (available from Alfa Aesar) in CH₃CN (500 mL) is refluxed for 5 hours. The reaction mixture is cooled to room temperature and diethyl ether (200 mL) is added to the solution. The precipitate which forms is collected by filtration. The solid is dried under vacuum to afford the desired product which can be used for the next step without purification.

144

Preparation of 2-(3-chlorophenyl)-N—{(S)-2-(4-nitrophenyl)-1-[2-(thiophen-2-yl)oxazol-4-yl]ethyl}acetamide (63): To a solution of (S)-2-(4-nitrophenyl)-1-[(thiophen-2-yl)oxazol-4-yl]ethanamine HBr, 47, (3.15 g, 10 mmol) 3-chlorophenyl-acetic acid (1.70 g, 10 mmol) and 1-hydroxybenzotriazole (HOBt) (0.70 g, 5.0 mmol) in DMF (50 mL) at 0° C., is added 1-(3-dimethylaminopropyl)-3-ethylcarbodiimide (EDCI) (1.90 g, 10 mmol) followed by triethylamine (4.2 mL, 30 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of —((S)-2-(2-(3-chlorophenyl)acetamido)-2-(2-(thiophen-2-yl)oxazol-4-yl)ethyl)phenylsulfamic acid (64): 2-(3-chlorophenyl)-N—{(S)-2-(4-nitrophenyl)-1-[2-(thiophen-2-yl)oxazol-4-yl]ethyl}acetamide, 63, (3 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue can be purified by reverse phase chromatography to afford the desired product as the ammonium salt.

The second aspect of Category X of the present disclosure relates to compounds having the formula:

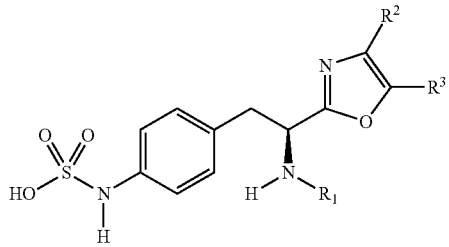

wherein R¹ is aryl and R² and R³ are further described herein below in Table XX.

TABLE XX

| No. | R² | R³ | R¹ |
|---|---|---|---|
| T833 | methyl | hydrogen | phenyl |
| T834 | methyl | hydrogen | benzyl |
| T835 | methyl | hydrogen | 2-fluorophenyl |
| T836 | methyl | hydrogen | 3-fluorophenyl |
| T837 | methyl | hydrogen | 4-fluorophenyl |
| T838 | methyl | hydrogen | 2-chlorophenyl |
| T839 | methyl | hydrogen | 3-chlorophenyl |
| T840 | methyl | hydrogen | 4-chlorophenyl |
| T841 | ethyl | hydrogen | phenyl |
| T842 | ethyl | hydrogen | benzyl |
| T843 | ethyl | hydrogen | 2-fluorophenyl |
| T844 | ethyl | hydrogen | 3-fluorophenyl |
| T845 | ethyl | hydrogen | 4-fluorophenyl |
| T846 | ethyl | hydrogen | 2-chlorophenyl |
| T847 | ethyl | hydrogen | 3-chlorophenyl |
| T848 | ethyl | hydrogen | 4-chlorophenyl |
| T849 | thien-2-yl | hydrogen | phenyl |

TABLE XX-continued

| No. | R² | R³ | R¹ |
|---|---|---|---|
| T850 | thien-2-yl | hydrogen | benzyl |
| T851 | thien-2-yl | hydrogen | 2-fluorophenyl |
| T852 | thien-2-yl | hydrogen | 3-fluorophenyl |
| T853 | thien-2-yl | hydrogen | 4-fluorophenyl |
| T854 | thien-2-yl | hydrogen | 2-chlorophenyl |
| T855 | thien-2-yl | hydrogen | 3-chlorophenyl |
| T856 | thiene-2-yl | hydrogen | 4-chlorophenyl |

Compounds according to the second aspect of Category X can be prepared by the procedure outlined in Scheme XXIII and described herein below in Example 24.

Scheme XXIII

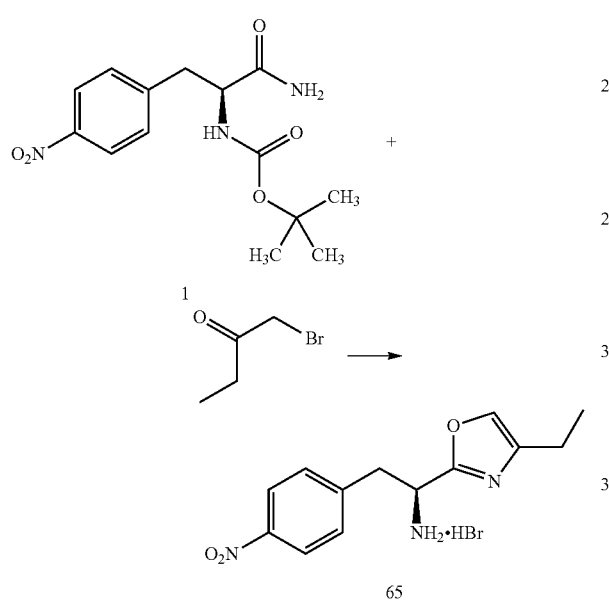

Reagents and Conditions: (a) CH₃CN; Reflux, 2 hr

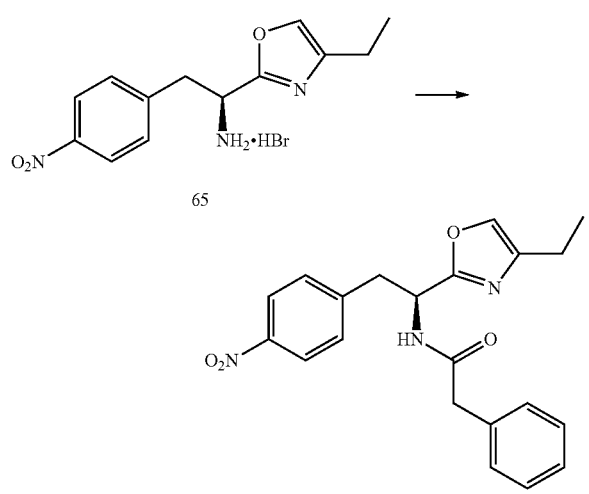

Reagents and Conditions: (b) C₆H₄CO₂H, EDCI, HOBt, DIPEA, DMF; Rt, 18 hr

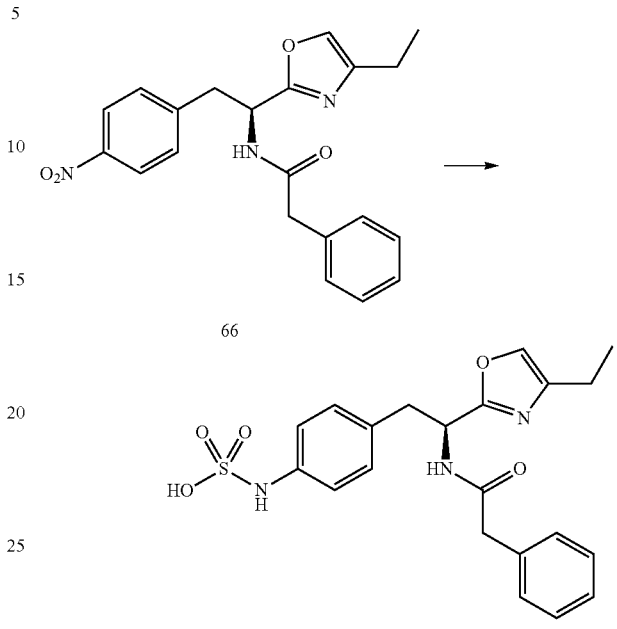

Reagents and Conditions: (c) (i) H₂:Pd/C, MeOH; (ii) SO₃-Pyridine, NH₄OH, Rt, 18 hr

EXAMPLE 24

{4-[2-(S)-(4-Ethyloxazol-2-yl)-2-phenylacetylaminoethyl]-phenyl}sulfamic Acid (67)

Preparation of (S)-1-(4-ethyloxazol-2-yl)-2-(4-nitrophenyl)ethanamine (65): A mixture of [1-(S)-carbamoyl-2-(4-nitrophenyl)ethyl-carbamic acid tert-butyl ester, 1, (10 g, 32.3 mmol) and 1-bromo-2-butanone (90%, 4.1 mL, 36 mmol) in CH₃CN (500 mL) is refluxed for 18 hours. The reaction mixture is cooled to room temperature and diethyl ether is added to the solution and the precipitate which forms is removed by filtration and is used without further purification.

Preparation of N-[1-(4-ethyloxazol-2-yl)-2-(4-nitrophenyl)ethyl]-2-phenyl-acetamide (66): To a solution of (S)-1-(4-ethyloxazol-2-yl)-2-(4-nitrophenyl)ethanamine, 65, (2.9 g, 11 mmol), phenylacetic acid (1.90 g, 14 mmol) and 1-hydroxybenzotriazole (HOBt) (0.94 g, 7.0 mmol) in DMF (100 mL) at 0° C., is added 1-(3-dimethylamino-propyl)-3-ethylcarbodiimide (EDCI) (2.68 g, 14 mmol) followed by triethylamine (6.0 mL, 42 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of {4-[2-(S)-(4-ethyloxazol-2-yl)-2-phenylacetylaminoethyl]-phenyl}sulfamic acid (67): N-[1-(4-ethyloxazol-2-yl)-2-(4-nitrophenyl)ethyl]-2-phenyl-acetamide, 66, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with $SO_3$-pyridine (0.177 g, 1.23). The reaction is stirred at room temperature for 5 minutes after which a 7% solution of $NH_4OH$ (10 mL) is added. The mixture is then concentrated and the resulting residue is purified by reverse phase chromatography to afford the desired product as the ammonium salt.

Non-limiting examples of the HPTP-β ($IC_{50}$ μM) activity for the disclosed compounds are listed in Table XXI.

HPTP-β inhibition can be tested by any method chosen by the formulator, for example, Amarasinge K. K. et al., "Design and Synthesis of Potent, Non-peptidic Inhibitors of HPTPbeta" *Bioorg Med Chem Lett.* 2006 Aug. 15; 16(16): 4252-6. Epub 2006 Jun. 12. Erratum in: *Bioorg Med Chem Lett.* 2008 Aug. 15; 18(16):4745. Evidokimov, Artem G [corrected to Evdokimov, Artem G]: PMID: 16759857; and Klopfenstein S. R. et al. "1,2,3,4-Tetrahydroisoquinolinyl Sulfamic Acids as Phosphatase PTP1B Inhibitors" *Bioorg Med Chem Lett.* 2006 Mar. 15; 16(6):1574-8, both of which are included herein by reference in their entirety.

TABLE XXI

| No. | Compound | HPTPβ $IC_{50}$ μM |
|---|---|---|
| AA1 | 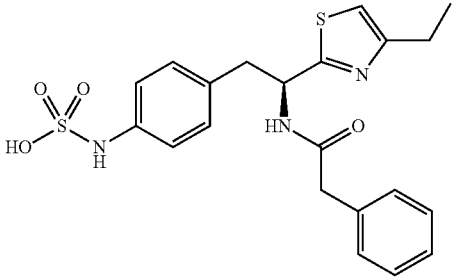 [SMILES: CCc1csc([C@H](Cc2ccc(NS(=O)(=O)O)cc2)NC(=O)Cc2ccccc2)n1]<br>(S)-{4-[2-(4-Ethylthiazol-2-yl)-2-(phenylacetylamino)ethyl]-phenyl}sulfamic acid | 0.000157 |
| AA2 | 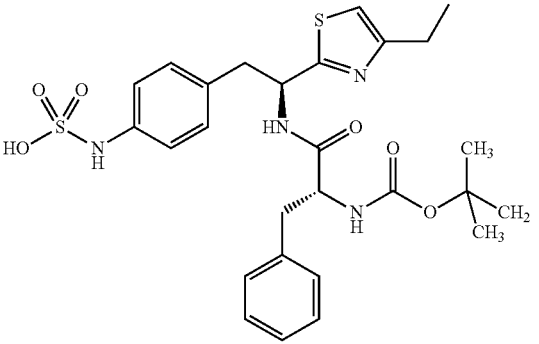 [SMILES: CCc1csc([C@H](Cc2ccc(NS(=O)(=O)O)cc2)NC(=O)[C@@H](Cc2ccccc2)NC(=O)OC(C)(C)C)n1]<br>4-{(S)-2-[(R)-2-(tert-butoxycarbonylamino)-3-phenylpropanamido]-2-(4-ethylthiazol-2-yl)ethyl}phenylsulfamic acid | 0.004 |
| AA3 | 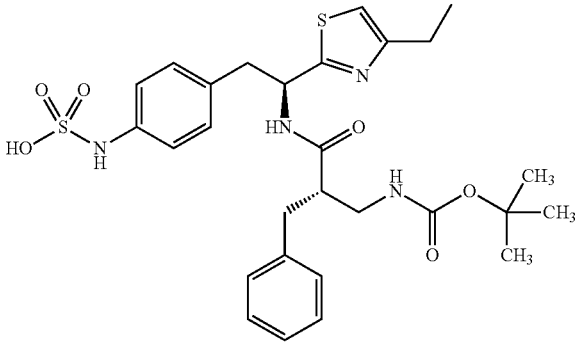 [SMILES: CCc1csc([C@H](Cc2ccc(NS(=O)(=O)O)cc2)NC(=O)[C@H](CNC(=O)OC(C)(C)C)Cc2ccccc2)n1]<br>{1-[1-(5-Ethylthiazol-2-yl)-(S)-2-(4-sulfoaminophenyl)ethyl-carbamoyl]-(S)-2-phenylethyl}methyl carbamic acid tert-butyl ester | 0.031 |

TABLE XXI-continued

| No. | Compound | HPTPβ IC$_{50}$ μM |
|---|---|---|
| AA4 | 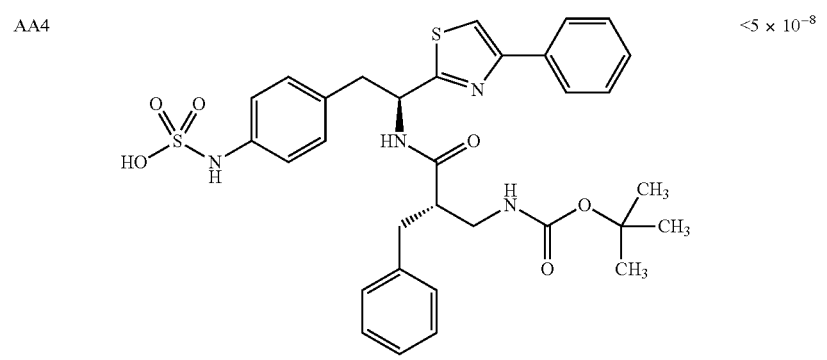{1-[1-(5-phenylthiazol-2-yl)-(S)-2-(4-sulfoaminophenyl)ethylcarbamoyl]-(S)-2-phenylethyl}methyl carbamic acid tert-butyl ester | $<5 \times 10^{-8}$ |
| AA5 | 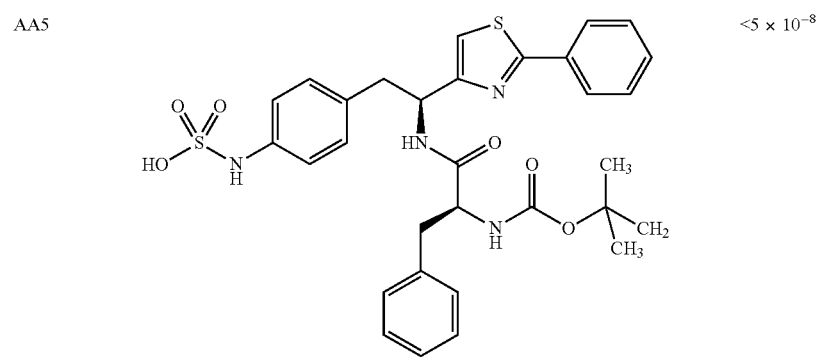4-{(S)-2-(S)-2-(tert-Butoxycarbonylamino)-3-phenylpropanamido-2-(2-phenylthiazol-4-yl)}phenylsulfamic acid | $<5 \times 10^{-8}$ |
| AA6 | 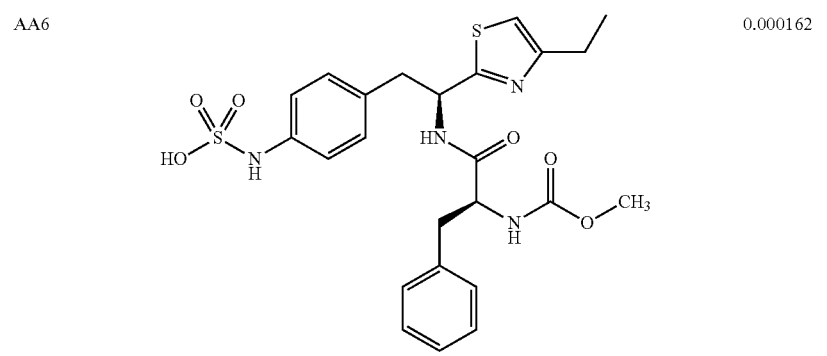4-{(S)-2-(4-Ethylthiazol-2-yl)-2-[(S)-2-(methoxycarbonylamino)-3-phenylpropanamido]ethyl}phenylsulfamic acid | 0.000162 |

TABLE XXI-continued
| No. | Compound | HPTPβ IC$_{50}$ μM |
|---|---|---|
| AA7 | 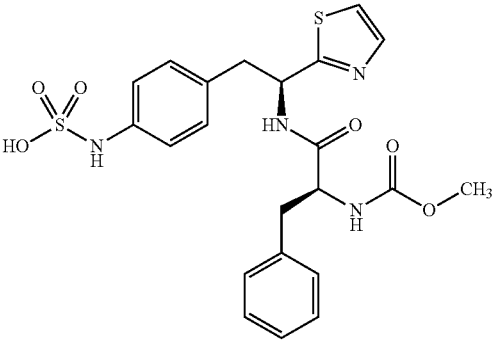 [SMILES: COC(=O)N[C@@H](Cc1ccccc1)C(=O)N[C@@H](Cc1ccc(NS(=O)(=O)O)cc1)c1nccs1]<br>4-{(S)-2-[(S)-2-(Methoxycarbonylamino)-3-phenylpropanamido]-2-(thiazol-2-yl)ethyl}phenylsulfamic acid | 0.006 |
| AA8 | 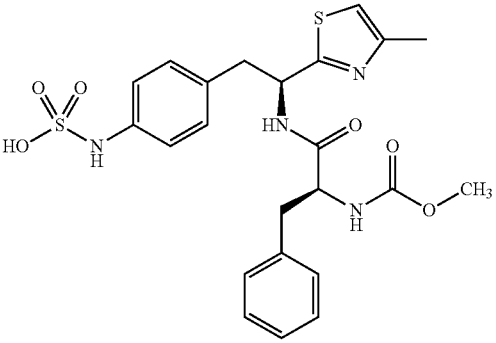 [SMILES: COC(=O)N[C@@H](Cc1ccccc1)C(=O)N[C@@H](Cc1ccc(NS(=O)(=O)O)cc1)c1nc(C)cs1]<br>4-{(S)-2-[(S)-2-(Methoxycarbonylamino)-3-phenylpropanamido]-2-(4-methylthiazol-2-yl)ethyl}phenylsulfamic acid | 0.001 |
| AA9 | 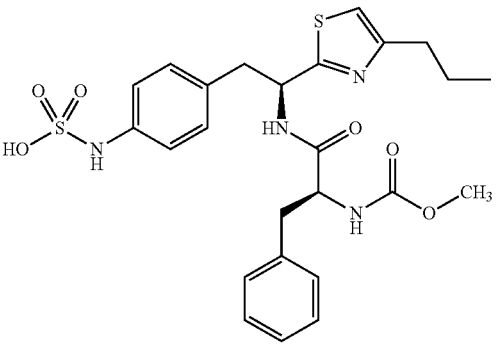 [SMILES: CCCc1csc([C@H](Cc2ccc(NS(=O)(=O)O)cc2)NC(=O)[C@H](Cc2ccccc2)NC(=O)OC)n1]<br>4-{(S)-2-[(S)-2-(Methoxycarbonylamino)-3-phenylpropanamido]-2-(4-propylthiazol-2-yl)ethyl}phenylsulfamic acid | 0.0001 |

TABLE XXI-continued

| No. | Compound | HPTPβ IC$_{50}$ μM |
|---|---|---|
| AA10 | 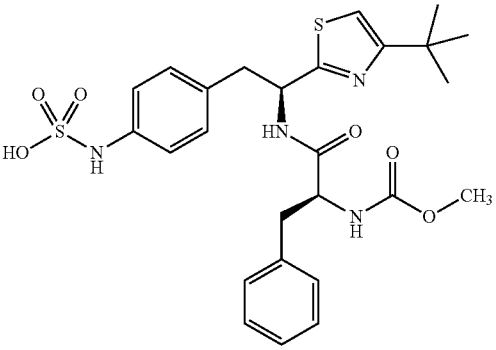 [SMILES: COC(=O)N[C@@H](Cc1ccccc1)C(=O)N[C@@H](Cc1ccc(NS(=O)(=O)O)cc1)c1nc(C(C)(C)C)cs1]<br>4-{(S)-2-(4-tert-Butylthiazol-2-yl)-2-[(S)-2-(methoxycarbonylamino)-3-phenylpropanamido]ethyl}phenylsulfamic acid | 0.0002 |
| AA11 | 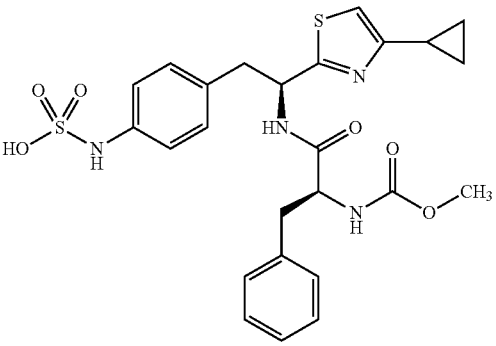 [SMILES: COC(=O)N[C@@H](Cc1ccccc1)C(=O)N[C@@H](Cc1ccc(NS(=O)(=O)O)cc1)c1nc(C2CC2)cs1]<br>4-{(S)-2-(4-Cyclopropylthiazol-2-yl)-2-[(S)-2-(methoxy-carbonylamino)-3-phenylpropanamido]ethyl}phenylsulfamic acid | 0.00001 |
| AA12 | 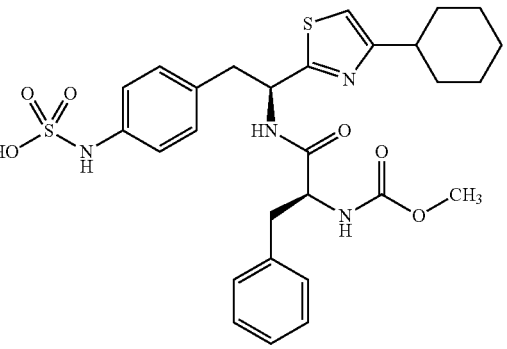<br>4-{(S)-2-(4-Cyclohexylthiazol-2-yl)-2-[(S)-2-(methoxycarbonylamino)-3-phenyl-propanamido]ethyl}phenylsulfamic acid | $<5 \times 10^{-8}$ |

TABLE XXI-continued
| No. | Compound | HPTPβ IC$_{50}$ μM |
|---|---|---|
| AA13 | 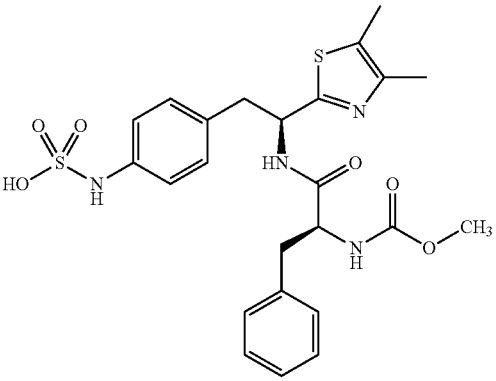 [SMILES: COC(=O)N[C@@H](Cc1ccccc1)C(=O)N[C@@H](Cc1ccc(NS(=O)(=O)O)cc1)c1nc(C)c(C)s1]<br>4-{(S)-2-(4,5-Dimethylthiazol-2-yl)-2-[(S)-2-(methoxycarbonylamino)-3-phenyl-propanamido]ethyl}phenylsulfamic acid | 0.001 |
| AA14 | 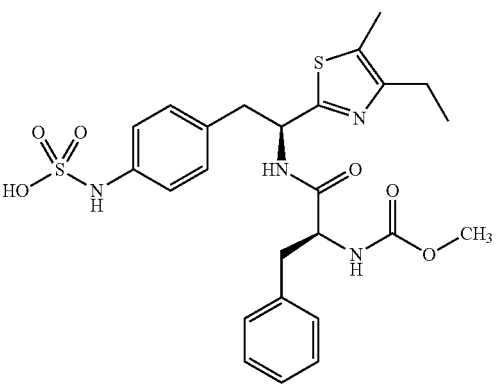 [SMILES: CCc1nc([C@H](Cc2ccc(NS(=O)(=O)O)cc2)NC(=O)[C@H](Cc2ccccc2)NC(=O)OC)sc1C]<br>4-{(S)-2-(4-Ethyl-5-methylthiazol-2-yl)-2-[(S)-2-(methoxy-carbonylamino)-3-phenyl-propanamido]ethyl}phenylsulfamic acid | 0.0001 |
| AA15 | 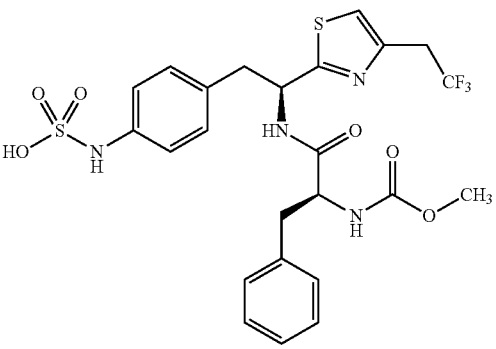 [SMILES: COC(=O)N[C@@H](Cc1ccccc1)C(=O)N[C@@H](Cc1ccc(NS(=O)(=O)O)cc1)c1nc(CC(F)(F)F)cs1]<br>4-{(S)-2-[(S)-2-(Methoxycarbonylamino)-3-phenylpropanamido]-2-[4-(2,2,2-trifluoroethyl)thiazol-2-yl]ethyl}phenylsulfamic acid | 0.0003 |

TABLE XXI-continued

| No. | Compound | HPTPβ IC$_{50}$ μM |
|---|---|---|
| AA16 | 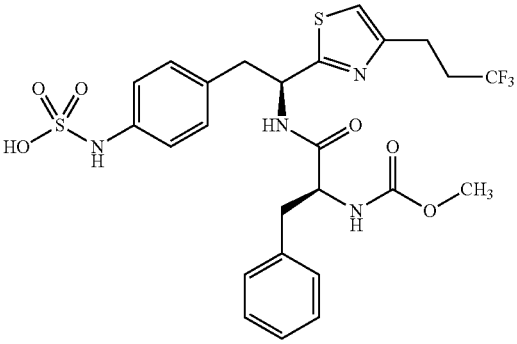 [SMILES: COC(=O)N[C@@H](Cc1ccccc1)C(=O)N[C@@H](Cc1ccc(NS(=O)(=O)O)cc1)c1nc(CCC(F)(F)F)cs1]<br>4-{(S)-2-[(S)-2-(Methoxycarbonylamino)-3-phenylpropanamido]-2-[4-(3,3,3-trifluoropropyl)thiazol-2-yl]ethyl}phenylsulfamic acid | 0.00008 |
| AA17 | 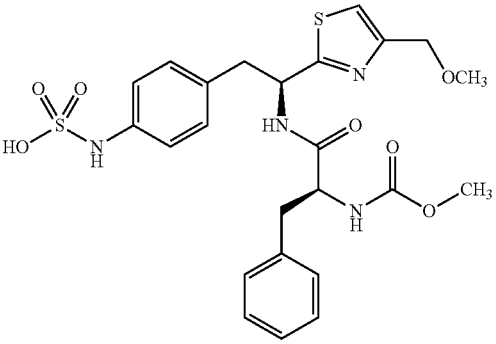 [SMILES: COCc1csc([C@H](Cc2ccc(NS(=O)(=O)O)cc2)NC(=O)[C@H](Cc2ccccc2)NC(=O)OC)n1]<br>4-{(S)-2-[(S)-2-(Methoxycarbonylamino)-3-phenylpropanamido]-2-[4-(methoxymethyl)thiazol-2-yl]ethyl}phenylsulfamic acid | 0.001 |
| AA18 | 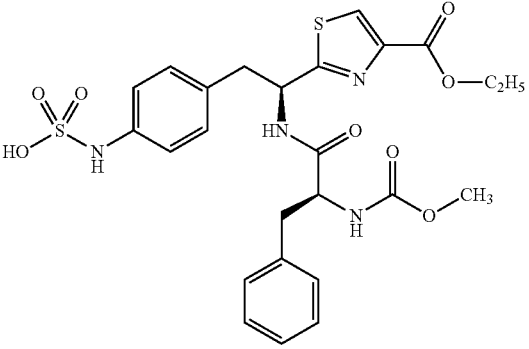 [SMILES: CCOC(=O)c1csc([C@H](Cc2ccc(NS(=O)(=O)O)cc2)NC(=O)[C@H](Cc2ccccc2)NC(=O)OC)n1]<br>4-{(S)-2-(4-(Ethoxycarbonyl)thiazol-2-yl)-2-[(S)-2-(methoxycarbonylamino)-3-phenylpropanamido]ethyl}phenylsulfamic acid | 0.0002 |

TABLE XXI-continued

| No. | Compound | HPTPβ IC$_{50}$ μM |
|---|---|---|
| AA19 | 4-{(S)-2-[(S)-2-(Methoxycarbonylamino)-3-phenylpropanamido]-2-(5-phenylthiazol-2-yl)ethyl}phenylsulfamic acid | 0.0003 |
| AA20 | 4-{(S)-2-(4-Ethyl-5-phenylthiazol-2-yl)-2-[(S)-2-(methoxy-carbonylamino)-3-phenyl-propanamido]ethyl}phenylsulfamic acid | <5 × 10$^{-8}$ |
| AA21 | 4-{(S)-2-[(S)-2-(Methoxycarbonylamino)-3-phenylpropanamido]-2-(4-phenylthiazol-2-yl)ethyl}phenylsulfamic acid | <2 × 10$^{-6}$ |

TABLE XXI-continued

| No. | Compound | HPTPβ IC$_{50}$ μM |
|---|---|---|
| AA22 | 4-{(S)-2-[(S)-2-(Methoxycarbonylamino)-3-phenylpropanamido]-2-[4-(thiophen-2-yl)thiazol-2-yl]ethyl}phenylsulfamic acid | <5 × 10$^{-8}$ |
| AA23 | 4-{(S)-2-[(S)-2-(Methoxycarbonylamino)-3-phenylpropanamido]-2-[4-(thiophen-3-yl)thiazol-2-yl]ethyl}phenylsulfamic acid | 0.00009 |
| AA24 | 4-{(S)-2-(5,6-Dihydro-4H-cyclopenta[d]thiazol-2-yl)-2-[(S)-2-(methoxycarbonylamino)-3-phenylpropanamido]ethyl}phenylsulfamic acid | 0.001 |

TABLE XXI-continued

| No. | Compound | HPTPβ IC$_{50}$ μM |
|---|---|---|
| AA25 | 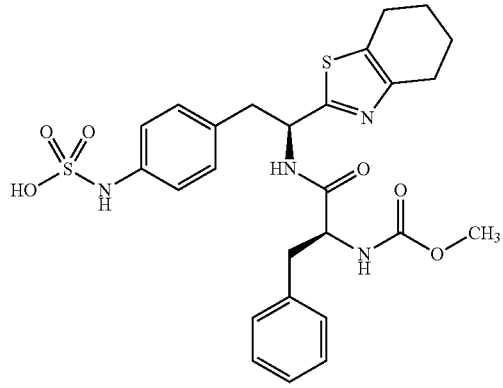 [SMILES: COC(=O)N[C@@H](Cc1ccccc1)C(=O)N[C@@H](Cc1ccc(NS(=O)(=O)O)cc1)c1nc2c(s1)CCCC2]

4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid | 0.0004 |
| AA26 | 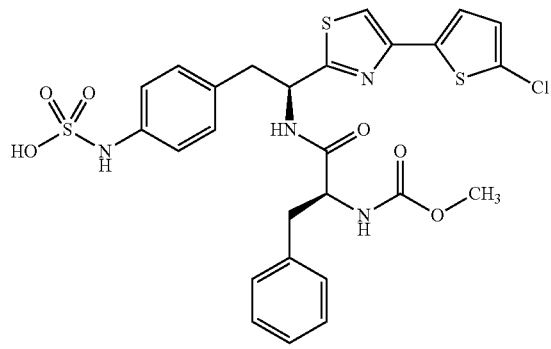 [SMILES: COC(=O)N[C@@H](Cc1ccccc1)C(=O)N[C@@H](Cc1ccc(NS(=O)(=O)O)cc1)c1nc(-c2ccc(Cl)s2)cs1]

4-{(S)-2-[4-(5-Chlorothiophen-2-yl)thiazol-2-yl]-2-[(S)-2-(methoxycarbonylamino)-3-phenylpropanamido]ethyl}phenyl-sulfamic acid | $<5 \times 10^{-8}$ |
| AA27 | 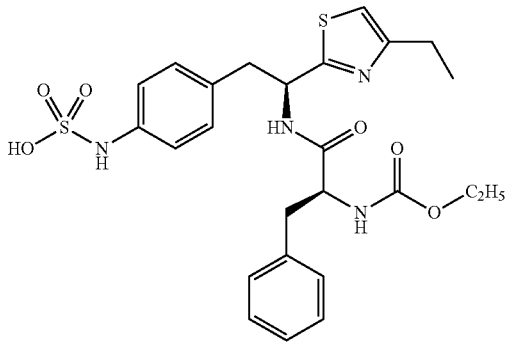 [SMILES: CCOC(=O)N[C@@H](Cc1ccccc1)C(=O)N[C@@H](Cc1ccc(NS(=O)(=O)O)cc1)c1nc(CC)cs1]

4-{(S)-2-[(S)-2-(Ethoxycarbonylamino)-3-phenylpropanamido]-2-(4-ethylthiazol-2-yl)ethyl}phenylsulfamic acid | 0.00014 |

TABLE XXI-continued
| No. | Compound | HPTPβ IC$_{50}$ μM |
|---|---|---|
| AA28 | 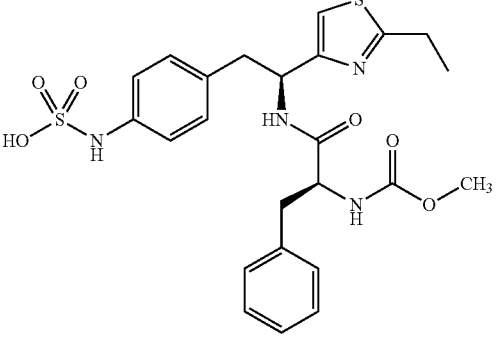<br>4-{(S)-2-[(S)-2-(Methoxycarbonylamino)-3-phenylpropanamido]-2-(2-ethylthiazol-4-yl)ethyl}phenylsulfamic acid | 0.0001 |
| AA29 | 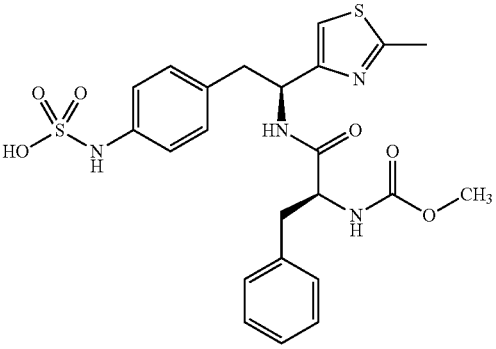 [SMILES: COC(=O)N[C@@H](Cc1ccccc1)C(=O)N[C@@H](Cc1ccc(NS(=O)(=O)O)cc1)c1csc(C)n1]<br>4-{(S)-2-[(S)-2-(Methoxycarbonylamino)-3-phenylpropanamido]-2-(2-methylthiazol-4-yl)ethyl}phenylsulfamic acid | 0.001 |
| AA30 | 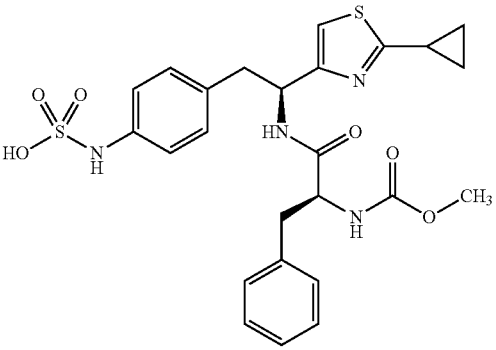 [SMILES: COC(=O)N[C@@H](Cc1ccccc1)C(=O)N[C@@H](Cc1ccc(NS(=O)(=O)O)cc1)c1csc(C2CC2)n1]<br>4-{(S)-2-(2-Cyclopropylthiazol-4-yl)-2-[(S)-2-(methoxycarbonylamino)-3-phenylpropanamido]ethyl}phenylsulfamic acid | 0.0002 |

TABLE XXI-continued

| No. | Compound | HPTPβ IC$_{50}$ μM |
|---|---|---|
| AA31 | 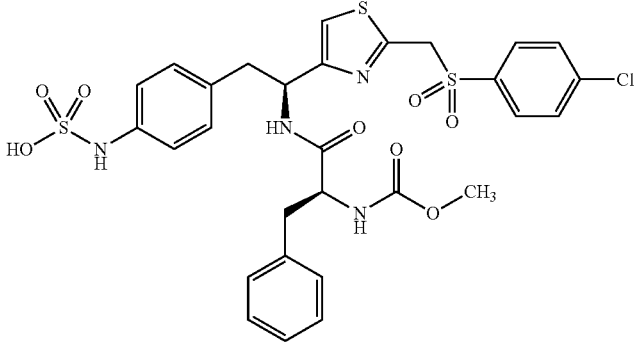 [SMILES: COC(=O)N[C@@H](Cc1ccccc1)C(=O)N[C@@H](Cc1ccc(NS(=O)(=O)O)cc1)c1csc(CS(=O)(=O)c2ccc(Cl)cc2)n1] 4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid | 0.00008 |
| AA32 | 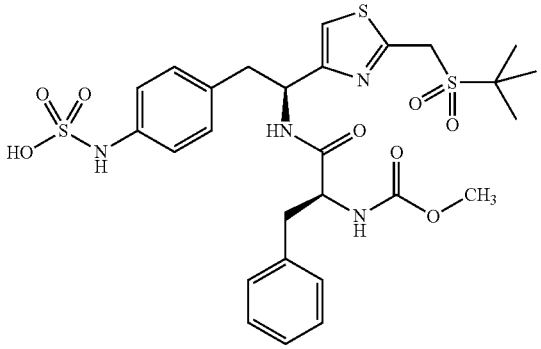 [SMILES: COC(=O)N[C@@H](Cc1ccccc1)C(=O)N[C@@H](Cc1ccc(NS(=O)(=O)O)cc1)c1csc(CS(=O)(=O)C(C)(C)C)n1] 4-{(S)-2-[2-(tert-Butylsulfonylmethyl)thiazol-4-yl]-2-[(S)-2-(methoxycarbonylamino)-3-phenylpropanamido]ethyl}phenylsulfamic acid | 0.002 |
| AA33 | 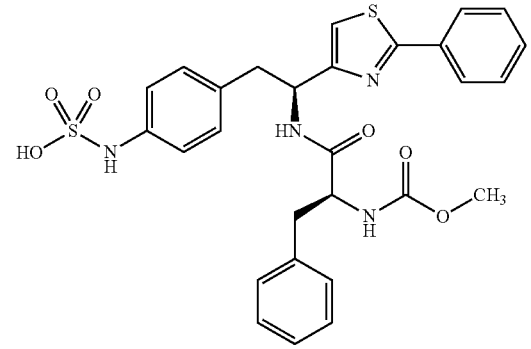 [SMILES: COC(=O)N[C@@H](Cc1ccccc1)C(=O)N[C@@H](Cc1ccc(NS(=O)(=O)O)cc1)c1csc(-c2ccccc2)n1] 4-{(S)-2-[(S)-2-(Methoxycarbonylamino)-3-phenylpropionamido]-2-(2-phenylthiazole-4-yl)ethyl}phenylsulfamic acid | 7 × 10$^{-7}$ |

TABLE XXI-continued

| No. | Compound | HPTPβ IC$_{50}$ μM |
|---|---|---|
| AA34 | 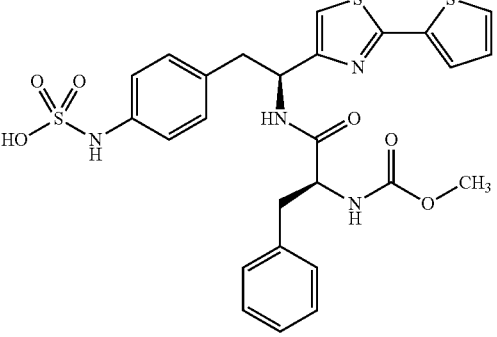 4-{(S)-2-[(S)-2-(Methoxycarbonylamino)-3-phenylpropanamido]-2-[2-(thiophen-2-yl)thiazol-4-yl]ethyl}phenylsulfamic acid | $5 \times 10^{-8}$ |
| AA35 | 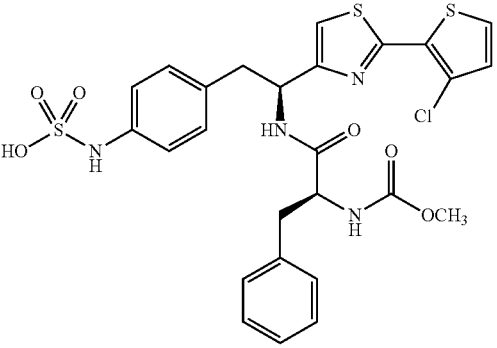 4-{(S)-2-[2-(3-Chlorothiophen-2-yl)thiazol-4-yl]-2-[(S)-2-(methoxycarbonylamino)-3-phenylpropanamido]ethyl}phenylsulfamic acid | $<5 \times 10^{-8}$ |
| AA36 | 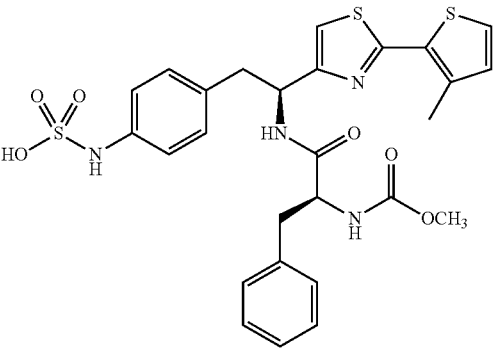 [SMILES: COC(=O)N[C@@H](Cc1ccccc1)C(=O)N[C@@H](Cc1ccc(NS(=O)(=O)O)cc1)c1csc(-c2sccc2C)n1] 4-{(S)-2-[(S)-2-(Methoxycarbonylamino)-3-phenylpropanamido]-2-[2-(3-methylthiophen-2-yl)thiazol-4-yl]ethyl}phenylsulfamic acid | $<5 \times 10^{-8}$ |

TABLE XXI-continued
| No. | Compound | HPTPβ IC$_{50}$ μM |
|---|---|---|
| AA37 | 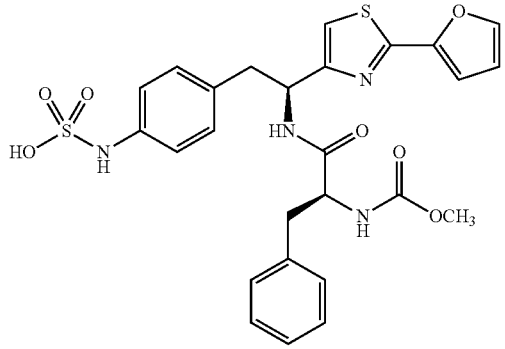<br>4-{[(S)-2-(2-(Furan-2-yl)thiazol-4-yl]-2-[(S)-2-(methoxy-carbonylamino)-3-phenylpropanamido]ethyl}phenylsulfamic acid | 0.0004 |
| AA38 | 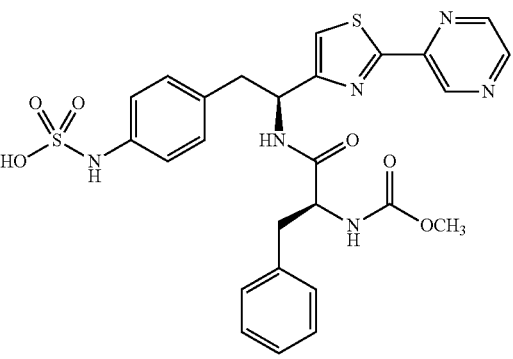 [SMILES: COC(=O)N[C@@H](Cc1ccccc1)C(=O)N[C@@H](Cc1ccc(NS(=O)(=O)O)cc1)c1csc(-c2cnccn2)n1]<br>4-{(S)-2-[(S)-2-(Methoxycarbonylamino)-3-phenylpropanamido]-2-[2-(pyrazin-2-yl)thiazol-4-yl]ethyl}phenylsulfamic acid | 0.003 |
| AA39 | 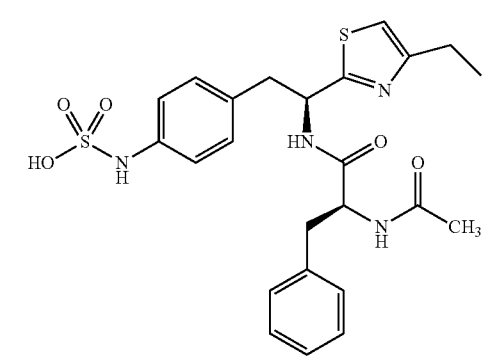 [SMILES: CCc1csc([C@H](Cc2ccc(NS(=O)(=O)O)cc2)NC(=O)[C@H](Cc2ccccc2)NC(C)=O)n1]<br>4-[(S)-2-((S)-2-Acetamido-3-phenylpropanamido)-2-(4-ethylthiazol-2-yl)ethyl]phenylsulfamic acid | 0.001 |

TABLE XXI-continued

| No. | Compound | HPTPβ IC$_{50}$ μM |
|---|---|---|
| AA40 | 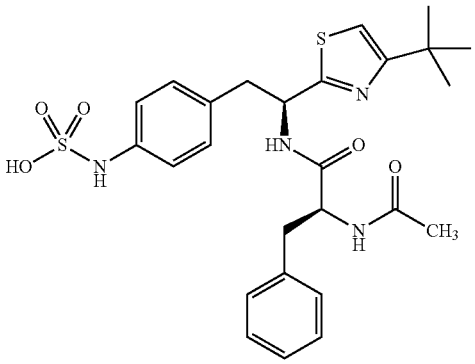 [SMILES: CC(=O)N[C@@H](Cc1ccccc1)C(=O)N[C@@H](Cc1ccc(NS(=O)(=O)O)cc1)c1nc(C(C)(C)C)cs1]<br>4-[(S)-2-((S)-2-Acetamido-3-phenylpropanamido)-2-(4-tert-butylthiazol-2-yl)ethyl]phenylsulfamic acid | 0.0003 |
| AA41 | 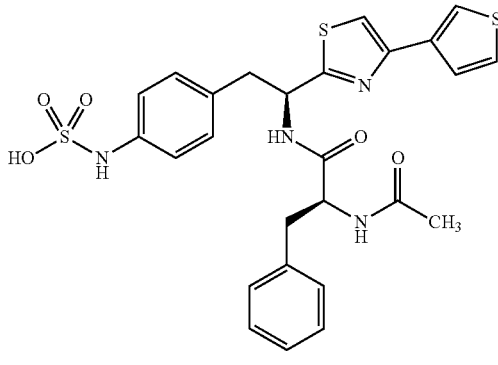 [SMILES: CC(=O)N[C@@H](Cc1ccccc1)C(=O)N[C@@H](Cc1ccc(NS(=O)(=O)O)cc1)c1nc(-c2ccsc2)cs1]<br>4-{(S)-2-((S)-2-Acetamido-3-phenylpropanamido)-2-[4-(thiophen-3-yl)thiazol-2-yl]ethyl}phenylsulfamic acid | 0.00024 |
| AA42 | 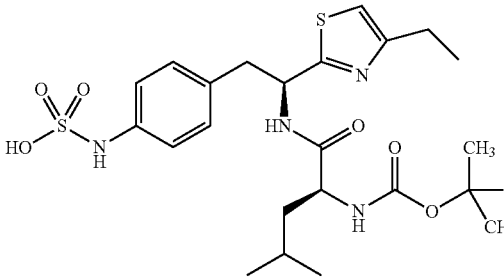<br>4-{(S)-2-[(S)-2-(tert-Butoxycarbonylamino)-3-methylbutanamido]-2-(4-ethylthiazol-2-yl)ethyl}phenylsulfamic acid | 0.006 |
| AA43 | 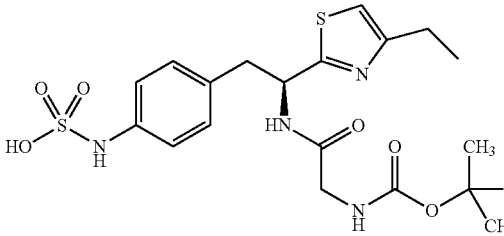<br>(S)-4-{2-[2-(tert-Butoxycarbonylamino)acetamido]-2-(4-ethylthiazol-2-yl)ethyl}phenylsulfamic acid | 0.028 |

TABLE XXI-continued

| No. | Compound | HPTPβ IC$_{50}$ μM |
|---|---|---|
| AA44 | (S)-4-{2-(4-Ethylthiazol-2-yl)-2-[2-(methoxycarbonylamino)acetamido]ethyl}phenylsulfamic acid | 0.020 |
| AA45 | 4-{(S)-2-(4-Ethylthiazol-2-yl)-2-[(S)-2-(methoxycarbonylamino)-3-methylbutanamido]-ethyl}phenylsulfamic acid | 0.003 |
| AA46 | 4-{(S)-2-[(S)-2-(tert-Butoxycarbonylamino)-4-methylpentanamido]-2-(4-ethylthiazol-2-yl)ethyl}phenylsulfamic acid | 0.001 |
| AA47 | 4-{(S)-2-(4-Ethylthiazol-2-yl)-2-[(S)-2-(methoxycarbonylamino)-4-methylpentanamido]ethyl}phenylsulfamic acid | 0.0003 |

TABLE XXI-continued

| No. | Compound | HPTPβ IC$_{50}$ μM |
|---|---|---|
| AA48 | 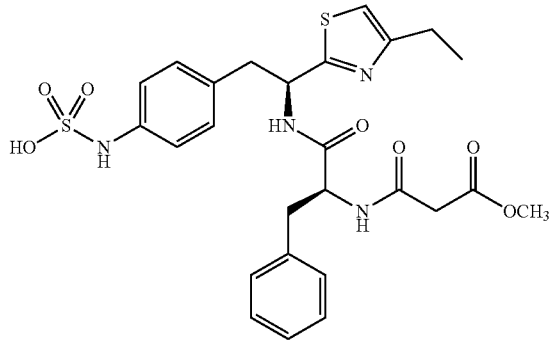 [SMILES: CCc1csc([C@H](Cc2ccc(NS(=O)(=O)O)cc2)NC(=O)[C@H](Cc2ccccc2)NC(=O)CC(=O)OC)n1]<br>4-((S)-2-(4-Ethylthiazol-2-yl)-2-{(S)-2-[2-methoxycarbonylamino)-acetamido]-3-phenylpropanamido}ethyl)phenylsulfamic acid | 0.0003 |
| AA49 | 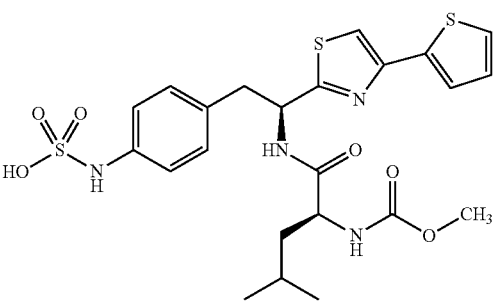 [SMILES: COC(=O)N[C@@H](CC(C)C)C(=O)N[C@@H](Cc1ccc(NS(=O)(=O)O)cc1)c1nc(-c2cccs2)cs1]<br>4-{(S)-2-[(S)-2-(Methoxycarbonylamino)-4-methylpentanamido]-2-[2-(thiophen-2-yl)thiazol-4-yl]ethyl}phenylsulfamic acid | $<5 \times 10^{-8}$ |
| AA50 | 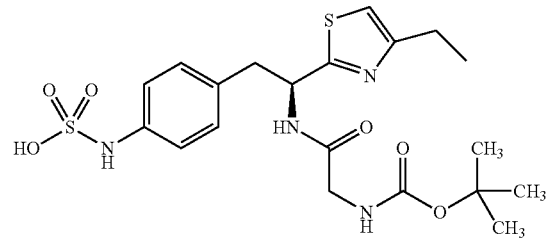 [SMILES: CCc1csc([C@H](Cc2ccc(NS(=O)(=O)O)cc2)NC(=O)CNC(=O)OC(C)(C)C)n1]<br>(S)-4-{2-[2-(tert-Butoxycarbonylamino)acetamido]-2-(4-ethylthiazol-2-yl)ethyl}-phenylsulfamic acid | 0.028 |
| AA51 | 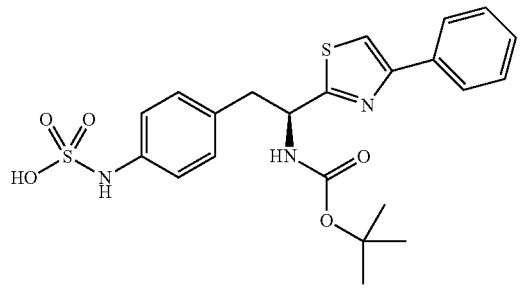 [SMILES: CC(C)(C)OC(=O)N[C@@H](Cc1ccc(NS(=O)(=O)O)cc1)c1nc(-c2ccccc2)cs1]<br>[1-(S)-(Phenylthiazol-2-yl)-2-(4-sulfoaminophenyl)ethyl]-carbamic acid tert-butyl ester | 0.049 |

TABLE XXI-continued

| No. | Compound | HPTPβ IC$_{50}$ μM |
|---|---|---|
| AA52 | (S)-4-(2-(4-Methylthiazol-2-yl)-2-pivalamidoethyl)phenyl-sulfamic acid | 0.112 |
| AA53 | (S)-4-(2-(4-Ethylthiazol-2-yl)-2-pivalamidoethyl)phenyl-sulfamic acid | 0.085 |
| AA54 | (S)-4-{2-[4-(hydroxymethyl)thiazol-2-yl]-2-pivalamidoethyl}phenyl-sulfamic acid | 0.266 |
| AA55 | (S)-4-{[2-(4-Ethoxycarbonyl)thiazol-2-yl]-2-pivalamidoethyl}phenylsulfamic acid | 0.584 |
| AA56 | (S)-4-(2-(4-Phenylthiazol-2-yl)-2-pivalamidoethyl)phenylsulfamic acid | 0.042 |

TABLE XXI-continued

| No. | Compound | HPTPβ IC$_{50}$ μM |
|---|---|---|
| AA57 | 4-((S)-2-(4-(3-Methoxyphenyl)thiazol-2-yl)-2-pivalamidoethyl)phenylsulfamic acid | 0.110 |
| AA58 | 4-((S)-2-(4-(2,4-Dimethoxyphenyl)thiazol-2-yl)-2-pivalamidoethyl)phenyl-sulfamic acid | 0.086 |
| AA59 | (S)-4-(2-(4-Benzylthiazol-2-yl)-2-pivalamidoethyl)phenylsulfamic acid | 0.113 |
| AA60 | (S)-4-(2-(4-(3-Methoxybenzyl)thiazol-2-yl)-2-pivalamidoethyl)phenylsulfamic acid | 0.132 |
| AA61 | 4-((S)-2-(4-(2,3-Dihydrobenzo[b][1,4]dioxin-6-yl)thiazol-2-yl)-2-pivalamidoethyl)phenylsulfamic acid | 0.138 |

TABLE XXI-continued

| No. | Compound | HPTPβ IC$_{50}$ μM |
|---|---|---|
| AA62 | (S)-4-(2-(5-Methyl-4-phenylthiazol-2-yl)-2-pivalamidoethyl)phenylsulfamic acid | 0.098 |
| AA63 | (S)-4-(2-(4-(Biphen-4-yl)thiazol-2-yl)-2-pivalamidoethyl)phenylsulfamic acid | 0.381 |
| AA64 | (S)-4-(2-tert-Butoxycarbonylamino)-2-(2-methylthiazol-4-yl)ethyl)phenylsulfamic acid | 0.033 |
| AA65 | (S)-4-(2-(tert-Butoxycarbonylamino)-2-(4-propylthiazol-2-yl)ethyl)phenyl sulfamic acid | 0.04 |

TABLE XXI-continued

| No. | Compound | HPTPβ IC$_{50}$ μM |
|---|---|---|
| AA66 | (S)-4-(2-(tert-Butoxycarbonylamino)-2-(4-tert-butylthiazol-2-yl)ethyl)phenyl sulfamic acid | 0.027 |
| AA67 | (S)-4-(2-(tert-Butoxycarbonylamino)-2-(4-(methoxymethyl)thiazol-2-yl)ethyl)-phenyl sulfamic acid | 0.18 |
| AA68 | (S)-4-(2-(tert-Butoxycarbonylamino)-2-(4-(hydroxymethyl)thiazol-2-yl)ethyl)phenylsulfamic acid | 0.644 |
| AA69 | (S)-4-(2-(tert-Butoxycarbonylamino)-2-(4-(2-ethoxy-2-oxoethyl)thiazol-2-yl)ethyl)phenylsulfamic acid | 0.167 |

TABLE XXI-continued

| No. | Compound | HPTPβ IC$_{50}$ μM |
|---|---|---|
| AA70 | (S)-4-(2-(tert-Butoxycarbonyl)-2-(4-(2-(2-methoxy-2-oxoyethyl amino)-2-oxoethyl)thiazole-2-yl)ethyl)phenylsulfamic acid | 0.132 |
| AA71 | (S)-4-(2-(tert-Butoxycarbonylamino)-2-(2-pivalamidothiazol-4-yl)ethyl)phenylsulfamic acid | 0.555 |
| AA72 | (S)-4-(2-(tert-Butoxycarbonylamino)-2-(5-phenylthiazol-2-yl)ethyl)-phenyl sulfamic acid | 0.308 |
| AA73 | 4-((S)-2-(tert-Butoxycarbonylamino)-2-(4-(3-(trifluoromethyl)phenyl)thiazol-2-yl)ethyl)-phenyl sulfamic acid | 0.253 |

TABLE XXI-continued

| No. | Compound | HPTPβ IC$_{50}$ μM |
|---|---|---|
| AA74 | 4-((S)-2-(tert-Butoxycarbonylamino)-2-(4-(thiophen-3-yl)thiazol-2-yl)ethyl)phenyl sulfamic acid | 0.045 |
| AA75 | (S)-{4-[2-(4-Ethylthiazol-2-yl)-2-(phenylacetylamido)ethyl]-phenyl}sulfamic acid | 0.05 |
| AA76 | (S)-4-(2-(4-Ethylthiazol-2-yl)-2-(2-(2-fluorophenyl)acetamido)ethyl)phenyl-sulfamic acid | 0.012 |
| AA77 | (S)-4-(2-(4-Ethylthiazol-2-yl)-2-(2-(3-fluorophenyl)acetamido)ethyl)phenyl-sulfamic acid | 0.0003 |

TABLE XXI-continued

| No. | Compound | HPTPβ IC$_{50}$ μM |
|---|---|---|
| AA78 | (S)-4-(2-(2-(2,3-Difluorophenyl)acetamido)-2-(4-ethylthiazol-2-yl)ethyl)phenyl-sulfamic acid | 0.028 |
| AA79 | (S)-4-(2-(2-(3,4-Difluorophenyl)acetamido)-2-(4-ethylthiazol-2-yl)ethyl)phenyl-sulfamic acid | 0.075 |
| AA80 | (S)-4-(2-(2-(2-Chlorophenyl)acetamido)-2-(4-ethylthiazol-2-yl)ethyl)phenyl-sulfamic acid | 0.056 |
| AA81 | (S)-4-(2-(2-(3-Chlorophenyl)acetamido)-2-(4-ethylthiazol-2-yl)ethyl)phenyl-sulfamic acid | 0.033 |

TABLE XXI-continued

| No. | Compound | HPTPβ IC$_{50}$ μM |
|---|---|---|
| AA82 | (S)-4-(2-(4-Ethylthiazol-2-yl)-2-(2-(3-hydroxyphenyl)acetamido)ethyl)phenyl-sulfamic acid | 0.04 |
| AA83 | (S)-4-(2-(4-Ethylthiazol-2-yl)-2-(2-(2-methoxyphenyl)acetamido)ethyl)phenyl-sulfamic acid | 0.014 |
| AA84 | (S)-4-(2-(4-Ethylthiazol-2-yl)-2-(2-(3-methoxyphenyl)acetamido)ethyl)phenyl-sulfamic acid | 0.008 |
| AA85 | (S)-4-(2-(4-Ethylthiazol-2-yl)-2-(3-phenylpropanamido)ethyl)phenylsulfamic acid | 0.002 |

TABLE XXI-continued

| No. | Compound | HPTPβ IC$_{50}$ μM |
|---|---|---|
| AA86 | (S)-4-(2-(2-(3,4-Dimethoxyphenyl)acetamido)-2-(4-ethylthiazol-2-yl)ethyl)-phenylsulfamic acid | 0.028 |
| AA87 | (S)-4-(2-(2-(2,3-Dimethoxyphenyl)acetamido)-2-(4-ethylthiazol-2-yl)ethyl)-phenylsulfamic acid | 0.037 |
| AA88 | (S)-4-(2-(3-(3-Chlorophenyl)propanamido)-2-(4-ethylthiazol-2-yl)ethyl)phenyl-sulfamic acid | 0.0002 |
| AA89 | (S)-4-(2-(4-Ethylthiazol-2-yl)-2-(3-(2-methoxyphenyl)propanamido)ethyl)phenyl-sulfamic acid | 0.003 |

TABLE XXI-continued

| No. | Compound | HPTPβ IC$_{50}$ μM |
|---|---|---|
| AA90 | 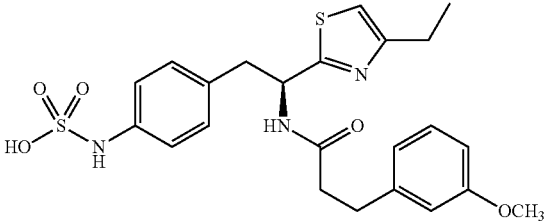 [SMILES: CCc1csc([C@H](Cc2ccc(NS(=O)(=O)O)cc2)NC(=O)CCc2cccc(OC)c2)n1]<br>(S)-4-(2-(4-Ethylthiazol-2-yl)-2-(3-(3-methoxyphenyl)propanamido)ethyl)phenyl-sulfamic acid | 0.01 |
| AA91 | 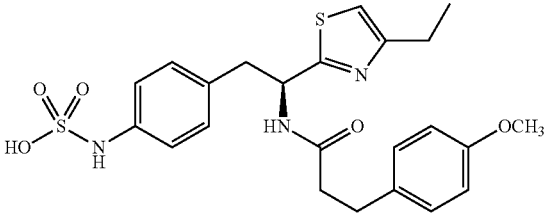 [SMILES: CCc1csc([C@H](Cc2ccc(NS(=O)(=O)O)cc2)NC(=O)CCc2ccc(OC)cc2)n1]<br>(S)-4-(2-(4-Ethylthiazol-2-yl)-2-(3-(4-methoxyphenyl)propanamido)ethyl)phenyl-sulfamic acid | 0.006 |
| AA92 | 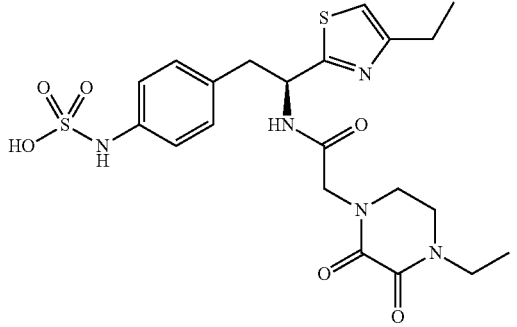 [SMILES: CCc1csc([C@H](Cc2ccc(NS(=O)(=O)O)cc2)NC(=O)CN2CCN(CC)C(=O)C2=O)n1]<br>(S)-4-{2-[2-(4-Ethyl-2,3-dioxopiperazin-1-yl)acetamide]-2-(4-ethylthiazol-2-yl)ethyl}phenylsulfamic acid | 0.002 |
| AA93 | 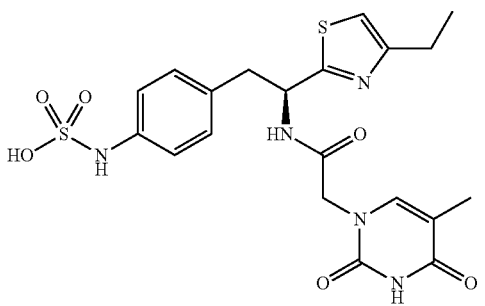 [SMILES: CCc1csc([C@H](Cc2ccc(NS(=O)(=O)O)cc2)NC(=O)Cn2cc(C)c(=O)[nH]c2=O)n1]<br>(S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid | 0.002 |

TABLE XXI-continued

| No. | Compound | HPTPβ IC$_{50}$ μM |
|---|---|---|
| AA94 | (S)-4-[2-(Benzo[d][1,3]dioxole-5-carboxamido)-2-(4-ethylthiazol-2-yl)ethyl]phenylsulfamic acid | 0.042 |
| AA95 | (S)-4-(2-(5-methyl-1,3,4-thiadiazol-2-ylamino)-2-(2-phenylthiazol-4-yl)ethyl)phenylsulfamic acid | 0.003 |
| AA96 | (S)-4-(2-(5-Phenyl-1,3,4-thiadiazol-2-ylamino)-2-(2-phenylthiazol-4-yl)ethyl)-phenylsulfamic acid | 0.046 |
| AA97 | 4-((S)-2-(5-Propyl-1,3,4-thiadiazol-2-ylamino)-2-(2-(thiophen-2-yl)thiazol-4-yl)ethyl)phenylsulfamic acid | 0.0002 |

TABLE XXI-continued

| No. | Compound | HPTPβ IC$_{50}$ μM |
|---|---|---|
| AA98 | 4-((S)-2-(5-Benzyl-1,3,4-thiadiazol-2-ylamino)-2-(2-(thiophen-2-yl)thiazol-4-yl)ethyl)phenylsulfamic acid | 0.0006 |
| AA99 | 4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid | 0.002 |
| AA100 | 4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid | $9 \times 10^{-6}$ |

Methods

Disclosed are methods for the treatment of diseases or conditions of the eye, especially diabetic macular edema, age-related macular degeneration (wet form), choroidal neovascularization, diabetic retinopathy, ocular ischemia, uveitis, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition. These diseases are characterized by an increased level of plasma Vascular Endothelial Growth Factor. As such, the present methods are directed to co-administration of the disclosed compounds which stabilizes the vasculature against leakage and one or more anti-VEGF agents.

One aspect of the disclosed methods relates to diseases that are a direct or indirect result of diabetes, inter alia, diabetic macular edema and diabetic retinopathy. The ocular vasculature of the diabetic becomes unstable over time leading to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This results in swelling that causes the subject's central vision to gradually become distorted. This condition is referred to as "macular edema." Another condition that may occur is non-proliferative retinopathy in which vascular changes, such as microaneurysms, outside the macular region of the eye may be observed.

These conditions may or may not progress to diabetic proliferative retinopathy which is characterized by increased neovascularization. These new blood vessels are fragile and are susceptible to bleeding. The result is scaring of the retina, as well as occlusion or total blockage of the light pathway through the eye due to the over formation of new blood vessels. Typically subjects having diabetic macular edema are suffering from the non-proliferative stage of diabetic retinopathy; however, it is not uncommon for subjects to only begin manifesting macular edema at the onset of the proliferative stage.

Diabetic retinopathy is the most common cause of vision loss in working-aged Americans (Klein R et al., "The Wisconsin Epidemiologic Study of Diabetic Retinopathy. II. Prevalence and risk of diabetic retinopathy when age at diagnosis is less than 30 years," *Arch. Ophthalmol.* 1984, 102:520-526). Severe vision loss occurs due to tractional retinal detachments that complicate retinal neovascularization (NV), but the most common cause of moderate vision loss is diabetic macular edema (DME). The pathogenesis of diabetic macular edema is not completely understood, but hypoxia is a contributing factor (Nguyen Q D et al., "Supplemental inspired oxygen improves diabetic macular edema; a pilot study," *Invest. Ophthalmol. Vis. Sci.* 2003, 45:617-624). *Vascular endothelial growth factor (Vegf)* is a hypoxia-regulated gene and VEGF levels are increased in hypoxic or ischemic retina. Injection of VEGF into mouse eyes causes breakdown of the inner blood-retinal barrier (See, Derevjanik N L et al. Quantitative assessment of the integrity of the blood-retinal barrier in mice, *Invest. Ophthalmol. Vis. Sci.* 2002, 43:2462-2467) and sustained release of VEGF in the eyes of monkeys causes macular edema (Ozaki H et al., "Intravitreal sustained release of VEGF causes retinal neovascularization in rabbits and breakdown of the blood-retinal barrier in rabbits and primates," *Exp Eye Res* 1997, 64:505-517). This combination of observations in patients and animal models led to the hypothesis that VEGF plays an important role in the pathogenesis of diabetic macular edema. This hypothesis has been confirmed by several clinical trials that have shown that VEGF antagonists reduce foveal thickening and improve vision in patients with diabetic macular edema (Nguyen Q D et al., "Vascular endothelial growth factor is a critical stimulus for diabetic macular edema," *Am. J. Ophthalmol.* 2006, 142:961-969; and Nguyen Q D et al. "Primary End Point (Six Months) Results of the Ranibizumab for Edema of the mAcula in Diabetes (READ-2) Study," *Ophthalmology* 2009, 116:2175-2181).

The effects of VEGF on vascular endothelial cells are modulated by Tie2 receptors, which are selectively expressed on vascular endothelial cells and are required for embryonic vascular development (Dumont D J et al., "Dominant-negative and targeted null mutations in the endothelial receptor tyrosine kinase, tek, reveal a critical role in vasculogenesis of the embryo," *Genes Dev.* 1994, 8:1897-1909). Angiopoietin 1 (Ang1) binds Tie2 with high affinity and initiates phosphorylation and downstream signaling (Davis S et al., "Isolation of angiopoietin-1, a ligand for the TIE2 receptor, by secretion-trap expression cloning," *Cell* 1996, 87:1161-1169). Mice deficient in Ang1 die around E12.5 with vascular defects similar to, but less severe than those seen in Tie2-deficient mice. Angiopoietin 2 (Ang2) binds Tie2 with high affinity, but does not stimulate phosphorylation in cultured endothelial cells. It acts as a competitive inhibitor of Ang1 and transgenic mice overexpressing Ang2 have a phenotype similar to Ang1-deficient mice. Several lines of evidence indicate that Ang2 is a developmentally- and hypoxia-regulated permissive factor for VEGF-induced neovascularization in the retina (Hackett S F et al., "Angiopoietin 2 expression in the retina: upregulation during physiologic and pathologic neovascularization," *J. Cell. Physiol.* 2000, 184:275-284). Double transgenic Tet/opsin/ang2 and Tet/opsin/ang1 mice with inducible expression of Ang2 or Ang1, respectively, have also helped to elucidate the role of Tie2 in the retina (Nambu H et al., "Angiopoietin 1 inhibits ocular neovascularization and breakdown of the blood-retinal barrier," *Gene Ther.* 2004, 11:865-873). In mice with ischemic retinopathy, increased expression of Ang2 when VEGF is high (P12-17) increases retinal neovascularization, but increased expression at P20 when VEGF levels have come down, hastens regression of retinal neovascularization and findings were similar in other models of ocular neovascularization. In contrast, increased expression of Ang1 suppressed neovascularization and reduced vascular leakage in several models. Therefore, Ang2 reduces stabilizing signals from the matrix making endothelial cells dependent upon VEGF and other soluble stimulators; when VEGF is high, neovascularization is stimulated and when VEGF is low, neovascularization regresses. In contrast, Ang1 increases stabilizing signals from the matrix and makes the vasculature unresponsive to soluble stimulators like VEGF.

Angiopoietin 2 binds Tie2, but does not stimulate phosphorylation and therefore acts as an antagonist under most circumstances. In the eye, angiopoietin 2 is upregulated at sites of neovascularization and acts as a permissive factor for VEGF. Increased expression of VEGF in the retina does not stimulate sprouting of neovascularization from the superficial or intermediate capillary beds of the retina or the choriocapillaris, but does stimulate sprouting from the deep capillary bed where there is constitutive expression of angiopoietin 2 (Hackett S F et al., "Angiopoietin-2 plays an important role in retinal angiogenesis," *J. Cell. Physiol.* 2002, 192:182-187). Co-expression of VEGF and angiopoietin 2 at the surface of the retina causes sprouting of neovascularization from the superficial retinal capillaries (Oshima Y et al., "Angiopoietin-2 enhances retinal vessel sensitivity to vascular endothelial growth factor," *J. Cell. Physiol.* 2004, 199:412-417). In double transgenic mice with inducible expression of angiopoietin 2 in the retina, expression of angiopoietin 2 when VEGF levels were high markedly enhanced neovascularization and expression of angiopoietin 2 when VEGF levels were low caused regression of neovascularization. In double transgenic mice with inducible expression of angiopoietin 1, the induced expression of angiopoietin 1 in the retina strongly suppressed VEGF-induced vascular leakage or neovascularization (Nambu H et al., "Angiopoietin 1 inhibits ocular neovascularization and breakdown of the blood-retinal barrier," *Gene Ther.* 2004, 11:865-873). In fact, in mice with high expression of VEGF in the retina which develop severe NV and retinal detachment, angiopoietin 1 is able to prevent the VEGF-induced detachments.

Regulation of Tie2 also occurs through an endothelial-specific phosphatase, vascular endothelial protein tyrosine phophatase (VE-PTP) in mice (Fachinger G et al., "Functional interaction of vascular endothelial-protein-tyrosine phosphatase with the angiopoietin receptor Tie-2," *Oncogene* 1999, 18:5948-5943) and its human orthologue human protein tyrosine phosphatase-β (HPTP-β) (Krueger N X et al., "Structural diversity and evolution of human receptor-like protein tyrosine phosphatases," *EMBO J.* 1990, 9:3241-3252). Mice deficient in VE-PTP die at E10 with severe defects in vascular remodeling and maturation of developing vasculature. Silencing of HPTP-β in cultured human endothelial cells, enhances Ang1-induced phosphorylation of Tie2 and survival-promoting activity while hypoxia increases expression of HPTP-β and reduces Ang1-induced phosphorylation of Tie2 (Yacyshyn O K et al., "Thyrosine phosphatase beta regulates angiopoietin-Tie2 signaling in human endothelial cells," *Angiogenesis* 2009, 12:25-33).

Diabetic retinopathy, if left untreated, can lead ultimately to blindness. Indeed, diabetic retinopathy is the leading cause of blindness in working-age populations.

Therefore, the disclosed methods relate to preventing, treating, controlling, abating, and/or otherwise minimizing ocular neovascularization in a subject having diabetes or a subject diagnosed with diabetes. In addition, subjects having or subjects diagnosed with diabetes can be alerted to or can be made aware of the risks of developing diabetes-related blindness, therefore the present methods can be used to prevent or delay the onset of non-proliferative retinopathy in subjects known to be at risk. Likewise, the present methods can be used for treating subjects having or being diagnosed with non-proliferative diabetic retinopathy to prevent progression of the condition.

The disclosed methods relate to preventing or controlling ocular neovascularization or treating a disease or condition that is related to the onset of ocular neovascularization by administering to a subject the disclosed compounds and one or more anti-VEGF agents as disclosed herein.

Unlike previous ocular treatments which comprise administration of an anti-VEGF agent, inter alia, ranibizumab (Lucentis™), bevacizumab (Avastin™) and aflibercept (Eylea™), wherein these vascular leak inhibitors are injected directly into the eye itself, the disclosed compounds acts systemically. The disclosed compounds can be used to increase or enhance the effect of anti-VEGF agents, thereby improving the rate and magnitude of the response and reducing the number of treatments.

In one aspect, the disclosed compounds is administered in combination with one or more pharmaceutical compounds or compositions useful for treating ocular diseases. In a first embodiment, the present disclosure relates to a method for treating an ocular disease, comprising administering:
 a) 4-{(S)-2-[(S)-2-(methoxycarbonylamino)-3-phenyl-propanamido]-2-[2-(thiophen-2-yl)thiazol-4-yl] ethyl}phenylsulfamic acid; and
 b) ranibizumab.

The compounds can be administered in any order convenient to the user or to the subject receiving treatment. In one iteration of this embodiment the disclosed compounds is administered first followed by administration of ranibizumab. In another iteration of this embodiment ranibizumab is administered first followed by administration of the disclosed compounds. The time period between dosing/administration of the first component of treatment can be any time period convenient to the formulator or subject receiving treatment. For example, the disclosed compounds can be administered minutes, hours, days or weeks prior to the administration of ranibizumab or more than one dosage of the disclosed compounds can be given to establish a therapeutic amount in the subject being treated.

In another iteration, the disclosed compounds and ranibizumab can be given in alternating administrations. For example, the disclosed compounds can be administered then after a time desired by the administrator ranibizumab is administered.

In a further iteration, the disclosed compounds is administered daily in one or more doses and the ramibizumab is administered according to a separate schedule. For example, in addition to daily dosing of the disclosed compounds, ranibizumab can be administered once a month, once every 2 months, once every 3 months, once every 4 months, once every 6 months, etc.

The dosage for ranibizumab can be in any amount necessary. In one embodiment, ranibizumab is administered in an amount from about 0.05 mg to about 1.5 mg. In a further embodiment, ranibizumab is administered in an amount from about 0.1 mg to about 1.5 mg. In another embodiment, ranibizumab is administered in an amount from about 0.05 mg to about 1 mg. In a still further embodiment, ranibizumab is administered in an amount from about 0.1 mg to about 1 mg. In one non-limiting example, ranibizumab is administered in an amount of approximately 0.5 mg. The amount of ranibizumab administered per treatment can be in any amount, for example, 0.05 mg, 0.06 mg, 0.07 mg, 0.08 mg, 0.09 mg, 0.1 mg, 0.12 mg, 0.13 mg, 0.14 mg, 0.15 mg, 0.16 mg, 0.17, mg, 0.18 mg, 0.19 mg, 0.2 mg, 0.21 mg, 0.22 mg, 0.23 mg, 0.24 mg, 0.25 mg, 0.26 mg, 0.27, mg, 0.28 mg, 0.29 mg, 0.3 mg, 0.31 mg, 0.32 mg, 0.33 mg, 0.34 mg, 0.35 mg, 0.36 mg, 0.37, mg, 0.38 mg, 0.39 mg, 0.4 mg, 0.41 mg, 0.42 mg, 0.43 mg, 0.44 mg, 0.45 mg, 0.46 mg, 0.47, mg, 0.48 mg, 0.49 mg, 0.5 mg, 0.51 mg, 0.52 mg, 0.53 mg, 0.54 mg, 0.55 mg, 0.56 mg, 0.57, mg, 0.58 mg, 0.59 mg, 0.6 mg, 0.61 mg, 0.62 mg, 0.63 mg, 0.64 mg, 0.65 mg, 0.66 mg, 0.67, mg, 0.68 mg, 0.69 mg, 0.7 mg, 0.71 mg, 0.72 mg, 0.73 mg, 0.74 mg, 0.75 mg, 0.76 mg, 0.77, mg, 0.78 mg, 0.79 mg, 0.8 mg, 0.81 mg, 0.82 mg, 0.83 mg, 0.84 mg, 0.85 mg, 0.86 mg, 0.87, mg, 0.88 mg, 0.89 mg, 0.9 mg, 0.91 mg, 0.92 mg, 0.93 mg, 0.94 mg, 0.95 mg, 0.96 mg, 0.97, mg, 0.98 mg, 0.99 mg and 1 mg.

In another aspect, the disclosed compounds is administered in combination with one or more pharmaceutical compounds or compositions useful for treating ocular diseases. In a first embodiment, the present disclosure relates to a method for treating an ocular disease, comprising administering:
 a) 4-{(S)-2-[(S)-2-(methoxycarbonylamino)-3-phenyl-propanamido]-2-[2-(thiophen-2-yl)thiazol-4-yl] ethyl}phenylsulfamic acid; and
 b) bevacizumab.

The compounds can be administered in any order convenient to the user or to the subject receiving treatment. In one iteration of this embodiment the disclosed compounds is administered first followed by administration of bevacizumab. In another iteration of this embodiment bevacizumab is administered first followed by administration of the disclosed compounds. The time period between dosing/administration of the first component of treatment can be any time period convenient to the formulator or subject receiving treatment. For example, the disclosed compounds can be administered minutes, hours, days or weeks prior to the administration of bevacizumab or more than one dosage of the disclosed compounds can be given to establish a therapeutic amount in the subject being treated.

In another iteration, the disclosed compounds and bevacizumab can be given in alternating administrations. For example, the disclosed compounds can be administered then after a time desired by the administrator bevacizumab is administered.

In a further iteration, the disclosed compounds is administered daily in one or more doses and the bevacizumab is administered according to a separate schedule. For example, in addition to daily dosing of the disclosed compounds, bevacizumab can be administered once a month, once every 2 months, once every 3 months, once every 4 months, once every 6 months, etc.

The dosage for bevacizumab can be in any amount necessary. In one embodiment, bevacizumab is administered in an amount from about 0.1 mg to about 5 mg. In a further embodiment, bevacizumab is administered in an amount from about 0.1 mg to about 3 mg. In another embodiment, bevacizumab is administered in an amount from about 0.5 mg to about 3 mg. In a still further embodiment, bevacizumab is administered in an amount from about 0.5 mg to about 2 mg. In one non-limiting example, bevacizumab is administered in an amount of 1.2 mg. The amount of bevacizumab administered per treatment can be in any amount, for example, 0.5 mg, 0.51 mg, 0.52 mg, 0.53 mg, 0.54 mg, 0.55 mg, 0.56 mg, 0.57, mg, 0.58 mg, 0.59 mg, 0.6 mg, 0.61 mg, 0.62 mg, 0.63 mg, 0.64 mg, 0.65 mg, 0.66 mg, 0.67, mg, 0.68 mg, 0.69 mg, 0.7 mg, 0.71 mg, 0.72 mg, 0.73 mg, 0.74 mg, 0.75 mg, 0.76 mg, 0.77, mg, 0.78 mg, 0.79 mg, 0.8 mg, 0.81 mg, 0.82 mg, 0.83 mg, 0.84 mg, 0.85 mg, 0.86 mg, 0.87, mg, 0.88 mg, 0.89 mg, 0.9 mg, 0.91 mg, 0.92 mg, 0.93 mg, 0.94 mg, 0.95 mg, 0.96 mg, 0.97, mg, 0.98 mg, 0.99 mg, 1 mg, 1.1 mg, 1.11 mg, 1.12 mg, 1.13 mg, 1.14 mg, 1.15 mg, 1.16 mg, 1.17, mg, 1.18 mg, 1.19 mg, 1.2 mg, 1.21 mg, 1.22 mg, 1.23 mg, 1.24 mg, 1.25 mg, 1.26 mg, 1.27, mg, 1.28 mg, 1.29 mg, 1.3 mg, 1.31 mg, 1.32 mg, 1.33 mg, 1.34 mg, 1.35 mg, 1.36 mg, 1.37, mg, 1.38 mg, 1.39 mg, 1.4 mg, 1.41, mg, 1.42 mg, 1.43 mg, 1.44 mg, 1.45 mg, 1.46 mg, 1.47, mg, 1.48 mg, 1.49 mg, 1.5 mg, 1.51 mg, 1.52 mg, 1.53 mg, 1.54 mg, 1.55 mg, 1.56 mg, 1.57, mg, 1.58 mg, 1.59 mg, and 1.6 mg.

In a further aspect, the disclosed compounds is administered in combination with one or more pharmaceutical compounds or compositions useful for treating ocular diseases. In a first embodiment, the present disclosure relates to a method for treating an ocular disease, comprising administering:
  a) 4-{(S)-2-[(S)-2-(methoxycarbonylamino)-3-phenyl-propanamido]-2-[2-(thiophen-2-yl)thiazol-4-yl]ethyl}phenylsulfamic acid; and
  b) aflibercept.

The compounds can be administered in any order convenient to the user or to the subject receiving treatment. In one iteration of this embodiment the disclosed compounds is administered first followed by administration of aflibercept. In another iteration of this embodiment aflibercept is administered first followed by administration of the disclosed compounds. The time period between dosing/administration of the first component of treatment can be any time period convenient to the formulator or subject receiving treatment. For example, the disclosed compounds can be administered minutes, hours, days or weeks prior to the administration of aflibercept or more than one dosage of the disclosed compounds can be given to establish a therapeutic amount in the subject being treated.

In another iteration, the disclosed compounds and aflibercept can be given in alternating administrations. For example, the disclosed compounds can be administered then after a time desired by the administrator aflibercept is administered.

In a further iteration, the disclosed compounds is administered daily in one or more doses and the aflibercept is administered according to a separate schedule. For example, in addition to daily dosing of the disclosed compounds, aflibercept can be administered once a month, once every 2 months, once every 3 months, once every 4 months, once every 6 months, etc.

The dosage for aflibercept can be in any amount necessary. In one embodiment, aflibercept is administered in an amount from about 0.05 mg to about 5 mg. In a further embodiment, aflibercept is administered in an amount from about 0.1 mg to about 3 mg. In another embodiment, aflibercept is administered in an amount from about 0.5 mg to about 2.5 mg. In a still further embodiment, aflibercept is administered in an amount from about 0.5 mg to about 2 mg. The amount of aflibercept administered per treatment can be in any amount, for example, 0.5 mg, 0.51 mg, 0.52 mg, 0.53 mg, 0.54 mg, 0.55 mg, 0.56 mg, 0.57, mg, 0.58 mg, 0.59 mg, 0.6 mg, 0.61 mg, 0.62 mg, 0.63 mg, 0.64 mg, 0.65 mg, 0.66 mg, 0.67, mg, 0.68 mg, 0.69 mg, 0.7 mg, 0.71 mg, 0.72 mg, 0.73 mg, 0.74 mg, 0.75 mg, 0.76 mg, 0.77, mg, 0.78 mg, 0.79 mg, 0.8 mg, 0.81 mg, 0.82 mg, 0.83 mg, 0.84 mg, 0.85 mg, 0.86 mg, 0.87, mg, 0.88 mg, 0.89 mg, 0.9 mg, 0.91 mg, 0.92 mg, 0.93 mg, 0.94 mg, 0.95 mg, 0.96 mg, 0.97, mg, 0.98 mg, 0.99 mg, 1 mg, 1.1 mg, 1.11 mg, 1.12 mg, 1.13 mg, 1.14 mg, 1.15 mg, 1.16 mg, 1.17, mg, 1.18 mg, 1.19 mg, 1.2 mg, 1.21 mg, 1.22 mg, 1.23 mg, 1.24 mg, 1.25 mg, 1.26 mg, 1.27, mg, 1.28 mg, 1.29 mg, 1.3 mg, 1.31 mg, 1.32 mg, 1.33 mg, 1.34 mg, 1.35 mg, 1.36 mg, 1.37, mg, 1.38 mg, 1.39 mg, 1.4 mg, 1.41 mg, 1.42 mg, 1.43 mg, 1.44 mg, 1.45 mg, 1.46 mg, 1.47, mg, 1.48 mg, 1.49 mg, 1.5 mg, 1.51 mg, 1.52 mg, 1.53 mg, 1.54 mg, 1.55 mg, 1.56 mg, 1.57, mg, 1.58 mg, 1.59 mg, 1.6 mg, 1.61 mg, 1.62 mg, 1.63 mg, 1.64 mg, 1.65 mg, 1.66 mg, 1.67, mg, 1.68 mg, 1.69 mg, 1.7 mg, 1.71 mg, 1.72 mg, 1.73 mg, 1.74 mg, 1.75 mg, 1.76 mg, 1.77, mg, 1.78 mg, 1.79 mg, 1.8 mg, 1.81 mg, 1.82 mg, 1.83 mg, 1.84 mg, 1.85 mg, 1.86 mg, 1.87, mg, 1.88 mg, 1.89 mg, 1.9 mg, 1.91 mg, 1.92 mg, 1.93 mg, 1.94 mg, 1.95 mg, 1.96 mg, 1.97, mg, 1.98 mg, 1.99 mg, and 2 mg.

The disclosed compounds can be administered in any amount necessary or convenient. For example, the compound can be administered in an amount from about 0.5 mg to about 50 mg per dose. In one embodiment, the compound can be administered in an amount from about 1 mg to about 20 mg per dose. In another embodiment, the compound can be administered in an amount from about 1 mg to about 15 mg per dose. In a further embodiment, the compound can be administered in an amount from about 1 mg to about 10 mg per dose. In a yet further embodiment, the compound can be administered in an amount from about 5 mg to about 50 mg per dose. In a still further embodiment, the compound can be administered in an amount from about 0.5 mg to about 15 mg per dose. In still another embodiment, the compound can be administered in an amount from about 0.5 mg to about 10 mg per dose. As such, the disclosed compounds can be administered in any amount from about 0.5 mg to about 25 mg per dose, for example, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, and 20 mg.

The disclosed compounds can be administered at any interval desired. For example, the compound can be administered once a week, 2 times a week, 3 times a week, 4 times a week, 6 times a week, 6 times a week, 7 times a week, 8 times a week, 9 times a week or 10 times a week. The interval between daily dosing can be any hourly interval, for example, every hour, every 2 hours, every 3 hours, every 4 hours, every 5 hours, every 6 hours, every 7 hours, every 8 hours, every 9 hours, every 10 hours, every 11 hours, and every 12 hours. The administration of the compound can have irregular dosing schedules to accommodate either the person administering the compound or the subject receiving the compound. As such, the compound can be administered once a day, twice a day, three times a day, and the like.

In addition, the amount administered can be of the same amount in each dose or the dosage can vary. For example, a first amount dosed in the morning and a second amount administered in the evening. The dosage for administration can be varied depending upon the schedule of the anti-VEGF administration.

The disclosed compounds can be administered in combination with any anti-VEGF agent in any combination, for example, at the beginning of the treatment, at any time during the treatment or at any time after treatment with the anti-VEGF agent has concluded. In addition, the dosage of the disclosed compounds can be adjusted during treatment. Also, the amount of anti-VEGF agent can be adjusted during treatment.

Further non-limiting examples of anti-VEGF agents includes dexamethasone, fluocinolone and triamcinolone. In addition, the disclosed methods can include implants which deliver an anti-VEGF agent. For example, the disclosed compounds can be co-administered either before, during or after an implant is provided to a subject suffering from a disease or condition described herein. For example, Ozurdex™ is an intraviteal implant which provides a supply of dexamethasone to a subject, Retisert™ and Iluvien™ are intraviteal implants which provides a supply of fluocinolone.

In one aspect, anti-VEGF treatments if typically given monthly, can have the frequency of treatment extended, for example, to once every 3 months, once every 6 months or yearly wherein the disclosed compounds is administered at any frequency between treatments.

Also disclosed herein are methods for decreasing the Central Foveal Thickness (CFT) in a patient having a disease or condition as disclosed herein. The method comprises administering to an eye:
 a) an amount of the disclosed compounds; and
 b) one or more anti-VEGF agents;
wherein the administration of the disclosed compounds and the anti-VEGF agent can be conducted in any manner desired by the administrator, for example, as further described herein.

In one aspect the decrease in Central Foveal Thickness is from about 50 µm to about 1000 µm. In one embodiment, the decrease in Central Foveal Thickness is from about 50 µm to about 750 µm. In another embodiment, the decrease in Central Foveal Thickness is from about 200 µm to about 1000 µm. In a further embodiment, the decrease in Central Foveal Thickness is from about 150 µm to about 500 µm. In a still further embodiment, the decrease in Central Foveal Thickness is from about 50 µm to about 500 µm. In a yet another embodiment, the decrease in Central Foveal Thickness is from about 250 µm to about 650 µm. In a yet still further embodiment, the decrease in Central Foveal Thickness is from about 200 µm to about 500 µm. In another still further embodiment, the decrease in Central Foveal Thickness is from about 400 µm to about 700 µm.

Further disclosed herein are methods for increasing the visual acuity of a subject having a disease or condition as disclosed herein.

Visual Acuity

Visual acuity (VA) is acuteness or clearness of vision, which is dependent on the sharpness of the retinal focus within the eye and the sensitivity of the interpretative faculty of the brain. Visual acuity is a measure of the spatial resolution of the visual processing system. VA is tested by requiring the person whose vision is being tested to identify characters typically numbers or letters on a chart from a set distance. Chart characters are represented as black symbols against a white background. The distance between the person's eyes and the testing chart is set at a sufficient distance to approximate infinity in the way the lens attempts to focus. Twenty feet, or six meters, is essentially infinity from an optical perspective.

Visual Acuity Testing

One non-limiting means for measuring Visual Acuity is the use of the ESV-3000 ETDRS testing device (see, U.S. Pat. No. 5,078,486) self-calibrated test lighting. The ESV-3000 device incorporates highly advanced LED light source technology. The auto-calibration circuitry constantly monitors the LED light source and calibrates the test luminance to 85 cd/m2 or 3 cd/m2.

Although designed for clinical trials where large-format ETDRS testing (up to 20/200) is performed at 4 meters, the device can be used in a non-research setting, i.e., hospital or clinic where ocular disease monitoring is conducted. To properly evaluate ETDRS, the test should be conducted under standardized lighting conditions, for, example, photopic test level of 85 cd/m2. This light level has been recommended by the National Academy of Sciences and by the American National Standards Institute for ETDRS and contrast sensitivity vision testing. Scoring of visual acuity can be accomplished in any manner chosen by the monitor. After providing a baseline evaluation, the increase or decrease in the number of letters that can be identified by the test subject provides a measure of sight increase or decrease during treatment.

In one aspect, disclosed herein is a method for increasing visual acuity in a subject having a disease or condition of the eye as disclosed herein. This method comprises administering to a patient having a disease or condition of the eye:
 a) an amount of the disclosed compounds; and
 b) one or more anti-VEGF agents;
wherein the administration of the disclosed compounds and the anti-VEGF agent can be conducted in any manner desired by the administrator, for example, as further described herein.

In one embodiment, the method provides a means for increasing the number of letters recognizable by a treated eye form about 1 to about 30 letters. In another embodiment, the number of letters recognizable is increased from about 5 to about 25 letters. In a further embodiment, the number of letters recognizable is increased from about 5 to about 20 letters. In another further embodiment, the number of letters recognizable is increased from about 5 to about 15 letters. In a still further embodiment, the number of letters recognizable is increased from about 5 to about 10 letters. In a yet another embodiment, the number of letters recognizable is increased from about 10 to about 25 letters. In a yet still further embodiment, the number of letters recognizable is increased from about 15 to about 25 letters. In yet still another embodiment, the number of letters recognizable is increased from about 20 to about 25 letters.

Description of the Figures

The disclosed Figures represent a control or baseline study used as a benchmark for determining the effectiveness of the disclosed methods for treating ocular diseases (FIGS. 1 and 3) and studies directed to the disclosed methods. Described herein below, four patients with visual acuity loss due to diabetic macular edema (central retinal thickness [CRT] of more than 325 microns and best corrected visual acuity less than 70 letters) were treated with subcutaneous injections of 5 mg of the disclosed compound twice a day for 28 days and then observed for an additional two months (days 28 through 84). At any time during the course of the study, investigators could administer additional therapy consisting of intravitreal injection of an anti-VEGF agent, for example, ranibizumab, bevacizumab and/or aflibercept if considered by the investigator to be medically necessary. Retinal thickness as measured by ocular coherence tomography and best corrected visual acuity as measured by a standard vision test were assessed at regular intervals during the 28 day active treatment phase and through the 2 month post-treatment observation phase, (Screening, Day 1 [baseline], Day 7, Day 14, Day 21, Day 28, Day 42, Day 56 and Day 84). The main efficacy outcomes for the study were change in CRT and visual acuity over time with treatment.

Figure 1:
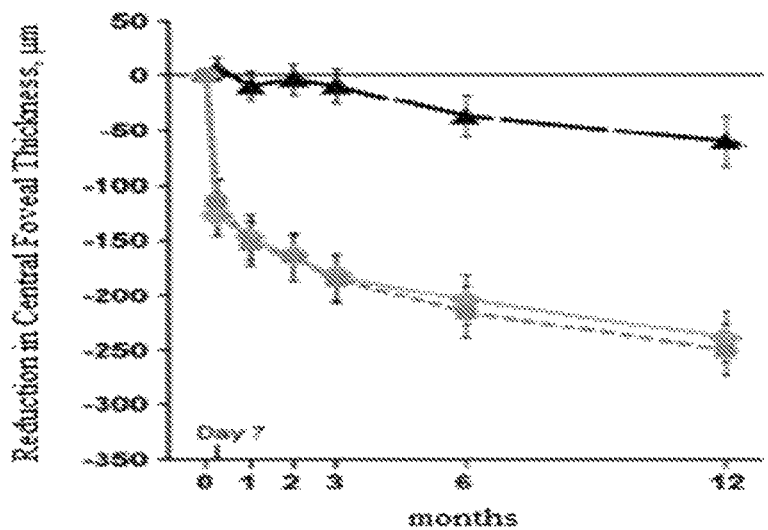
FIG. 1 depicts the results of two phase three studies to determine the effect of intravitreal injections of ranibizumab in patients with diabetic macular edema. Results of these studies were used as a benchmark for determining the effectiveness of the disclosed methods for treating ocular diseases. In this study patients received intravitreal injections with either 0.3 mg (♦) or 0.5 mg (■) ranibizumab monthly, whereas the control group (▲) received placebo. As depicted in FIG. 1 the reduction in Central Foveal Thickness (CFT) for both the 0.3 mg and 0.5 mg cohorts were essentially identical.

FIG. 1 depicts the results of two phase three studies to determine the effect of intravitreal injections of ranibizumab in patients with diabetic macular edema. Results of these studies were used as a benchmark for determining the effectiveness of the disclosed methods for treating ocular diseases. In this study patients received intravitreal injections with either 0.3 mg (♦) or 0.5 mg (■) ranibizumab monthly, whereas the control group (▲) received placebo. As depicted in FIG. 1 the reduction in Central Foveal Thickness (CFT) for both the 0.3 mg and 0.5 mg cohorts were essentially identical. As shown in FIG. 1, the two groups receiving ranibizumab had a reduction in Central Foveal Thickness of approximately 120 to 160 μm from day 7 to 1 month after the first injection of ranibizumab.

Figure 2:
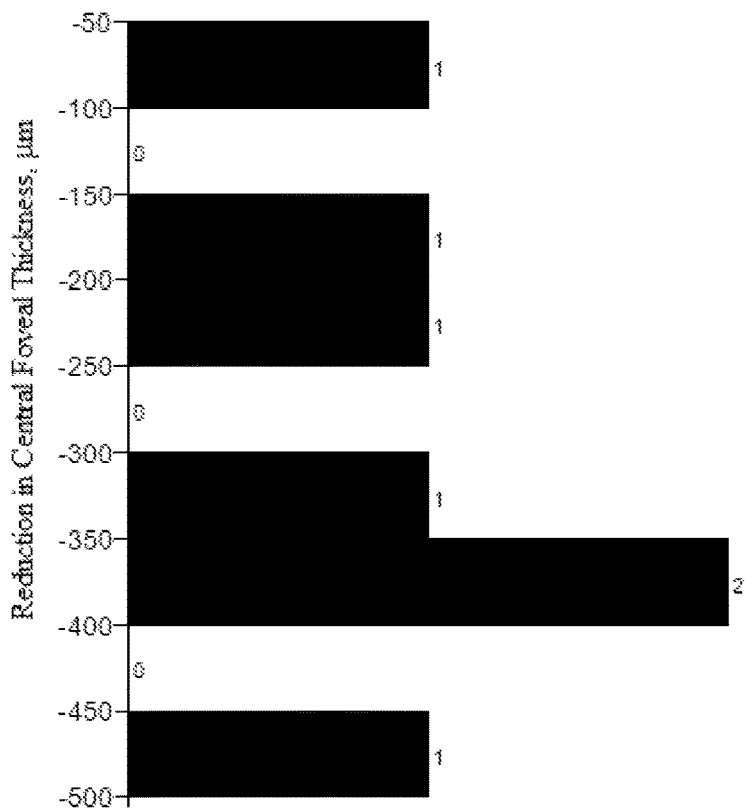
FIG. 2 depicts the results of a study wherein 4 patients received 5 mg of the disclosed compound subcutaneously twice daily for 28 days and subsequently were treated in one or both eyes (7 eyes total) with either ranibizumab (0.3 or 0.5 mg) or aflibercept (2 mg) by intravitreal injection at the discretion of the study investigator.

FIG. 2 depicts the results of a study wherein 4 patients received 5 mg of the disclosed compound subcutaneously twice daily for 28 days and subsequently were treated in one or both eyes (7 eyes total) with either ranibizumab (0.3 or 0.5 mg) or aflibercept (2 mg) by intravitreal injection at the discretion of the study investigator. FIG. 2 is read in this manner: 1 patient eye had a Central Foveal Reduction of between 50-100 μm, 1 patient eye had a Central Foveal Reduction of between 150-200 μm, 1 patient eye had a Central Foveal Reduction of between 200-250 μm, 1 patient eye had a Central Foveal Reduction of between 300-350 μm, 2 patient eyes had a Central Foveal Reduction of between 350-400 μm, and 1 patient eye had a Central Foveal Reduction of between 450-500 μm at 14-28 days post ranibizumab or aflibercept. The mean change in Central Foveal Thickness was −289 μm, approximately double the reduction seen after ranibizumab injection in the benchmark study in FIG. 1.

Figure 3:
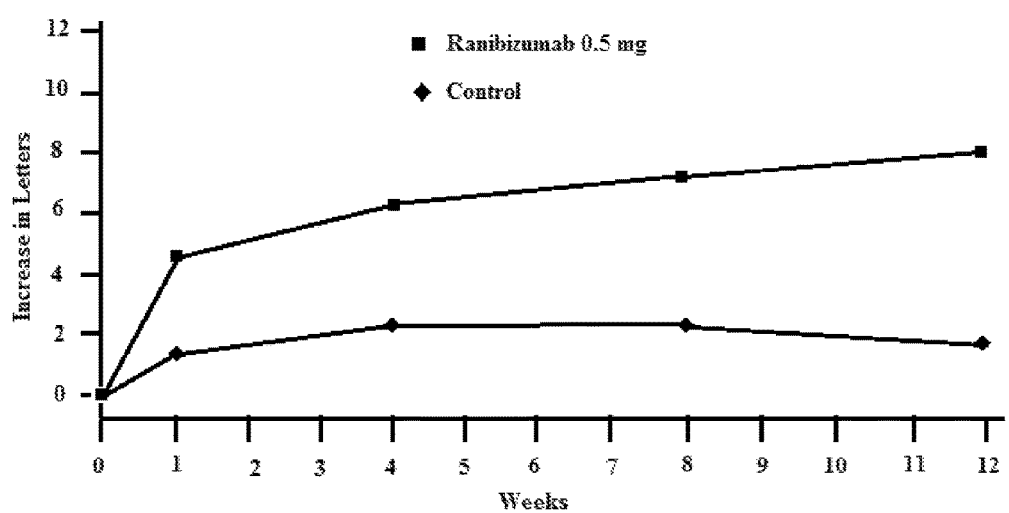
FIG. 3 depicts the results of two phase three studies to determine the effect of intravitreal injections of ranibizumab in patients with diabetic macular edema. Results of these studies were used as a benchmark for determining the effectiveness of the disclosed methods for treating ocular diseases. The control group is represented by (▲). Patients receiving 0.3 mg of ranibizumab monthly via ocular injection are represented by (♦). Patients receiving 0.5 mg of ranibizumab monthly via ocular injection are represented by (■).

FIG. 3 depicts the results of two phase three studies that to determine the effect of intravitreal injections of ranibizumab in patients with diabetic macular edema. Results of these studies were used as a benchmark for determining the effectiveness of the disclosed methods for treating ocular diseases. The control group is represented by (♦). Patients receiving 0.5 mg of ranibizumab monthly via ocular injection are represented by (■). As shown in FIG. 3, the two groups receiving ranibizumab had an increase in visual acuity of between approximately 4 to 6 letters from day 7 to 1 month after the first injection of ranibizumab.

Figure 4:
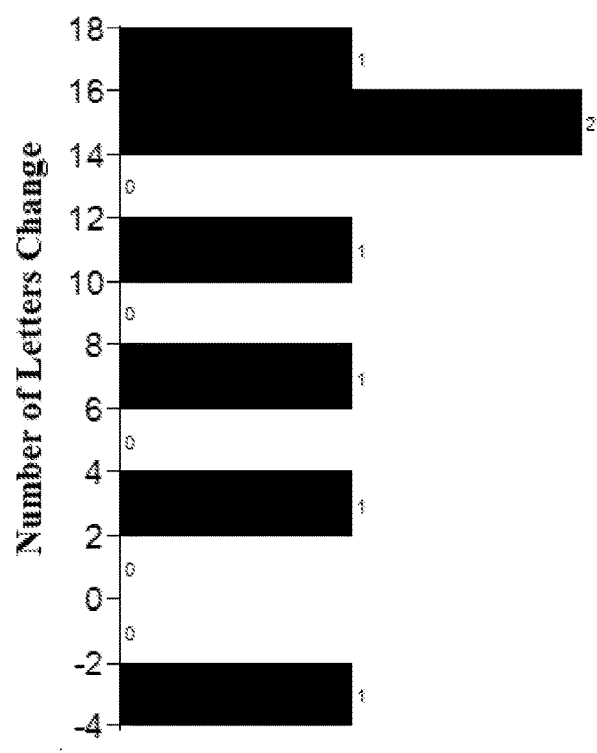
FIG. 4 depicts the increased visual acuity of a study wherein 4 patients received 5 mg of the disclosed compound subcutaneously twice daily for 28 days and subsequently were treated with either ranibizumab (0.3 or 0.5 mg) or aflibercept (2 mg) by intravitreal injection at the discretion of the study investigator.

FIG. 4 depicts the increased visual acuity of a study wherein 4 patients received 5 mg of the disclosed compound subcutaneously twice daily for 28 days and subsequently were treated with either ranibizumab (0.3 or 0.5 mg) or aflibercept (2 mg) by intravitreal injection at the discretion of the study investigator. FIG. 4 is read in this manner: 1 patient eye had an increase of from 16 to 18 letters improvement, 2 patient eyes had an increase of from 14 to 16 letters improvement, 1 patient eye had an increase of from 10 to 12 letters improvement, 1 patient eye had an increase of from 6 to 8 letters improvement, 1 patient eye had an increase of from 2 to 4 letters improvement, and 1 patient eye had a decrease of from 2 to 4 letters at 14-28 days post ranibizumab or aflibercept. The mean change in Visual Acuity was 9 letters, approximately 3 to 5 letters more improvement than seen in the benchmark study of ranibizumab alone depicted in FIG. 3.

Figure 5:
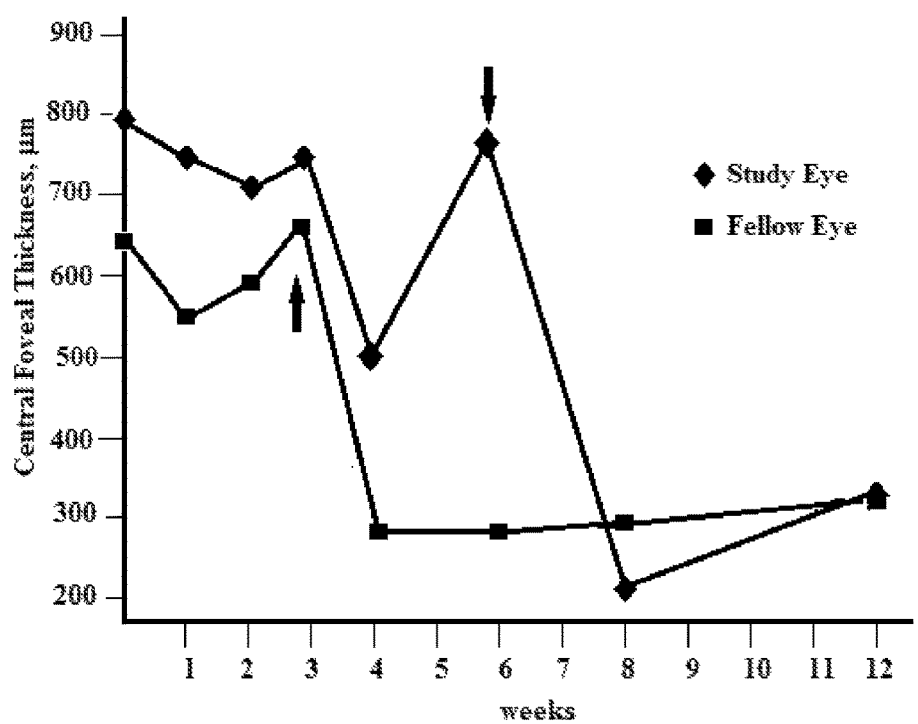
FIG. 5 represents the results of a single patient. The eye having the greater Central Foveal Thickness is chosen as the Study Eye. The patient from day one was given 5 mg of the disclosed compound subcutaneously twice daily. At week 3 (21 days, indicated by arrow) the fellow eye is treated with 0.5 mg of ranibizumab. At week 6 (42 days, indicated by arrow) the treated eye is treated with 0.5 mg of ranibizumab.

FIG. 5 represents the results of a single patient. The eye having the greater Central Foveal Thickness is chosen as the Study Eye. The patient from day one was given 5 mg of the disclosed compound subcutaneously twice daily. At week 3 (21 days, indicated by arrow) the fellow eye is treated with 0.5 mg of ranibizumab. At week 6 (42 days, indicated by arrow) the treated eye is treated with 0.5 mg of ranibizumab. As seen in FIG. 5, the Central Foveal Thickness of the fellow eye drops significantly (350 μm) by week 4 (28 days). Without wishing to be limited by theory, it is believed that when the fellow eye is treated with an injection of 0.5 mg of ranibizumab, the ranibizumab enters the study eye systemically. As a result, there is a pronounced reduction in CFT in the study eye from day 21 to day 28 (approximately 250 μm). As seen in FIG. 5, by the next monitoring point, week 6, the effects of the systemically received ranibizumab is no longer present and the CFT returns to approximately 775 μm. At week 6, the study eye is treated with an intravitreal injection of 0.5 mg of ranibizumab. As depicted in FIG. 5, by week 8, there is an overall reduction in CFT of approximately 500 μm, wherein the CFT of the subject eye is approximately 225 μm. Compared to the benchmark study depicted in FIG. 1 wherein the average change in CFT at one month after ranibizumab injection was approximately 160 mm, the combination disclosed method provided substantially greater reductions at 2-4 weeks following ranibizumab injection. FIG. 6 represents the results of a single patient. The eye having the greater Central Foveal Thickness is chosen as the Study Eye. The patient from day one was given 5 mg of the disclosed compound subcutaneously twice daily. At week 4 (28 days, indicated by arrow) the fellow eye is rescued with 2 mg of aflibercept. After rescue, the Fellow eye has a CFT reduction of approximately 400 μm. At week 6 (42 days, indicated by arrow) the study eye is rescued with 2 mg of aflibercept. After rescue, the Study eye has a CFT reduction of approximately 300 μm.

Unlike the results depicted for the ranibizumab protocol, there is no evidence of systemically delivered aflibercept to the Fellow Eye. From onset of the study, there was a reduction of CFT in the study eye and non-treated eye of approximately 300 μm and 280 μm respectively.

Unlike the results depicted for the ranibizumab protocol, there is no evidence of systemically delivered aflibercept to the Fellow Eye. From onset of the study, there was a reduction of CFT in the study eye and non-treated eye of approximately 300 μm and 280 μm respectively.

The disclosed methods include administration of the disclosed compounds in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

In another aspect, the disclosed compounds can be used prophylactically, i.e., as a preventative agent after treatment with an anti-VEGF agent has stopped. The disclosed compounds herein can be conveniently formulated into pharmaceutical compositions composed of one or more pharmaceutically acceptable carriers. See e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceutical carriers, most typically, are standard carriers for administration of compositions to humans and non-humans, including solutions such as sterile water, saline, and buffered solutions at physiological pH. Other compositions can be administered according to standard procedures used by those skilled in the art. For example, pharmaceutical compositions can also include one or more additional active ingredients such as antimicrobial agents, anti-inflammatory agents, anesthetics, and the like.

Non-limiting examples of pharmaceutically-acceptable carriers include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

The disclosed method also relates to the administration of the disclosed compounds, as well as compositions comprising the disclosed compounds. Administration can be systemic via subcutaneous or i.v. administration; or the HPTP-β inhibitor will be administered directly to the eye, e.g., local. Local methods of administration include, for example, by eye drops, subconjunctival injections or implants, intravitreal injections or implants, sub-Tenon's injections or implants, incorporation in surgical irrigating solutions, etc.

The disclosed methods relate to administering the disclosed compounds as part of a pharmaceutical composition. Compositions suitable for topical administration are known to the art (see, for example, US Patent Application 2005/0059639 included herein by reference in its entirety). In various embodiments, compositions of the invention can comprise a liquid comprising an active agent in solution, in suspension, or both. As used herein, liquid compositions include gels. In one embodiment, the liquid composition is aqueous. Alternatively, the composition can take form of an ointment. In another embodiment, the composition is an in situ gellable aqueous composition. In iteration, the composition is an in situ gellable aqueous solution. Such a composition can comprise a gelling agent in a concentration effective to promote gelling upon contact with the eye or lacrimal fluid in the exterior of the eye. Aqueous compositions of the invention have ophthalmically compatible pH and osmolality. The composition can comprise an ophthalmic depot formulation comprising an active agent for subconjunctival administration. The microparticles comprising active agent can be embedded in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, e.g. by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion generally comprise polymers and can be bioerodible or non-bioerodible.

In one embodiment of the disclosed methods, a human subject with at least one visually impaired eye is treated with form about 5 mg to about 50 mg of the disclosed compounds via intravitreal injection. Improvement of clinical symptoms are monitored by one or more methods known to the art, for example, indirect ophthalmoscopy, fundus photography, fluorescein angiopathy, electroretinography, external eye examination, slit lamp biomicroscopy, applanation tonometry, pachymetry, optical coherence tomography and autorefaction. As described herein, the dosing can occur at any frequency determined by the administrator. After cessation of the anti-VEGF agent treatment, subsequent doses can be administered weekly or monthly, e.g., with a frequency of 2-8 weeks or 1-12 months apart depending upon the response.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

The term "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human, animal being treated or route of administration. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present disclosure can be administered as frequently as necessary to achieve a therapeutic amount.

The disclosed compounds can also be present in liquids, emulsions, or suspensions for delivery of active therapeutic agents in aerosol form to cavities of the body such as the nose, throat, or bronchial passages. The ratio of disclosed compounds to the other compounding agents in these preparations will vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of one or more of the disclosed compounds in combination with a pharmaceutically acceptable carrier and, in addition, can include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. In one embodiment, a composition comprising the disclosed compounds in an amount of approximately 5 mg per 0.1 mL liquid is prepared. The liquid phase comprises sterile water and an appropriate amount of a saccharide or polysaccharide.

Compositions

Disclosed herein are compositions for administration to a subject having one or more of the diseases or conditions described herein. In one aspect, the compositions for delivering the disclosed compounds, comprise:

a) an effective amount of the disclosed compounds or a pharmaceutically acceptable salts thereof; and
b) one or more carriers or compatible excipients.

The compositions comprising the disclosed compounds can be administered by any method, for example, intravenously, orally, by patch, subcutaneous injection, and the like.

In one non-limiting example, solutions of the disclosed compounds are prepared as follows. Approximately 100 mg of a sterile powder of the disclosed compounds is dissolved in approximately 250 mg of hydroxypropyl beta cyclodextrin (HPβCD) to form a first solution. The first solution can be optionally diluted with from about 0.25 mL to about 1 mL of water. Depending upon the composition of the solution, the administrator of the compound can withdraw a sufficient amount such that the subject is injected subcutaneously with an amount that provides from about 5 mg to about 50 mg of the disclosed compounds. The formulator, however, can prepare a first solution or a diluted solution having any concentration convenient or desirable. Non-limiting examples according to this embodiment include the following TABLE I:

TABLE I

| Compound (mg) | HPβCD (mg) | Water (mL) |
|---|---|---|
| 50 | 250 | 0.25 |
| 50 | 250 | 0.5 |
| 50 | 250 | 0.75 |
| 50 | 250 | 1 |
| 100 | 250 | 0.25 |
| 100 | 250 | 0.5 |
| 100 | 250 | 0.75 |
| 100 | 250 | 1 |
| 50 | 250 | — |
| 50 | 250 | — |
| 50 | 250 | — |
| 50 | 250 | — |
| 100 | 250 | — |
| 100 | 250 | — |
| 100 | 250 | — |
| 100 | 250 | — |

In one aspect the disclosed methods comprise administering the disclosed compounds to a subject until a therapeutic level has been established. Once a therapeutic level has been established the subject then receives an anti-VEGF agent. After receiving the anti-VEGF agent, the subject is evaluated and when a benchmark reduction in symptoms is achieved, the anti-VEGF agent is discontinued and the subject continues to receive a therapeutic amount of the disclosed compounds.

EXAMPLE 2

A subject having a Central Retinal Thickness of greater than or equal to about 600 μm is given 15 mg of the disclosed compounds via subcutaneous injection twice daily for 2 weeks (14 days). On day 14 each eye is given an intravitreal injection of 0.5 mg ranibizumab. Ranibizumab is available as Lucentis™ from Genentech in single-use glass vials designed to provide 0.05 mL (10 mg/mL solution providing 0.5 mg of ranibizumab) for injection. Administration of the disclosed compounds is continued until the Central Retinal Thickness of each eye is less than about 150 μm.

EXAMPLE 3

A subject having a Central Retinal Thickness of greater than or equal to about 600 μm is given 5 mg of the disclosed compounds via subcutaneous injection twice daily for 4 weeks (28 days). On day 28 each eye is given an intravitreal injection of 0.5 mg ranibizumab. Administration of the disclosed compounds is continued until the Central Retinal Thickness of each eye is less than about 150 μm.

EXAMPLE 4

A subject having a Central Retinal Thickness of greater than or equal to about 600 μm is given 15 mg of the disclosed compounds via subcutaneous injection twice daily for 4 weeks (28 days). On day 28 each eye is given an intravitreal injection of 0.5 mg ranibizumab. Administration of the disclosed compounds is continued until the Central Retinal Thickness of each eye is less than about 150 μm.

EXAMPLE 5

A subject having a Central Retinal Thickness of greater than or equal to about 600 μm is given 30 mg of the disclosed compounds via subcutaneous injection twice daily for 2 weeks (14 days). On day 14 each eye is given an intravitreal injection of 0.5 mg ranibizumab. Administration of the disclosed compounds is continued until the Central Retinal Thickness of each eye is less than about 150 μm.

EXAMPLE 6

A subject having a Central Retinal Thickness of greater than or equal to about 600 μm is given 30 mg of the disclosed compounds via subcutaneous injection twice daily for 4 weeks (28 days). On day 28 each eye is given an intravitreal injection of 0.5 mg ranibizumab. Administration of the disclosed compounds is continued until the Central Retinal Thickness of each eye is less than about 150 μm.

EXAMPLE 7

A subject having a Central Retinal Thickness of greater than or equal to about 600 μm is given 15 mg of the disclosed compounds via subcutaneous injection twice daily for 2 weeks (14 days). On day 14 each eye is given an intravitreal injection of 0.3 mg ranibizumab. Ranibizumab is available as Lucentis™ from Genentech in single-use glass vials designed to provide 0.05 mL (6 mg/mL solution providing 0.3 mg of ranibizumab) for injection. Administration of the disclosed compounds is continued until the Central Retinal Thickness of each eye is less than about 150 μm.

EXAMPLE 8

A subject having a Central Retinal Thickness of greater than or equal to about 600 μm is given 5 mg of the disclosed compounds via subcutaneous injection twice daily for 4 weeks (28 days). On day 28 each eye is given an intravitreal injection of 0.3 mg ranibizumab. Administration of the disclosed compounds is continued until the Central Retinal Thickness of each eye is less than about 150 μm.

EXAMPLE 9

A subject having a Central Retinal Thickness of greater than or equal to about 600 μm is given 15 mg of the disclosed compounds via subcutaneous injection twice daily for 4 weeks (28 days). On day 28 each eye is given an intravitreal injection of 0.3 mg ranibizumab. Administration of the disclosed compounds is continued until the Central Retinal Thickness of each eye is less than about 150 μm.

EXAMPLE 10

A subject having a Central Retinal Thickness of greater than or equal to about 600 μm is given 30 mg of the disclosed compounds via subcutaneous injection twice daily for 2 weeks (14 days). On day 14 each eye is given an intravitreal injection of 0.3 mg ranibizumab. Administration of the disclosed compounds is continued until the Central Retinal Thickness of each eye is less than about 150 μm.

EXAMPLE 11

A subject having a Central Retinal Thickness of greater than or equal to about 600 μm is given 30 mg of the disclosed compounds via subcutaneous injection twice daily for 4 weeks (28 days). On day 28 each eye is given an intravitreal injection of 0.3 mg ranibizumab. Administration of the disclosed compounds is continued until the Central Retinal Thickness of each eye is less than about 150 μm.

EXAMPLE 12

A subject having a Central Retinal Thickness of greater than or equal to about 600 μm is given 30 mg of the disclosed compounds via subcutaneous injection twice daily for 2 weeks (14 days). On day 14 each eye is given an intravitreal injection of 2 mg aflibercept. Aflibercept is available as Eylea™ from Regeneron Pharmaceuticals, Inc. in single-use glass vials designed to provide 2 mg of aflibercept in a 0.05 mL injection. Administration of the disclosed compounds is continued until the Central Retinal Thickness of each eye is less than about 150 μm.

EXAMPLE 13

A subject having a Central Retinal Thickness of greater than or equal to about 600 μm is given 5 mg of the disclosed compounds via subcutaneous injection twice daily for 4 weeks (28 days). On day 28 each eye is given an intravitreal injection of 2 mg aflibercept. Administration of the disclosed compounds is continued until the Central Retinal Thickness of each eye is less than about 150 μm.

EXAMPLE 14

A subject having a Central Retinal Thickness of greater than or equal to about 600 μm is given 15 mg of the disclosed compounds via subcutaneous injection twice daily for 4 weeks (28 days). On day 28 each eye is given an intravitreal injection of 2 mg aflibercept. Administration of the disclosed compounds is continued until the Central Retinal Thickness of each eye is less than about 150 μm.

EXAMPLE 15

A subject having a Central Retinal Thickness of greater than or equal to about 600 μm is given 30 mg of the disclosed compounds via subcutaneous injection twice daily for 2 weeks (14 days). On day 14 each eye is given an intravitreal injection of 2 mg aflibercept. Administration of the disclosed compounds is continued until the Central Retinal Thickness of each eye is less than about 150 μm.

EXAMPLE 16

A subject having a Central Retinal Thickness of greater than or equal to about 600 μm is given 30 mg of the disclosed compounds via subcutaneous injection twice daily for 4 weeks (28 days). On day 28 each eye is given an intravitreal injection of 2 mg aflibercept. Administration of the disclosed compounds is continued until the Central Retinal Thickness of each eye is less than about 150 μm.

Kits

Disclosed herein are kits for practicing the disclosed methods. In general the kits comprise:

A) a composition for delivering the disclosed compounds; and

B) a composition for delivering an anti-VEGF agent.

The kits can be modified to fit the dosing regimen prescribed for the subject being treated. The following is a non-limiting example of a kit for use with a patient receiving an intravenously delivered composition comprising the disclosed compounds and an intravireally administered anti-VEGF agent. This particular example provides dosing of the disclosed compounds twice daily for 3 months and for an injection of ranibizumab at week 12.

A. 3 packages, each package containing 4 vials. Each vial comprising a sufficient amount of the disclosed compounds to provide 2 daily injections of 5 mg of the disclosed compounds for 7 days; and B. a vial of ranibizumab for injection at the end of week 12 which provides 0.5 mg of ranibizumab.

The artisan, however, can provide kits that comprise any combination of elements. In addition, when the disclosed compounds is provided orally, a single container with sufficient doses of the disclosed compounds can be supplied with the kit.

Also included with each kit labels providing instructions for use and disposal can be included, as well as instructions for use of the compositions to be delivered. The instructions can be modified from kit to kit to reflect the dosing regime prescribed.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for treating diabetic macular edema, comprising administering to a subject in need thereof a therapeutically effective amount of a compound having the formula:

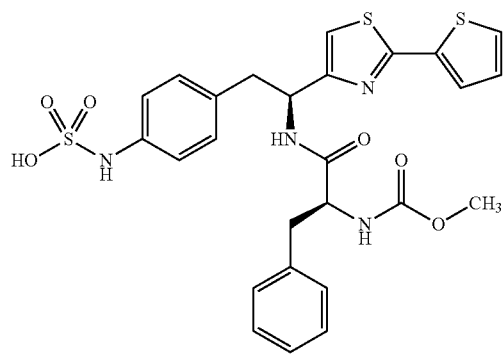

or
a pharmaceutically acceptable salt thereof; and
a therapeutically effective amount of at least one anti-VEGF agent, wherein the anti-VEGF agent is ranibizumab, bevacizumab, or aflibercept.

2. The method according to claim 1, the method further comprising treating a retinopathy in the subject.

3. The method according to claim 1, wherein the therapeutically effective amount of the compound or pharmaceutically-acceptable salt thereof is from about 0.5 mg to about 30 mg per treatment.

4. The method according to claim 1, wherein the anti-VEGF agent is ranibizumab.

5. The method according to claim 4, wherein the therapeutically effective amount of ranibizumab is about 0.05 mg to about 1.5 mg.

6. The method according to claim 1, wherein the anti-VEGF agent is bevacizumab.

7. The method according to claim 6, wherein the therapeutically effective amount of bevacizumab is about 0.1 mg to about 5 mg.

8. The method according to claim 1, wherein the anti-VEGF agent is aflibercept.

9. The method according to claim 8, wherein the therapeutically effective amount of aflibercept is about 0.05 mg to about 5 mg.

10. The method according to claim 1, wherein the administration reduces central foveal thickness in an eye of the subject.

11. The method according to claim 1, wherein the administration improves visual acuity in an eye of the subject.

12. The method according to claim 1, wherein the anti-VEGF agent is ranibizumab, and wherein the therapeutically effective amount of ranibizumab is about 0.3 mg.

13. The method according to claim 1, wherein the therapeutically effective amount of the compound or the pharmaceutically acceptable salt thereof is about 15 mg per treatment.

* * * * *